US008153795B2

(12) United States Patent
Sundermann et al.

(10) Patent No.: US 8,153,795 B2
(45) Date of Patent: Apr. 10, 2012

(54) SUBSTITUTED 1-OXA-3,8-DIAZASPIRO[4.5]-DECAN-2-ONE-COMPOUNDS AND THE USE THEREOF FOR PRODUCING DRUGS

(75) Inventors: Corinna Sundermann, Aachen (DE); Michael Przewosny, Aachen (DE); Bernd Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 951 days.

(21) Appl. No.: 11/994,001

(22) PCT Filed: Jun. 27, 2006

(86) PCT No.: PCT/EP2006/006215
§ 371 (c)(1),
(2), (4) Date: Jul. 2, 2008

(87) PCT Pub. No.: WO2007/000325
PCT Pub. Date: Jan. 4, 2007

(65) Prior Publication Data
US 2009/0105290 A1 Apr. 23, 2009

(30) Foreign Application Priority Data
Jun. 27, 2005 (DE) .................. 10 2005 030 051

(51) Int. Cl.
*C07D 491/10* (2006.01)
*A61K 31/44* (2006.01)
(52) U.S. Cl. ........................................ 546/19; 514/278
(58) Field of Classification Search .................. None
See application file for complete search history.

(56) References Cited

U.S. PATENT DOCUMENTS

| 4,244,961 A | * | 1/1981 | Kluge et al. ............ 514/278 |
| 4,255,432 A | | 3/1981 | Kluge et al. |
| 5,739,336 A | | 4/1998 | Weinhardt et al. |
| 7,265,108 B2 | * | 9/2007 | Ozaki et al. ............ 514/230.5 |

FOREIGN PATENT DOCUMENTS

| EP | 1 484 327 A1 | 12/2004 |
| WO | WO 99/65494 A | 12/1999 |
| WO | WO 03/057698 A2 | 7/2003 |

OTHER PUBLICATIONS

Caroon et al., J. Med. Chem., 1981, vol. 24, pp. 1320-1328.*
Smith et al., J. Med. Chem., 1995, vol. 38, pp. 3772-3779.*
Vippagunta, S. et al Adv. Drug Deliv. Rev., vol. 48, 2001, pp. 3-26.*
HCAPLUS 2002 353280.*
HCAPLUS 1997:4308.*
HCAPLUS 2003:818432.*
Smith, P. J. Med. Chem. 1995, vol. 38, pp. 3772-3779.*
HCAPLUS 2005:322737.*
Silverman, R. "The Organic Chemistry of Drug Design and Drug Action," 2004, Elsevier, pp. 29-32.*
Streitwieser, A. et al., Introduction to Organic Chemistry NY Macmillan, 1992, p. 39.*
German Search Report dated Aug. 1, 2006 with English translation (Nine (9) pages).
International Search Report dated Jan. 17, 2007 with English translation of relevant portions (Five (5) pages).
Joan M. Caroon et al., "Synthesis and Antihypertensive Activity of a Series of 8-Substituted 1-Oxa-3,8-diazaspiro[4.5]decan-2-ones[1]" Journal of Medicinal Chemistry, 1981, vol. 24, No. 11, pp. 1320-1328.

* cited by examiner

*Primary Examiner* — Janet Andres
*Assistant Examiner* — Heidi Reese
(74) *Attorney, Agent, or Firm* — Crowell & Moring LLP

(57) ABSTRACT

The present invention relates to substituted 1-oxa-3,8-diazaspiro[4.5]-decan-2-one compounds, to methods for the production thereof, to medicaments containing these compounds and to the use of these compounds for producing medicaments.

20 Claims, No Drawings

SUBSTITUTED 1-OXA-3,8-DIAZASPIRO[4.5]-DECAN-2-ONE-COMPOUNDS AND THE USE THEREOF FOR PRODUCING DRUGS

The present invention relates to substituted 1-oxa-3,8-diazaspiro[4.5]-decan-2-one compounds, to methods for the production thereof, to medicaments containing these compounds and to the use of these compounds for producing medicaments.

Pain is one of the basic clinical symptoms. There is a worldwide need for effective pain treatments. The urgency of the requirement for therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

Conventional opioids, such as for example morphine, are effective in the treatment of severe to very severe pain, but they often lead to unwanted accompanying symptoms, such as for example respiratory depression, vomiting, sedation, constipation or the development of tolerance. Moreover, they are frequently insufficiently effective in the case of neuropathic pain, suffered in particular by tumour patients.

One object of the present invention was accordingly to provide novel compounds which are suitable in particular as pharmaceutical active ingredients in medicaments, preferably in medicaments for the treatment of pain.

A further object of the present invention was to provide novel compounds which are suitable pharmacological active ingredients in medicaments for the treatment of disorders or diseases which are at least partially mediated by opioid receptors, in particular μ opioid receptors and/or serotonin (5-HT) receptors and/or noradrenalin receptors.

It has surprisingly now been found that substituted 1-oxa-3,8-diazaspiro[4.5]-decan-2-one compounds of the general formula I stated below exhibit an excellent affinity for the opioid receptor, in particular for the μ opioid receptor, for the serotonin (5-HT) receptor and for the noradrenalin receptor and are therefore particularly suitable for the prevention and/or treatment of disorders or diseases which are at least partially mediated by opioid receptors, in particular μ opioid receptors and/or serotonin (5-HT) receptors and/or noradrenalin receptors.

The present invention accordingly provides 1-oxa-3,8-diazaspiro[4.5]-decan-2-one compounds of the general formula I stated below,

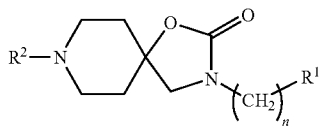

I in which n is equal to 1, 2, 3, 4 or 5;

$R^1$ denotes an optionally substituted 6- or 10-membered aryl residue or denotes an optionally substituted 5- to 14-membered heteroaryl residue, wherein the aryl and/or heteroaryl residue may in each case be fused with a saturated or unsaturated, optionally substituted mono- or bicyclic ring system;

$R^2$ denotes $-C(=S)-NH-R^3$;
$-C(=O)-NH-R^4$;
$-S(=O)_2-R^5$;
$-(CH_2)-C(=O)-NH-R^6$;
$-(CH_2)-R^7$;

denotes $-(CH_2)-D_{aa}-(CH_2)_{bb}-E_{cc}-(CH_2)_{dd}-R^7$ with aa=0 or 1; bb=0, 1 or 2;
cc=0 or 1 and dd=0 or 1; in which D and E mutually independently denote O, S, NH, N(CH$_3$), N(C$_2$H$_5$) or N[CH(CH$_3$)$_2$] and wherein the sum of aa and cc does not equal 0;
denotes $-C(=O)-R^8$
or $-S(=O)_2-NR^9R^{10}$;

$R^3$ denotes $-(CHR^{11})-(CH_2)_w-C(=O)-O-R^{12}$ with w=0 or 1;
denotes $-(CHR^{13})-(CH_2)_a-K_b-(CH_2)_c-L_d-R^{14}$ with a=0, 1 or 2; b=0 or 1; c=0, 1 or 2 and d=0 or 1; in which K and L mutually independently denote O, S, NH, N(CH$_3$), N(C$_2$H$_5$) or N[CH(CH$_3$)$_2$];
denotes a linear or branched, saturated or unsaturated, optionally substituted C$_{1-10}$ aliphatic residue;
denotes an unsaturated or saturated, optionally substituted 3-, 4-, 5-, 6-, 7-, 8- or 9-membered cycloaliphatic residue which may be bridged with 1 or 2 linear or branched, optionally substituted C$_{1-5}$ alkylene groups and/or fused with a saturated, unsaturated or aromatic, optionally substituted mono- or bicyclic ring system;
or denotes an optionally substituted 6- or 10-membered aryl residue or denotes an optionally substituted 5- to 14-membered heteroaryl residue, wherein the aryl and/or heteroaryl residue may in each case be fused with a saturated or unsaturated, optionally substituted mono- or bicyclic ring system;

$R^4$ denotes $-(CHR^{15})-(CH_2)_e-M_f-(CH_2)_g-P_h-R^{16}$ with e=0, 1 or 2; f=0 or 1; g=0, 1 or 2 and h=0 or 1; in which M and P mutually independently denote O, S, NH, N(CH$_3$), N(C$_2$H$_5$) or N[CH(CH$_3$)$_2$];
denotes a linear or branched, saturated or unsaturated, optionally substituted C$_{1-10}$ aliphatic residue;
denotes an unsaturated or saturated, optionally substituted 3-, 4-, 5-, 6-, 7-, 8- or 9-membered cycloaliphatic residue which may be bridged with 1 or 2 linear or branched, optionally substituted C$_{1-5}$ alkylene groups and/or fused with a saturated, unsaturated or aromatic, optionally substituted mono- or bicyclic ring system;
or denotes an optionally substituted 6- or 10-membered aryl residue or denotes an optionally substituted 5- to 14-membered heteroaryl residue, wherein the aryl and/or heteroaryl residue may in each case be fused with a saturated or unsaturated, optionally substituted mono- or bicyclic ring system;

$R^5$ denotes $-(CHR^{17})-(CH_2)_k-Q_l-(CH_2)_m-T_o-R^{18}$ with k=0, 1 or 2; l=0 or 1; m=0, 1 or 2 and o=0 or 1; in which Q and T mutually independently denote O, S, NH, N(CH$_3$), N(C$_2$H$_5$) or N[CH(CH$_3$)$_2$];
denotes a linear or branched, saturated or unsaturated, optionally substituted C$_{1-10}$ aliphatic residue;
denotes an unsaturated or saturated, optionally substituted 3-, 4-, 5-, 6-, 7-, 8- or 9-membered cycloaliphatic residue which may be bridged with 1 or 2 linear or branched, optionally substituted C$_{1-5}$ alkylene groups and/or fused with a saturated, unsaturated or aromatic, optionally substituted mono- or bicyclic ring system;
or denotes an optionally substituted 6- or 10-membered aryl residue or denotes an optionally substituted 5- to 14-membered heteroaryl residue, wherein the aryl and/ or heteroaryl residue may in each case be fused with a saturated or unsaturated, optionally substituted mono- or bicyclic ring system;

$R^6$ denotes a linear or branched, saturated or unsaturated, optionally substituted $C_{1-10}$ aliphatic residue;

denotes an unsaturated or saturated, optionally substituted 3-, 4-, 5-, 6-, 7-, 8- or 9-membered cycloaliphatic residue which may be bridged with 1 or 2 linear or branched, optionally substituted $C_{1-5}$ alkylene groups and/or fused with a saturated, unsaturated or aromatic, optionally substituted mono- or bicyclic ring system;

or denotes an optionally substituted 6- or 10-membered aryl residue or denotes an optionally substituted 5- to 14-membered heteroaryl residue, wherein the aryl and/or heteroaryl residue may in each case be fused with a saturated or unsaturated, optionally substituted mono- or bicyclic ring system;

$R^7$ denotes an unsaturated or saturated, optionally substituted 3-, 4-, 5-, 6-, 7-, 8- or 9-membered cycloaliphatic residue which may be bridged with 1 or 2 linear or branched, optionally substituted $C_{1-5}$ alkylene groups and/or fused with a saturated, unsaturated or aromatic, optionally substituted mono- or bicyclic ring system;

or denotes an optionally substituted 6- or 10-membered aryl residue or denotes an optionally substituted 5- to 14-membered heteroaryl residue, wherein the aryl and/or heteroaryl residue may in each case be fused with a saturated or unsaturated, optionally substituted mono- or bicyclic ring system;

$R^8$ denotes —(CHR$^{19}$)—V$_p$—(CH$_2$)$_q$—(CH$_2$)$_r$—W$_s$—R$^{20}$ with p=0 or 1; q=0, 1 or 2; r=0, 1 or 2 and s=0 or 1; in which V and W mutually independently in each case denote O, S, NH, N(CH$_3$), N(C$_2$H$_5$) or N[CH(CH$_3$)$_2$];

denotes —(CH=CH)—R$^{21}$;

denotes —(CR$^{22}$R$^{23}$)—Y$_t$—(CR$^{24}$R$^{25}$)$_u$—(CH$_2$)$_v$—C(=O)—OR$^{26}$ with t=0 or 1, u=0 or 1 and v=0 or 1, in which Y denotes O, S, NH, N(CH$_3$), N(C$_2$H$_5$) or N[CH(CH$_3$)$_2$];

denotes —(CHR$^{27}$)—O—C(=O)—R$^{28}$;

denotes —CH[(CH$_2$)R$^{29}$][NH—S(=O)$_2$—R$^{30}$];

denotes —CH[(CH$_2$)R$^{31}$][NH—C(=O)—O—R$^{32}$];

denotes a linear or branched, saturated or unsaturated, optionally substituted $C_{1-10}$ aliphatic residue;

denotes an unsaturated or saturated, optionally substituted 3-, 4-, 5-, 6-, 7-, 8- or 9-membered cycloaliphatic residue which may be bridged with 1 or 2 linear or branched, optionally substituted $C_{1-5}$ alkylene groups and/or fused with a saturated, unsaturated or aromatic, optionally substituted mono- or bicyclic ring system;

or denotes an optionally substituted 6- or 10-membered aryl residue or denotes an optionally substituted 5- to 14-membered heteroaryl residue, wherein the aryl and/or heteroaryl residue may in each case be fused with a saturated or unsaturated, optionally substituted mono- or bicyclic ring system;

$R^9$ and $R^{10}$, mutually independently, in each case denote a linear or branched, saturated or unsaturated, optionally substituted $C_{1-10}$ aliphatic residue;

$R^{11}$, $R^{13}$, $R^{15}$, $R^{17}$, $R^{19}$, $R^{22}$, $R^{23}$, $R^{24}$, $R^{25}$ and $R^{26}$, mutually independently, in each case denote
a hydrogen residue
or denote a linear or branched, saturated or unsaturated, optionally substituted $C_{1-10}$ aliphatic residue;

$R^{12}$, $R^{28}$ and $R^{32}$, mutually independently, in each case denote a linear or branched, saturated or unsaturated, optionally substituted $C_{1-10}$ aliphatic residue;

$R^{14}$, $R^{16}$, $R^{18}$ and $R^{20}$, mutually independently, in each case denote
a linear or branched, saturated or unsaturated, optionally substituted $C_{1-10}$ aliphatic residue;

denote an unsaturated or saturated, optionally substituted 3-, 4-, 5-, 6-, 7-, 8- or 9-membered cycloaliphatic residue which may be bridged with 1 or 2 linear or branched, optionally substituted $C_{1-5}$ alkylene groups and/or fused with a saturated, unsaturated or aromatic, optionally substituted mono- or bicyclic ring system;

or denote an optionally substituted 6- or 10-membered aryl residue or an optionally substituted 5- to 14-membered heteroaryl residue, wherein the aryl and/or heteroaryl residue may in each case be fused with a saturated or unsaturated, optionally substituted mono- or bicyclic ring system;

and $R^{21}$, $R^{27}$, $R^{29}$, $R^{30}$ and $R^{31}$, mutually independently, in each case denote
denote an unsaturated or saturated, optionally substituted 3-, 4-, 5-, 6-, 7-, 8- or 9-membered cycloaliphatic residue which may be bridged with 1 or 2 linear or branched, optionally substituted $C_{1-5}$ alkylene groups and/or fused with a saturated, unsaturated or aromatic, optionally substituted mono- or bicyclic ring system;

or denote an optionally substituted 6- or 10-membered aryl residue or an optionally substituted 5- to 14-membered heteroaryl residue, wherein the aryl and/or heteroaryl residue may in each case be fused with a saturated or unsaturated, optionally substituted mono- or bicyclic ring system;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The above-stated $C_{1-10}$ aliphatic residues may preferably in each case optionally be substituted with 1, 2, 3, 4 or 5 substituents mutually independently selected from the group consisting of F, Cl, Br, I, —CN, —NO$_2$, —OH, —SH and —NH$_2$.

If one or more of above-stated substituents denote(s) a linear or branched $C_{1-10}$ aliphatic residue, this residue may preferably be selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl.

Particularly preferred, optionally substituted $C_{1-10}$ aliphatic residues may be selected from the group consisting of methyl, ethyl, n-propyl, isopropyl, n-butyl, sec-butyl, isobutyl, tert-butyl, n-pentyl, sec-pentyl, 3-pentyl, n-hexyl, 3-heptyl, 4-heptyl, —CF$_3$, —CFH$_2$, —CF$_2$H, —CBr$_3$, —CCl$_3$, —CF$_2$—CF$_3$, —CH$_2$—CF$_3$, —CH$_2$—CN, —CH$_2$—NO$_2$, —CF$_2$—CF$_2$—CF$_3$, —CH$_2$—CH$_2$—CF$_3$, —CH$_2$—CH$_2$—CN, —CH$_2$—CH$_2$—NO$_2$, —CF$_2$—CF$_2$—CF$_2$—CF$_3$ and —CH$_2$—CH$_2$—CH$_2$—CN.

The above-stated cycloaliphatic residues may preferably in each case optionally be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —S—CF$_2$H, —S—CFH$_2$, —SH, —S—$C_{1-5}$-alkyl, —$C_{1-5}$-alkyl, —C(=O)—OH, —(CH$_2$)—C(=O)—OH; —C(=O)—O—$C_{1-5}$-alkyl, —(CH$_2$)—C(=O)—O—$C_{1-5}$-alkyl, —O—C(=O)—$C_{1-5}$-alkyl, —NH—$C_{1-5}$-alkyl, —N(—$C_{1-5}$-alkyl)$_2$, —NH-phenyl, —NH-pyridinyl, —N(—$C_{1-5}$-alkyl)-phenyl, —N(—$C_{1-5}$-alkyl)-pyridinyl, —NH—C(=O)—O—$C_{1-5}$-alkyl, —C(=O)—H, —C(=O)—$C_{1-5}$-alkyl, —C(=O)—$C_{1-5}$-perfluoroalkyl, —C(=O)—NH$_2$, —C(=O)—NH—$C_{1-5}$-alkyl, C(=O)—N—(—$C_{1-5}$-alkyl)$_2$, —S(=O)$_2$—$C_{1-5}$-alkyl, —S(=O)$_2$-phenyl, —NH—S(=O)$_2$—$C_{1-5}$-alkyl, —S(=O)$_2$—NH—$C_{1-5}$-alkyl, —S(=O)$_2$—NH$_2$, —S(=O)$_2$—NH-phenyl, cyclohexyl, cyclopentyl, pyridinyl, [1,2,5]-thiadiazolyl, pyridazinyl, —(CH$_2$)-benzo[b]furanyl, —O-phenyl, —O-benzyl, phenyl and benzyl, wherein in each case the cyclic moiety of the residues —S(=O)$_2$—NH-phenyl, —NH-phenyl, —NH-pyridinyl, —N(—$C_{1-5}$-alkyl)-phenyl, —N($C_{1-5}$-alkyl)-pyridinyl, pyridinyl, cyclopentyl, [1,2,5]-thiadiazolyl, cyclohexyl, pyridazinyl, —S(=O)$_2$-phenyl, —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —$C_{1-5}$-alkyl, —O—$C_{1-5}$-alkyl, —O—CF$_3$, —S—CF$_3$, phenyl and —O-benzyl.

The above-stated cycloaliphatic residues may preferably in each case optionally comprise 1, 2, 3, 4 or 5 heteroatom(s) mutually independently selected from the group consisting of oxygen, nitrogen and sulfur.

If one of the above-stated substituents denotes a cycloaliphatic residue, which may optionally be bridged with 1 or 2 linear or branched $C_{1-5}$ alkylene groups, said residue may preferably be selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, adamantyl and bicyclo[2.2.1]heptyl.

The above-stated cycloaliphatic residues may particularly preferably in each case optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, —(CH$_2$)—C(=O)—OH, —C(=O)—OH, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, phenyl and —S(=O)$_2$—NH$_2$, wherein the phenyl residue may in each case be substituted with 1, 2, 3, 4 or 5 substituents mutually independently selected from the group consisting of F, Cl, Br, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$.

The above-stated $C_{1-5}$ alkylene groups may preferably in each case optionally be substituted with 1, 2, 3, 4 or 5 substituents mutually independently selected from the group consisting of F, Cl, Br, I, —CN, —NO$_2$, —OH, —SH and —NH$_2$—.

If one of the above-stated substituents comprises a $C_{1-5}$ alkylene group, the latter may preferably be selected from the group consisting of —(CH$_2$)—, —(CH$_2$)$_2$—, —C(H)(CH$_3$)—, —C(CH$_3$)$_2$—, —(CH$_2$)$_3$—, —(CH$_2$)$_4$—, —(CH$_2$)$_5$—, —C(H)(C(H)(CH$_3$)$_2$)- and —C(C$_2$H$_5$)(H)—.

The rings of the above-stated mono- or polycyclic ring systems may likewise preferably in each case optionally be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—$C_{1-5}$-alkyl, —NH$_2$, —NO$_2$, —O—CF$_3$, —S—CF$_3$, —S—CF$_2$H, —S—CFH$_2$, —SH, —S—$C_{1-5}$-alkyl, —$C_{1-5}$-alkyl, —C(=O)—OH, —(CH$_2$)—C(=O)—OH; —C(=O)—O—$C_{1-5}$-alkyl, —(CH$_2$)—C(=O)—O—$C_{1-5}$-alkyl, —O—C(=O)—$C_{1-5}$-alkyl, —NH—$C_{1-5}$-alkyl, —N(—$C_{1-5}$-alkyl)$_2$, —NH-phenyl, —NH-pyridinyl, —N(—$C_{1-5}$-alkyl)-phenyl, —N(—$C_{1-5}$-alkyl)-pyridinyl, —NH—C(=O)—O—$C_{1-5}$-alkyl, —C(=O)—H, —C(=O)—$C_{1-5}$-alkyl, —C(=O)—$C_{1-5}$-perfluoroalkyl, —C(=O)—NH$_2$, —C(=O)—NH—$C_{1-5}$-alkyl, C(=O)—N—(—$C_{1-5}$-alkyl)$_2$, —S(=O)$_2$—$C_{1-5}$-alkyl, —S(=O)$_2$-phenyl, —NH—S(=O)$_2$—$C_{1-5}$-alkyl, —S(=O)$_2$—NH—$C_{1-5}$-alkyl, —S(=O)$_2$—NH$_2$, —S(=O)$_2$—NH-phenyl, cyclohexyl, cyclopentyl, pyridinyl, [1,2,5]-thiadiazolyl, pyridazinyl, —(CH$_2$)-benzo[b]furanyl, —O-phenyl, —O-benzyl, phenyl and benzyl, wherein in each case the cyclic moiety of the residues —S(=O)$_2$—NH-phenyl, —NH-phenyl, —NH-pyridinyl, —N(—$C_{1-5}$-alkyl)-phenyl, —N(—$C_{1-5}$-alkyl)-pyridinyl, pyridinyl, cyclopentyl, [1,2,5]-thiadiazolyl, cyclohexyl, pyridazinyl, —S(=O)$_2$-phenyl, —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —CN, —NO$_2$, —$C_{1-5}$-alkyl, —O—$C_{1-5}$-alkyl, —O—CF$_3$, —S—CF$_3$, phenyl and —O-benzyl.

The rings of the above-stated optionally substituted mono- or polycyclic ring systems may particularly preferably be unsubstituted or optionally substituted in each case with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, —(CH$_2$)—C(=O)—OH, —C(=O)—OH, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, phenyl and —S(=O)$_2$—NH$_2$; wherein the phenyl residue may in each case be substituted with 1, 2, 3, 4 or 5 substituents mutually independently selected from the group consisting of F, Cl, Br, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$.

For the purposes of the present invention, a mono- or polycyclic ring system is taken to mean mono- or polycyclic hydrocarbon residues which may be saturated, unsaturated or aromatic and may optionally comprise 1, 2, 3, 4 or 5 heteroatom(s) as ring member(s) which are mutually independently selected from the group consisting of oxygen, nitrogen and sulfur.

Such a mono- or polycyclic ring system may for example be fused (anellated) with an aryl residue or a heteroaryl residue.

If a polycyclic ring system, such as for example a bicyclic ring system, is present, the various rings may in each case mutually independently be of a different degree of saturation, i.e. be saturated, unsaturated or aromatic. A polycyclic ring system is preferably a bicyclic ring system.

The rings of the above-stated mono- or polycyclic ring systems may preferably in each case be 5-, 6- or 7-membered and may in each case comprise 1, 2 or 3 heteroatom(s) as ring member(s) which are mutually independently selected from the group consisting of oxygen, nitrogen and sulfur.

Examples of aryl residues which are fused with a mono- or polycyclic ring system and may be mentioned are [1,3]-benzodioxolyl, [1,4]-benzodioxanyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl and [3,4]-dihydro-2H-1,4-benzoxazinyl.

The above-stated optionally substituted aryl or heteroaryl residues may likewise preferably be unsubstituted or optionally substituted with 1, 2, 3, 4 or 5 substituents mutually independently selected from the group consisting of F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —S—CF$_2$H, —S—CFH$_2$, SH, —S—C$_{1-5}$-alkyl, —C$_{1-10}$-alkyl, —C(=O)—OH, —(CH$_2$)—C(=O)—OH, —C(=O)—O—C$_{1-5}$-alkyl, —(CH$_2$)—C(=O)—O—C$_{1-5}$-alkyl, —O—C(=O)—C$_{1-5}$-alkyl, —NH—C$_{1-5}$-alkyl, —N(—C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(—C$_{1-5}$-alkyl)$_2$, —S(=O)$_2$—C$_{1-5}$-alkyl, —S(=O)$_2$-phenyl, —NH—S(=O)$_2$—C$_{1-5}$-alkyl, —S(=O)$_2$—NH—C$_{1-5}$-alkyl, —S(=O)$_2$—NH$_2$, —S(=O)$_2$—NH-phenyl, cyclohexyl, cyclopentyl, pyridinyl, pyridazinyl, —(CH$_2$)-benzo[b]furanyl, —O-phenyl, —O-benzyl, phenyl and benzyl, wherein in each case the cyclic moiety of the residues pyridinyl, cyclopentyl, cyclohexyl, pyridazinyl, —S(=O)$_2$-phenyl, —S(=O)$_2$—NH-phenyl, —O-phenyl, —O-benzyl, phenyl, —(CH$_2$)-benzo[b]furanyl and benzyl may be substituted with 1, 2, 3, 4 or 5 substituents mutually independently selected from the group consisting of F, Cl, Br, —OH, —CF$_3$, —SF$_5$, —NO$_2$, —C$_{1-5}$-alkyl, —O—C$_{1-5}$-alkyl, —O—CF$_3$, —S—CF$_3$, phenyl and —O-benzyl.

The above-stated heteroaryl residues may preferably optionally in each case comprise 1, 2, 3, 4 or 5 heteroatom(s) mutually independently selected from the group consisting of oxygen, nitrogen and sulfur as ring member(s).

If one or more of the above-stated substituents denote(s) an aryl residue, the latter may preferably be selected from the group consisting of phenyl and naphthyl (1-naphthyl and 2-naphthyl).

If one or more of the above-stated substituents denotes a heteroaryl residue, the latter may preferably be selected from the group consisting of 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, oxazolyl, isoxazolyl, pyridazinyl, pyrazinyl, pyrimidinyl, indazolyl, quinazolinyl, quinolinyl and isoquinolinyl.

The aryl or heteroaryl residues may particularly preferably in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, —S(=O)$_2$—NH-phenyl, phenyl, —O-phenyl, —O-benzyl and benzyl, wherein in each case the cyclic moiety of the residues —S(=O)$_2$—NH-phenyl, phenyl, —O-phenyl, —O-benzyl and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl.

A substituted phenyl residue may very particularly preferably be selected from the group consisting of biphenyl, 2-trifluoromethylphenyl, 2-butoxyphenyl, 2-(1,1)-dimethylpropylphenyl, 2-nitrophenyl, 2-ethyl benzoate, 2-acetamidophenyl, 2-difluoromethylsulfanylphenyl, 2-dimethylaminophenyl, 2-diethylaminophenyl, 2-aminophenyl, 2-benzenesulfonamide, 2-trifluoromethylsulfanylphenyl, 2-ethylphenyl, 2-methyl benzoate, 2-methanesulfonylphenyl, 2-bromophenyl, 2-chlorophenyl, 2-fluorophenyl, 2-methylphenyl, 2-trifluoromethoxy, 2-methoxyphenyl, 2-ethoxyphenyl, 2-propylphenyl, 2-cyanophenyl, 2-acetylphenyl, 2-dimethylaminosulfonylphenyl, 3-chlorophenyl, 3-methylphenyl, 3-butoxyphenyl, 3-nitrophenyl, 3-trifluoromethylsulfanylphenyl, 3-trifluoromethylphenyl, 3-methanesulfonylphenyl, 3-benzenesulfonamide, 3-ethyl benzoate, 3-fluorophenyl, 3-difluoromethylsulfanylphenyl, 3-propylphenyl, 3-bromophenyl, 3-dimethylaminophenyl, 3-(1,1)-dimethylpropylphenyl, 3-acetaminophenyl, 3-diethylaminophenyl, 3-aminophenyl, 3-methoxyphenyl, 3-ethylphenyl, 3-ethoxyphenyl, 3-cyanophenyl, 3-trifluoromethoxyphenyl, 3-acetylphenyl, 3-phenylphenyl, 3-dimethylaminosulfonylphenyl, 4-methanesulfonylphenyl, 4-bromophenyl, 4-methoxyphenyl, 4-chlorophenyl, 4-benzenesulfonamide, 4-difluoromethylsulfanylphenyl, 4-fluorophenyl, 4-tert-butylphenyl, 4-cyanophenyl, 4-butoxyphenyl, 4-nitrophenyl, 4-trifluoromethylsulfanylphenyl, 4-methylphenyl, 4-phenylphenyl, 4-trifluoromethylphenyl, 4-dimethylaminophenyl, 4-propylphenyl, 4-diethylaminophenyl, 4-ethyl benzoate, 4-aminophenyl, 4-iodophenyl, 4-trifluoromethoxyphenyl, 4-(1,1)-dimethylpropylphenyl, 4-n-propylphenyl, 4-di-n-propylaminosulfonylphenyl, 4-(3, 5-dichlorophenylsulfamoyl)phenyl, 4-acetamidophenyl, 4-diethylaminosulfonylphenyl, 4-dimethylaminosulfonylphenyl, 4-ethylphenyl, 4-ethoxyphenyl, 4-methyl benzoate, 4-acetylphenyl, 2-fluoro-3-trifluoromethylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, (2,4)-dibromophenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, (3,4)-dichlorophenyl, 4-chloro-3-nitrophenyl, (3,4)-dimethoxyphenyl, 4-fluoro-3-trifluoromethylphenyl, 3-fluoro-4-trifluoromethylphenyl, (3,4)-difluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 4-methyl-3-nitrophenyl, (3,5)-dimethoxyphenyl, (3,5)-bis-trifluoromethylphenyl, (3,5)-difluorophenyl, (3,5)-dinitrophenyl, (3,5)-dichlorophenyl, 3-fluoro-5-trifluoromethylphenyl, 5-fluoro-3-trifluoromethylphenyl, (3,5)-dibromophenyl, 5-chloro-4-fluorophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (3,4,5)-trimethoxyphenyl, (2,3,4,5)-tetrafluorophenyl, 4-methoxy-2,3,6-trimethylphenyl, 4-methoxy-2,3,6-trimethylphenyl, 4-chloro-2,5-dimethylphenyl, 2-chloro-6-fluoro-3-methylphenyl, 6-chloro-2-fluoro-3-methyl and (2,3,4,5,6)-pentafluorophenyl.

An optionally substituted heteroaryl residue may very particularly preferably be selected from the group consisting of benzo[1,2,3]oxadiazol-5-yl, 5-tert-butyl-2-methyl-2H-pyrazol-3-yl, 5-tert-butyl-2-methylfuran-3-yl, 3-(2-chlorophenyl)-5-methylisoxazol-4-yl, 2-chloropyridin-3-yl, 2-chloropyridin-4-yl, 6-chloro-2H-chromen-3-yl, 6-chloropyridin-3-yl, 5-chlorobenzo[b]thiophen-3-yl, 3-chlorothiophen-2-yl, 3-cyano-4-methylthiophen-2-yl, (4,5)-dichlorothiophen-2-yl, (2,5)-dimethyl-2H-pyrazol-3-yl, 2-ethylsulfanylpyridin-3-yl, 3-(2-fluorophenyl)-5-methylisoxazol-4-yl, 2-furanyl, 3-furanyl, 1H-indol-3-yl, isoxazol-5-yl, 3-(4-methoxyphenyl)-[1,2,4]oxadiazol-5-yl, 2-methylsulfanylpyridin-3-yl, 5-methylisoxazol-4-yl, 5-methylisoxazol-3-yl, 5-methyl-2-phenyl-2H-[1,2,3]triazol-4-yl, 4-methyl[1,2,3]thiadiazol-5-yl, 2-methyl-6-trifluoromethylpyridin-3-yl, 1-phenyl-5-propyl-1H-pyrazol-4-yl, 4-phenyl-5-trifluoromethylthiophen-3-yl, 2-phenoxypyridin-3-yl, 4-phenylthiazolyl-2-yl, 2-pyridinyl, 3-pyridinyl, 4-pyridinyl, 2-thiophenyl, 3-thiophenyl, (1,2,3,4)-tetrahydroisoquinolin-7-yl and 5-trifluoromethyl-1H-pyrazol-4-yl.

Preferred substituted 1-oxa-3,8-diazaspiro[4.5]-decan-2-one compounds of the above-stated general formula I are likewise those in which $R^1$ denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, n-hexyl, n-heptyl, —NH—C(=O)—O—CH$_3$, —NH—C(=O)—O—C$_2$H$_5$, —NH—C(=O)—O—C(CH$_3$)$_3$, —NH—C(=O)—CH$_3$, —NH—C(=O)—C$_2$H$_5$, —NH—C(=O)—C(CH$_3$)$_3$, —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, phenyl and benzyl, wherein in each case the cyclic moiety of the residues phenyl and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

and in each case $R^2$ to $R^{32}$, aa, bb, cc, dd, a, b, c, d, e, f, g, h, k, l, m, n, o, p, q, r, s, t, u, v, w, D, E, K, L, M, P, Q, T, V, W and Y have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred substituted 1-oxa-3,8-diazaspiro[4.5]-decan-2-one compounds of the above-stated general formula I are furthermore those in which $R^2$ denotes —C(=S)—NH—R$^3$; —C(=O)—NH—R$^4$; —S(=O)$_2$—R$^5$; —(CH$_2$)—C(=O)—NH—R$^6$; —(CH$_2$)—R$^7$; für —(CH$_2$)—O—R$^7$, —(CH$_2$)—S—R$^7$, —(CH$_2$)—NH—R$^7$, —(CH$_2$)—N(CH$_3$)—R$^7$, —(CH$_2$)—(CH$_2$)—O—R$^7$, —(CH$_2$)—(CH$_2$)—S—R$^7$, —(CH$_2$)—NH—R$^7$, —(CH$_2$)—N(CH$_3$)—R$^7$, —(CH$_2$)—(CH$_2$)—(CH$_2$)—O—R$^7$, —(CH$_2$)—(CH$_2$)—(CH$_2$)—S—R$^7$, —(CH$_2$)—(CH$_2$)—(CH$_2$)—NH—R$^7$, —(CH$_2$)—(CH$_2$)—(CH$_2$)—N(CH$_3$)—R$^7$, —(CH$_2$)—O—(CH$_2$)—R$^7$, —(CH$_2$)—S—(CH$_2$)—R$^7$; —(CH$_2$)—NH—(CH$_2$)—R$^7$;   —C(=O)—R$^8$   or —S(=O)$_2$—NR$^9$R$^{10}$;

and in each case $R^1$, $R^3$ to $R^{10}$ and n have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred substituted 1-oxa-3,8-diazaspiro[4.5]-decan-2-one compounds of the above-stated general formula I are furthermore those in which $R^3$ denotes —(CHR$^{11}$)—C(=O)—O—R$^{12}$ or —(CHR$^{11}$)—(CH$_2$)—C(=O)—O—R$^{12}$;

denotes —(CHR$^{13}$)—R$^{14}$, —(CHR$^{13}$)—(CH$_2$)—R$^{14}$, —(CHR$^{13}$)—(CH$_2$)—(CH$_2$)—R$^{14}$, —(CHR$^{13}$)—O—R$^{14}$, —(CHR$^{13}$)—S—R$^{14}$, —(CHR$^{13}$)—NH—R$^{14}$, —(CHR$^{13}$)—N(CH$_3$)—R$^{14}$, —(CHR$^{13}$)—(CH$_2$)—O—R$^{14}$, —(CHR$^{13}$)—(CH$_2$)—S—R$^{14}$, —(CHR$^{13}$)—NH—R$^{14}$, —(CHR$^{13}$)—N(CH$_3$)—R$^{14}$, —(CHR$^{13}$)—(CH$_2$)—(CH$_2$)—O—R$^{14}$, —(CHR$^{13}$)—(CH$_2$)—(CH$_2$)—S—R$^{14}$, —(CHR$^{13}$)—(CH$_2$)—(CH$_2$)—NH—R$^{14}$, —(CHR$^{13}$)—(CH$_2$)—(CH$_2$)—N(CH$_3$)—R$^{14}$, —(CHR$^{13}$)—O—(CH$_2$)—R$^{14}$, —(CHR$^{13}$)—S—(CH$_2$)—R$^{14}$ or —(CHR$^{13}$)—NH—(CH$_2$)—R$^{14}$;

denotes a residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH) (C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein the residue may optionally be substituted with 1, 2, 3, 4 or 5 substituents mutually independently selected from the group consisting of F, Cl, Br, I, —CN, —NO$_2$, —OH, —SH and —NH$_2$;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein the residue may in each case optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, phenyl and benzyl, wherein in each case the cyclic moiety of the residues phenyl and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

and in each case R$^1$, R$^2$, R$^{11}$ to R$^{14}$, a, b, c, d, n, w, K and L have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred substituted 1-oxa-3,8-diazaspiro[4.5]-decan-2-one compounds of the above-stated general formula I are furthermore those in which R$^4$ denotes —(CHR$^{15}$)—R$^{16}$, —(CHR$^{15}$)—(CH$_2$)—R$^{16}$, —(CHR$^{15}$)—(CH$_2$)—(CH$_2$)—R$^{16}$, —(CHR$^{15}$)—O—R$^{16}$, —(CHR$^{15}$)—S—R$^{16}$, —(CHR$^{15}$)—NH—R$^{16}$, —(CHR$^{15}$)—N(CH$_3$)—R$^{16}$, —(CHR$^{15}$)—(CH$_2$)—O—R$^{16}$, —(CHR$^{15}$)—(CH$_2$)—S—R$^{16}$, —(CHR$^{15}$)—NH—R$^{16}$, —(CHR$^{15}$)—N(CH$_3$)—R$^{16}$, —(CHR$^{15}$)—(CH$_2$)—(CH$_2$)—O—R$^{16}$, —(CHR$^{15}$)—(CH$_2$)—(CH$_2$)—S—R$^{16}$, —(CHR$^{15}$)—(CH$_2$)—(CH$_2$)—NH—R$^{16}$, —(CHR$^{15}$)—(CH$_2$)—(CH$_2$)—N(CH$_3$)—R$^{16}$, —(CHR$^{15}$)—O—(CH$_2$)—R$^{16}$, —(CHR$^{15}$)—S—(CH$_2$)—R$^{16}$ or —(CHR$^{15}$)—NH—(CH$_2$)—R$^{16}$;

denotes a residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein the residue may optionally be substituted with 1, 2, 3, 4 or 5 substituents mutually independently selected from the group consisting of F, Cl, Br, I, —CN, —NO$_2$, —OH, —SH and —NH$_2$;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein the residue may in each case optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, phenyl and benzyl, wherein in each case the cyclic moiety of the residues phenyl and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

and in each case R$^1$, R$^2$, R$^{15}$, R$^{16}$, e, f, g, h, n, M and P have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Preferred substituted 1-oxa-3,8-diazaspiro[4.5]-decan-2-one compounds of the above-stated general formula I are likewise those in which R$^5$ denotes —(CHR$^{17}$)—R$^{18}$, —(CHR$^{17}$)—(CH$_2$)—R$^{18}$, —(CHR$^{17}$)—(CH$_2$)—(CH$_2$)—R$^{18}$, —(CHR$^{17}$)—O—R$^{18}$, —(CHR$^{17}$)—S—R$^{18}$, —(CHR$^{17}$)—NH—R$^{18}$, —(CHR$^{17}$)—N(CH$_3$)—R$^{18}$, —(CHR$^{17}$)—(CH$_2$)—O—R$^{18}$, —(CHR$^{17}$)—(CH$_2$)—S—R$^{18}$, —(CHR$^{17}$)—NH—R$^{18}$, —(CHR$^{17}$)—N(CH$_3$)—R$^{18}$, —(CHR$^{17}$)—(CH$_2$)—(CH$_2$)—O—R$^{18}$, —(CHR$^{17}$)(CH$_2$)—(CH$_2$)—S—R$^{18}$, —(CHR$^{17}$)—(CH$_2$)—(CH$_2$)—NH—R$^{18}$, —(CHR$^{17}$)—(CH$_2$)—(CH$_2$)—N(CH$_3$)—R$^{18}$, —(CHR$^{17}$)—O—(CH$_2$)—R$^{18}$, —(CHR$^{17}$)—S—(CH$_2$)—R$^{18}$ or —(CHR$^{17}$)—NH—(CH$_2$)—R$^{18}$;

denotes a residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein the residue may optionally be substituted with 1, 2, 3, 4 or 5 substituents mutually independently selected from the group consisting of F, Cl, Br, I, —CN, —NO$_2$, —OH, —SH and —NH$_2$;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein the residue may in each case optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—

C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, phenyl and benzyl, wherein in each case the cyclic moiety of the residues phenyl and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

and in each case R$^1$, R$^2$, R$^{17}$, R$^{18}$, k, l, m, n, o, Q and T have the above-stated meaning, in each case optionally in the form of a the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Preferred substituted 1-oxa-3,8-diazaspiro[4.5]-decan-2-one compounds of the above-stated general formula I are furthermore those in which R$^6$ denotes a residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein the residue may optionally be substituted with 1, 2, 3, 4 or 5 substituents mutually independently selected from the group consisting of F, Cl, Br, I, —CN, —NO$_2$, —OH, —SH and —NH$_2$;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein the residue may in each case optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, —S(=O)$_2$—NH-phenyl, phenyl and benzyl, wherein in each case the cyclic moiety of the residues —S(=O)$_2$—NH-phenyl, phenyl and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

and in each case R$^1$, R$^2$ and n have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred substituted 1-oxa-3,8-diazaspiro[4.5]-decan-2-one compounds of the above-stated general formula I are likewise those in which R$^7$ denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein the residue may in each case optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, —S(=O)$_2$—NH-phenyl, phenyl and benzyl, wherein in each case the cyclic moiety of the residues —S(=O)$_2$—NH-phenyl, phenyl and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

and in each case R$^1$, R$^2$, D, E, aa, bb, cc, dd and n have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred substituted 1-oxa-3,8-diazaspiro[4.5]-decan-2-one compounds of the above-stated general formula I are likewise those in which R$^8$ denotes —(CHR$^{19}$)—R$^{20}$, —(CHR$^{19}$)—(CH$_2$)—R$^{20}$, —(CHR$^{19}$)—(CH$_2$)—(CH$_2$)—R$^{20}$, —(CHR$^{19}$)—O—R$^{20}$, —(CHR$^{19}$)—S—R$^{20}$, —(CHR$^{19}$)—NH—R$^{20}$, —(CHR$^{19}$)—N(CH$_3$)—R$^{20}$, —(CHR$^{19}$)—(CH$_2$)—O—R$^{20}$, —(CHR$^{19}$)—(CH$_2$)—S—R$^{20}$, —(CHR$^{19}$)—NH—R$^{20}$, —(CHR$^{19}$)—N(CH$_3$)—R$^{20}$, —(CHR$^{19}$)—(CH$_2$)—(CH$_2$)—O—R$^{20}$, —(CHR$^{19}$)—(CH$_2$)—(CH$_2$)—S—R$^{20}$, —(CHR$^{19}$)—(CH$_2$)—(CH$_2$)—NH—R$^{20}$, —(CHR$^{19}$)—(CH$_2$)—(CH$_2$)—N(CH$_3$)—R$^{20}$, —(CHR$^{19}$)—O—(CH$_2$)—R$^{20}$, —(CHR$^{19}$)—S—(CH$_2$)—R$^{20}$, —(CHR$^{19}$)—NH—(CH$_2$)—R$^{20}$, —(CHR$^{19}$)—O—(CH$_2$)—(CH$_2$)—O—R$^{20}$, —(CHR$^{19}$)—O—(CH$_2$)—(CH$_2$)—S—R$^{20}$ or —(CHR$^{19}$)—S—(CH$_2$)—(CH$_2$)—S—R$^{20}$;

denotes —(CH=CH)—R$^{21}$;

denotes —(CR$^{22}$R$^{23}$)—C(=O)—O—R$^{26}$, —(CR$^{22}$R$^{23}$)—(CR$^{24}$R$^{25}$)—C(=O)—O—R$^{26}$, —(CR$^{22}$R$^{23}$)—(CR$^{24}$R$^{25}$)—(CH$_2$)—C(=O)—O—R$^{26}$, —(CR$^{22}$R$^{23}$)—O—(CR$^{24}$R$^{25}$)—C(=O)—O—R$^{26}$, —(CR$^{22}$R$^{23}$)—S—(CR$^{24}$R$^{25}$)—C(=O)—O—R$^{26}$ or —(CR$^{22}$R$^{23}$)—NH—(CR$^{24}$R$^{25}$)—C(=O)—O—R$^{26}$;

denotes —(CHR$^{27}$)—O—C(=O)—R$^{28}$;

denotes —CH[(CH$_2$)R$^{29}$][NH—S(=O)$_2$—R$^{30}$];

denotes —CH[(CH$_2$)R$^{31}$][NH—C(=O)—O—R$^{32}$];

denotes a residue selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein the residue may optionally be substituted with 1, 2, 3, 4 or 5 substituents mutually independently selected from the group consisting of F, Cl, Br, I, —CN, —NO$_2$, —OH, —SH and —NH$_2$;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, adamantyl and bicyclo[2.2.1]heptyl, wherein the residue in each case may optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, —(CH$_2$)—C(=O)—OH, —C(=O)—OH, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, phenyl and —S(=O)$_2$—NH$_2$; wherein the phenyl residue may in each case be substituted with 1, 2, 3, 4 or 5 substituents mutually independently selected from the group consisting of F, Cl, Br, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, —S(=O)$_2$—NH-phenyl, phenyl, —O-phenyl, —O-benzyl and benzyl, wherein in each case the cyclic moiety of the residues —S(=O)$_2$—NH-phenyl, phenyl, —O-phenyl, —O-benzyl and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

and in each case R$^1$, R$^2$, R$^{19}$ to R$^{32}$, p, q, n, r, s, t, u, v, V, W and Y have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred substituted 1-oxa-3,8-diazaspiro[4.5]-decan-2-one compounds of the above-stated general formula I are furthermore those in which R$^9$ and R$^{10}$, mutually independently, in each case denote a residue selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;

and in each case R$^1$, R$^2$ and n have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred substituted 1-oxa-3,8-diazaspiro[4.5]-decan-2-one compounds of the above-stated general formula I are likewise those in which R$^{11}$, R$^{13}$, R$^{15}$, R$^{17}$, R$^{19}$, R$^{22}$, R$^{23}$, R$^{24}$, R$^{25}$ and R$^{26}$, mutually independently in each case denote a hydrogen residue or a residue selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;

and in each case R$^1$ to R$^{10}$, R$^{12}$, R$^{14}$, R$^{16}$, R$^{18}$, R$^{20}$, R$^{21}$, R$^{27}$ to R$^{32}$, a, b, c, d, e, f, g, h, k, l, m, n, o, p, q, r, s, t, u, v, w, K, L, Q, T, V, W and Y have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Preferred substituted 1-oxa-3,8-diazaspiro[4.5]-decan-2-one compounds of the above-stated general formula I are furthermore those in which R$^{12}$, R$^{28}$ and R$^{32}$, mutually independently, in each case denote a residue selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;

and in each case R$^1$ to R$^{11}$, R$^{13}$ to R$^{27}$, R$^{29}$, R$^{30}$, R$^{31}$, a, b, c, d, e, f, g, h, k, l, m, n, o, p, q, r, s, t, u, v, w, K, L, Q, T, V, W and Y have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Preferred substituted 1-oxa-3,8-diazaspiro[4.5]-decan-2-one compounds of the above-stated general formula I are likewise those in which R$^{14}$, R$^{16}$, R$^{18}$ and R$^{20}$, mutually independently, in each case denote a residue selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, adamantyl and bicyclo[2.2.1]heptyl, wherein the residue may each case optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, —(CH$_2$)—C(=O)—OH, —C(=O)—OH, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—CH$_3$, —NH—C(=O)—C$_2$H$_5$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$) and S(=O)$_2$—NH$_2$;

and in each case R$^1$ to R$^{13}$, R$^{15}$, R$^{17}$, R$^{19}$, R$^{21}$ to R$^{32}$, a, b, c, d, e, f, g, h, k, l, m, n, o, p, q, r, s, t, u, v, w, K, L, Q, T, V, W and Y have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred substituted 1-oxa-3,8-diazaspiro[4.5]-decan-2-one compounds of the above-stated general formula I are likewise those in which R$^{21}$, R$^{27}$, R$^{29}$, R$^{30}$ and R$^{31}$, mutually independently, in each case denote a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—CH$_3$, —NH—C(=O)—C$_2$H$_5$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$) and S(=O)$_2$—NH$_2$;

and in each case R$^1$ to R$^{20}$, R$^{22}$ to R$^{26}$, R$^{28}$, R$^{32}$, a, b, c, d, e, f, g, h, k, l, m, n, o, p, q, r, s, t, u, v, w, K, L, Q, T, V, W and Y have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Particularly preferred substituted 1-oxa-3,8-diazaspiro[4.5]-decan-2-one compounds of the above-stated general formula I are those in which n is equal to 1, 2 or 3;

R$^1$ denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —SF$_5$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, methyl, ethyl, n-propyl, isopropyl, n-butyl, sec-butyl, isobutyl, tert-butyl, n-pentyl, n-hexyl, n-heptyl, phenyl and benzyl, wherein in each case the cyclic moiety of the residues phenyl and benzyl may be substituted with 1, 2, 3, 4 or 5 substituents mutually independently selected from the group consisting of F, Cl, Br, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$ and —O—C(CH$_3$)$_3$;

R$^2$ denotes —C(=S)—NH—R$^3$;
—C(=O)—NH—R$^4$;
—S(=O)$_2$—R$^5$;
—(CH$_2$)—C(=O)—NH—R$^6$;
—(CH$_2$)—R$^7$;
—(CH$_2$)—O—R$^7$, —(CH$_2$)—S—R$^7$, —(CH$_2$)—NH—R$^7$, —(CH$_2$)—N(CH$_3$)—R$^7$, —(CH$_2$)—(CH$_2$)—O—R$^7$, —(CH$_2$)—(CH$_2$)—S—R$^7$, —(CH$_2$)—NH—R$^7$, —(CH$_2$)—N(CH$_3$)—R$^7$, —(CH$_2$)—(CH$_2$)—(CH$_2$)—O—R$^7$, —(CH$_2$)—(CH$_2$)—(CH$_2$)—S—R$^7$, —(CH$_2$)—(CH$_2$)—(CH$_2$)—NH—R$^7$, —(CH$_2$)—(CH$_2$)—(CH$_2$)—N(CH$_3$)—R$^7$, —(CH$_2$)—O—(CH$_2$)—R$^7$, —(CH$_2$)—S—(CH$_2$)—R$^7$; —(CH$_2$)—NH—(CH$_2$)—R$^7$;
—C(=O)—R$^8$
or denotes —S(=O)$_2$—NR$^9$R$^{10}$;

R$^3$ denotes —(CHR$^{11}$)—C(=O)—O—R$^{12}$ or —(CHR$^{11}$)—(CH$_2$)—C(=O)—O—R$^{12}$;
—(CHR$^{13}$)—R$^{14}$, —(CHR$^{13}$)—(CH$_2$)—R$^{14}$, —(CHR$^{13}$)—(CH$_2$)—(CH$_2$)—R$^{14}$, —(CHR$^{13}$)—O—R$^{14}$, —(CHR$^{13}$)—(CH$_2$)—O—R$^{14}$, —(CHR$^{13}$)—(CH$_2$)—(CH$_2$)—O—R$^{14}$ or —(CHR$^{13}$)—O—(CH$_2$)—R$^{14}$;

denotes a residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$ and —C(=O)—C$_2$F$_5$;

R$^4$ denotes —(CHR$^{15}$)—R$^{16}$, —(CHR$^{15}$)—(CH$_2$)—R$^{16}$ or —(CHR$^{15}$)—(CH$_2$)—(CH$_2$)—R$^{16}$;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —NO$_2$, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, n-hexyl, n-heptyl, —C(=O)—O—CH$_3$, —C(=O)—O—CH$_2$—CH$_3$, —C(=O)—O—CH(CH$_3$)$_2$, —C(=O)—O—C(CH$_3$)$_3$, —C(=O)—CH$_3$, —C(=O)—C$_2$H$_5$, —C(=O)—C(CH$_3$)$_3$, —C(=O)—CF$_3$ and —C(=O)—C$_2$F$_5$;

R$^5$ denotes —(CHR$^{17}$)—R$^{18}$, —(CHR$^{17}$)—(CH$_2$)—R$^{18}$ or —(CHR$^{17}$)—(CH$_2$)—(CH$_2$)—R$^{18}$;

denotes a residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$);

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —C(=O)—O—CH$_3$, —C(=O)—O—CH$_2$—CH$_3$, —C(=O)—O—CH(CH$_3$)$_2$, —C(=O)—O—C(CH$_3$)$_3$, —C(=O)—CF$_3$, —C(=O)—C$_2$F$_5$, —S(=O)$_2$—CH$_3$ and —S(=O)$_2$—C$_2$H$_5$;

R$^6$ denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, —CF$_3$, —CN, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —S(=O)$_2$—NH-Phenyl, phenyl and benzyl, wherein in each case the cyclic moiety of the residues —S(=O)$_2$—NH-phenyl, phenyl and benzyl may be substituted with 1, 2, 3, 4 or 5 substituents mutually independently selected from the group consisting of F, Cl and Br;

R$^7$ denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,4]-oxadiazolyl, [1,2,3]-thiadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, —CN, —CF$_3$, —SF$_5$, —OH, —O—CH$_3$, —O—C$_2$H$_5$, —NO$_2$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, phenyl and benzyl, wherein in each case the cyclic moiety of the residues phenyl and benzyl may be substituted with 1, 2, 3, 4 or 5 substituents mutually independently selected from the group consisting of F, Cl, Br, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$;

R$^8$ denotes —(CHR$^{19}$)—R$^{20}$, —(CHR$^{19}$)—(CH$_2$)—R$^{20}$, —(CHR$^{19}$)—(CH$_2$)—(CH$_2$)—R$^{20}$, —(CHR$^{19}$)—O—R$^{20}$, —(CHR$^{19}$)—(CH$_2$)—O—R$^{20}$, —(CHR$^{19}$)—(CH$_2$)—(CH$_2$)—O—R$^{20}$, —(CHR$^{19}$)—O—(CH$_2$)—R$^{20}$ or —(CHR$^{19}$)—O—(CH$_2$)—(CH$_2$)—O—R$^{20}$;

denotes —(CH=CH)—R$^{21}$;

denotes —(CR$^{22}$R$^{23}$)—C(=O)—O—R$^{26}$, —(CR$^{22}$R$^{23}$)—(CR$^{24}$R$^{25}$)—C(=O)—O—R$^{26}$, —(CR$^{22}$R$^{23}$)—(CR$^{24}$R$^{25}$)—(CH$_2$)—C(=O)—O—R$^{26}$ or —(CR$^{22}$R$^{23}$)—O—(CR$^{24}$R$^{25}$)—C(=O)—O—R$^{26}$;

denotes —(CHR$^{27}$)—O—C(=O)—R$^{28}$;

denotes —CH[(CH$_2$)R$^{29}$][NH—S(=O)$_2$—R$^{30}$];

denotes —CH[(CH$_2$)R$^{31}$][NH—C(=O)—O—R$^{32}$];

denotes a residue selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, adamantyl and bicyclo[2.2.1]heptyl, wherein the residue may in each case optionally be substituted with 1, 2, 3, 4 or 5 substituents mutually independently selected from the group consisting of —C(=O)—CH$_3$, —C(=O)—C$_2$H$_5$, —C(=O)—C(CH$_3$)$_3$ and phenyl;

or denotes a residue selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein the residue may in each case optionally be substituted with 1, 2, 3, 4 or 5 substituents mutually independently selected from the group consisting of F, Cl, Br, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —S—CH$_3$, —S—C$_2$H$_5$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—CH$_3$, —NH—C(=O)—C$_2$H$_5$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —S(=O)$_2$—NH$_2$, phenyl, —O—phenyl, —O—benzyl and benzyl, wherein in each case the cyclic moiety of the residues phenyl, —O—phenyl, —O—benzyl, and benzyl may be substituted with 1, 2, 3, 4 or 5 substituents mutually independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O—benzyl;

R$^9$ and R$^{10}$, mutually independently, in each case denote a residue selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;

R$^{11}$, R$^{13}$, R$^{15}$, R$^{17}$, R$^{19}$, R$^{22}$, R$^{23}$, R$^{24}$, R$^{25}$ and R$^{26}$, mutually independently, in each case denote a hydrogen residue or a residue selected from the group consisting of methyl, ethyl, n-propyl, isopropyl, n-butyl, sec-butyl, isobutyl and tert-butyl;

R$^{12}$, R$^{28}$ and R$^{32}$, mutually independently, in each case denote a residue selected from the group consisting of methyl, ethyl, n-propyl, isopropyl, n-butyl, sec-butyl, isobutyl and tert-butyl;

R$^{14}$, R$^{16}$, R$^{18}$ and R$^{20}$, mutually independently, in each case denote a residue selected from the group consisting of methyl, ethyl, n-propyl, isopropyl, n-butyl, sec-butyl, isobutyl and tert-butyl;

denotes a residue selected from the group consisting of cyclopropyl, cyclobutyl, cyclopentyl, cyclohexyl, cycloheptyl, tetrahydrofuranyl, tetrahydrothiophenyl, tetrahydropyranyl and bicyclo[2.2.1]heptyl, wherein the residue may in each case optionally be substituted with 1, 2, 3, 4 or 5 substituents mutually independently selected from the group consisting of oxo (=O), thioxo (=S), methyl, ethyl, n-propyl, isopropyl, n-butyl, sec-butyl, isobutyl, tert-butyl, n-pentyl, n-hexyl, n-heptyl, —(CH$_2$)—C(=O)—OH and —C(=O)—OH;

or denote a residue selected from the group consisting of phenyl, and naphthyl, wherein the residue may in each case be substituted with 1, 2, 3, 4 or 5 substituents mutually independently selected from the group consisting of F, Cl, Br, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl and n-heptyl;

and

R$^{21}$, R$^{27}$, R$^{29}$, R$^{30}$ and R$^{31}$, mutually independently, in each case denote a residue selected from the group consisting of phenyl, naphthyl, indolyl and isoindolyl, wherein the residue may in each case be substituted with 1, 2, 3, 4 or 5 substituents mutually independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, —C(CH$_3$)$_2$—C$_2$H$_5$, n-hexyl and n-heptyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred substituted 1-oxa-3,8-diazaspiro[4.5]-decan-2-one compounds of the above-stated general formula I are those in which n is equal to 1 or 2;

R$^1$ denotes a residue selected from the group consisting of phenyl and naphthyl, wherein the residue may in each case optionally be substituted with 1, 2, 3, 4 or 5 substituents mutually independently selected from the group consisting of F, Cl, Br, I, —CN, —CF$_3$, —SF$_5$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, methyl, ethyl, n-propyl, isopropyl, n-butyl, sec-butyl, isobutyl, tert-butyl, n-pentyl, n-hexyl, n-heptyl, phenyl and benzyl;

R$^2$ denotes —C(=S)—NH—R$^3$;
—C(=O)—NH—R$^4$;
—S(=O)$_2$—R$^5$;
—(CH$_2$)—C(=O)—NH—R$^6$;
—(CH$_2$)—R$^7$;
—(CH$_2$)—O—R$^7$, —(CH$_2$)—(CH$_2$)—O—R$^7$, —(CH$_2$)—(CH$_2$)—(CH$_2$)—O—R$^7$;
—C(=O)—R$^8$
or denotes —S(=O)$_2$—NR$^9$R$^{10}$;

R$^3$ denotes —(CHR$^{11}$)—(CH$_2$)—C(=O)—O—R$^{12}$;
denotes —(CHR$^{13}$)—R$^{14}$, —(CHR$^{13}$)—(CH$_2$—R$^{14}$, —(CHR$^{13}$)—(CH$_2$)—(CH$_2$)—R$^{14}$ or —(CHR$^{13}$)—(CH$_2$)—O—R$^{14}$;

denotes a residue selected from the group consisting of vinyl, 1-propenyl, 2-propenyl, 1-butenyl, 2-butenyl and 3-butenyl;

or denotes a phenyl residue, [wherein] the residue may be substituted with 1, 2, 3, 4 or 5 substituents mutually independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$ and —C(=O)—C$_2$F$_5$;

R$^4$ denotes —(CHR$^{15}$)—R$^{16}$, —(CHR$^{15}$)—(CH$_2$)—R$^{16}$ or —(CHR$^{15}$)—(CH$_2$)—(CH$_2$)—R$^{16}$;

or denotes a residue selected from the group consisting of phenyl and naphthyl, wherein the residue may in each case optionally be substituted with 1, 2, 3, 4 or 5 substituents mutually independently selected from the group consisting of F, Cl, Br, —NO$_2$, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, n-hexyl, n-heptyl, —C(=O)—O—CH$_3$, —C(=O)—O—CH$_2$—CH$_3$, —C(=O)—O—CH(CH$_3$)$_2$, —C(=O)—O—C(CH$_3$)$_3$, —C(=O)—CH$_3$, —C(=O)—C$_2$H$_5$, —C(=O)—C(CH$_3$)$_3$, —C(=O)—CF$_3$ and —C(=O)—C$_2$F$_5$;

R$^5$ denotes —(CHR$^{17}$)—R$^{18}$, —(CHR$^{17}$)—(CH$_2$)—R$^{18}$ or —(CHR$^{17}$)—(CH$_2$)—(CH$_2$)—R$^{18}$;

denotes a residue selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, and —(CH$_2$)—(CH)(C$_2$H$_5$)—(CH$_2$)—(CH$_2$)—(CH$_2$)—(CH$_3$);

or denotes a residue selected from the group consisting of phenyl, naphthyl, pyrazolyl, thiophenyl, [1,2,3,4]-tetrahydroquinolinyl and [1,2,3,4]-tetrahydroisoquinolinyl, wherein the residue may in each case optionally be substituted with 1, 2, 3, 4 or 5 substituents mutually independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —C(=O)—O—CH$_3$, —C(=O)—O—CH$_2$—CH$_3$, —C(=O)—O—CH(CH$_3$)$_2$, —C(=O)—O—C(CH$_3$)$_3$, —C(=O)—CF$_3$, —C(=O)—C$_2$F$_5$, —S(=O)$_2$—CH$_3$ and —S(=O)$_2$—C$_2$H$_5$;

R$^6$ denotes a residue selected from the group consisting of phenyl, naphthyl, pyrazolyl, thiophenyl and thiazolyl, wherein the residue may in each case optionally be substituted with 1, 2, 3, 4 or 5 substituents mutually independently selected from the group consisting of F, Cl, Br, —CF$_3$, —CN, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —S(=O)$_2$—NH-phenyl, phenyl and benzyl, wherein in each case the cyclic moiety of the residues —S(=O)$_2$—NH-phenyl, phenyl and benzyl may be substituted with 1, 2, 3, 4 or 5 substituents mutually independently selected from the group consisting of F, Cl and Br;

R$^7$ denotes a residue selected from the group consisting of phenyl, naphthyl, benzo[b]furanyl, benzo[b]thiophenyl and [1,2,4]-oxadiazolyl, wherein the residue may in each case optionally be substituted with 1, 2, 3, 4 or 5 substituents mutually independently selected from the group consisting of F, Cl, Br, —CN, —CF$_3$, —SF$_5$, —OH, —O—CH$_3$, —O—C$_2$H$_5$, —NO$_2$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, phenyl and benzyl, wherein in each case the cyclic moiety of the residues phenyl and benzyl may be substituted with 1, 2, 3, 4 or 5 substituents mutually independently selected from the group consisting of F, Cl, Br, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$;

R$^8$ denotes —(CHR$^{19}$)—R$^{20}$, —(CHR$^{19}$)—(CH$_2$)—R$^{20}$, —(CHR$^{19}$)—(CH$_2$)—(CH$_2$)—R$^{20}$, —(CHR$^{19}$)—O—R$^{20}$, —(CHR$^{19}$)—(CH$_2$)—O—R$^{20}$, —(CHR$^{19}$)—(CH$_2$)—(CH$_2$)—O—R$^{20}$, —(CHR$^{19}$)—O—(CH$_2$)—R$^{20}$ or —(CHR$^{19}$)—O—(CH$_2$)—(CH$_2$)—O—R$^{20}$;

denotes —(CH=CH)—R$^{21}$;

denotes —(CR$^{22}$R$^{23}$)—C(=O)—O—R$^{26}$, —(CR$^{22}$R$^{23}$)—(CR$^{24}$R$^{25}$)C(=O)—O—R$^{26}$, —(CR$^{22}$R$^{23}$)—(CR$^{24}$R$^{25}$)—(CH$_2$)—C(=O)—O—R$^{26}$ or —(CR$^{22}$R$^{23}$)—O—(CR$^{24}$R$^{25}$)—C(=O)—O—R$^{26}$;

denotes —(CHR$^{27}$)—O—C(=O)—R$^{28}$;

denotes —CH[(CH$_2$)R$^{29}$][NH—S(=O)$_2$—R$^{30}$];

denotes —CH[(CH$_2$)R$^{31}$][NH—C(=O)—O—R$^{32}$];

denotes a residue selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;

denotes a residue selected from the group consisting of cyclopropyl, cyclobutyl, cyclopentyl, cyclohexyl, cycloheptyl, pyrrolidinyl, piperidinyl and adamantyl, wherein the residue may in each case optionally be substituted with 1, 2, 3, 4 or 5 substituents mutually independently selected from the group consisting of —C(=O)—CH$_3$, —C(=O)—C$_2$H$_5$, —C(=O)—C(CH$_3$)$_3$ and phenyl;

or denotes a residue selected from the group consisting of phenyl, naphthyl, 2H-chromenyl, thiophenyl, furanyl, pyrazolyl, triazolyl, pyridinyl, [1,2,3]-thiadiazolyl, [2,1,3]-benzoxadiazolyl, [1,2,3]-benzoxadiazolyl, oxazolyl and isoxazolyl, wherein the residue may in each case optionally be substituted with 1, 2, 3, 4 or 5 substituents mutually independently selected from the group consisting of F, Cl, Br, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —S—CH$_3$, —S—C$_2$H$_5$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—CH$_3$, —NH—C(=O)—C$_2$H$_5$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —S(=O)$_2$—NH$_2$, phenyl, —O-phenyl, —O-benzyl and benzyl, wherein in each case the cyclic moiety of the residues phenyl, —O-phenyl, —O-benzyl and benzyl may be substituted with 1, 2, 3, 4 or 5 substituents mutually independently selected from the group consisting of F, Cl and Br;

$R^9$ and $R^{10}$, mutually independently, in each case denote a residue selected from the group consisting of methyl, ethyl, n-propyl, isopropyl, n-butyl, sec-butyl, isobutyl and tert-butyl;

$R^{11}$, $R^{13}$, $R^{15}$, $R^{17}$, $R^{19}$, $R^{22}$, $R^{23}$, $R^{24}$, $R^{25}$ and $R^{26}$, mutually independently, in each case denote a hydrogen residue or a residue selected from the group consisting of methyl, ethyl and n-propyl;

$R^{12}$, $R^{28}$ and $R^{32}$, mutually independently, in each case denote a residue selected from the group consisting of methyl, ethyl, n-propyl, isopropyl, n-butyl, sec-butyl, isobutyl and tert-butyl;

$R^{14}$ denotes a residue selected from the group consisting of methyl, ethyl, n-propyl, isopropyl, n-butyl, sec-butyl, isobutyl and tert-butyl;

denotes a residue selected from the group consisting of cyclopropyl, cyclobutyl, cyclopentyl, cyclohexyl, cycloheptyl, tetrahydrofuranyl, tetrahydrothiophenyl and tetrahydropyranyl;

or denotes a phenyl residue which may be substituted with 1, 2, 3, 4 or 5 substituents selected from the group consisting of F, Cl and Br;

$R^{16}$ denotes a residue selected from the group consisting of phenyl and naphthyl, wherein the residue may in each case be substituted with 1, 2, 3, 4 or 5 substituents mutually independently selected from the group consisting of F, Cl and Br;

$R^{18}$ denotes a 7,7-dimethyl-2-oxobicyclo[2.2.1]hept-1-yl residue;

$R^{20}$ denotes a residue selected from the group consisting of methyl, ethyl, n-propyl, isopropyl, n-butyl, sec-butyl, isobutyl and tert-butyl;

denotes a residue selected from the group consisting of cyclopropyl, cyclobutyl, cyclopentyl, cyclohexyl and cycloheptyl; wherein the residue may in each case be substituted with a substituent selected from the group consisting of —$CH_2$—C(=O)—OH and —C(=O)—OH;

or denotes a phenyl residue which may be substituted with 1, 2, 3, 4 or 5 substituents mutually independently selected from the group consisting of F, Cl, Br, —O—$CH_3$, —O—$C_2H_5$, —O—CH($CH_3$)$_2$, —O—$CH_2$—$CH_2$—$CH_3$, —O—C($CH_3$)$_3$ and —O—$CH_2$—$CH_2$—$CH_2$—$CH_3$;

$R^{21}$ denotes a phenyl residue which may be substituted with 1, 2, 3, 4 or 5 substituents selected from the group consisting of F, Cl, and Br;

$R^{27}$ denotes a phenyl residue;

$R^{29}$ denotes a phenyl residue;

$R^{30}$ denotes a phenyl residue which may be substituted with 1, 2, 3, 4 or 5 substituents selected from the group consisting of methyl, ethyl, n-propyl, isopropyl, n-butyl, sec-butyl, and tert-butyl; and $R^{31}$ denotes an indolyl residue;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Still more preferred 1-oxa-3,8-diazaspiro[4.5]-decan-2-one compounds are those selected from the group consisting of

[1] 3-(4-methylbenzyl)-2-oxo-1-oxa-3,8-diazaspiro[4.5]decane-8-carbothioic acid pentafluorophenylamide

[2] 3-(3-bromobenzyl)-2-oxo-1-oxa-3,8-diazaspiro[4.5]decane-8-carbothioic acid (2,5-dichlorophenyl)amide

[3] 2-oxo-3-(4-trifluoromethylbenzyl)-1-oxa-3,8-diazaspiro[4.5]decane-8-carbothioic acid benzylamide

[4] 3-(3,5-dimethylbenzyl)-2-oxo-1-oxa-3,8-diazaspiro[4.5]decane-8-carbothioic acid (tetrahydrofuran-2-ylmethyl)amide

[5] 3-(3-bromobenzyl)-2-oxo-1-oxa-3,8-diazaspiro[4.5]decane-8-carbothioic acid (2-methoxyethyl)amide

[6] 3-(3-bromobenzyl)-2-oxo-1-oxa-3,8-diazaspiro[4.5]decane-8-carbothioic acid (2-methoxyphenyl)amide

[7] 3-(3,5-dimethylbenzyl)-2-oxo-1-oxa-3,8-diazaspiro[4.5]decane-8-carbothioic acid (3-acetylphenyl)amide

[8] 3-benzyl-2-oxo-1-oxa-3,8-diazaspiro[4.5]decane-8-carbothioic acid o-tolylamide

[9] 3-{[3-(3-bromobenzyl)-2-oxo-1-oxa-3,8-diazaspiro[4.5]decane-8-carbothioyl]amino}butanoic acid ethyl ester

[10] 3-naphthalen-2-ylmethyl-2-oxo-1-oxa-3,8-diazaspiro[4.5]decane-8-carbothioic acid allylamide

[11] 3-(3,4-difluorobenzyl)-2-oxo-1-oxa-3,8-diazaspiro[4.5]decane-8-carbothioic acid benzylamide

[12] 3-biphenyl-2-ylmethyl-2-oxo-1-oxa-3,8-diazaspiro[4.5]decane-8-carbothioic acid (1-phenylethyl)amide

[13] 3-(3,4-difluorobenzyl)-2-oxo-1-oxa-3,8-diazaspiro[4.5]decane-8-carbothioic acid (4-ethoxyphenyl)amide

[14] 3-(3-cyanobenzyl)-2-oxo-1-oxa-3,8-diazaspiro[4.5]decane-8-carbothioic acid (3,5-dichlorophenyl)amide

[15] 3-(3-cyanobenzyl)-2-oxo-1-oxa-3,8-diazaspiro[4.5]decane-8-carbothioic acid (3-trifluoromethylphenyl)amide

[16] 3-(3-bromobenzyl)-2-oxo-1-oxa-3,8-diazaspiro[4.5]decane-8-carbothioic acid benzylamide

[17] 3-(2-methoxy-5-nitrobenzyl)-2-oxo-1-oxa-3,8-diazaspiro[4.5]decane-8-carbothioic acid (tetrahydrofuran-2-ylmethyl)amide

[18] 3-biphenyl-2-ylmethyl-2-oxo-1-oxa-3,8-diazaspiro[4.5]decan-8-carbothioic acid phenylamide

[19] 3-(3-cyanobenzyl)-2-oxo-1-oxa-3,8-diazaspiro[4.5]decane-8-carbothioic acid cyclohexylmethylamide

[20] 3-(2-fluorobenzyl)-2-oxo-1-oxa-3,8-diazaspiro[4.5]decane-8-carbothioic acid (3-acetylphenyl)amide

[21] 3-(2-methoxy-5-nitrobenzyl)-2-oxo-1-oxa-3,8-diazaspiro[4.5]decane-8-carbothioic acid cyclohexylmethylamide

[22] 3-(3-cyanobenzyl)-2-oxo-1-oxa-3,8-diazaspiro[4.5]decane-8-carbothioic acid 4-chlorobenzylamide

[23] 3-(2-methoxy-5-nitrobenzyl)-2-oxo-1-oxa-3,8-diazaspiro[4.5]decane-8-carbothioic acid benzylamide

[24] 3-(2-fluorobenzyl)-2-oxo-1-oxa-3,8-diazaspiro[4.5]decane-8-carboxylic acid (4-ethoxyphenyl)amide

[25] 3-biphenyl-2-ylmethyl-2-oxo-1-oxa-3,8-diazaspiro[4.5]decane-8-carboxylic acid (2,5-dichlorophenyl)amide

[26] 3-(2-methoxy-5-nitrobenzyl)-2-oxo-1-oxa-3,8-diazaspiro[4.5]decane-8-carboxylic acid (2,5-difluorophenyl)amide

[27] 3-(4-methylbenzyl)-2-oxo-1-oxa-3,8-diazaspiro[4.5]decane-8-carboxylic acid (4-methyl-3-nitrophenyl)amide

[28] 3-(3,4-difluorobenzyl)-2-oxo-1-oxa-3,8-diazaspiro[4.5]decane-8-carboxylic acid 4-fluorobenzylamide

[29] 3-(3-bromobenzyl)-2-oxo-1-oxa-3,8-diazaspiro[4.5]decane-8-carboxylic acid (2,5-difluorophenyl)amide

[30] 4-[(3-naphthalen-2-ylmethyl-2-oxo-1-oxa-3,8-diazaspiro[4.5]decane-8-carbonyl)amino]benzoic acid ethyl ester

[31] 2-oxo-3-(4-trifluoromethylbenzyl)-1-oxa-3,8-diazaspiro[4.5]decane-8-carboxylic acid (4-chloro-3-trifluoromethylphenyl)amide

[32] 3-(2-cyanobenzyl)-2-oxo-1-oxa-3,8-diazaspiro[4.5]decane-8-carboxylic acid (2,5-difluorophenyl)amide

[33] 3-benzyl-2-oxo-1-oxa-3,8-diazaspiro[4.5]decane-8-carboxylic acid (3-cyanophenyl)amide
[34] 3-(3,4-difluorobenzyl)-2-oxo-1-oxa-3,8-diazaspiro[4.5]decane-8-carboxylic acid (4-methyl-3-nitrophenyl)amide
[35] 3-(3,4-difluorobenzyl)-2-oxo-1-oxa-3,8-diazaspiro[4.5]decane-8-carboxylic acid (3-methoxyphenyl)amide
[36] 3-(4-methylbenzyl)-2-oxo-1-oxa-3,8-diazaspiro[4.5]decane-8-carboxylic acid 3,4-dichlorobenzylamide
[37] 3-benzyl-2-oxo-1-oxa-3,8-diazaspiro[4.5]decane-8-carboxylic acid (4-chloro-3-trifluoromethylphenyl)amide
[38] 2-oxo-3-(4-trifluoromethylsulfanylbenzyl)-1-oxa-3,8-diazaspiro[4.5]decane-8-carboxylic acid (3-cyanophenyl)amide
[39] 3-benzyl-2-oxo-1-oxa-3,8-diazaspiro[4.5]decane-8-carboxylic acid (4-methoxyphenyl)amide
[40] 2-oxo-3-(4-trifluoromethylsulfanylbenzyl)-1-oxa-3,8-diazaspiro[4.5]decane-8-carboxylic acid (4-methyl-3-nitrophenyl)amide
[41] 3-(4-iodobenzyl)-2-oxo-1-oxa-3,8-diazaspiro[4.5]decane-8-carboxylic acid (4-butoxyphenyl)amide
[42] 3-(3-bromobenzyl)-2-oxo-1-oxa-3,8-diazaspiro[4.5]decane-8-carboxylic acid 3,4-dichlorobenzylamide
[43] 3-benzyl-2-oxo-1-oxa-3,8-diazaspiro[4.5]decane-8-carboxylic acid (1-phenylethyl)amide
[44] 3-naphthalen-2-ylmethyl-2-oxo-1-oxa-3,8-diazaspiro[4.5]decane-8-carboxylic acid 3,4-dichlorobenzylamide
[45] 3-(4-methylbenzyl)-2-oxo-1-oxa-3,8-diazaspiro[4.5]decane-8-carboxylic acid phenethylamide
[46] 2-oxo-3-(2-trifluoromethylbenzyl)-1-oxa-3,8-diazaspiro[4.5]decane-8-carboxylic acid (3-methoxyphenyl)amide
[47] 3-(4-cyanobenzyl)-2-oxo-1-oxa-3,8-diazaspiro[4.5]decane-8-carboxylic acid (4-methoxyphenyl)amide
[48] 2-oxo-3-(4-trifluoromethylbenzyl)-1-oxa-3,8-diazaspiro[4.5]decane-8-carboxylic acid (1-naphthalen-1-ylethyl)amide
[49] 2-oxo-3-(2-trifluoromethylbenzyl)-1-oxa-3,8-diazaspiro[4.5]decane-8-carboxylic acid phenethylamide
[50] 3-(4-iodobenzyl)-2-oxo-1-oxa-3,8-diazaspiro[4.5]decane-8-carboxylic acid (4-methyl-3-nitrophenyl)amide
[51] 3-(2-methoxy-5-nitrobenzyl)-2-oxo-1-oxa-3,8-diazaspiro[4.5]decane-8-carboxylic acid (3-cyanophenyl)amide
[52] 3-naphthalen-2-ylmethyl-2-oxo-1-oxa-3,8-diazaspiro[4.5]decane-8-carboxylic acid (4-methoxyphenyl)amide
[53] 3-{[3-(4-methylbenzyl)-2-oxo-1-oxa-3,8-diazaspiro[4.5]decane-8-carbonyl]amino}benzoic acid ethyl ester
[54] 2-oxo-3-(2-trifluoromethylbenzyl)-1-oxa-3,8-diazaspiro[4.5]decane-8-carboxylic acid (1-naphthalen-1-ylethyl)amide
[55] 3-naphthalen-2-ylmethyl-2-oxo-1-oxa-3,8-diazaspiro[4.5]decane-8-carboxylic acid (2,5-dimethoxyphenyl)amide
[56] 3-(4-cyanobenzyl)-2-oxo-1-oxa-3,8-diazaspiro[4.5]decane-8-carboxylic acid (3-acetylphenyl)amide
[57] 3-biphenyl-2-ylmethyl-2-oxo-1-oxa-3,8-diazaspiro[4.5]decane-8-carboxylic acid phenethylamide
[58] 3-(4-cyanobenzyl)-2-oxo-1-oxa-3,8-diazaspiro[4.5]decane-8-carboxylic acid (5-chloro-2-methoxyphenyl)amide
[59] 3-{[2-oxo-3-(2-trifluoromethylbenzyl)-1-oxa-3,8-diazaspiro[4.5]decane-8-carbonyl]amino}benzoic acid ethyl ester
[60] 3-benzyl-2-oxo-1-oxa-3,8-diazaspiro[4.5]decane-8-carboxylic acid (3-fluorophenyl)amide
[61] 3-{[3-(3-cyanobenzyl)-2-oxo-1-oxa-3,8-diazaspiro[4.5]decane-8-carbonyl]amino}benzoic acid ethyl ester
[62] 3-biphenyl-2-ylmethyl-2-oxo-1-oxa-3,8-diazaspiro[4.5]decane-8-carboxylic acid (3-methoxyphenyl)amide
[63] 3-(2-methoxy-5-nitrobenzyl)-2-oxo-1-oxa-3,8-diazaspiro[4.5]decane-8-carboxylic acid (1-naphthalen-1-ylethyl)amide
[64] {2-[3-(3,4-difluorobenzyl)-2-oxo-1-oxa-3,8-diazaspiro[4.5]dec-8-yl]-2-oxoethoxy}acetic acid
[65] 4-[3-(3,4-difluorobenzyl)-2-oxo-1-oxa-3,8-diazaspiro[4.5]dec-8-yl]-3,3-dimethyl-4-oxobutanoic acid
[66] [2-[3-(3-bromobenzyl)-2-oxo-1-oxa-3,8-diazaspiro[4.5]dec-8-yl]-1-(1H-indol-3-ylmethyl)-2-oxoethyl]carbamic acid tert-butyl ester
[67] 5-[3-(2-fluorobenzyl)-2-oxo-1-oxa-3,8-diazaspiro[4.5]dec-8-yl]-3-methyl-5-oxopentanoic acid
[68] 3,3-dimethyl-5-[3-(4-methylbenzyl)-2-oxo-1-oxa-3,8-diazaspiro[4.5]dec-8-yl]-5-oxopentanoic acid
[69] 5-[3-(3,4-difluorobenzyl)-2-oxo-1-oxa-3,8-diazaspiro[4.5]dec-8-yl]-3-methyl-5-oxopentanoic acid
[70] {2-oxo-2-[2-oxo-3-(4-trifluoromethylbenzyl)-1-oxa-3,8-diazaspiro[4.5]dec-8-yl]ethoxy}acetic acid
[71] (1-{2-[3-(2-cyanobenzyl)-2-oxo-1-oxa-3,8-diazaspiro[4.5]dec-8-yl]-2-oxoethyl}cyclopentyl)acetic acid
[72] (1-{2-[3-(3,4-difluorobenzyl)-2-oxo-1-oxa-3,8-diazaspiro[4.5]dec-8-yl]-2-oxoethyl}cyclopentyl)acetic acid
[73] 5-(3-biphenyl-2-ylmethyl-1-oxa-3,8-diazaspiro[4.5]dec-8-yl)-3-methyl-5-oxopentanoic acid
[74] 3-(3,4-difluorobenzyl)-8-(4-nitrobenzyl)-1-oxa-3,8-diazaspiro[4.5]decan-2-one
[75] N-[4-(3,5-dichlorophenylsulfamoyl)phenyl]-2-[3-(4-methylbenzyl)-2-oxo-1-oxa-3,8-diazaspiro[4.5]dec-8-yl]acetamide
[76] N-(2,5-dimethyl-2H-pyrazol-3-yl)-2-[3-(2-methoxy-5-nitrobenzyl)-2-oxo-1-oxa-3,8-diazaspiro[4.5]dec-8-yl]acetamide
[77] 3-(3,4-difluorobenzyl)-8-[3-(4-methoxyphenyl)-[1,2,4]oxadiazol-5-ylmethyl]-1-oxa-3,8-diazaspiro[4.5]decan-2-one
[78] 3-benzyl-8-(4-trifluoromethoxybenzyl)-1-oxa-3,8-diazaspiro[4.5]decan-2-one
[79] 8-(4-chlorobenzyl)-3-(3-methoxybenzyl)-1-oxa-3,8-diazaspiro[4.5]decan-2-one
[80] N-(3-cyano-4-methylthiophen-2-yl)-2-[3-(3,4-difluorobenzyl)-2-oxo-1-oxa-3,8-diazaspiro[4.5]dec-8-yl]acetamide
[81] 3-(3,4-difluorobenzyl)-8-(4-trifluoromethoxybenzyl)-1-oxa-3,8-diazaspiro[4.5]decan-2-one
[82] 2-[8-(4-chlorobenzyl)-2-oxo-1-oxa-3,8-diazaspiro[4.5]dec-3-ylmethyl]benzonitrile
[83] 8-(2-methylnaphthalen-1-ylmethyl)-3-(2-trifluoromethylbenzyl)-1-oxa-3,8-diazaspiro[4.5]decan-2-one
[84] 2-[8-(5-chlorobenzo[b]thiophen-3-ylmethyl)-2-oxo-1-oxa-3,8-diazaspiro[4.5]dec-3-ylmethyl]benzonitrile
[85] 2-[2-oxo-3-(4-trifluoromethylsulfanylbenzyl)-1-oxa-3,8-diazaspiro[4.5]dec-8-yl]-N-(4-phenyl-5-trifluoromethylthiophen-3-yl)acetamide
[86] 2-[3-(2-fluorobenzyl)-2-oxo-1-oxa-3,8-diazaspiro[4.5]dec-8-yl]-N-(4-phenylthiazol-2-yl)acetamide
[87] 2-[2-oxo-3-(2-trifluoromethylbenzyl)-1-oxa-3,8-diazaspiro[4.5]dec-8-yl]-N-(4-trifluoromethoxyphenyl)acetamide
[88] 3-(2-methoxy-5-nitrobenzyl)-8-(3-nitrobenzyl)-1-oxa-3,8-diazaspiro[4.5]decan-2-one
[89] 4-[8-(3-nitrobenzyl)-2-oxo-1-oxa-3,8-diazaspiro[4.5]dec-3-ylmethyl]benzonitrile
[90] 8-(1-bromonaphthalen-2-ylmethyl)-3-(4-methylbenzyl)-1-oxa-3,8-diazaspiro[4.5]decan-2-one

[91] N-{4-[3-(3-cyanobenzyl)-2-oxo-1-oxa-3,8-diazaspiro[4.5]decane-8-carbonyl]phenyl}acetamide
[92] 8-(4-ethoxybenzoyl)-3-(4-methylbenzyl)-1-oxa-3,8-diazaspiro[4.5]decan-2-one
[93] 3-[3-(4-cyanobenzyl)-2-oxo-1-oxa-3,8-diazaspiro[4.5]dec-8-yl]-3-oxopropionic acid methyl ester
[94] 2-[8-(2,4-difluorobenzoyl)-2-oxo-1-oxa-3,8-diazaspiro[4.5]dec-3-ylmethyl]benzonitrile
[95] 8-(3-dimethylaminobenzoyl)-3-(3,5-dimethylbenzyl)-1-oxa-3,8-diazaspiro[4.5]decan-2-one
[96] N-{4-[3-(3,4-difluorobenzyl)-2-oxo-1-oxa-3,8-diazaspiro[4.5]decane-8-carbonyl]phenyl}acetamide
[97] 8-(4-bromobenzoyl)-3-(4-fluorobenzyl)-1-oxa-3,8-diazaspiro[4.5]decan-2-one
[98] 4-[8-(adamantane-1-carbonyl)-2-oxo-1-oxa-3,8-diazaspiro[4.5]dec-3-ylmethyl]benzonitrile
[99] 3-(3,5-dimethylbenzyl)-8-(2-ethylsulfanylpyridine-3-carbonyl)-1-oxa-3,8-diazaspiro[4.5]decan-2-one
[100] 3-(3-bromobenzyl)-8-(4-chlorobenzoyl)-1-oxa-3,8-diazaspiro[4.5]decan-2-one
[101] 8-[3-(2-chlorophenyl)-5-methylisoxazole-4-carbonyl]-3-(3,5-dimethylbenzyl)-1-oxa-3,8-diazaspiro[4.5]decan-2-one
[102] 3-(3-bromobenzyl)-8-(4-ethylbenzylsulfonyl)-1-oxa-3,8-diazaspiro[4.5]decan-2-one
[103] 8-(4-butoxybenzylsulfonyl)-3-(3,5-dimethylbenzyl)-1-oxa-3,8-diazaspiro[4.5]decan-2-one
[104] 8-(biphenyl-4-carbonyl)-3-(3-bromobenzyl)-1-oxa-3,8-diazaspiro[4.5]decan-2-one
[105] acetic acid 2-[3-(3,5-dimethylbenzyl)-2-oxo-1-oxa-3,8-diazaspiro[4.5]dec-8-yl]-2-oxo-1-phenylethyl ester
[106] 4-[2-oxo-8-(2-phenylcyclopropanecarbonyl)-1-oxa-3,8-diazaspiro[4.5]dec-3-ylmethyl]benzonitrile
[107] 8-(2,5-dimethoxybenzylsulfonyl)-3-(3,5-dimethylbenzyl)-1-oxa-3,8-diazaspiro[4.5]decan-2-one
[108] 8-(2-chlorobenzoyl)-3-(3,5-dimethylbenzyl)-1-oxa-3,8-diazaspiro[4.5]decan-2-one
[109] 3-(3-bromobenzyl)-8-(4-nitrobenzoyl)-1-oxa-3,8-diazaspiro[4.5]decan-2-one
[110] N-{1-benzyl-2-[3-(3-cyanobenzyl)-2-oxo-1-oxa-3,8-diazaspiro[4.5]dec-8-yl]-2-oxoethyl}-4-methylbenzylsulfonamide
[111] 8-(2-ethylsulfanylpyridine-3-carbonyl)-3-(3-methoxybenzyl)-1-oxa-3,8-diazaspiro[4.5]decan-2-one
[112] 8-(2,4-dimethoxybenzoyl)-3-(3-methoxybenzyl)-1-oxa-3,8-diazaspiro[4.5]decan-2-one
[113] 3-(3,5-dimethylbenzyl)-8-[2-(3-methoxyphenyl)acetyl]-1-oxa-3,8-diazaspiro[4.5]decan-2-one
[114] 3-(3,5-dimethylbenzyl)-8-(4-methoxy-2,3,6-trimethylbenzylsulfonyl)-1-oxa-3,8-diazaspiro[4.5]decan-2-one
[115] 4-[8-(biphenyl-4-carbonyl)-2-oxo-1-oxa-3,8-diazaspiro[4.5]dec-3-ylmethyl]benzonitrile
[116] 8-(2-chlorobenzylsulfonyl)-3-(3,5-dimethylbenzyl)-1-oxa-3,8-diazaspiro[4.5]decan-2-one
[117] 8-(benzo[1,2,5]oxadiazole-5-carbonyl)-3-(3,5-dimethylbenzyl)-1-oxa-3,8-diazaspiro[4.5]decan-2-one
[118] 8-(biphenyl-4-carbonyl)-3-(4-iodobenzyl)-1-oxa-3,8-diazaspiro[4.5]decan-2-one
[119] 3-(3,5-dimethylbenzyl)-8-(pyridine-2-carbonyl)-1-oxa-3,8-diazaspiro[4.5]decan-2-one
[120] 8-(6-chloropyridine-3-carbonyl)-3-naphthalen-2-ylmethyl-1-oxa-3,8-diazaspiro[4.5]decan-2-one
[121] 3-(3-bromobenzyl)-8-(2-ethylsulfanylpyridine-3-carbonyl)-1-oxa-3,8-diazaspiro[4.5]decan-2-one
[122] 3-(3,5-dimethylbenzyl)-8-(5-methylisoxazole-3-carbonyl)-1-oxa-3,8-diazaspiro[4.5]decan-2-one
[123] 3-(2-methoxy-5-nitrobenzyl)-8-pentanoyl-1-oxa-3,8-diazaspiro[4.5]decan-2-one
[124] 8-(4-bromobenzoyl)-3-(3,5-dimethylbenzyl)-1-oxa-3,8-diazaspiro[4.5]decan-2-one
[125] 8-(5-tert-butyl-2-methylfuran-3-carbonyl)-3-(2-methoxy-5-nitrobenzyl)-1-oxa-3,8-diazaspiro[4.5]decan-2-one
[126] 8-(3-chlorobenzoyl)-3-(3,5-dimethylbenzyl)-1-oxa-3,8-diazaspiro[4.5]decan-2-one
[127] 8-(2-ethylsulfanylpyridine-3-carbonyl)-3-(2-trifluoromethylbenzyl)-1-oxa-3,8-diazaspiro[4.5]decan-2-one
[128] 3-(3,5-dimethylbenzyl)-8-(isoxazole-5-carbonyl)-1-oxa-3,8-diazaspiro[4.5]decan-2-one
[129] 3-(3-bromobenzyl)-8-(pyridine-2-carbonyl)-1-oxa-3,8-diazaspiro[4.5]decan-2-one
[130] 3-(3,5-dimethylbenzyl)-8-(thiophene-2-carbonyl)-1-oxa-3,8-diazaspiro[4.5]decan-2-one
[131] 8-(3-chloro-4-fluorobenzoyl)-3-(3,5-dimethylbenzyl)-1-oxa-3,8-diazaspiro[4.5]decan-2-one
[132] 8-(2,6-difluoro-3-methylbenzoyl)-3-(3,5-dimethylbenzyl)-1-oxa-3,8-diazaspiro[4.5]decan-2-one
[133] 4-[3-(3-bromobenzyl)-2-oxo-1-oxa-3,8-diazaspiro[4.5]dec-8-yl]-4-oxobutanoic acid methyl ester
[134] 3-[8-(2-ethylbutyryl)-2-oxo-1-oxa-3,8-diazaspiro[4.5]dec-3-ylmethyl]benzonitrile
[135] 3-[8-(3-bromobenzylsulfonyl)-2-oxo-1-oxa-3,8-diazaspiro[4.5]dec-3-ylmethyl]benzonitrile
[136] 3-(3,4-difluorobenzyl)-8-(4-methylbenzoyl)-1-oxa-3,8-diazaspiro[4.5]decan-2-one
[137] 3-(3-bromobenzyl)-8-(3,5-dimethoxybenzoyl)-1-oxa-3,8-diazaspiro[4.5]decan-2-one
[138] 8-(3-dimethylaminobenzoyl)-3-(2-methoxy-5-nitrobenzyl)-1-oxa-3,8-diazaspiro[4.5]decan-2-one
[139] 8-(2,6-dichlorobenzoyl)-3-(2-fluorobenzyl)-1-oxa-3,8-diazaspiro[4.5]decan-2-one
[140] 3-(2-methoxy-5-nitrobenzyl)-8-(2-phenoxypyridine-3-carbonyl)-1-oxa-3,8-diazaspiro[4.5]decan-2-one
[141] 8-[2-(3-methoxyphenyl)acetyl]-3-naphthalen-2-ylmethyl-1-oxa-3,8-diazaspiro[4.5]decan-2-one
[142] 4-{2-oxo-8-[2-(2,2,2-trifluoroacetyl)-1,2,3,4-tetrahydroisoquinoline-7-sulfonyl]-1-oxa-3,8-diazaspiro[4.5]dec-3-ylmethyl}benzonitrile
[143] 8-(3,5-bis-trifluoromethylbenzoyl)-3-(4-trifluoromethylbenzyl)-1-oxa-3,8-diazaspiro[4.5]decan-2-one
[144] 3-(3-bromobenzyl)-8-(2-phenoxypyridine-3-carbonyl)-1-oxa-3,8-diazaspiro[4.5]decan-2-one
[145] 3-(2-methoxy-5-nitrobenzyl)-8-[2-(3-methoxyphenyl)acetyl]-1-oxa-3,8-diazaspiro[4.5]decan-2-one
[146] 3-(3,4-difluorobenzyl)-8-(2-phenoxypyridine-3-carbonyl)-1-oxa-3,8-diazaspiro[4.5]decan-2-one
[147] 3-[8-(4-bromo-3-methylbenzoyl)-2-oxo-1-oxa-3,8-diazaspiro[4.5]dec-3-ylmethyl]benzonitrile
[148] 3-(3-bromobenzyl)-8-(4-propylbenzoyl)-1-oxa-3,8-diazaspiro[4.5]decan-2-one
[149] 3-biphenyl-2-ylmethyl-8-(3-chlorobenzylsulfonyl)-1-oxa-3,8-diazaspiro[4.5]decan-2-one
[150] 8-[2-(3,4-dimethoxyphenyl)acetyl]-3-(2-methoxy-5-nitrobenzyl)-1-oxa-3,8-diazaspiro[4.5]decan-2-one
[151] 2-[8-(2-chloro-4-nitrobenzoyl)-2-oxo-1-oxa-3,8-diazaspiro[4.5]dec-3-ylmethyl]benzonitrile
[152] 3-[2-oxo-8-(2,4,6-trimethylbenzylsulfonyl)-1-oxa-3,8-diazaspiro[4.5]dec-3-ylmethyl]benzonitrile
[153] 3-benzyl-8-(4-fluorobenzylsulfonyl)-1-oxa-3,8-diazaspiro[4.5]decan-2-one
[154] 3-(4-fluorobenzyl)-8-(toluene-4-sulfonyl)-1-oxa-3,8-diazaspiro[4.5]decan-2-one

[155] 4-[2-oxo-8-(toluene-4-sulfonyl)-1-oxa-3,8-diazaspiro[4.5]dec-3-ylmethyl]benzonitrile
[156] 3-(2-fluorobenzyl)-8-(toluene-4-sulfonyl)-1-oxa-3,8-diazaspiro[4.5]decan-2-one
[157] 3-(3,4-difluorobenzyl)-8-(toluene-4-sulfonyl)-1-oxa-3,8-diazaspiro[4.5]decan-2-one
[158] 3-(4-tert-butylbenzyl)-8-(toluene-4-sulfonyl)-1-oxa-3,8-diazaspiro[4.5]decan-2-one
[159] 8-(toluene-4-sulfonyl)-3-(4-trifluoromethylsulfanylbenzyl)-1-oxa-3,8-diazaspiro[4.5]decan-2-one
[160] 2-[3-(4-fluorobenzyl)-2-oxo-1-oxa-3,8-diazaspiro[4.5]decan-8-sulfonyl]benzoic acid methyl ester
[161] 2-[3-(3-methoxybenzyl)-2-oxo-1-oxa-3,8-diazaspiro[4.5]decan-8-sulfonyl]benzoic acid methyl ester
[162] 2-[3-(3-bromobenzyl)-2-oxo-1-oxa-3,8-diazaspiro[4.5]decan-8-sulfonyl]benzoic acid methyl ester
[163] 3-benzyl-8-(2-methanesulfonylbenzylsulfonyl)-1-oxa-3,8-diazaspiro[4.5]decan-2-one
[164] 8-(2-methanesulfonylbenzylsulfonyl)-3-(2-methoxy-5-nitrobenzyl)-1-oxa-3,8-diazaspiro[4.5]decan-2-one
[165] 3-(4-methylbenzyl)-2-oxo-1-oxa-3,8-diazaspiro[4.5]decane-8-sulfonic acid dimethylamide
[166] 4-[8-(7,7-dimethyl-2-oxobicyclo[2.2.1]hept-1-ylmethanesulfonyl)-2-oxo-1-oxa-3,8-diazaspiro[4.5]dec-3-ylmethyl]benzonitrile
[167] 3-(4-fluorobenzyl)-8-(4-methoxybenzylsulfonyl)-1-oxa-3,8-diazaspiro[4.5]decan-2-one
[168] 3-(4-methylbenzyl)-8-(4-trifluoromethoxybenzylsulfonyl)-1-oxa-3,8-diazaspiro[4.5]decan-2-one
[169] 8-(4-trifluoromethoxybenzylsulfonyl)-3-(4-trifluoromethylsulfanylbenzyl)-1-oxa-3,8-diazaspiro[4.5]decan-2-one
[170] 8-(propane-1-sulfonyl)-3-(4-trifluoromethylsulfanylbenzyl)-1-oxa-3,8-diazaspiro[4.5]decan-2-one
[171] 3-(2-methoxy-5-nitrobenzyl)-8-(4-propylbenzylsulfonyl)-1-oxa-3,8-diazaspiro[4.5]decan-2-one
[172] 3-biphenyl-2-ylmethyl-8-(4-propylbenzylsulfonyl)-1-oxa-3,8-diazaspiro[4.5]decan-2-one
[173] 8-(3-bromobenzylsulfonyl)-3-(2-fluorobenzyl)-1-oxa-3,8-diazaspiro[4.5]decan-2-one
[174] 8-(3-bromobenzylsulfonyl)-3-(3-bromobenzyl)-1-oxa-3,8-diazaspiro[4.5]decan-2-one
[175] 2-{8-[4-(1,1-dimethylpropyl)benzylsulfonyl]-2-oxo-1-oxa-3,8-diazaspiro[4.5]dec-3-ylmethyl}benzonitrile
[176] 3-benzyl-8-[4-(1,1-dimethylpropyl)benzylsulfonyl]-1-oxa-3,8-diazaspiro[4.5]decan-2-one
[177] 8-[4-(1,1-dimethylpropyl)benzylsulfonyl]-3-(4-iodobenzyl)-1-oxa-3,8-diazaspiro[4.5]decan-2-one
[178] 8-[4-(1,1-dimethylpropyl)benzylsulfonyl]-3-(2-methoxy-5-nitrobenzyl)-1-oxa-3,8-diazaspiro[4.5]decan-2-one
[179] 8-[4-(1,1-dimethylpropyl)benzylsulfonyl]-3-(4-trifluoromethylbenzyl)-1-oxa-3,8-diazaspiro[4.5]decan-2-one
[180] 3-biphenyl-2-ylmethyl-8-[4-(1,1-dimethylpropyl)benzylsulfonyl]-1-oxa-3,8-diazaspiro[4.5]decan-2-one
[181] 8-(4,5-dichlorothiophene-2-sulfonyl)-3-(3-methoxybenzyl)-1-oxa-3,8-diazaspiro[4.5]decan-2-one
[182] 8-(4,5-dichlorothiophene-2-sulfonyl)-3-(4-trifluoromethylbenzyl)-1-oxa-3,8-diazaspiro[4.5]decan-2-one
[183] 3-(3-bromobenzyl)-8-(4,5-dichlorothiophene-2-sulfonyl)-1-oxa-3,8-diazaspiro[4.5]decan-2-one
[184] 2-[8-(4-methoxy-2,3,6-trimethylbenzylsulfonyl)-2-oxo-1-oxa-3,8-diazaspiro[4.5]dec-3-ylmethyl]benzonitrile
[185] 3-(2-fluorobenzyl)-8-(4-methoxy-2,3,6-trimethylbenzylsulfonyl)-1-oxa-3,8-diazaspiro[4.5]decan-2-one
[186] 3-(4-tert-butylbenzyl)-8-[2-(2,2,2-trifluoroacetyl)-1,2,3,4-tetrahydroisoquinoline-7-sulfonyl]-1-oxa-3,8-diazaspiro[4.5]decan-2-one
[187] 8-(butane-1-sulfonyl)-3-(3-methoxybenzyl)-1-oxa-3,8-diazaspiro[4.5]decan-2-one
[188] 3-(4-methylbenzyl)-8-(thiophene-2-sulfonyl)-1-oxa-3,8-diazaspiro[4.5]decan-2-one
[189] 8-(4-chloro-2,5-dimethylbenzylsulfonyl)-3-(4-methylbenzyl)-1-oxa-3,8-diazaspiro[4.5]decan-2-one
[190] 3-benzyl-8-(4-chloro-2,5-dimethylbenzylsulfonyl)-1-oxa-3,8-diazaspiro[4.5]decan-2-one
[191] 8-(4-chloro-2,5-dimethylbenzylsulfonyl)-3-(4-trifluoromethylbenzyl)-1-oxa-3,8-diazaspiro[4.5]decan-2-one
[192] 3-biphenyl-2-ylmethyl-8-(4-chloro-2,5-dimethylbenzylsulfonyl)-1-oxa-3,8-diazaspiro[4.5]decan-2-one
[193] 8-(4-chloro-2,5-dimethylbenzylsulfonyl)-3-(4-trifluoromethylsulfanylbenzyl)-1-oxa-3,8-diazaspiro[4.5]decan-2-one
[194] 3-(4-fluorobenzyl)-8-(2-trifluoromethylbenzylsulfonyl)-1-oxa-3,8-diazaspiro[4.5]decan-2-one
[195] 3-(3-methoxybenzyl)-8-(2-trifluoromethylbenzylsulfonyl)-1-oxa-3,8-diazaspiro[4.5]decan-2-one
[196] 3-benzyl-8-(2-methyl-5-nitrobenzylsulfonyl)-1-oxa-3,8-diazaspiro[4.5]decan-2-one
[197] 3-(4-tert-butylbenzyl)-8-(2-methyl-5-nitrobenzylsulfonyl)-1-oxa-3,8-diazaspiro[4.5]decan-2-one
[198] 3-(4-tert-butylbenzyl)-8-(toluene-3-sulfonyl)-1-oxa-3,8-diazaspiro[4.5]decan-2-one
[199] 8-(furan-2-carbonyl)-3-(4-trifluoromethylbenzyl)-1-oxa-3,8-diazaspiro[4.5]decan-2-one
[200] 3-(3-bromobenzyl)-8-(furan-2-carbonyl)-1-oxa-3,8-diazaspiro[4.5]decan-2-one
[201] 4-[8-(naphthalene-1-carbonyl)-2-oxo-1-oxa-3,8-diazaspiro[4.5]dec-3-ylmethyl]benzonitrile
[202] 3-(3,4-difluorobenzyl)-8-(naphthalene-1-carbonyl)-1-oxa-3,8-diazaspiro[4.5]decan-2-one
[203] 3-(3-bromobenzyl)-8-(naphthalene-1-carbonyl)-1-oxa-3,8-diazaspiro[4.5]decan-2-one
[204] 2-[8-(3-nitrobenzoyl)-2-oxo-1-oxa-3,8-diazaspiro[4.5]dec-3-ylmethyl]benzonitrile
[205] 4-[8-(3-nitrobenzoyl)-2-oxo-1-oxa-3,8-diazaspiro[4.5]dec-3-ylmethyl]benzonitrile
[206] 3-(3-bromobenzyl)-8-(3,5-difluorobenzoyl)-1-oxa-3,8-diazaspiro[4.5]decan-2-one
[207] 8-(2-benzyloxy-acetyl)-3-(2-fluorobenzyl)-1-oxa-3,8-diazaspiro[4.5]decan-2-one
[208] 8-(2-chlorobenzoyl)-3-(2-trifluoromethylbenzyl)-1-oxa-3,8-diazaspiro[4.5]decan-2-one
[209] 8-(2-chlorobenzoyl)-3-(4-iodobenzyl)-1-oxa-3,8-diazaspiro[4.5]decan-2-one
[210] 8-(2-chlorobenzoyl)-3-(2-methoxy-5-nitrobenzyl)-1-oxa-3,8-diazaspiro[4.5]decan-2-one
[211] 3-biphenyl-2-ylmethyl-8-(2-chlorobenzoyl)-1-oxa-3,8-diazaspiro[4.5]decan-2-one
[212] 8-(2,6-dichlorobenzoyl)-3-naphthalen-2-ylmethyl-1-oxa-3,8-diazaspiro[4.5]decan-2-one
[213] 3-(4-tert-butylbenzyl)-8-(2,6-dichlorobenzoyl)-1-oxa-3,8-diazaspiro[4.5]decan-2-one
[214] 3-(3-bromobenzyl)-8-(2,6-dichlorobenzoyl)-1-oxa-3,8-diazaspiro[4.5]decan-2-one
[215] 8-(2,6-dichlorobenzoyl)-3-(4-trifluoromethylsulfanylbenzyl)-1-oxa-3,8-diazaspiro[4.5]decan-2-one
[216] 2-[8-(2-methylbenzoyl)-2-oxo-1-oxa-3,8-diazaspiro[4.5]dec-3-ylmethyl]benzonitrile
[217] 8-(2-methylbenzoyl)-3-(4-methylbenzyl)-1-oxa-3,8-diazaspiro[4.5]decan-2-one

[218] 8-(2-methylbenzoyl)-3-(2-trifluoromethylbenzyl)-1-oxa-3,8-diazaspiro[4.5]decan-2-one
[219] 3-(2-methoxy-5-nitrobenzyl)-8-(2-methylbenzoyl)-1-oxa-3,8-diazaspiro[4.5]decan-2-one
[220] 3-(3,4-difluorobenzyl)-8-(2-methylbenzoyl)-1-oxa-3,8-diazaspiro[4.5]decan-2-one
[221] 8-(2-methylbenzoyl)-3-(4-trifluoromethylbenzyl)-1-oxa-3,8-diazaspiro[4.5]decan-2-one
[222] 8-(2-methylbenzoyl)-3-(4-trifluoromethylsulfanylbenzyl)-1-oxa-3,8-diazaspiro[4.5]decan-2-one
[223] 8-(3-bromobenzoyl)-3-(4-fluorobenzyl)-1-oxa-3,8-diazaspiro[4.5]decan-2-one
[224] 8-(3-bromobenzoyl)-3-(2-trifluoromethylbenzyl)-1-oxa-3,8-diazaspiro[4.5]decan-2-one
[225] 8-(3-bromobenzoyl)-3-(2-fluorobenzyl)-1-oxa-3,8-diazaspiro[4.5]decan-2-one
[226] 8-(3-bromobenzoyl)-3-(3,4-difluorobenzyl)-1-oxa-3,8-diazaspiro[4.5]decan-2-one
[227] 8-(3-bromobenzoyl)-3-naphthalen-2-ylmethyl-1-oxa-3,8-diazaspiro[4.5]decan-2-one
[228] 8-(3-bromobenzoyl)-3-(4-tert-butylbenzyl)-1-oxa-3,8-diazaspiro[4.5]decan-2-one
[229] 3-benzyl-8-(3-fluorobenzoyl)-1-oxa-3,8-diazaspiro[4.5]decan-2-one
[230] 8-(3-fluorobenzoyl)-3-(2-fluorobenzyl)-1-oxa-3,8-diazaspiro[4.5]decan-2-one
[231] 3-(3,4-difluorobenzyl)-8-(3-fluorobenzoyl)-1-oxa-3,8-diazaspiro[4.5]decan-2-one
[232] 8-(3-fluorobenzoyl)-3-(4-trifluoromethylbenzyl)-1-oxa-3,8-diazaspiro[4.5]decan-2-one
[233] 3-(3-bromobenzyl)-8-(3-fluorobenzoyl)-1-oxa-3,8-diazaspiro[4.5]decan-2-one
[234] 8-(3-chlorobenzoyl)-3-(3,5-dimethylbenzyl)-1-oxa-3,8-diazaspiro[4.5]decan-2-one
[235] 3-benzyl-8-(3-chlorobenzoyl)-1-oxa-3,8-diazaspiro[4.5]decan-2-one
[236] 4-[8-(3,4-dichlorobenzoyl)-2-oxo-1-oxa-3,8-diazaspiro[4.5]dec-3-ylmethyl]benzonitrile
[237] 3-(4-iodobenzyl)-8-(3-methoxybenzoyl)-1-oxa-3,8-diazaspiro[4.5]decan-2-one
[238] 3-(2-fluorobenzyl)-8-(3-methoxybenzoyl)-1-oxa-3,8-diazaspiro[4.5]decan-2-one
[239] 3-(4-tert-butylbenzyl)-8-(3-methoxybenzoyl)-1-oxa-3,8-diazaspiro[4.5]decan-2-one
[240] 3-benzyl-8-(3-methylbenzoyl)-1-oxa-3,8-diazaspiro[4.5]decan-2-one
[241] 3-(2-methoxy-5-nitrobenzyl)-8-(3-methylbenzoyl)-1-oxa-3,8-diazaspiro[4.5]decan-2-one
[242] 3-(4-tert-butylbenzyl)-8-(3-methylbenzoyl)-1-oxa-3,8-diazaspiro[4.5]decan-2-one
[243] 8-(3-methylbenzoyl)-3-(4-trifluoromethylbenzyl)-1-oxa-3,8-diazaspiro[4.5]decan-2-one
[244] 3-(3,4-difluorobenzyl)-8-(2-phenyl-butyryl)-1-oxa-3,8-diazaspiro[4.5]decan-2-one
[245] 3-benzyl-8-[3-(2-chlorophenyl)-5-methylisoxazole-4-carbonyl]-1-oxa-3,8-diazaspiro[4.5]decan-2-one
[246] 4-[8-(2,3-dichlorobenzoyl)-2-oxo-1-oxa-3,8-diazaspiro[4.5]dec-3-ylmethyl]benzonitrile
[247] 8-[2-(4-chlorophenyl)acetyl]-3-(3,4-difluorobenzyl)-1-oxa-3,8-diazaspiro[4.5]decan-2-one
[248] 3-biphenyl-2-ylmethyl-8-[2-(4-chlorophenyl)acetyl]-1-oxa-3,8-diazaspiro[4.5]decan-2-one
[249] 8-[2-(4-chlorophenyl)acetyl]-3-(4-trifluoromethylsulfanylbenzyl)-1-oxa-3,8-diazaspiro[4.5]decan-2-one
[250] 3-(4-tert-butylbenzyl)-8-[3-(2-chlorophenyl)acryloyl]-1-oxa-3,8-diazaspiro[4.5]decan-2-one
[251] 3-biphenyl-2-ylmethyl-8-[3-(2-chlorophenyl)acryloyl]-1-oxa-3,8-diazaspiro[4.5]decan-2-one
[252] 3-(3-bromobenzyl)-8-[3-(2-chlorophenyl)acryloyl]-1-oxa-3,8-diazaspiro[4.5]decan-2-one
[253] 4-[8-(2,3-difluorobenzoyl)-2-oxo-1-oxa-3,8-diazaspiro[4.5]dec-3-ylmethyl]benzonitrile
[254] 8-(2,3-difluorobenzoyl)-3-(2-trifluoromethylbenzyl)-1-oxa-3,8-diazaspiro[4.5]decan-2-one
[255] 8-(2,3-difluorobenzoyl)-3-(4-iodobenzyl)-1-oxa-3,8-diazaspiro[4.5]decan-2-one
[256] 2-[2-oxo-8-(2-propylpentanoyl)-1-oxa-3,8-diazaspiro[4.5]dec-3-ylmethyl]benzonitrile
[257] 3-(3,4-difluorobenzyl)-8-(2-propylpentanoyl)-1-oxa-3,8-diazaspiro[4.5]decan-2-one
[258] 8-(2-chloro-4-nitrobenzoyl)-3I-(4-methylbenzyl)-1-oxa-3,8-diazaspiro[4.5]decan-2-one
[259] 8-(2-chloro-4-nitrobenzoyl)-3I-(2-trifluoromethylbenzyl)-1-oxa-3,8-diazaspiro[4.5]decan-2-one
[260] 3-(4-tert-butylbenzyl)-8-(2-chloro-4-nitrobenzoyl)-1-oxa-3,8-diazaspiro[4.5]decan-2-one
[261] 8-(2-chloro-4-nitrobenzoyl)-3I-(4-trifluoromethylbenzyl)-1-oxa-3,8-diazaspiro[4.5]decan-2-one
[262] 3-biphenyl-2-ylmethyl-8-(2-chloro-4-nitrobenzoyl)-1-oxa-3,8-diazaspiro[4.5]decan-2-one
[263] 3-(3-bromobenzyl)-8-(2-chloro-4-nitrobenzoyl)-1-oxa-3,8-diazaspiro[4.5]decan-2-one
[264] 8-(2-chloro-4-nitrobenzoyl)-3I-(4-trifluoromethylsulfanylbenzyl)-1-oxa-3,8-diazaspiro[4.5]decan-2-one
[265] 8-(2-chloropyridine-3-carbonyl)-3-(4-fluorobenzyl)-1-oxa-3,8-diazaspiro[4.5]decan-2-one
[266] 2-[8-(2-chloropyridine-3-carbonyl)-2-oxo-1-oxa-3,8-diazaspiro[4.5]dec-3-ylmethyl]benzonitrile
[267] 8-(2-chloropyridine-3-carbonyl)-3-(4-methylbenzyl)-1-oxa-3,8-diazaspiro[4.5]decan-2-one
[268] 8-(2-chloropyridine-3-carbonyl)-3-(4-trifluoromethylbenzyl)-1-oxa-3,8-diazaspiro[4.5]decan-2-one
[269] 3-(3-methoxybenzyl)-8-(2-methylsulfanylpyridine-3-carbonyl)-1-oxa-3,8-diazaspiro[4.5]decan-2-one
[270] 3-(4-methylbenzyl)-8-(2-methylsulfanylpyridine-3-carbonyl)-1-oxa-3,8-diazaspiro[4.5]decan-2-one
[271] 3-(4-iodobenzyl)-8-(2-methylsulfanylpyridine-3-carbonyl)-1-oxa-3,8-diazaspiro[4.5]decan-2-one
[272] 3-(3,4-difluorobenzyl)-8-(2-methylsulfanylpyridine-3-carbonyl)-1-oxa-3,8-diazaspiro[4.5]decan-2-one
[273] 3-(4-tert-butylbenzyl)-8-(2-methylsulfanylpyridine-3-carbonyl)-1-oxa-3,8-diazaspiro[4.5]decan-2-one
[274] 8-(2-methylsulfanylpyridine-3-carbonyl)-3-(4-trifluoromethylbenzyl)-1-oxa-3,8-diazaspiro[4.5]decan-2-one
[275] 8-(2-ethylsulfanylpyridine-3-carbonyl)-3-(4-fluorobenzyl)-1-oxa-3,8-diazaspiro[4.5]decan-2-one
[276] 3-[8-(2-ethylsulfanylpyridine-3-carbonyl)-2-oxo-1-oxa-3,8-diazaspiro[4.5]dec-3-ylmethyl]benzonitrile
[277] 2-[8-(2-ethylsulfanylpyridine-3-carbonyl)-2-oxo-1-oxa-3,8-diazaspiro[4.5]dec-3-ylmethyl]benzonitrile
[278] 8-(2-ethylsulfanylpyridine-3-carbonyl)-3-(4-methylbenzyl)-1-oxa-3,8-diazaspiro[4.5]decan-2-one
[279] 3-benzyl-8-(2-ethylsulfanylpyridine-3-carbonyl)-1-oxa-3,8-diazaspiro[4.5]decan-2-one
[280] 8-(2-ethylsulfanylpyridine-3-carbonyl)-3-(2-fluorobenzyl)-1-oxa-3,8-diazaspiro[4.5]decan-2-one
[281] 4-[8-(6-chloropyridine-3-carbonyl)-2-oxo-1-oxa-3,8-diazaspiro[4.5]dec-3-ylmethyl]benzonitrile
[282] 8-(6-chloropyridine-3-carbonyl)-3-(2-trifluoromethylbenzyl)-1-oxa-3,8-diazaspiro[4.5]decan-2-one
[283] 8-(6-chloropyridine-3-carbonyl)-3-(4-iodobenzyl)-1-oxa-3,8-diazaspiro[4.5]decan-2-one

[284] 3-(4-tert-butylbenzyl)-8-(6-chloropyridine-3-carbonyl)-1-oxa-3,8-diazaspiro[4.5]decan-2-one
[285] 3-biphenyl-2-ylmethyl-8-(6-chloropyridine-3-carbonyl)-1-oxa-3,8-diazaspiro[4.5]decan-2-one
[286] 3-(3-methoxybenzyl)-8-(4-trifluoromethoxybenzoyl)-1-oxa-3,8-diazaspiro[4.5]decan-2-one
[287] 3-(3,4-difluorobenzyl)-8-(4-trifluoromethoxybenzoyl)-1-oxa-3,8-diazaspiro[4.5]decan-2-one
[288] 8-[3-(2-chloro-6-fluorophenyl)-5-methylisoxazole-4-carbonyl]-3-(4-fluorobenzyl)-1-oxa-3,8-diazaspiro[4.5]decan-2-one
[289] 8-[3-(2-chloro-6-fluorophenyl)-5-methylisoxazole-4-carbonyl]-3-(3-methoxybenzyl)-1-oxa-3,8-diazaspiro[4.5]decan-2-one
[290] 8-[3-(2-chloro-6-fluorophenyl)-5-methylisoxazole-4-carbonyl]-3-(4-trifluoromethylbenzyl)-1-oxa-3,8-diazaspiro[4.5]decan-2-one
[291] 8-[3-(2-chloro-6-fluorophenyl)-5-methylisoxazole-4-carbonyl]-3-(4-trifluoromethylsulfanylbenzyl)-1-oxa-3,8-diazaspiro[4.5]decan-2-one
[292] 3-(4-methylbenzyl)-8-(3-trifluoromethoxybenzoyl)-1-oxa-3,8-diazaspiro[4.5]decan-2-one
[293] 3-(4-iodobenzyl)-8-(3-trifluoromethoxybenzoyl)-1-oxa-3,8-diazaspiro[4.5]decan-2-one
[294] 3-(3,4-difluorobenzyl)-8-(3-trifluoromethoxybenzoyl)-1-oxa-3,8-diazaspiro[4.5]decan-2-one
[295] 3-naphthalen-2-ylmethyl-8-(3-trifluoromethoxybenzoyl)-1-oxa-3,8-diazaspiro[4.5]decan-2-one
[296] 4-[8-(isoxazole-5-carbonyl)-2-oxo-1-oxa-3,8-diazaspiro[4.5]dec-3-ylmethyl]benzonitrile
[297] 8-(isoxazole-5-carbonyl)-3-(2-trifluoromethylbenzyl)-1-oxa-3,8-diazaspiro[4.5]decan-2-one
[298] 8-(isoxazole-5-carbonyl)-3-(2-methoxy-5-nitrobenzyl)-1-oxa-3,8-diazaspiro[4.5]decan-2-one
[299] 3-(3-bromobenzyl)-8-(isoxazole-5-carbonyl)-1-oxa-3,8-diazaspiro[4.5]decan-2-one
[300] 2-[8-(2-chloro-6-fluorobenzoyl)-2-oxo-1-oxa-3,8-diazaspiro[4.5]dec-3-ylmethyl]benzonitrile
[301] 4-[8-(2-chloro-6-fluorobenzoyl)-2-oxo-1-oxa-3,8-diazaspiro[4.5]dec-3-ylmethyl]benzonitrile
[302] 8-(2-chloro-6-fluorobenzoyl)-3-(4-methylbenzyl)-1-oxa-3,8-diazaspiro[4.5]decan-2-one
[303] 3-biphenyl-2-ylmethyl-8-(2-chloro-6-fluorobenzoyl)-1-oxa-3,8-diazaspiro[4.5]decan-2-one
[304] 8-(2,5-dimethylfuran-3-carbonyl)-3-(3-methoxybenzyl)-1-oxa-3,8-diazaspiro[4.5]decan-2-one
[305] 4-[8-(2,5-dimethylfuran-3-carbonyl)-2-oxo-1-oxa-3,8-diazaspiro[4.5]dec-3-ylmethyl]benzonitrile
[306] 4-[8-(4-bromo-3-methylbenzoyl)-2-oxo-1-oxa-3,8-diazaspiro[4.5]dec-3-ylmethyl]benzonitrile
[307] 8-(4-bromo-3-methylbenzoyl)-3-(4-methylbenzyl)-1-oxa-3,8-diazaspiro[4.5]decan-2-one
[308] 3-benzyl-8-(4-bromo-3-methylbenzoyl)-1-oxa-3,8-diazaspiro[4.5]decan-2-one
[309] 8-(4-bromo-3-methylbenzoyl)-3-(2-trifluoromethylbenzyl)-1-oxa-3,8-diazaspiro[4.5]decan-2-one
[310] 8-(4-bromo-3-methylbenzoyl)-3-(3,4-difluorobenzyl)-1-oxa-3,8-diazaspiro[4.5]decan-2-one
[311] 8-(4-bromo-3-methylbenzoyl)-3-(4-tert-butylbenzyl)-1-oxa-3,8-diazaspiro[4.5]decan-2-one
[312] 3-biphenyl-2-ylmethyl-8-(4-bromo-3-methylbenzoyl)-1-oxa-3,8-diazaspiro[4.5]decan-2-one
[313] 8-(4-bromo-3-methylbenzoyl)-3-(4-trifluoromethylsulfanylbenzyl)-1-oxa-3,8-diazaspiro[4.5]decan-2-one
[314] 8-(2,6-difluoro-3-methylbenzoyl)-3-(3-methoxybenzyl)-1-oxa-3,8-diazaspiro[4.5]decan-2-one
[315] 2-[8-(2,6-difluoro-3-methylbenzoyl)-2-oxo-1-oxa-3,8-diazaspiro[4.5]dec-3-ylmethyl]benzonitrile
[316] 4-[8-(2,6-difluoro-3-methylbenzoyl)-2-oxo-1-oxa-3,8-diazaspiro[4.5]dec-3-ylmethyl]benzonitrile
[317] 8-(2,6-difluoro-3-methylbenzoyl)-3-(2-trifluoromethylbenzyl)-1-oxa-3,8-diazaspiro[4.5]decan-2-one
[318] 8-(2,6-difluoro-3-methylbenzoyl)-3-(2-fluorobenzyl)-1-oxa-3,8-diazaspiro[4.5]decan-2-one
[319] 8-(2-chloro-6-fluoro-3-methylbenzoyl)-3-(4-fluorobenzyl)-1-oxa-3,8-diazaspiro[4.5]decan-2-one
[320] 8-(2-chloro-6-fluoro-3-methylbenzoyl)-3-(3-methoxybenzyl)-1-oxa-3,8-diazaspiro[4.5]decan-2-one
[321] 8-(2-chloro-6-fluoro-3-methylbenzoyl)-3-(4-trifluoromethylsufanylbenzyl)-1-oxa-3,8-diazaspiro[4.5]decan-2-one
[322] 3-biphenyl-2-ylmethyl-8-(6-chloro-2-fluoro-3-methylbenzoyl)-1-oxa-3,8-diazaspiro[4.5]decan-2-one
[323] 3-benzyl-8-(3-difluoromethylsulfanylbenzoyl)-1-oxa-3,8-diazaspiro[4.5]decan-2-one
[324] 8-(3-difluoromethylsulfanylbenzoyl)-3-naphthalen-2-ylmethyl-1-oxa-3,8-diazaspiro[4.5]decan-2-one
[325] 8-(3-difluoromethylsulfanylbenzoyl)-3-(4-trifluoromethylbenzyl)-1-oxa-3,8-diazaspiro[4.5]decan-2-one
[326] 3-(3-bromobenzyl)-8-(3-difluoromethylsulfanylbenzoyl)-1-oxa-3,8-diazaspiro[4.5]decan-2-one
[327] 3-[8-(3-chloro-2-fluorobenzoyl)-2-oxo-1-oxa-3,8-diazaspiro[4.5]dec-3-ylmethyl]benzonitrile
[328] 8-(3-chloro-2-fluorobenzoyl)-3-(4-iodobenzyl)-1-oxa-3,8-diazaspiro[4.5]decan-2-one
[329] 8-(3-chloro-2-fluorobenzoyl)-3-naphthalen-2-ylmethyl-1-oxa-3,8-diazaspiro[4.5]decan-2-one
[330] 3-(3-methoxybenzyl)-8-(4-trifluoromethylsulfanylbenzoyl)-1-oxa-3,8-diazaspiro[4.5]decan-2-one
[331] 2-[2-oxo-8-(4-trifluoromethylsulfanylbenzoyl)-1-oxa-3,8-diazaspiro[4.5]dec-3-ylmethyl]benzonitrile
[332] 4-[2-oxo-8-(4-trifluoromethylsulfanylbenzoyl)-1-oxa-3,8-diazaspiro[4.5]dec-3-ylmethyl]benzonitrile
[333] 3-(4-iodobenzyl)-8-(4-trifluoromethylsulfanylbenzoyl)-1-oxa-3,8-diazaspiro[4.5]decan-2-one
[334] 3-naphthalen-2-ylmethyl-8-(4-trifluoromethylsulfanylbenzoyl)-1-oxa-3,8-diazaspiro[4.5]decan-2-one
[335] 3-(4-trifluoromethylbenzyl)-8-(4-trifluoromethylsulfanylbenzoyl)-1-oxa-3,8-diazaspiro[4.5]decan-2-one
[336] 8-(2-chloro-5-trifluoromethylbenzoyl)-3-(2-trifluoromethylbenzyl)-1-oxa-3,8-diazaspiro[4.5]decan-2-one
[337] 8-(2-chloro-5-trifluoromethylbenzoyl)-3-(2-fluorobenzyl)-1-oxa-3,8-diazaspiro[4.5]decan-2-one
[338] 8-(2-chloro-5-trifluoromethylbenzoyl)-3-(3,4-difluorobenzyl)-1-oxa-3,8-diazaspiro[4.5]decan-2-one
[339] 8-(2,3-difluoro-4-methylbenzoyl)-3-(3-methoxybenzyl)-1-oxa-3,8-diazaspiro[4.5]decan-2-one
[340] 4-[8-(2,3-difluoro-4-methylbenzoyl)-2-oxo-1-oxa-3,8-diazaspiro[4.5]dec-3-ylmethyl]benzonitrile
[341] 3-benzyl-8-(2,3-difluoro-4-methylbenzoyl)-1-oxa-3,8-diazaspiro[4.5]decan-2-one
[342] 8-(2,3-difluoro-4-methylbenzoyl)-3-(4-iodobenzyl)-1-oxa-3,8-diazaspiro[4.5]decan-2-one
[343] 3-(3,4-difluorobenzyl)-8-(2,3-difluoro-4-methylbenzoyl)-1-oxa-3,8-diazaspiro[4.5]decan-2-one
[344] 8-(2,3-difluoro-4-methylbenzoyl)-3-naphthalen-2-ylmethyl-1-oxa-3,8-diazaspiro[4.5]decan-2-one
[345] 3-biphenyl-2-ylmethyl-8-(2,3-difluoro-4-methylbenzoyl)-1-oxa-3,8-diazaspiro[4.5]decan-2-one
[346] 3-(3-bromobenzyl)-8-(2,3-difluoro-4-methylbenzoyl)-1-oxa-3,8-diazaspiro[4.5]decan-2-one
[347] 3-benzyl-8-[2-(2-methoxyethoxy)acetyl]-1-oxa-3,8-diazaspiro[4.5]decan-2-one

[348] 3-(2-fluorobenzyl)-8-[2-(2-methoxyethoxy)acetyl]-1-oxa-3,8-diazaspiro[4.5]decan-2-one
[349] 3-(3,4-difluorobenzyl)-8-[2-(2-methoxyethoxy)acetyl]-1-oxa-3,8-diazaspiro[4.5]decan-2-one
[350] 3-(4-tert-butylbenzyl)-8-[2-(2-methoxyethoxy)acetyl]-1-oxa-3,8-diazaspiro[4.5]decan-2-one
[351] 8-[2-(2-methoxyethoxy)acetyl]-3-(4-trifluoromethylsulfanylbenzyl)-1-oxa-3,8-diazaspiro[4.5]decan-2-one
[352] 8-(1-acetylpiperidine-4-carbonyl)-3-(3,4-difluorobenzyl)-1-oxa-3,8-diazaspiro[4.5]decan-2-one
[353] 4-{8-[2-(3-chlorophenoxy)acetyl]-2-oxo-1-oxa-3,8-diazaspiro[4.5]dec-3-ylmethyl}benzonitrile
[354] 8-[2-(3-chlorophenoxy)acetyl]-3-(3,4-difluorobenzyl)-1-oxa-3,8-diazaspiro[4.5]decan-2-one
[355] 3-(3-bromobenzyl)-8-[2-(3-chlorophenoxy)acetyl]-1-oxa-3,8-diazaspiro[4.5]decan-2-one
[356] 8-[2-(3-chlorophenoxy)acetyl]-3-(4-trifluoromethylsulfanylbenzyl)-1-oxa-3,8-diazaspiro[4.5]decan-2-one
[357] 4-[3-(3-methoxybenzyl)-2-oxo-1-oxa-3,8-diazaspiro[4.5]decane-8-carbonyl]benzylsulfonamide
[358] N-{4-[3-(3,4-difluorobenzyl)-2-oxo-1-oxa-3,8-diazaspiro[4.5]decane-8-carbonyl]phenyl}acetamide
[359] 8-(3-dimethylaminobenzoyl)-3-(3,5-dimethylbenzyl)-1-oxa-3,8-diazaspiro[4.5]decan-2-one
[360] 3-(4-tert-butylbenzyl)-8-(3-dimethylaminobenzoyl)-1-oxa-3,8-diazaspiro[4.5]decan-2-one
[361] 3-(3-bromobenzyl)-8-(3-dimethylaminobenzoyl)-1-oxa-3,8-diazaspiro[4.5]decan-2-one
[362] 3-(4-methylbenzyl)-8-(4-phenoxybutyryl)-1-oxa-3,8-diazaspiro[4.5]decan-2-one
[363] 8-(4-phenoxybutyryl)-3-(2-trifluoromethylbenzyl)-1-oxa-3,8-diazaspiro[4.5]decan-2-one
[364] 3-(2-fluorobenzyl)-8-(4-phenoxybutyryl)-1-oxa-3,8-diazaspiro[4.5]decan-2-one
[365] 8-(2,3-dimethylbenzoyl)-3-(4-fluorobenzyl)-1-oxa-3,8-diazaspiro[4.5]decan-2-one
[366] 3-[8-(2,3-dimethylbenzoyl)-2-oxo-1-oxa-3,8-diazaspiro[4.5]dec-3-ylmethyl]benzonitrile
[367] 8-(2,3-dimethylbenzoyl)-3-(3,5-dimethylbenzyl)-1-oxa-3,8-diazaspiro[4.5]decan-2-one
[368] 8-(2,3-dimethylbenzoyl)-3-(4-methylbenzyl)-1-oxa-3,8-diazaspiro[4.5]decan-2-one
[369] 8-(2,3-dimethylbenzoyl)-3-(2-trifluoromethylbenzyl)-1-oxa-3,8-diazaspiro[4.5]decan-2-one
[370] 8-(2,3-dimethylbenzoyl)-3-(2-methoxy-5-nitrobenzyl)-1-oxa-3,8-diazaspiro[4.5]decan-2-one
[371] 8-(2,3-dimethylbenzoyl)-3-(4-trifluoromethylbenzyl)-1-oxa-3,8-diazaspiro[4.5]decan-2-one
[372] 3-biphenyl-2-ylmethyl-8-(2,3-dimethylbenzoyl)-1-oxa-3,8-diazaspiro[4.5]decan-2-one
[373] 4-[8-(5-methyl-2-phenyl-2H-[1,2,3]triazole-4-carbonyl)-2-oxo-1-oxa-3,8-diazaspiro[4.5]dec-3-ylmethyl]benzonitrile
[374] 3-benzyl-8-(5-methyl-2-phenyl-2H-[1,2,3]triazole-4-carbonyl)-1-oxa-3,8-diazaspiro[4.5]decan-2-one
[375] 3-(3,4-difluorobenzyl)-8-(5-methyl-2-phenyl-2H-[1,2,3]triazole-4-carbonyl)-1-oxa-3,8-diazaspiro[4.5]decan-2-one
[376] 8-(5-methyl-2-phenyl-2H-[1,2,3]triazole-4-carbonyl)-3-naphthalen-2-ylmethyl-1-oxa-3,8-diazaspiro[4.5]decan-2-one
[377] 3-biphenyl-2-ylmethyl-8-(5-methyl-2-phenyl-2H-[1,2,3]triazole-4-carbonyl)-1-oxa-3,8-diazaspiro[4.5]decan-2-one
[378] 3-(4-tert-butylbenzyl)-8-[3-(2,6-dichlorophenyl)-5-methylisoxazole-4-carbonyl]-1-oxa-3,8-diazaspiro[4.5]decan-2-one
[379] 3-[2-oxo-8-(2-phenoxypyridine-3-carbonyl)-1-oxa-3,8-diazaspiro[4.5]dec-3-ylmethyl]benzonitrile
[380] 2-[2-oxo-8-(2-phenoxypyridine-3-carbonyl)-1-oxa-3,8-diazaspiro[4.5]dec-3-ylmethyl]benzonitrile
[381] 3-(4-fluorobenzyl)-8-(pyridine-2-carbonyl)-1-oxa-3,8-diazaspiro[4.5]decan-2-one
[382] 3-(3-methoxybenzyl)-8-(pyridine-2-carbonyl)-1-oxa-3,8-diazaspiro[4.5]decan-2-one
[383] 3-(3,5-dimethylbenzyl)-8-(pyridine-2-carbonyl)-1-oxa-3,8-diazaspiro[4.5]decan-2-one
[384] 2-[2-oxo-8-(pyridine-2-carbonyl)-1-oxa-3,8-diazaspiro[4.5]dec-3-ylmethyl]benzonitrile
[385] 3-(2-fluorobenzyl)-8-(pyridine-2-carbonyl)-1-oxa-3,8-diazaspiro[4.5]decan-2-one
[386] 3-(3,4-difluorobenzyl)-8-(pyridine-2-carbonyl)-1-oxa-3,8-diazaspiro[4.5]decan-2-one
[387] 3-biphenyl-2-ylmethyl-8-(pyridine-2-carbonyl)-1-oxa-3,8-diazaspiro[4.5]decan-2-one
[388] 4-[8-(3-chlorothiophene-2-carbonyl)-2-oxo-1-oxa-3,8-diazaspiro[4.5]dec-3-ylmethyl]benzonitrile
[389] 8-(3-chlorothiophene-2-carbonyl)-3-(3,4-difluorobenzyl)-1-oxa-3,8-diazaspiro[4.5]decan-2-one
[390] 3-biphenyl-2-ylmethyl-8-(3-chlorothiophene-2-carbonyl)-1-oxa-3,8-diazaspiro[4.5]decan-2-one
[391] 8-[1-(4-chlorophenyl)-5-trifluoromethyl-1H-pyrazole-4-carbonyl]-3-(2-fluorobenzyl)-1-oxa-3,8-diazaspiro[4.5]decan-2-one
[392] 8-[1-(4-chlorophenyl)-5-trifluoromethyl-1H-pyrazole-4-carbonyl]-3-(3,4-difluorobenzyl)-1-oxa-3,8-diazaspiro[4.5]decan-2-one
[393] 8-[1-(4-chlorophenyl)-5-trifluoromethyl-1H-pyrazole-4-carbonyl]-3-(4-trifluoromethylsulfanylbenzyl)-1-oxa-3,8-diazaspiro[4.5]decan-2-one
[394] 3-(4-tert-butylbenzyl)-8-(5-tert-butyl-2-methyl-2H-pyrazole-3-carbonyl)-1-oxa-3,8-diazaspiro[4.5]decan-2-one
[395] 3-[8-(5-methylisoxazole-3-carbonyl)-2-oxo-1-oxa-3,8-diazaspiro[4.5]dec-3-ylmethyl]benzonitrile
[396] 3-(3,5-dimethylbenzyl)-8-(5-methylisoxazole-3-carbonyl)-1-oxa-3,8-diazaspiro[4.5]decan-2-one
[397] 2-[8-(5-methylisoxazole-3-carbonyl)-2-oxo-1-oxa-3,8-diazaspiro[4.5]dec-3-ylmethyl]benzonitrile
[398] 4-[8-(5-methylisoxazole-3-carbonyl)-2-oxo-1-oxa-3,8-diazaspiro[4.5]dec-3-ylmethyl]benzonitrile
[399] 3-benzyl-8-(5-methylisoxazole-3-carbonyl)-1-oxa-3,8-diazaspiro[4.5]decan-2-one
[400] 3-(3,4-difluorobenzyl)-8-(5-methylisoxazole-3-carbonyl)-1-oxa-3,8-diazaspiro[4.5]decan-2-one
[401] 3-biphenyl-2-ylmethyl-8-(5-methylisoxazole-3-carbonyl)-1-oxa-3,8-diazaspiro[4.5]decan-2-one
[402] 8-(4-methyl[1,2,3]thiadiazole-5-carbonyl)-3-(2-trifluoromethylbenzyl)-1-oxa-3,8-diazaspiro[4.5]decan-2-one
[403] 3-(4-tert-butylbenzyl)-8-(4-methyl[1,2,3]thiadiazole-5-carbonyl)-1-oxa-3,8-diazaspiro[4.5]decan-2-one
[404] 8-(4-methyl[1,2,3]thiadiazole-5-carbonyl)-3-(4-trifluoromethylsulfanylbenzyl)-1-oxa-3,8-diazaspiro[4.5]decan-2-one
[405] 4-[2-oxo-8-(1-phenyl-5-propyl-1H-pyrazole-4-carbonyl)-1-oxa-3,8-diazaspiro[4.5]dec-3-ylmethyl]benzonitrile
[406] 3-(3,4-difluorobenzyl)-8-(1-phenyl-5-propyl-1H-pyrazole-4-carbonyl)-1-oxa-3,8-diazaspiro[4.5]decan-2-one
[407] 3-naphthalen-2-ylmethyl-8-(1-phenyl-5-propyl-1H-pyrazole-4-carbonyl)-1-oxa-3,8-diazaspiro[4.5]decan-2-one

[408] 8-(1-phenyl-5-propyl-1H-pyrazole-4-carbonyl)-3-(4-trifluoromethylsulfanylbenzyl)-1-oxa-3,8-diazaspiro[4.5]decan-2-one
[409] 3-[8-(2-chloropyridine-4-carbonyl)-2-oxo-1-oxa-3,8-diazaspiro[4.5]dec-3-ylmethyl]benzonitrile
[410] 8-(2-chloropyridine-4-carbonyl)-3-(3-methoxybenzyl)-1-oxa-3,8-diazaspiro[4.5]decan-2-one
[411] 8-(5-tert-butyl-2-methylfuran-3-carbonyl)-3-(4-fluorobenzyl)-1-oxa-3,8-diazaspiro[4.5]decan-2-one
[412] 3-[8-(5-tert-butyl-2-methylfuran-3-carbonyl)-2-oxo-1-oxa-3,8-diazaspiro[4.5]dec-3-ylmethyl]benzonitrile
[413] 2-[8-(5-tert-butyl-2-methylfuran-3-carbonyl)-2-oxo-1-oxa-3,8-diazaspiro[4.5]dec-3-ylmethyl]benzonitrile
[414] 4-[8-(5-tert-butyl-2-methylfuran-3-carbonyl)-2-oxo-1-oxa-3,8-diazaspiro[4.5]dec-3-ylmethyl]benzonitrile
[415] 8-(5-tert-butyl-2-methylfuran-3-carbonyl)-3-(2-trifluoromethylbenzyl)-1-oxa-3,8-diazaspiro[4.5]decan-2-one
[416] 8-(5-tert-butyl-2-methylfuran-3-carbonyl)-3-naphthalen-2-ylmethyl-1-oxa-3,8-diazaspiro[4.5]decan-2-one
[417] 3-biphenyl-2-ylmethyl-8-(5-tert-butyl-2-methylfuran-3-carbonyl)-1-oxa-3,8-diazaspiro[4.5]decan-2-one
[418] 3-(3-bromobenzyl)-8-(5-tert-butyl-2-methylfuran-3-carbonyl)-1-oxa-3,8-diazaspiro[4.5]decan-2-one
[419] 8-(benzo[1,2,5]oxadiazole-5-carbonyl)-3-(3,4-difluorobenzyl)-1-oxa-3,8-diazaspiro[4.5]decan-2-one
[420] 8-(benzo[1,2,5]oxadiazole-5-carbonyl)-3-(4-trifluoromethylbenzyl)-1-oxa-3,8-diazaspiro[4.5]decan-2-one
[421] 3-[8-(2-methyl-6-trifluoromethylpyridine-3-carbonyl)-2-oxo-1-oxa-3,8-diazaspiro[4.5]dec-3-ylmethyl]benzonitrile
[422] 2-[8-(2-methyl-6-trifluoromethylpyridine-3-carbonyl)-2-oxo-1-oxa-3,8-diazaspiro[4.5]dec-3-ylmethyl]benzonitrile
[423] 4-[8-(2-methyl-6-trifluoromethylpyridine-3-carbonyl)-2-oxo-1-oxa-3,8-diazaspiro[4.5]dec-3-ylmethyl]benzonitrile
[424] 8-(2-methyl-6-trifluoromethylpyridine-3-carbonyl)-3-(2-trifluoromethylbenzyl)-1-oxa-3,8-diazaspiro[4.5]decan-2-one
[425] 3-(3,4-difluorobenzyl)-8-(2-methyl-6-trifluoromethylpyridine-3-carbonyl)-1-oxa-3,8-diazaspiro[4.5]decan-2-one
[426] 3-(3-bromobenzyl)-8-(2-methyl-6-trifluoromethylpyridine-3-carbonyl)-1-oxa-3,8-diazaspiro[4.5]decan-2-one
[427] 8-(6-chloro-2H-chromene-3-carbonyl)-3-(3,4-difluorobenzyl)-1-oxa-3,8-diazaspiro[4.5]decan-2-one
[428] 8-(2-chloropyridine-4-carbonyl)-3-(2-fluorobenzyl)-1-oxa-3,8-diazaspiro[4.5]decan-2-one
[429] 8-(2-chloropyridine-4-carbonyl)-3-naphthalen-2-ylmethyl-1-oxa-3,8-diazaspiro[4.5]decan-2-one
[430] 8-acetyl-3-(2-fluorobenzyl)-1-oxa-3,8-diazaspiro[4.5]decan-2-one
[431] 8-acetyl-3-(3-bromobenzyl)-1-oxa-3,8-diazaspiro[4.5]decan-2-one
and
[432] 3-(2-methoxy-5-nitrobenzyl)-8-(3-phenoxypropyl)-1-oxa-3,8-diazaspiro[4.5]decan-2-one;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The present invention also provides a method for producing compounds of the above-stated general formula I, in accordance with which at least one compound of the general formula II,

in which PG denotes a protective group, preferably a tert-butyloxycarbonyl or benzyloxycarbonyl group, is reacted in a reaction medium, in the presence of at least one base, preferably in the presence of at least one metal hydride salt, particularly preferably in the presence of potassium hydride and/or sodium hydride, with at least one compound of the general formula $R^1$—$(CH_2)_n$—X, in which $R^1$ and n has the above-stated meaning and X denotes a leaving group, preferably a halogen atom, particularly preferably a chlorine or bromine atom, to yield at least one compound of the general formula III,

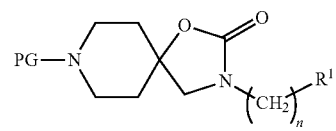

in which $R^1$, PG and n have the above-stated meaning, and this is optionally purified and/or isolated, and at least one compound of the general formula III is reacted by elimination of the protective group, preferably the tert-butoxycarbonyl residue-group in a reaction medium, preferably in the presence of at least one acid or in the presence of at least one base or by elimination of benzyloxycarbonyl group in a reaction medium, preferably in the presence of hydrogen and catalyst, preferably palladium on carbon, to yield at least one compound of the general formula IV, optionally in the form of a corresponding salt, preferably in the form of a corresponding hydrochloride,

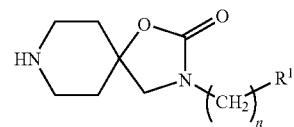

in which $R^1$ and n have the above-stated meaning, and this is optionally purified and/or isolated, and at least one compound of the general formula IV is reacted in a reaction medium with at least one isothiocyanate of the general formula $R^3$—N=C=S, in which $R^3$ has the above-stated meaning, optionally in the presence of at least one base, preferably in the presence of at least one base selected from the group consisting of triethylamine, (4,4)-dimethylaminopyridine, pyridine, diisopropylethylamine and N-methylmorpholine, to yield at least one compound of the general formula I, in which $R^1$ and n have the above-stated meaning and $R^2$ denotes —C(=S)—NH—$R^3$, in which $R^3$ has the above-stated meaning, and this is optionally purified and/or isolated;

or at least one compound of the general formula IV is reacted in a reaction medium with at least one isocyanate of the general formula $R^4$—N═C═O, in which $R^4$ has the above-stated meaning, optionally in the presence of at least one base, preferably in the presence of at least one base selected from the group consisting of triethylamine, (4,4)-dimethylaminopyridine, pyridine, diisopropylethylamine and N-methylmorpholine, to yield at least one compound of the general formula I, in which $R^1$ and n have the above-stated meaning and $R^2$ denotes —C(═O)—NH—$R^4$, in which $R^4$ has the above-stated meaning, and this is optionally purified and/or isolated;

or at least one compound of the general formula IV is reacted in a reaction medium, optionally in the presence of at least one base, preferably in the presence of at least one base selected from the group consisting of triethylamine, (4,4)-dimethylaminopyridine, pyridine, diisopropylethylamine and N-methylmorpholine, with at least one sulfonic acid derivative of the general formula $R^5$—S(═O)$_2$—X, in which $R^5$ has the above-stated meaning and X denotes a leaving group, preferably a halogen atom, particularly preferably a chlorine or bromine atom, to yield at least one compound of the general formula I, in which $R^1$ and n have the above-stated meaning and $R^2$ denotes —S(═O)$_2$—$R^5$, in which $R^5$ has the above-stated meaning, and this is optionally purified and/or isolated;

or at least one compound of the general formula IV is reacted in a reaction medium, optionally in the presence of at least one base, preferably in the presence of at least one base selected from the group consisting of triethylamine, (4,4)-dimethylaminopyridine, pyridine, diisopropylethylamine and N-methylmorpholine, with at least one compound of the general formula X—(CH$_2$)—C(═O)—NHR$^6$, in which $R^6$ has the above-stated meaning and X denotes a leaving group, preferably a halogen atom, particularly preferably a chlorine or bromine atom, to yield at least one compound of the general formula I, in which $R^1$ and n have the above-stated meaning and $R^2$ denotes —(CH$_2$)—C(═O)—NH—$R^6$, in which $R^6$ has the above-stated meaning, and this is optionally purified and/or isolated;

or at least one compound of the general formula IV is reacted in a reaction medium, in the presence of at least one reducing agent, with at least one compound of the general formula $R^7$—C(═O)—H, in which $R^7$ has the above-stated meaning, to yield at least one compound of the general formula I, in which $R^1$ and n have the above-stated meaning and $R^2$ denotes —(CH$_2$)—$R^7$, in which $R^7$ has the above-stated meaning, and this is optionally purified and/or isolated;

or at least one compound of the general formula IV is reacted in a reaction medium, optionally in the presence of at least one base, preferably in the presence of at least one base selected from the group consisting of triethylamine, (4,4)-dimethylaminopyridine, pyridine, diisopropylethylamine and N-methylmorpholine, with at least one compound of the general formula X—(CH$_2$)—$R^7$ or at least one compound of the general formula X—(CH$_2$)-D$_{aa}$-(CH$_2$)$_{bb}$-E$_{cc}$-(CH$_2$)$_{dd}$—$R^7$, in which $R^7$, D, E, aa, bb, cc and dd have the above-stated meaning and X denotes a leaving group, preferably a halogen atom, particularly preferably a chlorine or bromine atom, to yield at least one compound of the general formula I, in which $R^1$ and n have the above-stated meaning and $R^2$ denotes —(CH$_2$)—$R^7$ or —(CH$_2$)-D$_{aa}$-(CH$_2$)$_{bb}$-E$_{cc}$-(CH$_2$)$_{dd}$—$R^7$, in which $R^7$, D, E, aa, bb, cc and dd have the above-stated meaning, and this is optionally purified and/or isolated;

or at least one compound of the general formula IV is reacted in a reaction medium, optionally in the presence of at least one base, preferably in the presence of at least one base selected from the group consisting of triethylamine, (4,4)-dimethylaminopyridine, pyridine, diisopropylethylamine and N-methylmorpholine, with at least one carboxylic acid derivative of the general formula $R^8$—C(═O)—X, in which $R^8$ has the above-stated meaning and X denotes a leaving group, preferably a halogen atom, particularly preferably a chlorine or bromine atom, to yield at least one compound of the general formula I, in which $R^1$ and n have the above-stated meaning and $R^2$ denotes —C(═O)—$R^8$, in which $R^8$ has the above-stated meaning, and this is optionally purified and/or isolated;

or at least one compound of the general formula IV is reacted in a reaction medium, in the presence of at least one coupling reagent, optionally in the presence of at least one base, preferably in the presence of at least one base selected from the group consisting of triethylamine, (4,4)-dimethylaminopyridine, pyridine, diisopropylethylamine and N-methylmorpholine, with at least one carboxylic acid of the general formula $R^8$—C(═O)—OH, in which $R^8$ has the above-stated meaning, to yield at least one compound of the general formula I, in which $R^1$ and n have the above-stated meaning and $R^2$ denotes —C(═O)—$R^8$, in which $R^8$ has the above-stated meaning, and this is optionally purified and/or isolated;

or at least one compound of the general formula IV is reacted in a reaction medium, optionally in the presence of at least one base, preferably in the presence of at least one base selected from the group consisting of triethylamine, (4,4)-dimethylaminopyridine, pyridine, diisopropylethylamine and N-methylmorpholine, with at least one sulfonic acid derivative of the general formula X—S(═O)$_2$—NR$^9$R$^{10}$, in which $R^9$ and $R^{10}$ have the above stated meaning and X denotes a leaving group, preferably a halogen atom, particularly preferably a chlorine or bromine atom, to yield at least one compound of the general formula I, in which $R^1$ and n have the above-stated meaning and $R^2$ denotes —S(═O)$_2$—NR$^9$R$^{10}$, in which $R^9$ and $R^{10}$ have the above-stated meaning, and this is optionally purified and/or isolated.

The method according to the invention for producing the substituted 1-oxa-3,8-diazaspiro[4.5]-decan-2-one compounds of the above-stated general formula I is also shown in Scheme 1 below.

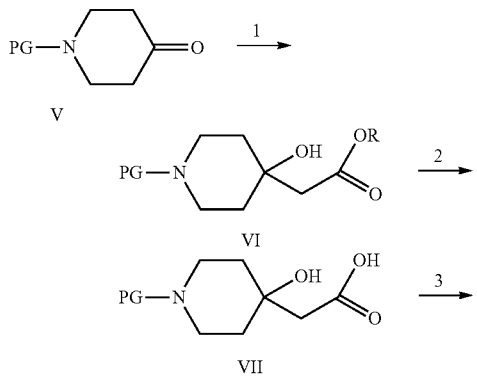

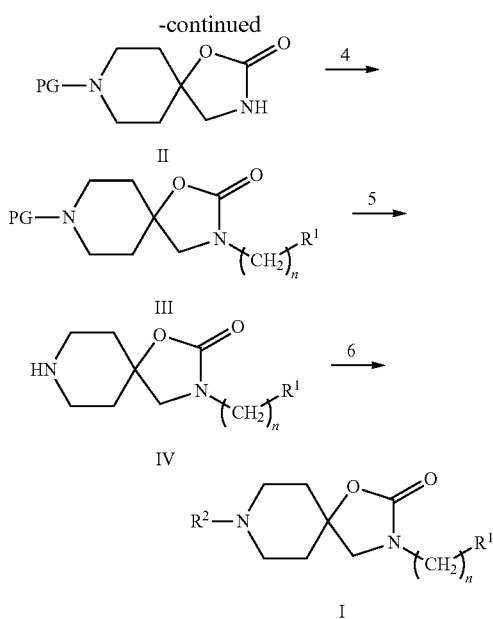

In stage 1, compounds of the general formula V, in which PG denotes a tert-butoxycarbonyl group or benzyloxycarbonyl group, are reacted in a reaction medium preferably selected from the group consisting of dichloromethane, acetonitrile, toluene, diethyl ether, tetrahydrofuran and corresponding mixtures in the presence of at least one base, preferably in the presence of lithium and/or potassium hexamethyldisilazide, with compounds of the general formula $CH_3$—C(=O)—O—R, in which R denotes a linear or branched —$C_{1-10}$ alkyl residue, at temperatures of preferably −80 to 20° C. to yield compounds of the general formula VI.

In stage 2, compounds of the general formula VI are reacted in a reaction medium, preferably selected from the group consisting of methanol, ethanol, isopropanol, water and corresponding mixtures, with an inorganic base, preferably with at least one base selected from the group consisting of lithium hydroxide, potassium hydroxide and sodium hydroxide at temperatures of preferably 20 to 30° C. to yield compounds of the general formula VII.

In stage 3, compounds of the general formula VII are reacted in a reaction medium preferably selected from the group consisting of dichloromethane, acetonitrile, toluene, dioxane, diethyl ether, tetrahydrofuran and corresponding mixtures in the presence of at least one organic base, preferably in the presence of triethylamine, 4,4-dimethylaminopyridine, pyridine, N-methylmorpholine and diisopropylethylamine with diphenylphosphoryl azide at temperatures of preferably 20 to 120° C. to yield compounds of the general formula (II).

In stage 4, compounds of the general formula (II) are reacted in a reaction medium, preferably selected from the group consisting of dichloromethane, dimethylformamide, toluene, tetrahydrofuran, acetonitrile, diethyl ether, dioxane and corresponding mixtures in the presence of at least one base, preferably in the presence of at least one metal hydride salt, particularly preferably in the presence of potassium and/or sodium hydride, with compounds of the general formula $R^1$—$(CH_2)_n$—X, in which $R^1$ and n have the above-stated meaning and X denotes a leaving group, preferably a halogen atom, particularly preferably a chlorine or bromine atom, to yield compounds of the general formula (III).

In stage 5, compounds of the general formula (III), in which PG denotes a tert-butyloxycarbonyl group, are reacted in a reaction medium preferably selected from the group consisting of dichloromethane, acetonitrile, methanol, ethanol, isopropanol, water, diethyl ether, tetrahydrofuran and corresponding mixtures in the presence of at least one acid preferably selected from the group consisting of hydrochloric acid, sulfuric acid, trifluoroacetic acid and acetic acid at temperatures of preferably 0 to 50° C. to yield compounds of the general formula IV. The reaction of the compound of the general formula (III) particularly preferably proceeds with trifluoroacetic acid in dichloromethane at temperatures of preferably 20 to 30° C. to yield a compound of the general formula IV.

Alternatively, compounds of the general formula (III), in which PG denotes a benzyloxycarbonyl group, are reacted in a reaction medium preferably selected from the group consisting of diethyl ether, tetrahydrofuran, dioxane, acetonitrile, toluene and corresponding mixtures in the presence of hydrogen and palladium on carbon at temperatures of preferably 20 to 80° C. to yield a compound of the general formula IV.

If compounds of the general formula IV are present in the form of a corresponding hydrochloride or as a salt of trifluoroacetic acid, these are converted into the corresponding bases of the general formula IV in a reaction medium, preferably selected from the group consisting of dioxane, tetrahydrofuran, diethyl ether, methanol, ethanol, isopropanol, water and corresponding mixtures, in the presence of an inorganic base, preferably with addition of a metal hydroxide, for example sodium hydroxide, potassium hydroxide or lithium hydroxide, at temperatures of preferably 0° C. to 30° C.

In stage 6, compounds of the general formula IV are reacted with isothiocyanates of the general formula S=C=N—$R^3$, in which $R^3$ has the above-stated meaning, in a reaction medium, preferably selected from the group consisting of acetonitrile, toluene, tetrahydrofuran, benzene, ethanol, methanol, water and corresponding mixtures, optionally in the presence of at least one base, preferably in the presence of at least one base selected from the group consisting of triethylamine, 4,4-dimethylaminopyridine, pyridine, N-methylmorpholine and diisopropylethylamine, to yield compounds of the general formula I, in which $R^2$ denotes C(=S)—NH—$R^3$.

Alternatively in stage 6, compounds of the general formula IV are reacted with an isocyanate of the general formula $R^4$—N=C=O, in which $R^4$ has the above-stated meaning, in a reaction medium, preferably selected from the group consisting of acetonitrile, tetrahydrofuran, toluene, benzene, ethanol, methanol, water and corresponding mixtures, optionally in the presence of at least one base, preferably in the presence of at least one base selected from the group consisting of triethylamine, N-methylmorpholine, pyridine, 4,4-dimethylaminopyridine and diisopropylethylamine, to yield compounds of the general formula I, in which $R^2$ denotes —C(=O)—$NHR^{14}$.

Compounds of the general formula IV may likewise be reacted with sulfonic acid derivatives of the general formula X—S(=O)$_2$—$R^5$ or X—S(=O)$_2$—$NR^9R^{10}$, in which $R^5$, $R^9$ and $R^{10}$ have the above-stated meaning and X denotes a leaving group, preferably a halogen atom, particularly preferably a chlorine or bromine atom, in a reaction medium, preferably selected from the group consisting of diethyl ether, tetrahydrofuran, acetonitrile, methanol, ethanol, dimethylformamide, dichloromethane and corresponding mixtures, optionally in the presence of an organic base, preferably selected from the group consisting of triethylamine, 4,4-dimethylaminopyridine, pyridine, N-methylmorpholine and diisopropylethylamine, at temperatures of preferably 70° C. to 100° C. to yield compounds of the general formula I, in which $R^2$ denotes $S(=O)_2$—$R^5$ or —$S(=O)_2$—$NR^9R^{10}$.

Alternatively in stage 6, compounds of the general formula IV are reacted with compounds of the general formula $R^7$—C(=O)—H, in which $R^7$ has the above-stated meaning, in a reaction medium, preferably selected from the group consisting of diethyl ether, tetrahydrofuran, methanol, ethanol, dichloromethane, toluene and corresponding mixtures, with addition of at least one reducing agent, preferably with addition of at least one reducing agent selected from the group consisting of sodium borohydride, sodium acetoxyborohydride, sodium cyanoborohydride and borane-pyridine complex (pyridine-borane, $BH_3.C_5H_5N$), particularly preferably in the presence of borane-pyridine complex, to yield compounds of the general formula I, in which $R^2$ denotes —$(CH_2)$—$R^7$.

Alternatively in stage 6, compounds of the general formula IV are reacted in a reaction medium, preferably selected from the group consisting of diethyl ether, tetrahydrofuran, acetonitrile, methanol, ethanol, dimethylformamide, dichloromethane and corresponding mixtures, optionally in the presence of at least one base, preferably in the presence of at least one base selected from the group consisting of triethylamine, (4,4)-dimethylaminopyridine, pyridine, diisopropylethylamine and N-methylmorpholine, with compounds of the general formula X—$(CH_2)$—$R^7$ or X—$(CH_2)$—C(=O)—NH—$R^6$ or X—$(CH_2)$-$D_{aa}$-$(CH_2)_{bb}$-$E_{cc}$-$(CH_2)_{dd}$—$R^7$, in which $R^6$, $R^7$, D, E, aa, bb, cc and dd have the above-stated meaning and X denotes a leaving group, preferably a halogen atom, particularly preferably a chlorine or bromine atom, to yield compounds of the general formula I, in which $R^2$ denotes —$(CH_2)$—$R^7$, $(CH_2)$—C(=O)—NH—$R^6$ or —$(CH_2)$-$D_{aa}$-$(CH_2)_{bb}$-$E_{cc}$-$(CH_2)_{dd}$—$R^7$.

In stage 6, compounds of the general formula IV are reacted with carboxylic acid derivatives of the general formula X—C(=O)—$R^8$, in which $R^8$ has the above-stated meaning and X denotes a leaving group, preferably a halogen atom, particularly preferably a chlorine or bromine atom, in a reaction medium, preferably selected from the group consisting of diethyl ether, tetrahydrofuran, acetonitrile, methanol, ethanol, dimethylformamide, dichloromethane and corresponding mixtures, optionally in the presence of an organic base, preferably selected from the group consisting of triethylamine, 4,4-dimethylaminopyridine, N-methylmorpholine, pyridine and diisopropylethylamine, at temperatures of preferably 70° C. to 100° C. to yield compounds of the general formula I, in which $R^2$ denotes —C(=O)—$R^8$.

Alternatively, compounds of the above-stated general formula IV are reacted with carboxylic acids of the general formula OH—C(=O)—$R^8$, in which $R^8$ has the above-stated meaning, in a reaction medium, preferably selected from the group consisting of diethyl ether, tetrahydrofuran, acetonitrile, methanol, ethanol, dimethylformamide, dichloromethane and corresponding mixtures, optionally in the presence of at least one coupling reagent, preferably selected from the group consisting of 1-benzotriazolyloxy-tris(dimethylamino)phosphonium hexafluorophosphate (BOP), dicyclohexylcarbodiimide (DCC), N'-(3-dimethylaminopropyl)-N-ethylcarbodiimide (EDCI), N-[(dimethylamino)-1H-1,2,3-triazolo[4,5b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU) and 1-hydroxy-7-azabenzotriazole (HOAt), optionally in the presence of a base, preferably selected from the group consisting of triethylamine, pyridine, N-methylmorpholine, 4,4-dimethylaminopyridine and diisopropylethylamine at temperatures of preferably 70° C. to 10° C. to yield compounds of the general formula I, in which $R^2$ denotes —C(=O)—$R^8$.

The above-described reactions may in each case be carried out under the conventional conditions familiar to a person skilled in the art for example with regard to pressure or sequence of addition of the components. Optimum control of the process under the respective conditions may optionally be established by a person skilled in the art by simple preliminary testing.

The intermediate and final products obtained from the above-described reactions may in each case, if desired and/or necessary, be purified and/or isolated using conventional methods known to a person skilled in the art. Suitable purification methods are, for example, extraction methods and chromatographic methods such as column chromatography or preparative chromatography.

All the above-described process steps and in each case also the purification and/or isolation of intermediate or final products may be performed in part or entirely under an inert gas atmosphere, preferably under a nitrogen atmosphere.

The substituted 1-oxa-3,8-diazaspiro[4.5]-decan-2-one compounds according to the invention of the above-stated general formula I and corresponding stereoisomers may be isolated not only in the form of the free bases thereof, the free acids thereof but also in the form of corresponding salts, in particular physiologically acceptable salts.

The free bases of the particular substituted 1-oxa-3,8-diazaspiro[4.5]-decan-2-one compounds according to the invention of the above-stated general formula I and corresponding stereoisomers may, for example, be converted into the corresponding salts, preferably physiologically acceptable salts, by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid.

The free bases of the particular substituted 1-oxa-3,8-diazaspiro[4.5]-decan-2-one compounds of the above-stated general formula I and corresponding stereoisomers may likewise be converted into the corresponding physiologically acceptable salts with the free acid or a salt of a sugar substitute, such as for example saccharin, cyclamate or acesulfame.

Correspondingly, the free acids of the substituted 1-oxa-3,8-diazaspiro[4.5]-decan-2-one compounds the above-stated general formula I and corresponding stereoisomers may be converted into the corresponding physiologically acceptable salts by reaction with a suitable base. Alkali metal salts, alkaline earth metal salts or ammonium salts $[NH_xR_{4-x}]^+$, in which x=0, 1, 2, 3 or 4 and R denotes a linear or branched $C_{1-4}$ alkyl residue, may be stated by way of example.

The substituted 1-oxa-3,8-diazaspiro[4.5]-decan-2-one compounds according to the invention of the above-stated general formula I and corresponding stereoisomers may optionally, like the corresponding acids, the corresponding bases or salts of these compounds also be obtained in the form of the solvates thereof, preferably in the form of the hydrates thereof using conventional methods known to a person skilled in the art.

If the substituted 1-oxa-3,8-diazaspiro[4.5]-decan-2-one compounds according to the invention of the above-stated general formula I are obtained after the production thereof in the form of a mixture of the stereoisomers thereof, preferably in the form of the racemates thereof or other mixtures of their various enantiomers and/or diastereomers, these may be separated and optionally isolated by conventional methods known to a person skilled in the art. Examples are chromatographic separation methods, in particular liquid chromatography methods at standard pressure or at elevated pressure, preferably MPLC and HPLC methods, and fractional crystallisation methods. Individual enantiomers, for example diastereomeric salts formed by means of HPLC on a chiral stationary phase or by means of crystallisation with chiral acids, such as (+)-tartaric acid, (−)-tartaric acid or (+)-10-camphorsulfonic acid, may here in particular be separated from one another.

The substituted 1-oxa-3,8-diazaspiro[4.5]-decan-2-one compounds according to the invention of the above-stated general formula I and corresponding stereoisomers as well as in each case the corresponding acids, bases, salts and solvates are toxicologically safe and are therefore suitable as pharmaceutical active ingredients in medicaments.

The present invention accordingly also provides a medicament containing at least one 1-oxa-3,8-diazaspiro[4.5]-decan-2-one compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

The medicaments according to the invention are in particular suitable for noradrenalin receptor regulation, in particular for inhibiting noradrenalin reuptake (noradrenalin uptake), for 5-HT receptor regulation, in particular for inhibiting 5-hydroxytryptophan reuptake (5-HT uptake) and/or for μ opioid receptor regulation, in particular for inhibiting the μ opioid receptor.

The medicaments according to the invention are likewise preferably suitable for the prevention and/or treatment of disorders or diseases, which are at least partially mediated by noradrenalin receptors, 5-HT receptors and/or μ opioid receptors.

The medicament according to the invention is preferably suitable for the prevention and/or treatment of pain, preferably of pain selected from the group consisting of acute pain, chronic pain, visceral pain and neuropathic pain; for the prevention and/or treatment of one or more diseases selected from the group consisting of disorders of food intake, preferably selected from the group consisting of bulimia, anorexia, obesity and cachexia; water retention conditions; migraine; chronic paroxysmal hemicrania; depression; urinary incontinence; coughing; asthma; glaucoma; tinnitus; inflammation; neurodegenerative diseases, preferably selected from the group consisting of Parkinson's disease, Huntington's chorea, Alzheimer's disease and multiple sclerosis; cognitive dysfunction, preferably memory disorders; cognitive deficiency states (attention deficit syndrome, ADS); epilepsy; catalepsy; narcolepsy; diarrhoea; gastritis; stomach ulcer; pruritus; anxiety states; panic attacks; schizophrenia; cerebral ischaemic episodes; muscle spasms; cramps; gastro-oesophageal reflux syndrome; alcohol and/or drug abuse, preferably nicotine and/or cocaine abuse, and/or abuse of medicines; alcohol and/or drug dependency, preferably nicotine and/or cocaine dependency, and/or dependency on medicines, preferably for the prevention and/or reduction of withdrawal symptoms associated with alcohol and/or drug dependency, preferably nicotine and/or cocaine dependency and/or dependency on medicines; for the prevention and/or reduction of the development of tolerance to medicines and/or drugs, in particular medicines based on opioids; for regulating food intake; for modulating locomotor activity, for suppression of the urinary reflex; for regulating the cardiovascular system, preferably for vasodilating the arteries; for local anaesthesia; for increasing vigilance; for increasing libido; for diuresis, and/or for antinatriuresis.

The medicament according to the invention is particularly preferably suitable for the treatment and/or prevention of one or more diseases selected from the group consisting of pain, preferably of pain selected from the group consisting of acute pain, chronic pain, and neuropathic pain, urinary incontinence, depression and anxiety states.

The present invention also provides the use of at least one substituted 1-oxa-3,8-diazaspiro[4.5]-decan-2-one compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for noradrenalin receptor regulation, in particular for inhibiting noradrenalin reuptake (NA uptake), for 5-HT receptor regulation, in particular for inhibiting 5-hydroxytryptophan reuptake (5-HT uptake) and/or for μ opioid receptor regulation, in particular for μ opioid receptor inhibition.

It is preferred to use at least one substituted 1-oxa-3,8-diazaspiro[4.5]-decan-2-one compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for the prevention and/or treatment of disorders or diseases which are at least partially mediated by noradrenalin receptors, 5-HT receptors and/or μ opioid receptors.

It is particularly preferred to use at least one substituted 1-oxa-3,8-diazaspiro[4.5]-decan-2-one compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for the prevention and/or treatment of pain, preferably of pain selected from the group consisting of acute pain, chronic pain, visceral pain and neuropathic pain; for the prevention and/or treatment of one or more diseases selected from the group consisting of disorders of food intake, preferably selected from the group consisting of bulimia, anorexia, obesity and cachexia; water retention conditions; migraine; chronic paroxysmal hemicrania; depression; urinary incontinence; coughing; asthma; glaucoma; tinnitus; inflammation; neurodegenerative diseases, preferably selected from the group consisting of Parkinson's disease, Huntington's chorea, Alzheimer's disease and multiple sclerosis; cognitive dysfunction, preferably memory disorders; cognitive deficiency states (attention deficit syndrome, ADS); epilepsy;

catalepsy; narcolepsy; diarrhoea; gastritis; stomach ulcer; pruritus; anxiety states; panic attacks; schizophrenia; cerebral ischaemic episodes; muscle spasms; cramps; gastro-oesophageal reflux syndrome; alcohol and/or drug abuse, preferably nicotine and/or cocaine abuse, and/or abuse of medicines; alcohol and/or drug dependency, preferably nicotine and/or cocaine dependency, and/or dependency on medicines, preferably for the prevention and/or reduction of withdrawal symptoms associated with alcohol and/or drug dependency, preferably nicotine and/or cocaine dependency and/or dependency on medicines; for the prevention and/or reduction of the development of tolerance to medicines and/or drugs, in particular medicines based on opioids; for regulating food intake; for modulating locomotor activity, for suppression of the urinary reflex; for regulating the cardiovascular system, preferably for vasodilating the arteries; for local anaesthesia; for increasing vigilance; for increasing libido; for diuresis, and/or for antinatriuresis.

It is very particularly preferred to use at least one substituted 1-oxa-3,8-diazaspiro[4.5]-decan-2-one compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for the production of a medicament for the treatment and/or prevention of one or more diseases selected from the group consisting of pain, preferably of pain selected from the group consisting of acute pain, chronic pain, and neuropathic pain, urinary incontinence, depression and anxiety states.

The medicament according to the invention is suitable for administration to adults and children including small children and babies.

The medicament according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted 1-oxa-3,8-diazaspiro[4.5]-decan-2-one compound of the above-stated general formula I, optionally in the form of one of the pure stereoisomers thereof, in particular enantiomers or diastereomers, the racemates thereof or in the form of mixtures of the stereoisomers, in particular the enantiomers or diastereomers, in any desired mixing ratio, or optionally in the form of a corresponding salt or in each case in the form of a corresponding solvate, the medicament according to the invention conventionally contains further physiologically acceptable pharmaceutical auxiliary substances, which may preferably be selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the medicament is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

The substituted 1-oxa-3,8-diazaspiro[4.5]-decan-2-one compounds according to the invention used in the medicament according to the invention in a depot in dissolved form or in a dressing, optionally with the addition of skin penetration promoters, may be suitable percutaneous administration preparations.

Orally or percutaneously administrable formulations may also release the particular substituted 1-oxa-3,8-diazaspiro[4.5]-decan-2-one compounds according to the invention in delayed manner.

Production of the medicaments according to the invention proceeds with the assistance of conventional means, devices, methods and processes known from the prior art, as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure.

The quantity of the particular substituted 1-oxa-3,8-diazaspiro[4.5]-decan-2-one compounds of the above-stated general formula I to be administered to patients may vary and is for example dependent on the weight or age of the patient and on the mode of administration, the indication and the severity of the complaint. Conventionally, at least one such compound according to the invention is administered in a quantity of 0.005 to 100 mg/kg, preferably of 0.05 to 75 mg/kg, of patient body weight.

Pharmacological Methods:
a) Method for Determining Noradrenalin and 5-HT Uptake Inhibition:

Synaptosomes from rat brain regions are freshly isolated for in vitro studies, as described in the publication "The isolation of nerve endings from brain" by E. G. Gray and V. P. Whittaker, J. Anatomy 96, pages 79-88, 1962. The corresponding literature description is hereby introduced as a reference and is deemed to be part of the disclosure.

The tissue (hypothalamus for the determination of noradrenalin uptake inhibition and medulla and pons for the determination of 5-HT uptake inhibition) is homogenised in ice-cooled 0.32 M sucrose (100 mg of tissue/1 mL) in a glass homogeniser with Teflon pestle using five complete up and down strokes at 840 revolutions/minute.

The homogenate is centrifuged at 4° C. for 10 minutes at 1000 g. After subsequent centrifugation at 17000 g for 55 minutes, the synaptosomes ($P_2$ fraction) are obtained, which are resuspended in 0.32 M glucose (0.5 mL/100 mg of original weight).

The particular uptake is measured in a 96-well microtitre plate. The volume is 250 µl and the incubation proceeds at room temperature (approx. 20-25° C.) under an $O_2$ atmosphere.

The incubation time is 7.5 minutes for [$^3$H]-NA and 5 minutes for [$^3$H]-5-HT. The 96 samples are then filtered through a Unifilter GF/B® microtitre plate (Packard) and washed with 200 mL of incubated buffer using a "Brabdel MPXRI-96T Cell-Harvester". The Unifilter GF/B plate is dried for 1 hour at 55° C. The plate is then sealed with a Back Seal® (Packard) and 35 µl of scintillation fluid are added per well (Ultima Gold®, Packard). After sealing with a top Seal® (Packard) and establishing an equilibrium (around 5 hours), radioactivity is determined in a "Trilux 1450 Microbeta" (Wallac).

The quantity of protein used in the above determination corresponds to the values known from the literature, as for example described in "Protein measurement with the folin phenol reagent", Lowry et al., J. Biol. Chem., 193, 265-275, 1951.

A detailed description of the method may additionally be found in the literature, for example in M. Ch. Frink, H.-H. Hennies, W. Engelberger, M. Haurand and B. Wilffert (1996) Arzneim.-Forsch./Drug Res. 46 (III), 11, 1029-1036.

The corresponding literature descriptions are hereby introduced in each case as a reference and are deemed to be part of the present disclosure.

The following characteristics were determined for the NA or 5-HT transporter:
NA uptake: Km=0.32±0.11 µM
5HT uptake: Km=0.084±0.011 µM b) Method for Determining Affinity for the Human µ Opioid Receptor Receptor affinity for the human µ opioid receptor is determined in a homogeneous batch in microtitre plates. To this end, dilution series of the particular substituted 1-oxa-3,8-diazaspiro[4.5]-decan-2-one compounds to be tested were incubated at room temperature for 90 minutes in a total volume of 250 µl with a receptor membrane preparation (15-40 µg of protein per 250 µl of incubation batch) of CHO-K1 cells, which express the human µ opioid receptor (RB-HOM receptor membrane preparation from NEN, Zaventem, Belgium) in the presence of 1 nmol/l of the radioactive ligand [$^3$H]-naloxone (NET719, from NEN, Zaventem, Belgium) and of 1 mg of WGA-SPA beads (wheat germ agglutinin SPA beads from Amersham/Pharmacia, Freiburg, Germany). The incubation buffer used is 50 mmol/l tris-HCl supplemented with 0.05 wt. % of sodium azide and 0.06 wt. % of bovine serum albumin. Nonspecific binding is determined by additionally adding 25 µmol/l of naloxone. Once the ninety minute incubation time had elapsed, the microtitre plates were centrifuged off for 20 minutes at 1000 g and the radioactivity measured in a β counter (Microbeta-Trilux, from PerkinElmer Wallac, Freiburg, Germany). The percentage displacement of the radioactive ligand from its binding to the human µ opioid receptor is determined at a concentration of the substances to be tested of 1 µmol/l and stated as percentage inhibition of specific binding.

The invention is explained below with reference to Examples. These explanations are given merely by way of example and do not restrict the general concept of the invention.

EXAMPLES

The yields of the compounds produced have not been optimised.

All temperatures are uncorrected.

"Ether" means diethyl ether, "EtOAc" ethyl acetate, "DCM" dichloromethane, "DMF" N,N-dimethylformamide, "EtOH" ethanol, "MeOH" methanol.

"Equivalents" means molar equivalents, "m.p." melting point or melting range, "RT" room temperature, i.e. approx. 20° C., "min" minutes, "h" hours, "sat." saturated and aq. "aqueous".

The chemicals and solvents used were purchased from conventional suppliers (Acros, Avocado, Aldrich, Bachem, Fluka, Lancaster, Maybridge, Merck, Sigma, TCI, Oakwood etc.) or synthesised by conventional methods familiar to a person skilled in the art.

Silica gel 60 (0.04-0.063 mm) from E. Merck, Darmstadt, was used as the stationary phase for the column chromatography.

Thin-layer chromatography was performed with precoated silica gel 60 F 254 HPTLC plates from E. Merck, Darmstadt.

The mobile solvent mixture ratios for chromatographic investigations are always stated in volume/volume. Analysis was carried out by NMR and HPLC-MS.

Synthesis of
2-oxo-1-oxa-3,8-diazaspiro[4.5]decane-8-carboxylic acid tert-butyl ester (A3)

1. Synthesis of 4-ethoxycarbonylmethyl-4-hydroxypiperidine-1-carboxylic acid tert-butyl ester (A1)

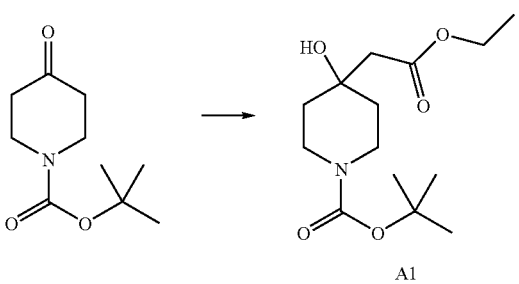

A 1.0 M solution of lithium hexamethyldisilazide (LiHMDS) in THF (40 mL, 40 mmol) was cooled to −70° C. under a nitrogen atmosphere. EtOAc (3.91 mL, 40 mmol) was slowly added dropwise thereto. The reaction mixture was stirred for 10 min at −70° C. stirred and a solution of 1-(tert-butyloxycarbonyl)-4-piperidone (7.34 g, 36.84 mmol, Lancaster, order number: 13361) in THF (16 mL) was slowly added dropwise thereto. After heating the reaction solution to 0° C., water (50 mL) was added and the reaction mixture repeatedly extracted with ether. The combined organic phases were washed with sat. aq. NaCl solution, dried over Na$_2$SO$_4$ and the solvent was removed under a vacuum. 11.31 g of the desired product 4-ethoxycarbonylmethyl-4-hydroxypiperidine-1-carboxylic acid tert-butyl ester (A1) were obtained and further reacted without purification.

2. Synthesis of
4-carboxymethyl-4-hydroxypiperidine-1-carboxylic acid tert-butyl ester (A2)

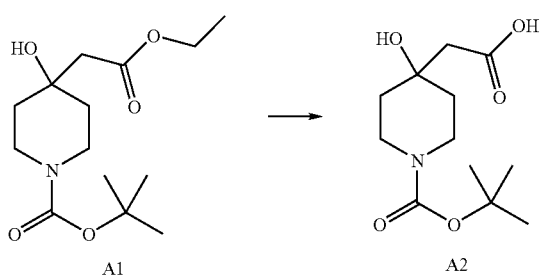

A 2.0 M solution of sodium hydroxide in water (28 mL) was added to a solution of A1 (11.31 g) in methanol (40 mL). The reaction mixture was stirred for 1 h at RT. The organic solvent was removed under a vacuum and the remaining aqueous reaction mixture was repeatedly extracted with ether. The aqueous phase was acidified with 2.0 M hydrochloric acid solution in water and repeatedly extracted with DCM. The combined DCM organic phases were washed with sat. aq. NaCl solution, dried over $Na_2SO_4$ and the solvent was removed under a vacuum. 7.9 g of the desired product 4-carboxymethyl-4-hydroxypiperidine-1-carboxylic acid tert-butyl ester (A2) were obtained and further reacted without purification.

3. Synthesis of 2-oxo-1-oxa-3,8-diazaspiro[4.5]decane-8-carboxylic acid tert-butyl ester (A3)

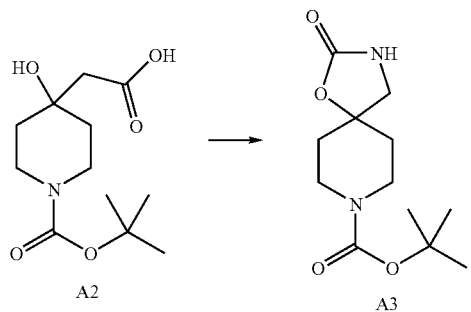

Triethylamine (5.59 mL, 39.78 mmol) and diphenylphosphoryl azide (10.86 mL, 5.1 mmol) were added in succession under a nitrogen atmosphere to a solution of A2 (7.9 g) in dry toluene (205 mL). The reaction mixture was heated to 80 to 90° C., evolution of gas being observed which ceased after 90 min. Stirring was continued for a further 2 h at 115° C. After cooling, the reaction mixture was diluted with EtOAc and repeatedly washed with water. The combined aqueous phases were extracted with EtOAc and the combined organic phases were washed with sat. aq. NaCl solution, dried over $Na_2SO_4$ and the solvent was removed under a vacuum. The residue was washed repeatedly with ether. 5.72 g (60.6% of theoretical over three stages starting from 1-(tert-butyloxycarbonyl)-4-piperidone) of the desired product 2-oxo-1-oxa-3,8-diazaspiro[4.5]decane-8-carboxylic acid tert-butyl ester (A3) remained as a white solid.

Compounds of the above-stated general formula I, in which $R^2$ denotes —C(=S)—NH—$R^3$ or —C(=O)—NH—$R^4$, may be produced in a similar manner to Examples 29, 33 and 52. The starting materials required for this purpose are known to a person skilled in the art.

Example 33

3-benzyl-2-oxo-1-oxa-3,8-diazaspiro[4.5]decane-8-carboxylic acid (3-cyanophenyl)amide

1. Synthesis of 3-benzyl-2-oxo-1-oxa-3,8-diazaspiro[4.5]decane-8-carboxylic acid tert-butyl ester (A4)

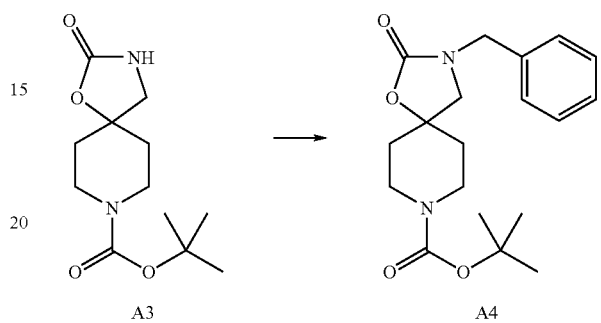

Sodium hydride (82 mg, 60% dispersion in mineral oil, weight percent) was suspended under a nitrogen atmosphere in DMF (5 mL). Compound A3 (0.5 g, 1.95 mmol) was added thereto and the reaction mixture was stirred for 10 min at RT. Benzyl bromide (235 µL, 1.97 mmol) was added thereto. The reaction mixture was stirred for 18 h at RT, combined with water and extracted with EtOAc. The combined organic phases were washed with sat. aq. NaCl solution, dried over $Na_2SO_4$ and the solvent was removed under a vacuum. The residue was dissolved in a mixture of ether and heptane. After removal of the ether, the desired product 3-benzyl-2-oxo-1-oxa-3,8-diazaspiro[4.5]decane-8-carboxylic acid tert-butyl ester (A4) (0.54 g, 80% of theoretical) was obtained as a white solid by filtration.

2. Synthesis of 3-benzyl-2-oxo-1-oxa-3,8-diazaspiro[4.5]decane-8-carboxylic acid (3-cyanophenyl)amide (33)

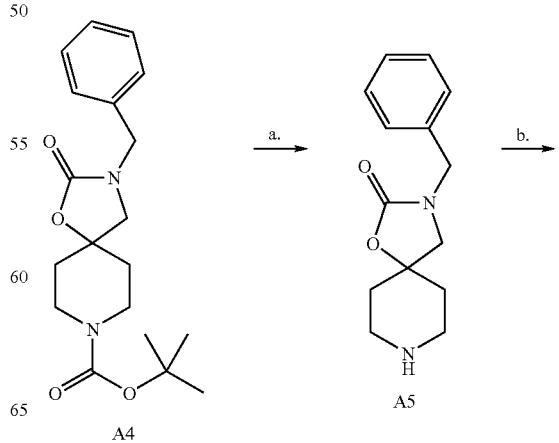

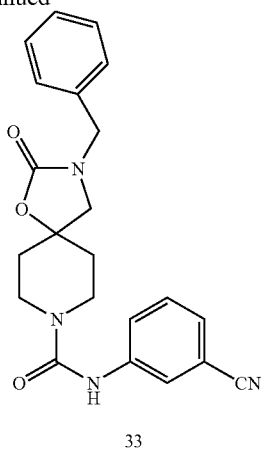

33 a. Compound A4 (0.57 g, 1.65 mmol) was dissolved in DCM (3 mL) and combined with trifluoroacetic acid (3 mL). The reaction mixture was stirred for 5 min at RT and the solvent was then removed under a vacuum. The residue was combined repeatedly with toluene and the solvent was then removed again. The residue was then combined with sat. aq. NaHCO₃ solution and repeatedly extracted with EtOAc. The combined organic phases were dried over Na₂SO₄ and the solvent was removed under a vacuum.

b. The residue from stage a. was redissolved in anhydrous THF (5 mL) and combined with a little triethylamine. The reaction mixture was combined with 3-cyanophenyl isocyanate (249 mg, 1.73 mmol), stirred for 18 h at RT and combined with water and EtOAc. The organic phase was separated off and the aqueous phase repeatedly extracted with EtOAc. The combined organic phases were dried over Na₂SO₄ and the solvent was removed under a vacuum. The residue was purified by column chromatography (SiO₂, heptane/EtOAc 1:1). After crystallisation from heptane and DCM, 242 mg (37% of theoretical) of the desired product 3-benzyl-2-oxo-1-oxa-3,8-diazaspiro[4.5]decane-8-carboxylic acid (3-cyanophenyl)amide (33) were obtained.

Example 29

3-(3-bromobenzyl)-2-oxo-1-oxa-3,8-diazaspiro[4.5]decane-8-carboxylic acid (2,5-difluorophenyl)amide 1. Synthesis of 3-(3-bromobenzyl)-2-oxo-1-oxa-3,8-diazaspiro[4.5]decane-8-carboxylic acid tert-butyl ester (A6)

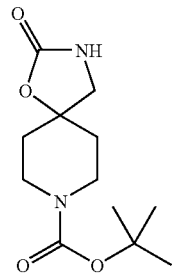

A3

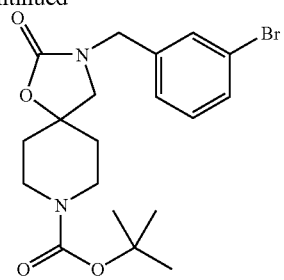

A6

Sodium hydride (246 mg, 60% dispersion in mineral oil, weight percent) was suspended under a nitrogen atmosphere in DMF (15 mL). Compound A3 (1.5 g, 5.85 mmol) was added thereto and the reaction mixture was stirred for 10 min at RT. 3-Bromobenzyl bromide (1.48 g, 5.91 mmol) was added thereto. The reaction mixture was stirred for 18 h at RT, combined with water and extracted with EtOAc. The combined organic phases were washed with sat. aq. NaCl solution, dried over Na₂SO₄ and the solvent was removed under a vacuum. The residue was dissolved in a mixture of ether and heptane. After removal of the ether, the desired product 3-(3-bromobenzyl)-2-oxo-1-oxa-3,8-diazaspiro[4.5]decane-8-carboxylic acid tert-butyl ester (A6) (2.33 g, 93% of theoretical) was obtained as a white solid by filtration.

2. Synthesis of 3-(3-bromobenzyl)-2-oxo-1-oxa-3,8-diazaspiro[4.5]decane-8-carboxylic acid (2,5-difluorophenyl)amide (29)

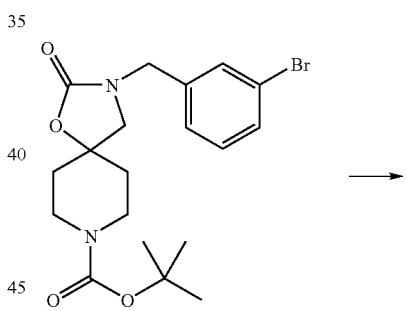

A6

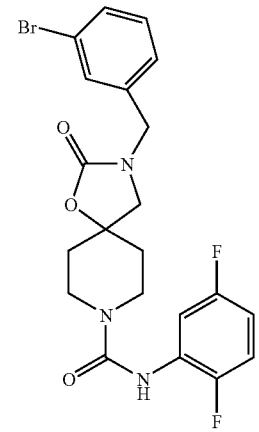

29

The compound A6 (0.50 g, 1.18 mmol) was dissolved in DCM (3 mL) and combined with trifluoroacetic acid (3 mL).

The reaction mixture was stirred for 5 min at RT and the solvent was then removed under a vacuum. The residue was combined repeatedly with toluene and the solvent was then removed again. The residue was then combined with sat. aq. NaHCO₃ solution and repeatedly extracted with EtOAc. The combined organic phases were dried over Na₂SO₄ and the solvent was removed under a vacuum. The residue was redissolved in anhydrous THF (5 mL) and combined with a little triethylamine. The reaction mixture was combined with 2,5-difluorophenyl isocyanate (145 µL, 1.23 mmol), stirred for 18 h at RT and combined with water and EtOAc. The organic phase was separated off and the aqueous phase repeatedly extracted with EtOAc. The combined organic phases were washed with sat. aq. NaCl solution, dried over Na₂SO₄ and the solvent was removed under a vacuum. The residue was purified by column chromatography (SiO₂, heptane/EtOAc 2:1). After crystallisation from heptane and DCM, 483 mg (85% of theoretical) of the desired product 3-(3-bromobenzyl)-2-oxo-1-oxa-3,8-diazaspiro[4.5]decane-8-carboxylic acid (2,5-difluorophenyl)amide (29) were obtained.

Example 52

3-naphthalen-2-ylmethyl-2-oxo-1-oxa-3,8-diazaspiro[4.5]decane-8-carboxylic acid (4-methoxyphenyl)amide 1. Synthesis of 3-naphthalen-2-ylmethyl-2-oxo-1-oxa-3,8-diazaspiro[4.5]decane-8-carboxylic acid tert-butyl ester (A7)

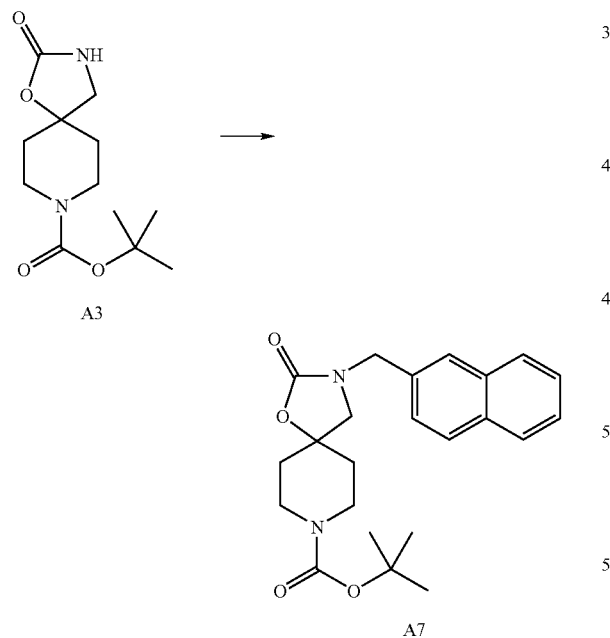

Sodium hydride (82 mg, 60% dispersion in mineral oil, weight percent) was suspended under a nitrogen atmosphere in DMF (5 mL). Compound A3 (0.5 g, 1.95 mmol) was added thereto and the reaction mixture was stirred for 10 min at RT. 2-Bromomethylnaphthol (436 mg, 1.97 mmol) was added thereto. The reaction mixture was stirred for 18 h at RT, combined with water and extracted with EtOAc. The combined organic phases were washed with sat. aq. NaCl solution, dried over Na₂SO₄ and the solvent was removed under a vacuum. The residue was dissolved in a mixture of ether and heptane. After removal of the ether, the desired product 3-naphthalen-2-ylmethyl-2-oxo-1-oxa-3,8-diazaspiro[4.5]decane-8-carboxylic acid tert-butyl ester (A7) (260 mg, 34% of theoretical) was obtained as a white solid by filtration.

2. Synthesis of 3-naphthalen-2-ylmethyl-2-oxo-1-oxa-3,8-diazaspiro[4.5]decane-8-carboxylic acid (4-methoxyphenyl)amide (52)

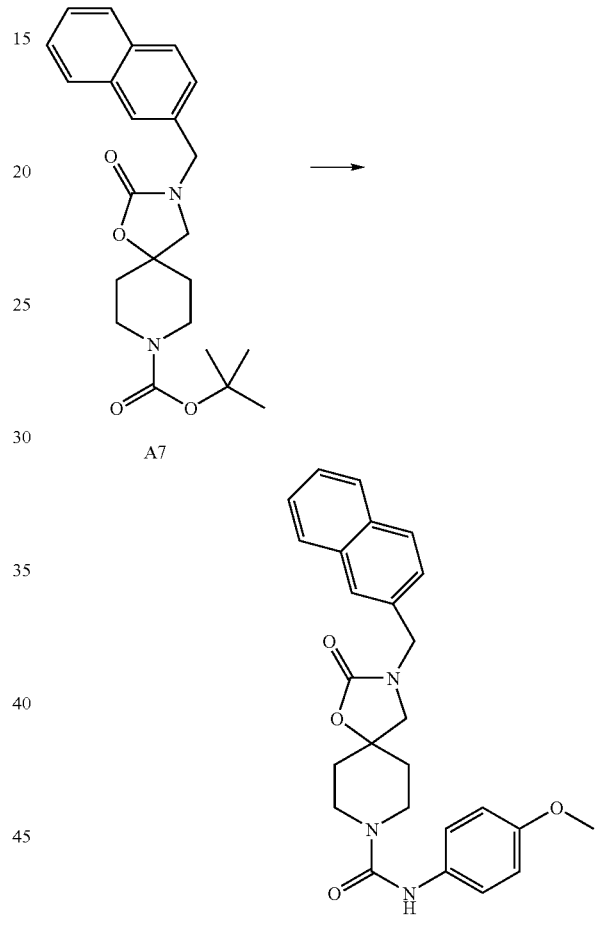

Compound A7 (0.50 g, 1.26 mmol) was dissolved in DCM (3 mL) and combined with trifluoroacetic acid (3 mL). The reaction mixture was stirred for 5 min at RT and the solvent was then removed under a vacuum. The residue was combined repeatedly with toluene and the solvent was then removed again. The residue was then combined with sat. aq. NaHCO₃ solution and repeatedly extracted with EtOAc. The combined organic phases were dried over Na₂SO₄ and the solvent was removed under a vacuum. The residue was redissolved in anhydrous THF (5 mL) and combined with a little triethylamine. The reaction mixture was combined with 4-methoxyphenyl isocyanate (202 mg, 1.35 mmol), stirred for 18 h at RT and combined with water and EtOAc. The organic phase was separated off and the aqueous phase repeatedly extracted with EtOAc. The combined organic phases were dried over Na₂SO₄ and the solvent was removed under a vacuum. The residue was purified by column chromatography (SiO$_2$, heptane/EtOAc 2:1). After crystallisation from heptane and DCM, 237 mg (42% of theoretical) of the desired product 3-naphthalen-2-ylmethyl-2-oxo-1-oxa-3,8-diazaspiro[4.5]decane-8-carboxylic acid (4-methoxyphenyl) amide (52) were obtained.

Compounds of the above-stated general formula I, in which R$^2$ denotes —S(=O)$_2$—R$^5$, —S(=O)$_2$—NR$^9$R$^{10}$ or —C(=O)—R$^8$, may be produced in a similar manner to Examples 137 and 144. The starting materials required for this purpose are known to a person skilled in the art.

Example 137

3-(3-bromobenzyl)-8-(3,5-dimethoxybenzoyl)-1-oxa-3,8-diazaspiro[4.5]decan-2-one

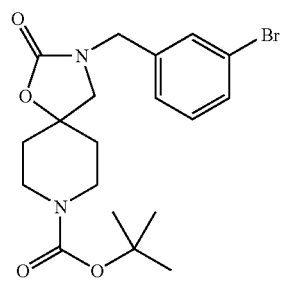
A7

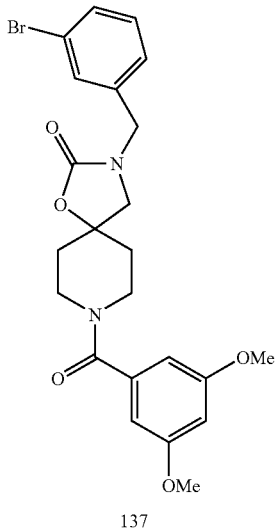
137

Compound A7 (0.50 g, 1.18 mmol) was dissolved in DCM (3 mL) and combined with trifluoroacetic acid (3 mL). The reaction mixture was stirred for 5 min at RT and the solvent was then removed under a vacuum. The residue was combined repeatedly with toluene and the solvent was then removed again. The residue was then combined with sat. aq. NaHCO$_3$ solution and repeatedly extracted with EtOAc. The combined organic phases were washed with sat. aq. NaCl solution, dried over Na$_2$SO$_4$ and the solvent was removed under a vacuum. The residue was redissolved in anhydrous DCM (5 mL) and combined with triethylamine (148 µL, 1.76 mmol). The reaction mixture was combined with 3,5-dimethoxybenzoyl chloride (technical (92%), 282 mg, 1.29 mmol), stirred for 18 h at RT and combined with water and EtOAc. The organic phase was separated off and the aqueous phase repeatedly extracted with EtOAc. The combined organic phases were washed with sat. aq. NaCl solution, dried over Na$_2$SO$_4$ and the solvent was removed under a vacuum. The residue was purified by column chromatography (SiO$_2$, heptane/EtOAc 1:2). 350 mg (60% of theoretical) of the desired product 3-(3-bromobenzyl)-8-(3,5-dimethoxybenzoyl)-1-oxa-3,8-diazaspiro[4.5]decan-2-one (137) were obtained.

Example 144

3-(3-bromobenzyl)-8-(2-phenoxypyridine-3-carbonyl)-1-oxa-3,8-diazaspiro[4.5]decan-2-one

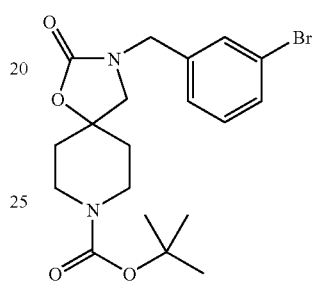
A7

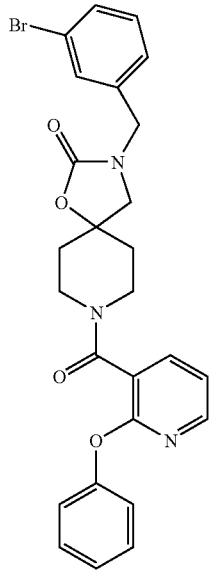
144

Compound A7 (0.50 g, 1.18 mmol) was dissolved in DCM (3 mL) and combined with trifluoroacetic acid (3 mL). The reaction mixture was stirred for 5 min at RT and the solvent was then removed under a vacuum. The residue was combined repeatedly with toluene and the solvent was then removed again. The residue was then combined with sat. aq. NaHCO$_3$ solution and repeatedly extracted with EtOAc. The combined organic phases were dried over Na$_2$SO$_4$ and the solvent was removed under a vacuum. The residue was redissolved in anhydrous DCM (5 mL) and combined with triethylamine (148 µL, 1.76 mmol). The reaction mixture was combined with 2-phenoxypyridine-3-carbonyl chloride (technical (80%), 377 mg, 1.29 mmol), stirred for 18 h at RT and combined with water and EtOAc. The organic phase was separated off and the aqueous phase repeatedly extracted with EtOAc. The combined organic phases were washed with sat. aq. NaCl solution, dried over $Na_2SO_4$ and the solvent was removed under a vacuum. The residue was purified by column chromatography ($SiO_2$, heptane/EtOAc 1:2). 539 mg (88% of theoretical) of the desired product 3-(3-bromobenzyl)-8-(2-phenoxypyridine-3-carbonyl)-1-oxa-3,8-diazaspiro[4.5]decan-2-one (144) were obtained.

Compounds of the above-stated general formula I, in which $R^2$ denotes —$(CH_2)$—$R^7$, —$(CH_2)$—C(=O)—NH—$R^6$ and —$(CH_2)$-$D_{aa}$-$(CH_2)_{bb}$-$E_{cc}$-$(CH_2)_{dd}$—$R^7$, may be produced in a similar manner to Example 432. The starting materials required for this purpose are known to a person skilled in the art.

Example 432

3-(2-methoxy-5-nitrobenzyl)-8-(3-phenoxypropyl)-1-oxa-3,8-diazaspiro[4.5]decan-2-one 1. Synthesis of 3-(2-methoxy-5-nitrobenzyl)-2-oxo-1-oxa-3,8-diazaspiro[4.5]decane-8-carboxylic acid tert-butyl ester (A8)

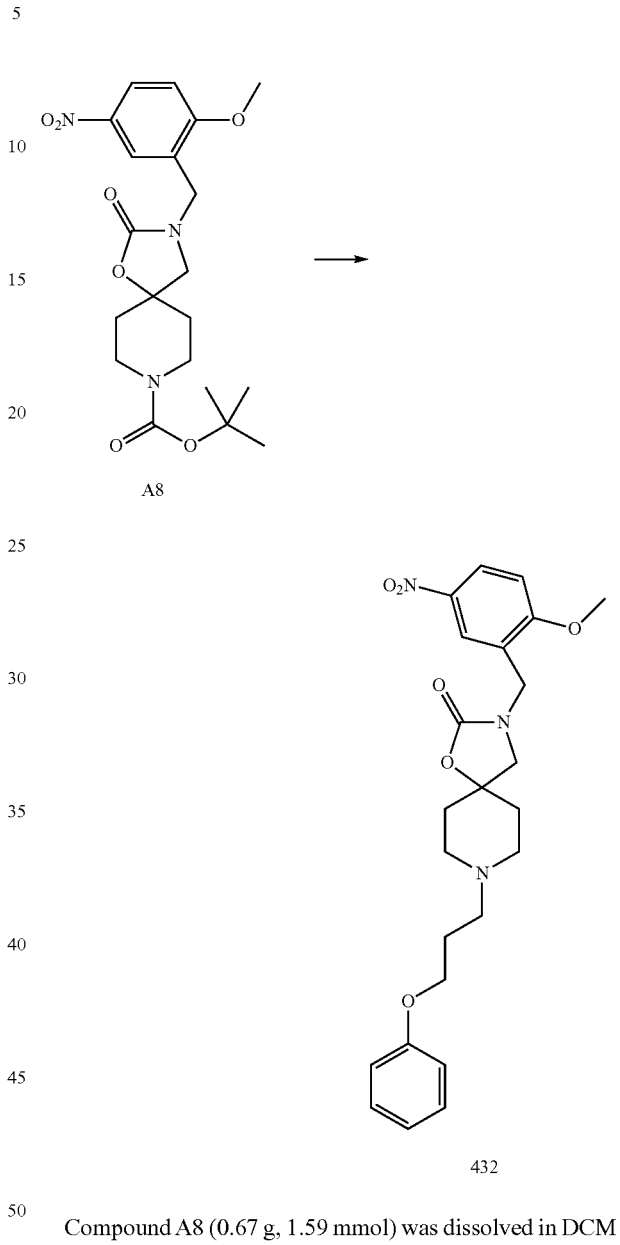

Sodium hydride (82 mg, 60% dispersion in mineral oil, weight percent) was suspended under a nitrogen atmosphere in DMF (5 mL). Compound A3 (0.5 g, 1.95 mmol) was added thereto and the reaction mixture was stirred for 10 min at RT. 2-Methoxy-5-nitrobenzyl bromide (485 mg, 1.97 mmol) was added thereto. The reaction mixture was stirred for 18 h at RT, combined with water and extracted with EtOAc. The combined organic phases were washed with sat. aq. NaCl solution, dried over $Na_2SO_4$ and the solvent was removed under a vacuum. The residue was dissolved in a mixture of ether and heptane. After removal of the ether, the desired product 3-(2-methoxy-5-nitrobenzyl)-2-oxo-1-oxa-3,8-diazaspiro[4.5] decane-8-carboxylic acid tert-butyl ester (A87) (670 mg, 81% of theoretical) was obtained as a white solid by filtration.

2. Synthesis of 3-(2-methoxy-5-nitrobenzyl)-8-(3-phenoxypropyl)-1-oxa-3,8-diazaspiro[4.5]decan-2-one (432)

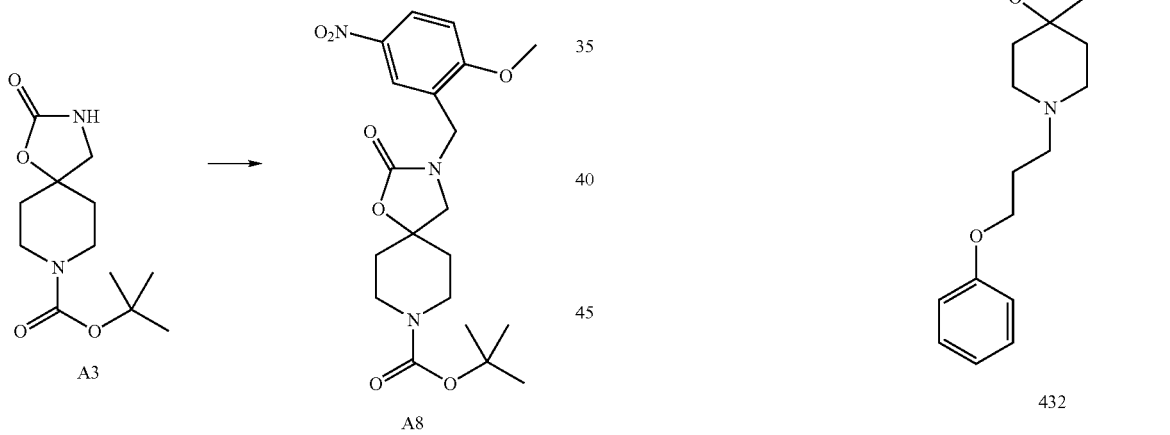

Compound A8 (0.67 g, 1.59 mmol) was dissolved in DCM (3 mL) and combined with trifluoroacetic acid (3 mL). The reaction mixture was stirred for 5 min at RT and the solvent was then removed under a vacuum. The residue was combined repeatedly with toluene and the solvent was then removed again. The residue was then combined with sat. aq. $NaHCO_3$ solution and repeatedly extracted with EtOAc. The combined organic phases were dried over $Na_2SO_4$ and the solvent was removed under a vacuum. The residue was redissolved in anhydrous THF (5 mL) and combined with diisopropylethylamine (333 μL, 1.91 mmol). The reaction mixture was combined with 3-phenoxypropyl bromide (277 μL, 1.75 mmol), stirred for 18 h at RT and combined with water and EtOAc. The organic phase was separated off and the aqueous phase repeatedly extracted with EtOAc. The combined organic phases were dried over $Na_2SO_4$ and the solvent was removed under a vacuum. The residue was purified by column chromatography (SiO₂, DCM/MeOH 98:2). 433 mg (58% of theoretical) of the desired product 3-(2-methoxy-5-nitrobenzyl)-8-(3-phenoxypropyl)-1-oxa-3,8-diazaspiro[4.5]decan-2-one (432) were obtained.

The production, not described in detail above, of the other compounds according to the Examples stated below also proceeded in a similar manner to the above-stated production methods, the educts used in each case being known to a person skilled in the art on the basis of these methods.

[1] 3-(4-methylbenzyl)-2-oxo-1-oxa-3,8-diazaspiro[4.5]decane-8-carbothioic acid pentafluorophenylamide
[2] 3-(3-bromobenzyl)-2-oxo-1-oxa-3,8-diazaspiro[4.5]decane-8-carbothioic acid (2,5-dichlorophenyl)amide
[3] 2-oxo-3-(4-trifluoromethylbenzyl)-1-oxa-3,8-diazaspiro[4.5]decane-8-carbothioic acid benzylamide
[4] 3-(3,5-dimethylbenzyl)-2-oxo-1-oxa-3,8-diazaspiro[4.5]decane-8-carbothioic acid (tetrahydrofuran-2-ylmethyl)amide
[5] 3-(3-bromobenzyl)-2-oxo-1-oxa-3,8-diazaspiro[4.5]decane-8-carbothioic acid (2-methoxyethyl)amide
[6] 3-(3-bromobenzyl)-2-oxo-1-oxa-3,8-diazaspiro[4.5]decane-8-carbothioic acid (2-methoxyphenyl)amide
[7] 3-(3,5-dimethylbenzyl)-2-oxo-1-oxa-3,8-diazaspiro[4.5]decane-8-carbothioic acid (3-acetylphenyl)amide
[8] 3-benzyl-2-oxo-1-oxa-3,8-diazaspiro[4.5]decane-8-carbothioic acid o-tolylamide
[9] 3-{[3-(3-bromobenzyl)-2-oxo-1-oxa-3,8-diazaspiro[4.5]decane-8-carbothioyl]amino}butanoic acid ethyl ester
[10] 3-naphthalen-2-ylmethyl-2-oxo-1-oxa-3,8-diazaspiro[4.5]decane-8-carbothioic acid allylamide
[11] 3-(3,4-difluorobenzyl)-2-oxo-1-oxa-3,8-diazaspiro[4.5]decane-8-carbothioic acid benzylamide
[12] 3-biphenyl-2-ylmethyl-2-oxo-1-oxa-3,8-diazaspiro[4.5]decane-8-carbothioic acid (1-phenylethyl)amide
[13] 3-(3,4-difluorobenzyl)-2-oxo-1-oxa-3,8-diazaspiro[4.5]decane-8-carbothioic acid (4-ethoxyphenyl)amide
[14] 3-(3-cyanobenzyl)-2-oxo-1-oxa-3,8-diazaspiro[4.5]decane-8-carbothioic acid (3,5-dichlorophenyl)amide
[15] 3-(3-cyanobenzyl)-2-oxo-1-oxa-3,8-diazaspiro[4.5]decane-8-carbothioic acid (3-trifluoromethylphenyl)amide
[16] 3-(3-bromobenzyl)-2-oxo-1-oxa-3,8-diazaspiro[4.5]decane-8-carbothioic acid benzylamide
[17] 3-(2-methoxy-5-nitrobenzyl)-2-oxo-1-oxa-3,8-diazaspiro[4.5]decane-8-carbothioic acid (tetrahydrofuran-2-ylmethyl)amide
[18] 3-biphenyl-2-ylmethyl-2-oxo-1-oxa-3,8-diazaspiro[4.5]decan-8-carbothioic acid phenylamide
[19] 3-(3-cyanobenzyl)-2-oxo-1-oxa-3,8-diazaspiro[4.5]decane-8-carbothioic acid cyclohexylmethylamide
[20] 3-(2-fluorobenzyl)-2-oxo-1-oxa-3,8-diazaspiro[4.5]decane-8-carbothioic acid (3-acetylphenyl)amide
[21] 3-(2-methoxy-5-nitrobenzyl)-2-oxo-1-oxa-3,8-diazaspiro[4.5]decane-8-carbothioic acid cyclohexylmethylamide
[22] 3-(3-cyanobenzyl)-2-oxo-1-oxa-3,8-diazaspiro[4.5]decane-8-carbothioic acid 4-chlorobenzylamide
[23] 3-(2-methoxy-5-nitrobenzyl)-2-oxo-1-oxa-3,8-diazaspiro[4.5]decane-8-carbothioic acid benzylamide
[24] 3-(2-fluorobenzyl)-2-oxo-1-oxa-3,8-diazaspiro[4.5]decane-8-carboxylic acid (4-ethoxyphenyl)amide
[25] 3-biphenyl-2-ylmethyl-2-oxo-1-oxa-3,8-diazaspiro[4.5]decane-8-carboxylic acid (2,5-dichlorophenyl)amide
[26] 3-(2-methoxy-5-nitrobenzyl)-2-oxo-1-oxa-3,8-diazaspiro[4.5]decane-8-carboxylic acid (2,5-difluorophenyl)amide
[27] 3-(4-methylbenzyl)-2-oxo-1-oxa-3,8-diazaspiro[4.5]decane-8-carboxylic acid (4-methyl-3-nitrophenyl)amide
[28] 3-(3,4-difluorobenzyl)-2-oxo-1-oxa-3,8-diazaspiro[4.5]decane-8-carboxylic acid 4-fluorobenzylamide
[29] 3-(3-bromobenzyl)-2-oxo-1-oxa-3,8-diazaspiro[4.5]decane-8-carboxylic acid (2,5-difluorophenyl)amide
[30] 4-[(3-naphthalen-2-ylmethyl-2-oxo-1-oxa-3,8-diazaspiro[4.5]decane-8-carbonyl)amino]benzoic acid ethyl ester
[31] 2-oxo-3-(4-trifluoromethylbenzyl)-1-oxa-3,8-diazaspiro[4.5]decane-8-carboxylic acid (4-chloro-3-trifluoromethylphenyl)amide
[32] 3-(2-cyanobenzyl)-2-oxo-1-oxa-3,8-diazaspiro[4.5]decane-8-carboxylic acid (2,5-difluorophenyl)amide
[33] 3-benzyl-2-oxo-1-oxa-3,8-diazaspiro[4.5]decane-8-carboxylic acid (3-cyanophenyl)amide
[34] 3-(3,4-difluorobenzyl)-2-oxo-1-oxa-3,8-diazaspiro[4.5]decane-8-carboxylic acid (4-methyl-3-nitrophenyl)amide
[35] 3-(3,4-difluorobenzyl)-2-oxo-1-oxa-3,8-diazaspiro[4.5]decane-8-carboxylic acid (3-methoxyphenyl)amide
[36] 3-(4-methylbenzyl)-2-oxo-1-oxa-3,8-diazaspiro[4.5]decane-8-carboxylic acid 3,4-dichlorobenzylamide -continued

[37] 3-benzyl-2-oxo-1-oxa-3,8-diazaspiro[4.5]decane-8-carboxylic acid (4-chloro-3-trifluoromethylphenyl)amide
[38] 2-oxo-3-(4-trifluoromethylsulfanylbenzyl)-1-oxa-3,8-diazaspiro[4.5]decane-8-carboxylic acid (3-cyanophenyl)amide
[39] 3-benzyl-2-oxo-1-oxa-3,8-diazaspiro[4.5]decane-8-carboxylic acid (4-methoxyphenyl)amide
[40] 2-oxo-3-(4-trifluoromethylsulfanylbenzyl)-1-oxa-3,8-diazaspiro[4.5]decane-8-carboxylic acid (4-methyl-3-nitrophenyl)amide
[41] 3-(4-iodobenzyl)-2-oxo-1-oxa-3,8-diazaspiro[4.5]decane-8-carboxylic acid (4-butoxyphenyl)amide
[42] 3-(3-bromobenzyl)-2-oxo-1-oxa-3,8-diazaspiro[4.5]decane-8-carboxylic acid 3,4-dichlorobenzylamide
[43] 3-benzyl-2-oxo-1-oxa-3,8-diazaspiro[4.5]decane-8-carboxylic acid (1-phenylethyl)amide
[44] 3-naphthalen-2-ylmethyl-2-oxo-1-oxa-3,8-diazaspiro[4.5]decane-8-carboxylic acid 3,4-dichlorobenzylamide
[45] 3-(4-methylbenzyl)-2-oxo-1-oxa-3,8-diazaspiro[4.5]decane-8-carboxylic acid phenethylamide
[46] 2-oxo-3-(2-trifluoromethylbenzyl)-1-oxa-3,8-diazaspiro[4.5]decane-8-carboxylic acid (3-methoxyphenyl)amide
[47] 3-(4-cyanobenzyl)-2-oxo-1-oxa-3,8-diazaspiro[4.5]decane-8-carboxylic acid (4-methoxyphenyl)amide
[48] 2-oxo-3-(4-trifluoromethylbenzyl)-1-oxa-3,8-diazaspiro[4.5]decane-8-carboxylic acid (1-naphthalen-1-yl-ethyl)amide
[49] 2-oxo-3-(2-trifluoromethylbenzyl)-1-oxa-3,8-diazaspiro[4.5]decane-8-carboxylic acid phenethylamide
[50] 3-(4-iodobenzyl)-2-oxo-1-oxa-3,8-diazaspiro[4.5]decane-8-carboxylic acid (4-methyl-3-nitrophenyl)amide
[51] 3-(2-methoxy-5-nitrobenzyl)-2-oxo-1-oxa-3,8-diazaspiro[4.5]decane-8-carboxylic acid (3-cyanophenyl)amide
[52] 3-naphthalen-2-ylmethyl-2-oxo-1-oxa-3,8-diazaspiro[4.5]decane-8-carboxylic acid (4-methoxyphenyl)amide
[53] 3-{[3-(4-methylbenzyl)-2-oxo-1-oxa-3,8-diazaspiro[4.5]decane-8-carbonyl]amino}benzoic acid ethyl ester
[54] 2-oxo-3-(2-trifluoromethylbenzyl)-1-oxa-3,8-diazaspiro[4.5]decane-8-carboxylic acid (1-naphthalen-1-yl-ethyl)amide
[55] 3-naphthalen-2-ylmethyl-2-oxo-1-oxa-3,8-diazaspiro[4.5]decane-8-carboxylic acid (2,5-dimethoxyphenyl)amide
[56] 3-(4-cyanobenzyl)-2-oxo-1-oxa-3,8-diazaspiro[4.5]decane-8-carboxylic acid (3-acetylphenyl)amide
[57] 3-biphenyl-2-ylmethyl-2-oxo-1-oxa-3,8-diazaspiro[4.5]decane-8-carboxylic acid phenethylamide
[58] 3-(4-cyanobenzyl)-2-oxo-1-oxa-3,8-diazaspiro[4.5]decane-8-carboxylic acid (5-chloro-2-methoxyphenyl)amide
[59] 3-{[2-oxo-3-(2-trifluoromethylbenzyl)-1-oxa-3,8-diazaspiro[4.5]decane-8-carbonyl]amino}benzoic acid ethyl ester
[60] 3-benzyl-2-oxo-1-oxa-3,8-diazaspiro[4.5]decane-8-carboxylic acid (3-fluorophenyl)amide
[61] 3-{[3-(3-cyanobenzyl)-2-oxo-1-oxa-3,8-diazaspiro[4.5]decane-8-carbonyl]amino}benzoic acid ethyl ester
[62] 3-biphenyl-2-ylmethyl-2-oxo-1-oxa-3,8-diazaspiro[4.5]decane-8-carboxylic acid (3-methoxyphenyl)amide
[63] 3-(2-methoxy-5-nitrobenzyl)-2-oxo-1-oxa-3,8-diazaspiro[4.5]decane-8-carboxylic acid (1-naphthalen-1-yl-ethyl)amide
[64] {2-[3-(3,4-difluorobenzyl)-2-oxo-1-oxa-3,8-diazaspiro[4.5]dec-8-yl]-2-oxoethoxy}acetic acid
[65] 4-[3-(3,4-difluorobenzyl)-2-oxo-1-oxa-3,8-diazaspiro[4.5]dec-8-yl]-3,3-dimethyl-4-oxobutanoic acid
[66] [2-[3-(3-bromobenzyl)-2-oxo-1-oxa-3,8-diazaspiro[4.5]dec-8-yl]-1-(1H-indol-3-ylmethyl)-2-oxoethyl]carbamic acid tert-butyl ester
[67] 5-[3-(2-fluorobenzyl)-2-oxo-1-oxa-3,8-diazaspiro[4.5]dec-8-yl]-3-methyl-5-oxopentanoic acid
[68] 3,3-dimethyl-5-[3-(4-methylbenzyl)-2-oxo-1-oxa-3,8-diazaspiro[4.5]dec-8-yl]-5-oxopentanoic acid
[69] 5-[3-(3,4-difluorobenzyl)-2-oxo-1-oxa-3,8-diazaspiro[4.5]dec-8-yl]-3-methyl-5-oxopentanoic acid
[70] {2-oxo-2-[2-oxo-3-(4-trifluoromethylbenzyl)-1-oxa-3,8-diazaspiro[4.5]dec-8-yl]ethoxy}acetic acid
[71] (1-{2-[3-(2-cyanobenzyl)-2-oxo-1-oxa-3,8-diazaspiro[4.5]dec-8-yl]-2-oxoethyl}cyclopentyl)acetic acid
[72] (1-{2-[3-(3,4-difluorobenzyl)-2-oxo-1-oxa-3,8-diazaspiro[4.5]dec-8-yl]-2-oxoethyl}cyclopentyl)acetic acid
[73] 5-(3-biphenyl-2-ylmethyl-2-oxo-1-oxa-3,8-diazaspiro[4.5]dec-8-yl)-3-methyl-5-oxopentanoic acid
[74] 3-(3,4-difluorobenzyl)-8-(4-nitrobenzyl)-1-oxa-3,8-diazaspiro[4.5]decan-2-one
[75] N-[4-(3,5-dichlorophenylsulfamoyl)phenyl]-2-[3-(4-methylbenzyl)-2-oxo-1-oxa-3,8-diazaspiro[4.5]dec-8-yl]acetamide
[76] N-(2,5-dimethyl-2H-pyrazol-3-yl)-2-[3-(2-methoxy-5-nitrobenzyl)-2-oxo-1-oxa-3,8-diazaspiro[4.5]dec-8-yl]acetamide -continued

[77] 3-(3,4-difluorobenzyl)-8-[3-(4-methoxyphenyl)-[1,2,4]oxadiazol-5-ylmethyl]-1-oxa-3,8-diazaspiro[4.5]decan-2-one
[78] 3-benzyl-8-(4-trifluoromethoxybenzyl)-1-oxa-3,8-diazaspiro[4.5]decan-2-one
[79] 8-(4-chlorobenzyl)-3-(3-methoxybenzyl)-1-oxa-3,8-diazaspiro[4.5]decan-2-one
[80] N-(3-cyano-4-methylthiophen-2-yl,)-2-[3-(3,4-difluorobenzyl)-2-oxo-1-oxa-3,8-diazaspiro[4.5]dec-8-yl]acetamide
[81] 3-(3,4-difluorobenzyl)-8-(4-trifluoromethoxybenzyl)-1-oxa-3,8-diazaspiro[4.5]decan-2-one
[82] 2-[8-(4-chlorobenzyl)-2-oxo-1-oxa-3,8-diazaspiro[4.5]dec-3-ylmethyl]benzonitrile
[83] 8-(2-methylnaphthalen-1-ylmethyl)-3-(2-trifluoromethylbenzyl)-1-oxa-3,8-diazaspiro[4.5]decan-2-one
[84] 2-[8-(5-chlorobenzo[b]thiophen-3-ylmethyl)-2-oxo-1-oxa-3,8-diazaspiro[4.5]dec-3-ylmethyl]benzonitrile
[85] 2-[2-oxo-3-(4-trifluoromethylsulfanylbenzyl)-1-oxa-3,8-diazaspiro[4.5]dec-8-yl]-N-(4-phenyl-5-trifluoromethylthiophen-3-yl)acetamide
[86] 2-[3-(2-fluorobenzyl)-2-oxo-1-oxa-3,8-diazaspiro[4.5]dec-8-yl]-N-(4-phenylthiazol-2-yl)acetamide
[87] 2-[2-oxo-3-(2-trifluoromethylbenzyl)-1-oxa-3,8-diazaspiro[4.5]dec-8-yl]-N-(4-trifluoromethoxyphenyl)acetamide
[88] 3-(2-methoxy-5-nitrobenzyl)-8-(3-nitrobenzyl)-1-oxa-3,8-diazaspiro[4.5]decan-2-one
[89] 4-[8-(3-nitrobenzyl)-2-oxo-1-oxa-3,8-diazaspiro[4.5]dec-3-ylmethyl]benzonitrile
[90] 8-(1-bromonaphthalen-2-ylmethyl)-3-(4-methylbenzyl)-1-oxa-3,8-diazaspiro[4.5]decan-2-one
[91] N-{4-[3-(3-cyanobenzyl)-2-oxo-1-oxa-3,8-diazaspiro[4.5]decane-8-carbonyl]phenyl}acetamide
[92] 8-(4-ethoxybenzoyl)-3-(4-methylbenzyl)-1-oxa-3,8-diazaspiro[4.5]decan-2-one
[93] 3-[3-(4-cyanobenzyl)-2-oxo-1-oxa-3,8-diazaspiro[4.5]dec-8-yl]-3-oxopropionic acid methyl ester
[94] 2-[8-(2,4-difluorobenzoyl)-2-oxo-1-oxa-3,8-diazaspiro[4.5]dec-3-ylmethyl]benzonitrile
[95] 8-(3-dimethylaminobenzoyl)-3-(3,5-dimethylbenzyl)-1-oxa-3,8-diazaspiro[4.5]decan-2-one
[96] N-{4-[3-(3,4-difluorobenzyl)-2-oxo-1-oxa-3,8-diazaspiro[4.5]decane-8-carbonyl]phenyl}acetamide
[97] 8-(4-bromobenzoyl)-3-(4-fluorobenzyl)-1-oxa-3,8-diazaspiro[4.5]decan-2-one
[98] 4-[8-(adamantane-1-carbonyl)-2-oxo-1-oxa-3,8-diazaspiro[4.5]dec-3-ylmethyl]benzonitrile
[99] 3-(3,5-dimethylbenzyl)-8-(2-ethylsulfanylpyridine-3-carbonyl)-1-oxa-3,8-diazaspiro[4.5]decan-2-one
[100] 3-(3-bromobenzyl)-8-(4-chlorobenzoyl)-1-oxa-3,8-diazaspiro[4.5]decan-2-one
[101] 8-[3-(2-chlorophenyl)-5-methylisoxazole-4-carbonyl]-3-(3,5-dimethylbenzyl)-1-oxa-3,8-diazaspiro[4.5]decan-2-one
[102] 3-(3-bromobenzyl)-8-(4-ethylbenzylsulfonyl)-1-oxa-3,8-diazaspiro[4.5]decan-2-one
[103] 8-(4-butoxybenzylsulfonyl)-3-(3,5-dimethylbenzyl)-1-oxa-3,8-diazaspiro[4.5]decan-2-one
[104] 8-(biphenyl-4-carbonyl)-3-(3-bromobenzyl)-1-oxa-3,8-diazaspiro[4.5]decan-2-one
[105] acetic acid 2-[3-(3,5-dimethylbenzyl)-2-oxo-1-oxa-3,8-diazaspiro[4.5]dec-8-yl]-2-oxo-1-phenylethyl ester
[106] 4-[2-oxo-8-(2-phenylcyclopropanecarbonyl)-1-oxa-3,8-diazaspiro[4.5]dec-3-ylmethyl]benzonitrile
[107] 8-(2,5-dimethoxybenzylsulfonyl)-3-(3,5-dimethylbenzyl)-1-oxa-3,8-diazaspiro[4.5]decan-2-one
[108] 8-(2-chlorobenzoyl)-3-(3,5-dimethylbenzyl)-1-oxa-3,8-diazaspiro[4.5]decan-2-one
[109] 3-(3-bromobenzyl)-8-(4-nitrobenzoyl)-1-oxa-3,8-diazaspiro[4.5]decan-2-one
[110] N-{1-benzyl-2-[3-(3-cyanobenzyl)-2-oxo-1-oxa-3,8-diazaspiro[4.5]dec-8-yl]-2-oxoethyl}-4-methylbenzylsulfonamide
[111] 8-(2-ethylsulfanylpyridine-3-carbonyl)-3-(3-methoxybenzyl)-1-oxa-3,8-diazaspiro[4.5]decan-2-one
[112] 8-(2,4-dimethoxybenzoyl)-3-(3-methoxybenzyl)-1-oxa-3,8-diazaspiro[4.5]decan-2-one
[113] 3-(3,5-dimethylbenzyl)-8-[2-(3-methoxyphenyl)acetyl]-1-oxa-3,8-diazaspiro[4.5]decan-2-one
[114] 3-(3,5-dimethylbenzyl)-8-(4-methoxy-2,3,6-trimethylbenzylsulfonyl)-1-oxa-3,8-diazaspiro[4.5]decan-2-one
[115] 4-[8-(biphenyl-4-carbonyl)-2-oxo-1-oxa-3,8-diazaspiro[4.5]dec-3-ylmethyl]benzonitrile
[116] 8-(2-chlorobenzylsulfonyl)-3-(3,5-dimethylbenzyl)-1-oxa-3,8-diazaspiro[4.5]decan-2-one
[117] 8-(benzo[1,2,5]oxadiazole-5-carbonyl)-3-(3,5-dimethylbenzyl)-1-oxa-3,8-diazaspiro[4.5]decan-2-one
[118] 8-(biphenyl-4-carbonyl)-3-(4-iodobenzyl)-1-oxa-3,8-diazaspiro[4.5]decan-2-one
[119] 3-(3,5-dimethylbenzyl)-8-(pyridine-2-carbonyl)-1-oxa-3,8-diazaspiro[4.5]decan-2-one
[120] 8-(6-chloropyridine-3-carbonyl)-3-naphthalen-2-ylmethyl-1-oxa-3,8-diazaspiro[4.5]decan-2-one
[121] 3-(3-bromobenzyl)-8-(2-ethylsulfanylpyridine-3-carbonyl)-1-oxa-3,8-diazaspiro[4.5]decan-2-one
[122] 3-(3,5-dimethylbenzyl)-8-(5-methylisoxazole-3-carbonyl)-1-oxa-3,8-diazaspiro[4.5]decan-2-one
[123] 3-(2-methoxy-5-nitrobenzyl)-8-pentanoyl-1-oxa-3,8-diazaspiro[4.5]decan-2-one
[124] 8-(4-bromobenzoyl)-3-(3,5-dimethylbenzyl)-1-oxa-3,8-diazaspiro[4.5]decan-2-one
[125] 8-(5-tert-butyl-2-methylfuran-3-carbonyl)-3-(2-methoxy-5-nitrobenzyl)-1-oxa-3,8-diazaspiro[4.5]decan-2-one
[126] 8-(3-chlorobenzoyl)-3-(3,5-dimethylbenzyl)-1-oxa-3,8-diazaspiro[4.5]decan-2-one -continued

[127] 8-(2-ethylsulfanylpyridine-3-carbonyl)-3-(2-trifluoromethylbenzyl)-1-oxa-3,8-diazaspiro[4.5]decan-2-one
[128] 3-(3,5-dimethylbenzyl)-8-(isoxazole-5-carbonyl)-1-oxa-3,8-diazaspiro[4.5]decan-2-one
[129] 3-(3-bromobenzyl)-8-(pyridine-2-carbonyl)-1-oxa-3,8-diazaspiro[4.5]decan-2-one
[130] 3-(3,5-dimethylbenzyl)-8-(thiophene-2-carbonyl)-1-oxa-3,8-diazaspiro[4.5]decan-2-one
[131] 8-(3-chloro-4-fluorobenzoyl)-3-(3,5-dimethylbenzyl)-1-oxa-3,8-diaza-spiro[4.5]decan-2-one
[132] 8-(2,6-difluoro-3-methylbenzoyl)-3-(3,5-dimethylbenzyl)-1-oxa-3,8-diazaspiro[4.5]decan-2-one
[133] 4-[3-(3-bromobenzyl)-2-oxo-1-oxa-3,8-diazaspiro[4.5]dec-8-yl]-4-oxobutanoic acid methyl ester
[134] 3-[8-(2-ethylbutyryl)-2-oxo-1-oxa-3,8-diazaspiro[4.5]dec-3-ylmethyl]benzonitrile
[135] 3-[8-(3-bromobenzylsulfonyl)-2-oxo-1-oxa-3,8-diazaspiro[4.5]dec-3-ylmethyl]benzonitrile
[136] 3-(3,4-difluorobenzyl)-8-(4-methylbenzoyl)-1-oxa-3,8-diazaspiro[4.5]decan-2-one
[137] 3-(3-bromobenzyl)-8-(3,5-dimethoxybenzoyl)-1-oxa-3,8-diazaspiro[4.5]decan-2-one
[138] 8-(3-dimethylaminobenzoyl)-3-(2-methoxy-5-nitrobenzyl)-1-oxa-3,8-diazaspiro[4.5]decan-2-one
[139] 8-(2,6-dichlorobenzoyl)-3-(2-fluorobenzyl)-1-oxa-3,8-diazaspiro[4.5]decan-2-one
[140] 3-(2-methoxy-5-nitrobenzyl)-8-(2-phenoxypyridine-3-carbonyl)-1-oxa-3,8-diazaspiro[4.5]decan-2-one
[141] 8-[2-(3-methoxyphenyl)acetyl]-3-naphthalen-2-ylmethyl-1-oxa-3,8-diazaspiro[4.5]decan-2-one
[142] 4-{2-oxo-8-[2-(2,2,2-trifluoroacetyl)-1,2,3,4-tetrahydroisoquinoline-7-sulfonyl]-1-oxa-3,8-diazaspiro[4.5]dec-3-ylmethyl}benzonitrile
[143] 8-(3,5-bis-trifluoromethylbenzoyl)-3-(4-trifluoromethylbenzyl)-1-oxa-3,8-diazaspiro[4.5]decan-2-one
[144] 3-(3-bromobenzyl)-8-(2-phenoxypyridine-3-carbonyl)-1-oxa-3,8-diazaspiro[4.5]decan-2-one
[145] 3-(2-methoxy-5-nitrobenzyl)-8-[2-(3-methoxyphenyl)acetyl]-1-oxa-3,8-diazaspiro[4.5]decan-2-one
[146] 3-(3,4-difluorobenzyl)-8-(2-phenoxypyridine-3-carbonyl)-1-oxa-3,8-diazaspiro[4.5]decan-2-one
[147] 3-[8-(4-bromo-3-methylbenzoyl)-2-oxo-1-oxa-3,8-diazaspiro[4.5]dec-3-ylmethyl]benzonitrile
[148] 3-(3-bromobenzyl)-8-(4-propylbenzoyl)-1-oxa-3,8-diazaspiro[4.5]decan-2-one
[149] 3-biphenyl-2-ylmethyl-8-(3-chlorobenzylsulfonyl)-1-oxa-3,8-diazaspiro[4.5]decan-2-one
[150] 8-[2-(3,4-dimethoxyphenyl)acetyl]-3-(2-methoxy-5-nitrobenzyl)-1-oxa-3,8-diazaspiro[4.5]decan-2-one
[151] 2-[8-(2-chloro-4-nitrobenzoyl)-2-oxo-1-oxa-3,8-diazaspiro[4.5]dec-3-ylmethyl]benzonitrile
[152] 3-[2-oxo-8-(2,4,6-trimethylbenzylsulfonyl)-1-oxa-3,8-diazaspiro[4.5]dec-3-ylmethyl]benzonitrile
[153] 3-benzyl-8-(4-fluorobenzylsulfonyl)-1-oxa-3,8-diazaspiro[4.5]decan-2-one
[154] 3-(4-fluorobenzyl)-8-(toluene-4-sulfonyl)-1-oxa-3,8-diazaspiro[4.5]decan-2-one
[155] 4-[2-oxo-8-(toluene-4-sulfonyl)-1-oxa-3,8-diazaspiro[4.5]dec-3-ylmethyl]benzonitrile
[156] 3-(2-fluorobenzyl)-8-(toluene-4-sulfonyl)-1-oxa-3,8-diazaspiro[4.5]decan-2-one
[157] 3-(3,4-difluorobenzyl)-8-(toluene-4-sulfonyl)-1-oxa-3,8-diazaspiro[4.5]decan-2-one
[158] 3-(4-tert-butylbenzyl)-8-(toluene-4-sulfonyl)-1-oxa-3,8-diazaspiro[4.5]decan-2-one
[159] 8-(toluene-4-sulfonyl)-3-(4-trifluoromethylsulfanylbenzyl)-1-oxa-3,8-diazaspiro[4.5]decan-2-one
[160] 2-[3-(4-fluorobenzyl)-2-oxo-1-oxa-3,8-diazaspiro[4.5]decan-8-sulfonyl]benzoic acid methyl ester
[161] 2-[3-(3-methoxybenzyl)-2-oxo-1-oxa-3,8-diazaspiro[4.5]decan-8-sulfonyl]benzoic acid methyl ester
[162] 2-[3-(3-bromobenzyl)-2-oxo-1-oxa-3,8-diazaspiro[4.5]decan-8-sulfonyl]benzoic acid methyl ester
[163] 3-benzyl-8-(2-methanesulfonylbenzylsulfonyl)-1-oxa-3,8-diazaspiro[4.5]decan-2-one
[164] 8-(2-methanesulfonylbenzylsulfonyl)-3-(2-methoxy-5-nitrobenzyl)-1-oxa-3,8-diazaspiro[4.5]decan-2-one
[165] 3-(4-methylbenzyl)-2-oxo-1-oxa-3,8-diazaspiro[4.5]decane-8-sulfonic acid dimethylamide
[166] 4-[8-(7,7-dimethyl-2-oxobicyclo[2.2.1]hept-1-ylmethanesulfonyl)-2-oxo-1-oxa-3,8-diazaspiro[4.5]dec-3-ylmethyl]benzonitrile
[167] 3-(4-fluorobenzyl)-8-(4-methoxybenzylsulfonyl)-1-oxa-3,8-diazaspiro[4.5]decan-2-one
[168] 3-(4-methylbenzyl)-8-(4-trifluoromethoxybenzylsulfonyl)-1-oxa-3,8-diazaspiro[4.5]decan-2-one
[169] 8-(4-trifluoromethoxybenzylsulfonyl)-3-(4-trifluoromethylsulfanylbenzyl)-1-oxa-3,8-diazaspiro[4.5]decan-2-one
[170] 8-(propane-1-sulfonyl)-3-(4-trifluoromethylsulfanylbenzyl)-1-oxa-3,8-diazaspiro[4.5]decan-2-one
[171] 3-(2-methoxy-5-nitrobenzyl)-8-(4-propylbenzylsulfonyl)-1-oxa-3,8-diazaspiro[4.5]decan-2-one
[172] 3-biphenyl-2-ylmethyl-8-(4-propylbenzylsulfonyl)-1-oxa-3,8-diazaspiro[4.5]decan-2-one
[173] 8-(3-bromobenzylsulfonyl)-3-(2-fluorobenzyl)-1-oxa-3,8-diazaspiro[4.5]decan-2-one
[174] 8-(3-bromobenzylsulfonyl)-3-(3-bromobenzyl)-1-oxa-3,8-diazaspiro[4.5]decan-2-one -continued

[175] 2-{8-[4-(1,1-dimethylpropyl)benzylsulfonyl]-2-oxo-1-oxa-3,8-diazaspiro[4.5]dec-3-ylmethyl}benzonitrile
[176] 3-benzyl-8-[4-(1,1-dimethylpropyl)benzylsulfonyl]-1-oxa-3,8-diazaspiro[4.5]decan-2-one
[177] 8-[4-(1,1-dimethylpropyl)benzylsulfonyl]-3-(4-iodobenzyl)-1-oxa-3,8-diazaspiro[4.5]decan-2-one
[178] 8-[4-(1,1-dimethylpropyl)benzylsulfonyl]-3-(2-methoxy-5-nitrobenzyl)-1-oxa-3,8-diazaspiro[4.5]decan-2-one
[179] 8-[4-(1,1-dimethylpropyl)benzylsulfonyl]-3-(4-trifluoromethylbenzyl)-1-oxa-3,8-diazaspiro[4.5]decan-2-one
[180] 3-biphenyl-2-ylmethyl-8-[4-(1,1-dimethylpropyl)benzylsulfonyl]-1-oxa-3,8-diazaspiro[4.5]decan-2-one
[181] 8-(4,5-dichlorothiophene-2-sulfonyl)-3-(3-methoxybenzyl)-1-oxa-3,8-diazaspiro[4.5]decan-2-one
[182] 8-(4,5-dichlorothiophene-2-sulfonyl)-3-(4-trifluoromethylbenzyl)-1-oxa-3,8-diazaspiro[4.5]decan-2-one
[183] 3-(3-bromobenzyl)-8-(4,5-dichlorothiophene-2-sulfonyl)-1-oxa-3,8-diazaspiro[4.5]decan-2-one
[184] 2-[8-(4-methoxy-2,3,6-trimethylbenzylsulfonyl)-2-oxo-1-oxa-3,8-diazaspiro[4.5]dec-3-ylmethyl]benzonitrile
[185] 3-(2-fluorobenzyl)-8-(4-methoxy-2,3,6-trimethylbenzylsulfonyl)-1-oxa-3,8-diazaspiro[4.5]decan-2-one
[186] 3-(4-tert-butylbenzyl)-8-[2-(2,2,2-trifluoroacetyl)-1,2,3,4-tetrahydroisoquinoline-7-sulfonyl]-1-oxa-3,8-diazaspiro[4.5]decan-2-one
[187] 8-(butane-1-sulfonyl)-3-(3-methoxybenzyl)-1-oxa-3,8-diazaspiro[4.5]decan-2-one
[188] 3-(4-methylbenzyl)-8-(thiophene-2-sulfonyl)-1-oxa-3,8-diazaspiro[4.5]decan-2-one
[189] 8-(4-chloro-2,5-dimethylbenzylsulfonyl)-3-(4-methylbenzyl)-1-oxa-3,8-diazaspiro[4.5]decan-2-one
[190] 3-benzyl-8-(4-chloro-2,5-dimethylbenzylsulfonyl)-1-oxa-3,8-diazaspiro[4.5]decan-2-one
[191] 8-(4-chloro-2,5-dimethylbenzylsulfonyl)-3-(4-trifluoromethylbenzyl)-1-oxa-3,8-diazaspiro[4.5]decan-2-one
[192] 3-biphenyl-2-ylmethyl-8-(4-chloro-2,5-dimethylbenzylsulfonyl)-1-oxa-3,8-diazaspiro[4.5]decan-2-one
[193] 8-(4-chloro-2,5-dimethylbenzylsulfonyl)-3-(4-trifluoromethylsulfanylbenzyl)-1-oxa-3,8-diazaspiro[4.5]decan-2-one
[194] 3-(4-fluorobenzyl)-8-(2-trifluoromethylbenzylsulfonyl)-1-oxa-3,8-diazaspiro[4.5]decan-2-one
[195] 3-(3-methoxybenzyl)-8-(2-trifluoromethylbenzylsulfonyl)-1-oxa-3,8-diazaspiro[4.5]decan-2-one
[196] 3-benzyl-8-(2-methyl-5-nitrobenzylsulfonyl)-1-oxa-3,8-diazaspiro[4.5]decan-2-one
[197] 3-(4-tert-butylbenzyl)-8-(2-methyl-5-nitrobenzylsulfonyl)-1-oxa-3,8-diazaspiro[4.5]decan-2-one
[198] 3-(4-tert-butylbenzyl)-8-(toluene-3-sulfonyl)-1-oxa-3,8-diazaspiro[4.5]decan-2-one
[199] 8-(furan-2-carbonyl)-3-(4-trifluoromethylbenzyl)-1-oxa-3,8-diazaspiro[4.5]decan-2-one
[200] 3-(3-bromobenzyl)-8-(furan-2-carbonyl)-1-oxa-3,8-diazaspiro[4.5]decan-2-one
[201] 4-[8-(naphthalene-1-carbonyl)-2-oxo-1-oxa-3,8-diazaspiro[4.5]dec-3-ylmethyl]benzonitrile
[202] 3-(3,4-difluorobenzyl)-8-(naphthalene-1-carbonyl)-1-oxa-3,8-diazaspiro[4.5]decan-2-one
[203] 3-(3-bromobenzyl)-8-(naphthalene-1-carbonyl)-1-oxa-3,8-diazaspiro[4.5]decan-2-one
[204] 2-[8-(3-nitrobenzoyl)-2-oxo-1-oxa-3,8-diazaspiro[4.5]dec-3-ylmethyl]benzonitrile
[205] 4-[8-(3-nitrobenzoyl)-2-oxo-1-oxa-3,8-diazaspiro[4.5]dec-3-ylmethyl]benzonitrile
[206] 3-(3-bromobenzyl)-8-(3,5-difluorobenzoyl)-1-oxa-3,8-diazaspiro[4.5]decan-2-one
[207] 8-(2-benzyloxy-acetyl)-3-(2-fluorobenzyl)-1-oxa-3,8-diazaspiro[4.5]decan-2-one
[208] 8-(2-chlorobenzoyl)-3-(2-trifluoromethylbenzyl)-1-oxa-3,8-diazaspiro[4.5]decan-2-one
[209] 8-(2-chlorobenzoyl)-3-(4-iodobenzyl)-1-oxa-3,8-diazaspiro[4.5]decan-2-one
[210] 8-(2-chlorobenzoyl)-3-(2-methoxy-5-nitrobenzyl)-1-oxa-3,8-diazaspiro[4.5]decan-2-one
[211] 3-biphenyl-2-ylmethyl-8-(2-chlorobenzoyl)-1-oxa-3,8-diazaspiro[4.5]decan-2-one
[212] 8-(2,6-dichlorobenzoyl)-3-naphthalen-2-ylmethyl-1-oxa-3,8-diazaspiro[4.5]decan-2-one
[213] 3-(4-tert-butylbenzyl)-8-(2,6-dichlorobenzoyl)-1-oxa-3,8-diazaspiro[4.5]decan-2-one
[214] 3-(3-bromobenzyl)-8-(2,6-dichlorobenzoyl)-1-oxa-3,8-diazaspiro[4.5]decan-2-one
[215] 8-(2,6-dichlorobenzoyl)-3-(4-trifluoromethylsulfanylbenzyl)-1-oxa-3,8-diazaspiro[4.5]decan-2-one
[216] 2-[8-(2-methylbenzoyl)-2-oxo-1-oxa-3,8-diazaspiro[4.5]dec-3-ylmethyl]benzonitrile
[217] 8-(2-methylbenzoyl)-3-(4-methylbenzyl)-1-oxa-3,8-diazaspiro[4.5]decan-2-one
[218] 8-(2-methylbenzoyl)-3-(2-trifluoromethylbenzyl)-1-oxa-3,8-diazaspiro[4.5]decan-2-one
[219] 3-(2-methoxy-5-nitrobenzyl)-8-(2-methylbenzoyl)-1-oxa-3,8-diazaspiro[4.5]decan-2-one
[220] 3-(3,4-difluorobenzyl)-8-(2-methylbenzoyl)-1-oxa-3,8-diazaspiro[4.5]decan-2-one
[221] 8-(2-methylbenzoyl)-3-(4-trifluoromethylbenzyl)-1-oxa-3,8-diazaspiro[4.5]decan-2-one
[222] 8-(2-methylbenzoyl)-3-(4-trifluoromethylsulfanylbenzyl)-1-oxa-3,8-diazaspiro[4.5]decan-2-one
[223] 8-(3-bromobenzoyl)-3-(4-fluorobenzyl)-1-oxa-3,8-diazaspiro[4.5]decan-2-one
[224] 8-(3-bromobenzoyl)-3-(2-trifluoromethylbenzyl)-1-oxa-3,8-diazaspiro[4.5]decan-2-one
[225] 8-(3-bromobenzoyl)-3-(2-fluorobenzyl)-1-oxa-3,8-diazaspiro[4.5]decan-2-one
[226] 8-(3-bromobenzoyl)-3-(3,4-difluorobenzyl)-1-oxa-3,8-diazaspiro[4.5]decan-2-one
[227] 8-(3-bromobenzoyl)-3-naphthalen-2-ylmethyl-1-oxa-3,8-diazaspiro[4.5]decan-2-one -continued

[228] 8-(3-bromobenzoyl)-3-(4-tert-butylbenzyl)-1-oxa-3,8-diazaspiro[4.5]decan-2-one
[229] 3-benzyl-8-(3-fluorobenzoyl)-1-oxa-3,8-diazaspiro[4.5]decan-2-one
[230] 8-(3-fluorobenzoyl)-3-(2-fluorobenzyl)-1-oxa-3,8-diazaspiro[4.5]decan-2-one
[231] 3-(3,4-difluorobenzyl)-8-(3-fluorobenzoyl)-1-oxa-3,8-diazaspiro[4.5]decan-2-one
[232] 8-(3-fluorobenzoyl)-3-(4-trifluoromethylbenzyl)-1-oxa-3,8-diazaspiro[4.5]decan-2-one
[233] 3-(3-bromobenzyl)-8-(3-fluorobenzoyl)-1-oxa-3,8-diazaspiro[4.5]decan-2-one
[234] 8-(3-chlorobenzoyl)-3-(3,5-dimethylbenzyl)-1-oxa-3,8-diazaspiro[4.5]decan-2-one
[235] 3-benzyl-8-(3-chlorobenzoyl)-1-oxa-3,8-diazaspiro[4.5]decan-2-one
[236] 4-[8-(3,4-dichlorobenzoyl)-2-oxo-1-oxa-3,8-diazaspiro[4.5]dec-3-ylmethyl]benzonitrile
[237] 3-(4-iodobenzyl)-8-(3-methoxybenzoyl)-1-oxa-3,8-diazaspiro[4.5]decan-2-one
[238] 3-(2-fluorobenzyl)-8-(3-methoxybenzoyl)-1-oxa-3,8-diazaspiro[4.5]decan-2-one
[239] 3-(4-tert-butylbenzyl)-8-(3-methoxybenzoyl)-1-oxa-3,8-diazaspiro[4.5]decan-2-one
[240] 3-benzyl-8-(3-methylbenzoyl)-1-oxa-3,8-diazaspiro[4.5]decan-2-one
[241] 3-(2-methoxy-5-nitrobenzyl)-8-(3-methylbenzoyl)-1-oxa-3,8-diazaspiro[4.5]decan-2-one
[242] 3-(4-tert-butylbenzyl)-8-(3-methylbenzoyl)-1-oxa-3,8-diazaspiro[4.5]decan-2-one
[243] 8-(3-methylbenzoyl)-3-(4-trifluoromethylbenzyl)-1-oxa-3,8-diazaspiro[4.5]decan-2-one
[244] 3-(3,4-difluorobenzyl)-8-(2-phenyl-butyryl)-1-oxa-3,8-diazaspiro[4.5]decan-2-one
[245] 3-benzyl-8-[3-(2-chlorophenyl)-5-methylisoxazole-4-carbonyl]-1-oxa-3,8-diazaspiro[4.5]decan-2-one
[246] 4-[8-(2,3-dichlorobenzoyl)-2-oxo-1-oxa-3,8-diazaspiro[4.5]dec-3-ylmethyl]benzonitrile
[247] 8-[2-(4-chlorophenyl)acetyl]-3-(3,4-difluorobenzyl)-1-oxa-3,8-diazaspiro[4.5]decan-2-one
[248] 3-biphenyl-2-ylmethyl-8-[2-(4-chlorophenyl)acetyl]-1-oxa-3,8-diazaspiro[4.5]decan-2-one
[249] 8-[2-(4-chlorophenyl)acetyl]-3-(4-trifluoromethylsulfanylbenzyl)-1-oxa-3,8-diazaspiro[4.5]decan-2-one
[250] 3-(4-tert-butylbenzyl)-8-[3-(2-chlorophenyl)acryloyl]-1-oxa-3,8-diazaspiro[4.5]decan-2-one
[251] 3-biphenyl-2-ylmethyl-8-[3-(2-chlorophenyl)acryloyl]-1-oxa-3,8-diazaspiro[4.5]decan-2-one
[252] 3-(3-bromobenzyl)-8-[3-(2-chlorophenyl)acryloyl]-1-oxa-3,8-diazaspiro[4.5]decan-2-one
[253] 4-[8-(2,3-difluorobenzoyl)-2-oxo-1-oxa-3,8-diazaspiro[4.5]dec-3-ylmethyl]benzonitrile
[254] 8-(2,3-difluorobenzoyl)-3-(2-trifluoromethylbenzyl)-1-oxa-3,8-diazaspiro[4.5]decan-2-one
[255] 8-(2,3-difluorobenzoyl)-3-(4-iodobenzyl)-1-oxa-3,8-diazaspiro[4.5]decan-2-one
[256] 2-[2-oxo-8-(2-propylpentanoyl)-1-oxa-3,8-diazaspiro[4.5]dec-3-ylmethyl]benzonitrile
[257] 3-(3,4-difluorobenzyl)-8-(2-propylpentanoyl)-1-oxa-3,8-diazaspiro[4.5]decan-2-one
[258] 8-(2-chloro-4-nitrobenzoyl)-3l-(4-methylbenzyl)-1-oxa-3,8-diazaspiro[4.5]decan-2-one
[259] 8-(2-chloro-4-nitrobenzoyl)-3l-(2-trifluoromethylbenzyl)-1-oxa-3,8-diazaspiro[4.5]decan-2-one
[260] 3-(4-tert-butylbenzyl)-8-(2-chloro-4-nitrobenzoyl)-1-oxa-3,8-diazaspiro[4.5]decan-2-one
[261] 8-(2-chloro-4-nitrobenzoyl)-3l-(4-trifluoromethylbenzyl)-1-oxa-3,8-diazaspiro[4.5]decan-2-one
[262] 3-biphenyl-2-ylmethyl-8-(2-chloro-4-nitrobenzoyl)-1-oxa-3,8-diazaspiro[4.5]decan-2-one
[263] 3-(3-bromobenzyl)-8-(2-chloro-4-nitrobenzoyl)-1-oxa-3,8-diazaspiro[4.5]decan-2-one
[264] 8-(2-chloro-4-nitrobenzoyl)-3l-(4-trifluoromethylsulfanylbenzyl)-1-oxa-3,8-diazaspiro[4.5]decan-2-one
[265] 8-(2-chloropyridine-3-carbonyl)-3-(4-fluorobenzyl)-1-oxa-3,8-diazaspiro[4.5]decan-2-one
[266] 2-[8-(2-chloropyridine-3-carbonyl)-2-oxo-1-oxa-3,8-diazaspiro[4.5]dec-3-ylmethyl]benzonitrile
[267] 8-(2-chloropyridine-3-carbonyl)-3-(4-methylbenzyl)-1-oxa-3,8-diazaspiro[4.5]decan-2-one
[268] 8-(2-chloropyridine-3-carbonyl)-3-(4-trifluoromethylbenzyl)-1-oxa-3,8-diazaspiro[4.5]decan-2-one
[269] 3-(3-methoxybenzyl)-8-(2-methylsulfanylpyridine-3-carbonyl)-1-oxa-3,8-diazaspiro[4.5]decan-2-one
[270] 3-(4-methylbenzyl)-8-(2-methylsulfanylpyridine-3-carbonyl)-1-oxa-3,8-diazaspiro[4.5]decan-2-one
[271] 3-(4-iodobenzyl)-8-(2-methylsulfanylpyridine-3-carbonyl)-1-oxa-3,8-diazaspiro[4.5]decan-2-one
[272] 3-(3,4-difluorobenzyl)-8-(2-methylsulfanylpyridine-3-carbonyl)-1-oxa-3,8-diazaspiro[4.5]decan-2-one
[273] 3-(4-tert-butylbenzyl)-8-(2-methylsulfanylpyridine-3-carbonyl)-1-oxa-3,8-diazaspiro[4.5]decan-2-one
[274] 8-(2-methylsulfanylpyridine-3-carbonyl)-3-(4-trifluoromethylbenzyl)-1-oxa-3,8-diazaspiro[4.5]decan-2-one
[275] 8-(2-ethylsulfanylpyridine-3-carbonyl)-3-(4-fluorobenzyl)-1-oxa-3,8-diazaspiro[4.5]decan-2-one
[276] 3-[8-(2-ethylsulfanylpyridine-3-carbonyl)-2-oxo-1-oxa-3,8-diazaspiro[4.5]dec-3-ylmethyl]benzonitrile
[277] 2-[8-(2-ethylsulfanylpyridine-3-carbonyl)-2-oxo-1-oxa-3,8-diazaspiro[4.5]dec-3-ylmethyl]benzonitrile
[278] 8-(2-ethylsulfanylpyridine-3-carbonyl)-3-(4-methylbenzyl)-1-oxa-3,8-diazaspiro[4.5]decan-2-one
[279] 3-benzyl-8-(2-ethylsulfanylpyridine-3-carbonyl)-1-oxa-3,8-diazaspiro[4.5]decan-2-one

[280] 8-(2-ethylsulfanylpyridine-3-carbonyl)-3-(2-fluorobenzyl)-1-oxa-3,8-diazaspiro[4.5]decan-2-one
[281] 4-[8-(6-chloropyridine-3-carbonyl)-2-oxo-1-oxa-3,8-diazaspiro[4.5]dec-3-ylmethyl]benzonitrile
[282] 8-(6-chloropyridine-3-carbonyl)-3-(2-trifluoromethylbenzyl)-1-oxa-3,8-diazaspiro[4.5]decan-2-one
[283] 8-(6-chloropyridine-3-carbonyl)-3-(4-iodobenzyl)-1-oxa-3,8-diazaspiro[4.5]decan-2-one
[284] 3-(4-tert-butylbenzyl)-8-(6-chloropyridine-3-carbonyl)-1-oxa-3,8-diazaspiro[4.5]decan-2-one
[285] 3-biphenyl-2-ylmethyl-8-(6-chloropyridine-3-carbonyl)-1-oxa-3,8-diazaspiro[4.5]decan-2-one
[286] 3-(3-methoxybenzyl)-8-(4-trifluoromethoxybenzoyl)-1-oxa-3,8-diazaspiro[4.5]decan-2-one
[287] 3-(3,4-difluorobenzyl)-8-(4-trifluoromethoxybenzoyl)-1-oxa-3,8-diazaspiro[4.5]decan-2-one
[288] 8-[3-(2-chloro-6-fluorophenyl)-5-methylisoxazole-4-carbonyl]-3-(4-fluorobenzyl)-1-oxa-3,8-diazaspiro[4.5]decan-2-one
[289] 8-[3-(2-chloro-6-fluorophenyl)-5-methylisoxazole-4-carbonyl]-3-(3-methoxybenzyl)-1-oxa-3,8-diazaspiro[4.5]decan-2-one
[290] 8-[3-(2-chloro-6-fluorophenyl)-5-methylisoxazole-4-carbonyl]-3-(4-trifluoromethylbenzyl)-1-oxa-3,8-diazaspiro[4.5]decan-2-one
[291] 8-[3-(2-chloro-6-fluorophenyl)-5-methylisoxazole-4-carbonyl]-3-(4-trifluoromethylsulfanylbenzyl)-1-oxa-3,8-diazaspiro[4.5]decan-2-one
[292] 3-(4-methylbenzyl)-8-(3-trifluoromethoxybenzoyl)-1-oxa-3,8-diazaspiro[4.5]decan-2-one
[293] 3-(4-iodobenzyl)-8-(3-trifluoromethoxybenzoyl)-1-oxa-3,8-diazaspiro[4.5]decan-2-one
[294] 3-(3,4-difluorobenzyl)-8-(3-trifluoromethoxybenzoyl)-1-oxa-3,8-diazaspiro[4.5]decan-2-one
[295] 3-naphthalen-2-ylmethyl-8-(3-trifluoromethoxybenzoyl)-1-oxa-3,8-diazaspiro[4.5]decan-2-one
[296] 4-[8-(isoxazole-5-carbonyl)-2-oxo-1-oxa-3,8-diazaspiro[4.5]dec-3-ylmethyl]benzonitrile
[297] 8-(isoxazole-5-carbonyl)-3-(2-trifluoromethylbenzyl)-1-oxa-3,8-diazaspiro[4.5]decan-2-one
[298] 8-(isoxazole-5-carbonyl)-3-(2-methoxy-5-nitrobenzyl)-1-oxa-3,8-diazaspiro[4.5]decan-2-one
[299] 3-(3-bromobenzyl)-8-(isoxazole-5-carbonyl)-1-oxa-3,8-diazaspiro[4.5]decan-2-one
[300] 2-[8-(2-chloro-6-fluorobenzoyl)-2-oxo-1-oxa-3,8-diazaspiro[4.5]dec-3-ylmethyl]benzonitrile
[301] 4-[8-(2-chloro-6-fluorobenzoyl)-2-oxo-1-oxa-3,8-diazaspiro[4.5]dec-3-ylmethyl]benzonitrile
[302] 8-(2-chloro-6-fluorobenzoyl)-3-(4-methylbenzyl)-1-oxa-3,8-diazaspiro[4.5]decan-2-one
[303] 3-biphenyl-2-ylmethyl-8-(2-chloro-6-fluorobenzoyl)-1-oxa-3,8-diazaspiro[4.5]decan-2-one
[304] 8-(2,5-dimethylfuran-3-carbonyl)-3-(3-methoxybenzyl)-1-oxa-3,8-diazaspiro[4.5]decan-2-one
[305] 4-[8-(2,5-dimethylfuran-3-carbonyl)-2-oxo-1-oxa-3,8-diazaspiro[4.5]dec-3-ylmethyl]benzonitrile
[306] 4-[8-(4-bromo-3-methylbenzoyl)-2-oxo-1-oxa-3,8-diazaspiro[4.5]dec-3-ylmethyl]benzonitrile
[307] 8-(4-bromo-3-methylbenzoyl)-3-(4-methylbenzyl)-1-oxa-3,8-diazaspiro[4.5]decan-2-one
[308] 3-benzyl-8-(4-bromo-3-methylbenzoyl)-1-oxa-3,8-diazaspiro[4.5]decan-2-one
[309] 8-(4-bromo-3-methylbenzoyl)-3-(2-trifluoromethylbenzyl)-1-oxa-3,8-diazaspiro[4.5]decan-2-one
[310] 8-(4-bromo-3-methylbenzoyl)-3-(3,4-difluorobenzyl)-1-oxa-3,8-diazaspiro[4.5]decan-2-one
[311] 8-(4-bromo-3-methylbenzoyl)-3-(4-tert-butylbenzyl)-1-oxa-3,8-diazaspiro[4.5]decan-2-one
[312] 3-biphenyl-2-ylmethyl-8-(4-bromo-3-methylbenzoyl)-1-oxa-3,8-diazaspiro[4.5]decan-2-one
[313] 8-(4-bromo-3-methylbenzoyl)-3-(4-trifluoromethylsulfanylbenzyl)-1-oxa-3,8-diazaspiro[4.5]decan-2-one
[314] 8-(2,6-difluoro-3-methylbenzoyl)-3-(3-methoxybenzyl)-1-oxa-3,8-diazaspiro[4.5]decan-2-one
[315] 2-[8-(2,6-difluoro-3-methylbenzoyl)-2-oxo-1-oxa-3,8-diazaspiro[4.5]dec-3-ylmethyl]benzonitrile
[316] 4-[8-(2,6-difluoro-3-methylbenzoyl)-2-oxo-1-oxa-3,8-diazaspiro[4.5]dec-3-ylmethyl]benzonitrile
[317] 8-(2,6-difluoro-3-methylbenzoyl)-3-(2-trifluoromethylbenzyl)-1-oxa-3,8-diazaspiro[4.5]decan-2-one
[318] 8-(2,6-difluoro-3-methylbenzoyl)-3-(2-fluorobenzyl)-1-oxa-3,8-diazaspiro[4.5]decan-2-one
[319] 8-(2-chloro-6-fluoro-3-methylbenzoyl)-3-(4-fluorobenzyl)-1-oxa-3,8-diazaspiro[4.5]decan-2-one
[320] 8-(2-chloro-6-fluoro-3-methylbenzoyl)-3-(3-methoxybenzyl)-1-oxa-3,8-diazaspiro[4.5]decan-2-one -continued

[321] 8-(2-chloro-6-fluoro-3-methylbenzoyl)-3-(4-trifluoromethylsulfanylbenzyl)-1-oxa-3,8-diazaspiro[4.5]decan-2-one
[322] 3-biphenyl-2-ylmethyl-8-(6-chloro-2-fluoro-3-methylbenzoyl)-1-oxa-3,8-diazaspiro[4.5]decan-2-one
[323] 3-benzyl-8-(3-difluoromethylsulfanylbenzoyl)-1-oxa-3,8-diazaspiro[4.5]decan-2-one
[324] 8-(3-difluoromethylsulfanylbenzoyl)-3-naphthalen-2-ylmethyl-1-oxa-3,8-diazaspiro[4.5]decan-2-one
[325] 8-(3-difluoromethylsulfanylbenzoyl)-3-(4-trifluoromethylbenzyl)-1-oxa-3,8-diazaspiro[4.5]decan-2-one
[326] 3-(3-bromobenzyl)-8-(3-difluoromethylsulfanylbenzoyl)-1-oxa-3,8-diazaspiro[4.5]decan-2-one
[327] 3-[8-(3-chloro-2-fluorobenzoyl)-2-oxo-1-oxa-3,8-diazaspiro[4.5]dec-3-ylmethyl]benzonitrile
[328] 8-(3-chloro-2-fluorobenzoyl)-3-(4-iodobenzyl)-1-oxa-3,8-diazaspiro[4.5]decan-2-one
[329] 8-(3-chloro-2-fluorobenzoyl)-3-naphthalen-2-ylmethyl-1-oxa-3,8-diazaspiro[4.5]decan-2-one
[330] 3-(3-methoxybenzyl)-8-(4-trifluoromethylsulfanylbenzoyl)-1-oxa-3,8-diazaspiro[4.5]decan-2-one
[331] 2-[2-oxo-8-(4-trifluoromethylsulfanylbenzoyl)-1-oxa-3,8-diazaspiro[4.5]dec-3-ylmethyl]benzonitrile
[332] 4-[2-oxo-8-(4-trifluoromethylsulfanylbenzoyl)-1-oxa-3,8-diazaspiro[4.5]dec-3-ylmethyl]benzonitrile
[333] 3-(4-iodobenzyl)-8-(4-trifluoromethylsulfanylbenzoyl)-1-oxa-3,8-diazaspiro[4.5]decan-2-one
[334] 3-naphthalen-2-ylmethyl-8-(4-trifluoromethylsulfanylbenzoyl)-1-oxa-3,8-diazaspiro[4.5]decan-2-one
[335] 3-(4-trifluoromethylbenzyl)-8-(4-trifluoromethylsulfanylbenzoyl)-1-oxa-3,8-diazaspiro[4.5]decan-2-one
[336] 8-(2-chloro-5-trifluoromethylbenzoyl)-3-(2-trifluoromethylbenzyl)-1-oxa-3,8-diazaspiro[4.5]decan-2-one
[337] 8-(2-chloro-5-trifluoromethylbenzoyl)-3-(2-fluorobenzyl)-1-oxa-3,8-diazaspiro[4.5]decan-2-one
[338] 8-(2-chloro-5-trifluoromethylbenzoyl)-3-(3,4-difluorobenzyl)-1-oxa-3,8-diazaspiro[4.5]decan-2-one
[339] 8-(2,3-difluoro-4-methylbenzoyl)-3-(3-methoxybenzyl)-1-oxa-3,8-diazaspiro[4.5]decan-2-one
[340] 4-[8-(2,3-difluoro-4-methylbenzoyl)-2-oxo-1-oxa-3,8-diazaspiro[4.5]dec-3-ylmethyl]benzonitrile
[341] 3-benzyl-8-(2,3-difluoro-4-methylbenzoyl)-1-oxa-3,8-diazaspiro[4.5]decan-2-one
[342] 8-(2,3-difluoro-4-methylbenzoyl)-3-(4-iodobenzyl)-1-oxa-3,8-diazaspiro[4.5]decan-2-one
[343] 3-(3,4-difluorobenzyl)-8-(2,3-difluoro-4-methylbenzoyl)-1-oxa-3,8-diazaspiro[4.5]decan-2-one
[344] 8-(2,3-difluoro-4-methylbenzoyl)-3-naphthalen-2-ylmethyl-1-oxa-3,8-diazaspiro[4.5]decan-2-one
[345] 3-biphenyl-2-ylmethyl-8-(2,3-difluoro-4-methylbenzoyl)-1-oxa-3,8-diazaspiro[4.5]decan-2-one
[346] 3-(3-bromobenzyl)-8-(2,3-difluoro-4-methylbenzoyl)-1-oxa-3,8-diazaspiro[4.5]decan-2-one
[347] 3-benzyl-8-[2-(2-methoxyethoxy)acetyl]-1-oxa-3,8-diazaspiro[4.5]decan-2-one
[348] 3-(2-fluorobenzyl)-8-[2-(2-methoxyethoxy)acetyl]-1-oxa-3,8-diazaspiro[4.5]decan-2-one
[349] 3-(3,4-difluorobenzyl)-8-[2-(2-methoxyethoxy)acetyl]-1-oxa-3,8-diazaspiro[4.5]decan-2-one
[350] 3-(4-tert-butylbenzyl)-8-[2-(2-methoxyethoxy)acetyl]-1-oxa-3,8-diazaspiro[4.5]decan-2-one
[351] 8-[2-(2-methoxyethoxy)acetyl]-3-(4-trifluoromethylsulfanylbenzyl)-1-oxa-3,8-diazaspiro[4.5]decan-2-one
[352] 8-(1-acetylpiperidine-4-carbonyl)-3-(3,4-difluorobenzyl)-1-oxa-3,8-diazaspiro[4.5]decan-2-one
[353] 4-{8-[2-(3-chlorophenoxy)acetyl]-2-oxo-1-oxa-3,8-diazaspiro[4.5]dec-3-ylmethyl}benzonitrile
[354] 8-[2-(3-chlorophenoxy)acetyl]-3-(3,4-difluorobenzyl)-1-oxa-3,8-diazaspiro[4.5]decan-2-one
[355] 3-(3-bromobenzyl)-8-[2-(3-chlorophenoxy)acetyl]-1-oxa-3,8-diazaspiro[4.5]decan-2-one
[356] 8-[2-(3-chlorophenoxy)acetyl]-3-(4-trifluoromethylsulfanylbenzyl)-1-oxa-3,8-diazaspiro[4.5]decan-2-one
[357] 4-[3-(3-methoxybenzyl)-2-oxo-1-oxa-3,8-diazaspiro[4.5]decane-8-carbonyl]benzylsulfonamide
[358] N-{4-[3-(3,4-difluorobenzyl)-2-oxo-1-oxa-3,8-diazaspiro[4.5]decane-8-carbonyl]phenyl}acetamide
[359] 8-(3-dimethylaminobenzoyl)-3-(3,5-dimethylbenzyl)-1-oxa-3,8-diazaspiro[4.5]decan-2-one
[360] 3-(4-tert-butylbenzyl)-8-(3-dimethylaminobenzoyl)-1-oxa-3,8-diazaspiro[4.5]decan-2-one
[361] 3-(3-bromobenzyl)-8-(3-dimethylaminobenzoyl)-1-oxa-3,8-diazaspiro[4.5]decan-2-one
[362] 3-(4-methylbenzyl)-8-(4-phenoxybutyryl)-1-oxa-3,8-diazaspiro[4.5]decan-2-one
[363] 8-(4-phenoxybutyryl)-3-(2-trifluoromethylbenzyl)-1-oxa-3,8-diazaspiro[4.5]decan-2-one

- [364] 3-(2-fluorobenzyl)-8-(4-phenoxybutyryl)-1-oxa-3,8-diazaspiro[4.5]decan-2-one
- [365] 8-(2,3-dimethylbenzoyl)-3-(4-fluorobenzyl)-1-oxa-3,8-diazaspiro[4.5]decan-2-one
- [366] 3-[8-(2,3-dimethylbenzoyl)-2-oxo-1-oxa-3,8-diazaspiro[4.5]dec-3-ylmethyl]benzonitrile
- [367] 8-(2,3-dimethylbenzoyl)-3-(3,5-dimethylbenzyl)-1-oxa-3,8-diazaspiro[4.5]decan-2-one
- [368] 8-(2,3-dimethylbenzoyl)-3-(4-methylbenzyl)-1-oxa-3,8-diazaspiro[4.5]decan-2-one
- [369] 8-(2,3-dimethylbenzoyl)-3-(2-trifluoromethylbenzyl)-1-oxa-3,8-diazaspiro[4.5]decan-2-one
- [370] 8-(2,3-dimethylbenzoyl)-3-(2-methoxy-5-nitrobenzyl)-1-oxa-3,8-diazaspiro[4.5]decan-2-one
- [371] 8-(2,3-dimethylbenzoyl)-3-(4-trifluoromethylbenzyl)-1-oxa-3,8-diazaspiro[4.5]decan-2-one
- [372] 3-biphenyl-2-ylmethyl-8-(2,3-dimethylbenzoyl)-1-oxa-3,8-diazaspiro[4.5]decan-2-one
- [373] 4-[8-(5-methyl-2-phenyl-2H-[1,2,3]triazole-4-carbonyl)-2-oxo-1-oxa-3,8-diazaspiro[4.5]dec-3-ylmethyl]benzonitrile
- [374] 3-benzyl-8-(5-methyl-2-phenyl-2H-[1,2,3]triazole-4-carbonyl)-1-oxa-3,8-diazaspiro[4.5]decan-2-one
- [375] 3-(3,4-difluorobenzyl)-8-(5-methyl-2-phenyl-2H-[1,2,3]triazole-4-carbonyl)-1-oxa-3,8-diazaspiro[4.5]decan-2-one
- [376] 8-(5-methyl-2-phenyl-2H-[1,2,3]triazole-4-carbonyl)-3-naphthalen-2-ylmethyl-1-oxa-3,8-diazaspiro[4.5]decan-2-one
- [377] 3-biphenyl-2-ylmethyl-8-(5-methyl-2-phenyl-2H-[1,2,3]triazole-4-carbonyl)-1-oxa-3,8-diazaspiro[4.5]decan-2-one
- [378] 3-(4-tert-butylbenzyl)-8-[3-(2,6-dichlorophenyl)-5-methylisoxazole-4-carbonyl]-1-oxa-3,8-diazaspiro[4.5]decan-2-one
- [379] 3-[2-oxo-8-(2-phenoxypyridine-3-carbonyl)-1-oxa-3,8-diazaspiro[4.5]dec-3-ylmethyl]benzonitrile
- [380] 2-[2-oxo-8-(2-phenoxypyridine-3-carbonyl)-1-oxa-3,8-diazaspiro[4.5]dec-3-ylmethyl]benzonitrile
- [381] 3-(4-fluorobenzyl)-8-(pyridine-2-carbonyl)-1-oxa-3,8-diazaspiro[4.5]decan-2-one
- [382] 3-(3-methoxybenzyl)-8-(pyridine-2-carbonyl)-1-oxa-3,8-diazaspiro[4.5]decan-2-one
- [383] 3-(3,5-dimethylbenzyl)-8-(pyridine-2-carbonyl)-1-oxa-3,8-diazaspiro[4.5]decan-2-one
- [384] 2-[2-oxo-8-(pyridine-2-carbonyl)-1-oxa-3,8-diazaspiro[4.5]dec-3-ylmethyl]benzonitrile
- [385] 3-(2-fluorobenzyl)-8-(pyridine-2-carbonyl)-1-oxa-3,8-diazaspiro[4.5]decan-2-one
- [386] 3-(3,4-difluorobenzyl)-8-(pyridine-2-carbonyl)-1-oxa-3,8-diazaspiro[4.5]decan-2-one
- [387] 3-biphenyl-2-ylmethyl-8-(pyridine-2-carbonyl)-1-oxa-3,8-diazaspiro[4.5]decan-2-one
- [388] 4-[8-(3-chlorothiophene-2-carbonyl)-2-oxo-1-oxa-3,8-diazaspiro[4.5]dec-3-ylmethyl]benzonitrile
- [389] 8-(3-chlorothiophene-2-carbonyl)-3-(3,4-difluorobenzyl)-1-oxa-3,8-diazaspiro[4.5]decan-2-one
- [390] 3-biphenyl-2-ylmethyl-8-(3-chlorothiophene-2-carbonyl)-1-oxa-3,8-diazaspiro[4.5]decan-2-one
- [391] 8-[1-(4-chlorophenyl)-5-trifluoromethyl-1H-pyrazole-4-carbonyl]-3-(2-fluorobenzyl)-1-oxa-3,8-diazaspiro[4.5]decan-2-one
- [392] 8-[1-(4-chlorophenyl)-5-trifluoromethyl-1H-pyrazole-4-carbonyl]-3-(3,4-difluorobenzyl)-1-oxa-3,8-diazaspiro[4.5]decan-2-one
- [393] 8-[1-(4-chlorophenyl)-5-trifluoromethyl-1H-pyrazole-4-carbonyl]-3-(4-trifluoromethylsulfanylbenzyl)-1-oxa-3,8-diazaspiro[4.5]decan-2-one
- [394] 3-(4-tert-butylbenzyl)-8-(5-tert-butyl,-2-methyl-2H-pyrazole-3-carbonyl)-1-oxa-3,8-diazaspiro[4.5]decan-2-one
- [395] 3-[8-(5-methylisoxazole-3-carbonyl)-2-oxo-1-oxa-3,8-diazaspiro[4.5]dec-3-ylmethyl]benzonitrile
- [396] 3-(3,5-dimethylbenzyl)-8-(5-methylisoxazole-3-carbonyl)-1-oxa-3,8-diazaspiro[4.5]decan-2-one
- [397] 2-[8-(5-methylisoxazole-3-carbonyl)-2-oxo-1-oxa-3,8-diazaspiro[4.5]dec-3-ylmethyl]benzonitrile
- [398] 4-[8-(5-methylisoxazole-3-carbonyl)-2-oxo-1-oxa-3,8-diazaspiro[4.5]dec-3-ylmethyl]benzonitrile
- [399] 3-benzyl-8-(5-methylisoxazole-3-carbonyl)-1-oxa-3,8-diazaspiro[4.5]decan-2-one
- [400] 3-(3,4-difluorobenzyl)-8-(5-methylisoxazole-3-carbonyl)-1-oxa-3,8-diazaspiro[4.5]decan-2-one
- [401] 3-biphenyl-2-ylmethyl-8-(5-methylisoxazole-3-carbonyl)-1-oxa-3,8-diazaspiro[4.5]decan-2-one
- [402] 8-(4-methyl[1,2,3]thiadiazole-5-carbonyl)-3-(2-trifluoromethylbenzyl)-1-oxa-3,8-diazaspiro[4.5]decan-2-one
- [403] 3-(4-tert-butylbenzyl)-8-(4-methyl[1,2,3]thiadiazole-5-carbonyl)-1-oxa-3,8-diazaspiro[4.5]decan-2-one
- [404] 8-(4-methyl[1,2,3]thiadiazole-5-carbonyl)-3-(4-trifluoromethylsulfanylbenzyl)-1-oxa-3,8-diazaspiro[4.5]decan-2-one
- [405] 4-[2-oxo-8-(1-phenyl-5-propyl-1H-pyrazole-4-carbonyl)-1-oxa-3,8-diazaspiro[4.5]dec-3-ylmethyl]benzonitrile
- [406] 3-(3,4-difluorobenzyl)-8-(1-phenyl-5-propyl-1H-pyrazole-4-carbonyl)-1-oxa-3,8-diazaspiro[4.5]decan-2-one
- [407] 3-naphthalen-2-ylmethyl-8-(1-phenyl-5-propyl-1H-pyrazole-4-carbonyl)-1-oxa-3,8-diazaspiro[4.5]decan-2-one
- [408] 8-(1-phenyl-5-propyl-1H-pyrazole-4-carbonyl)-3-(4-trifluoromethylsulfanylbenzyl)-1-oxa-3,8-diazaspiro[4.5]decan-2-one
- [409] 3-[8-(2-chloropyridine-4-carbonyl)-2-oxo-1-oxa-3,8-diazaspiro[4.5]dec-3-ylmethyl]benzonitrile
- [410] 8-(2-chloropyridine-4-carbonyl)-3-(3-methoxybenzyl)-1-oxa-3,8-diazaspiro[4.5]decan-2-one -continued

[411] 8-(5-tert-butyl-2-methylfuran-3-carbonyl)-3-(4-fluorobenzyl)-1-oxa-3,8-diazaspiro[4.5]decan-2-one
[412] 3-[8-(5-tert-butyl-2-methylfuran-3-carbonyl)-2-oxo-1-oxa-3,8-diazaspiro[4.5]dec-3-ylmethyl]benzonitrile
[413] 2-[8-(5-tert-butyl-2-methylfuran-3-carbonyl)-2-oxo-1-oxa-3,8-diazaspiro[4.5]dec-3-ylmethyl]benzonitrile
[414] 4-[8-(5-tert-butyl-2-methylfuran-3-carbonyl)-2-oxo-1-oxa-3,8-diazaspiro[4.5]dec-3-ylmethyl]benzonitrile
[415] 8-(5-tert-butyl-2-methylfuran-3-carbonyl)-3-(2-trifluoromethylbenzyl)-1-oxa-3,8-diazaspiro[4.5]decan-2-one
[416] 8-(5-tert-butyl-2-methylfuran-3-carbonyl)-3-naphthalen-2-ylmethyl-1-oxa-3,8-diazaspiro[4.5]decan-2-one
[417] 3-biphenyl-2-ylmethyl-8-(5-tert-butyl-2-methylfuran-3-carbonyl)-1-oxa-3,8-diazaspiro[4.5]decan-2-one
[418] 3-(3-bromobenzyl)-8-(5-tert-butyl-2-methylfuran-3-carbonyl)-1-oxa-3,8-diazaspiro[4.5]decan-2-one
[419] 8-(benzo[1,2,5]oxadiazole-5-carbonyl)-3-(3,4-difluorobenzyl)-1-oxa-3,8-diazaspiro[4.5]decan-2-one
[420] 8-(benzo[1,2,5]oxadiazole-5-carbonyl)-3-(4-trifluoromethylbenzyl)-1-oxa-3,8-diazaspiro[4.5]decan-2-one
[421] 3-[8-(2-methyl-6-trifluoromethylpyridine-3-carbonyl)-2-oxo-1-oxa-3,8-diazaspiro[4.5]dec-3-ylmethyl]benzonitrile
[422] 2-[8-(2-methyl-6-trifluoromethylpyridine-3-carbonyl)-2-oxo-1-oxa-3,8-diazaspiro[4.5]dec-3-ylmethyl]benzonitrile
[423] 4-[8-(2-methyl-6-trifluoromethylpyridine-3-carbonyl)-2-oxo-1-oxa-3,8-diazaspiro[4.5]dec-3-ylmethyl]benzonitrile
[424] 8-(2-methyl-6-trifluoromethylpyridine-3-carbonyl)-3-(2-trifluoromethylbenzyl)-1-oxa-3,8-diazaspiro[4.5]decan-2-one
[425] 3-(3,4-difluorobenzyl)-8-(2-methyl-6-trifluoromethylpyridine-3-carbonyl)-1-oxa-3,8-diazaspiro[4.5]decan-2-one
[426] 3-(3-bromobenzyl)-8-(2-methyl-6-trifluoromethylpyridine-3-carbonyl)-1-oxa-3,8-diazaspiro[4.5]decan-2-one
[427] 8-(6-chloro-2H-chromene-3-carbonyl)-3-(3,4-difluorobenzyl)-1-oxa-3,8-diazaspiro[4.5]decan-2-one
[428] 8-(2-chloropyridine-4-carbonyl)-3-(2-fluorobenzyl)-1-oxa-3,8-diazaspiro[4.5]decan-2-one
[429] 8-(2-chloropyridine-4-carbonyl)-3-naphthalen-2-ylmethyl-1-oxa-3,8-diazaspiro[4.5]decan-2-one
[430] 8-acetyl-3-(2-fluorobenzyl)-1-oxa-3,8-diazaspiro[4.5]decan-2-one
[431] 8-acetyl-3-(3-bromobenzyl)-1-oxa-3,8-diazaspiro[4.5]decan-2-one
[432] 3-(2-methoxy-5-nitrobenzyl)-8-(3-phenoxypropyl)-1-oxa-3,8-diazaspiro[4.5]decan-2-one;

Pharmacological Data:

The 5-HT uptake inhibition and noradrenalin uptake inhibition of the substituted 1-oxa-3,8-diazaspiro[4.5]-decan-2-one compounds according to the invention of the general formula I were determined as described above.

The investigated 1-oxa-3,8-diazaspiro[4.5]-decan-2-one compounds of the general formula I exhibit excellent inhibition of 5-HT and noradrenalin reuptake.

| Compound according to Example | 5-HT uptake, % inhibition, 10 μM | NA uptake, inhibition, 10 μM |
|---|---|---|
| 1 | 66 | |
| 2 | 60 | 64 |
| 3 | 69 | |
| 4 | 76 | |
| 5 | | 70 |
| 6 | 63 | 56 |
| 7 | 55 | 50 |
| 8 | 62 | 50 |
| 9 | | 81 |
| 10 | 50 | 78 |
| 11 | 58 | |
| 12 | 60 | |
| 13 | 44 | 53 |
| 14 | 57 | 49 |
| 15 | 57 | 55 |
| 16 | 54 | |
| 17 | 50 | 45 |
| 18 | | 55 |
| 19 | 69 | 48 |
| 20 | | 48 |
| 21 | 55 | |
| 22 | 48 | |
| 23 | 60 | |
| 24 | | 58 |
| 25 | 53 | |
| 26 | 70 | |
| 27 | 62 | 68 |
| 28 | 45 | 53 |
| 29 | 84 | 82 |
| 30 | 65 | |
| 32 | 56 | |
| 33 | 59 | 93 |
| 34 | | 41 |
| 35 | 56 | 63 |
| 36 | 56 | 60 |
| 37 | | 47 |
| 38 | 52 | |
| 39 | 42 | 76 |
| 40 | 54 | |
| 41 | 49 | |
| 42 | 60 | 83 |
| 43 | 49 | |
| 44 | 57 | 61 |
| 45 | 51 | |
| 46 | 43 | |
| 47 | 49 | |
| 48 | 43 | |

-continued

| Compound according to Example | 5-HT uptake, % inhibition, 10 μM | NA uptake, inhibition, 10 μM |
|---|---|---|
| 49 | | 48 |
| 50 | 64 | |
| 51 | 89 | |
| 52 | 94 | 96 |
| 53 | 68 | 81 |
| 54 | 75 | |
| 55 | 61 | |
| 56 | 60 | |
| 57 | 50 | 55 |
| 58 | 49 | |
| 59 | 47 | |
| 60 | | 58 |
| 61 | 69 | 77 |
| 62 | 57 | 67 |
| 63 | 84 | 41 |
| 65 | 55 | |
| 66 | 53 | |
| 71 | 62 | |
| 72 | 45 | |
| 73 | 57 | |
| 74 | 66 | 57 |
| 75 | | 67 |
| 76 | 51 | |
| 77 | 50 | 64 |
| 78 | 51 | 53 |
| 79 | 67 | 57 |
| 80 | 47 | 45 |
| 81 | 75 | |
| 82 | 56 | |
| 83 | 41 | |
| 84 | 62 | |
| 85 | 90 | |
| 86 | 56 | 79 |
| 87 | 72 | 59 |
| 88 | 70 | |
| 89 | 63 | 57 |
| 90 | 77 | |
| 91 | 68 | |
| 92 | 67 | 73 |
| 99 | 73 | |
| 101 | 84 | |
| 102 | 67 | |
| 103 | 83 | |
| 104 | 89 | 73 |
| 105 | 74 | |
| 106 | 63 | |
| 107 | 76 | |
| 108 | 77 | |
| 109 | 81 | 78 |
| 110 | 64 | |
| 111 | 71 | |
| 112 | 66 | |
| 113 | 68 | |
| 114 | 73 | |
| 115 | 84 | |
| 116 | 76 | |
| 117 | 73 | |
| 118 | 66 | |
| 119 | 67 | |
| 120 | 66 | |
| 121 | 77 | |
| 122 | 68 | |
| 123 | 71 | |
| 124 | 72 | |
| 125 | 63 | |
| 126 | 64 | |
| 127 | 63 | |
| 128 | 62 | |
| 129 | 77 | |
| 130 | 70 | |
| 131 | 63 | |
| 132 | 65 | |
| 133 | 64 | |
| 134 | 64 | |
| 135 | 69 | |
| 136 | 67 | |
| 137 | 74 | 84 |

-continued

| Compound according to Example | 5-HT uptake, % inhibition, 10 μM | NA uptake, inhibition, 10 μM |
|---|---|---|
| 138 | 65 | |
| 139 | 70 | |
| 140 | 64 | |
| 141 | 78 | |
| 142 | 67 | |
| 143 | 66 | |
| 144 | 81 | |
| 145 | 77 | |
| 146 | 63 | |
| 147 | 73 | |
| 148 | 73 | 75 |
| 150 | 84 | |
| 151 | 71 | |

The affinity of the substituted 1-oxa-3,8-diazaspiro[4.5]-decan-2-one compounds according to the invention for the human μ opioid receptor was likewise determined as described above.

The compounds according to the invention also exhibit excellent affinity for the human μ opioid receptor.

| Compound according to Example | μ opioid receptor, % inhibition (1 μM) |
|---|---|
| 64 | 48 |
| 65 | 56 |
| 67 | 41 |
| 68 | 46 |
| 69 | 50 |
| 70 | 42 |
| 92 | 70 |
| 93 | 65 |
| 94 | 62 |
| 95 | 75 |
| 96 | 78 |
| 97 | 67 |
| 98 | 75 |
| 100 | 64 |
| 149 | 61 |

The invention claimed is:

1. A substituted 1-oxa-3,8-diazaspiro[4.5]-decan-2-one compound corresponding to formula I

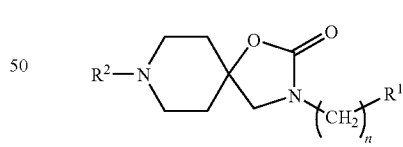

wherein
n is 1, 2, 3, 4 or 5;
$R^1$ denotes an optionally substituted 6- or 10-membered aryl group or an optionally substituted 5- to 14-membered heteroaryl group, wherein the aryl or heteroaryl group optionally may be fused with a saturated or unsaturated, optionally substituted mono- or bicyclic ring system;
$R^2$ denotes
—C(=S)—NH—$R^3$;
—C(=O)—NH—$R^4$;
—S(=O)$_2$—$R^5$;
—(CH$_2$)—C(=O)—NH—$R^6$;

—(CH$_2$)-D$_{aa}$-(CH$_2$)$_{bb}$-E$_{cc}$-(CH$_2$)$_{dd}$—R$^7$, wherein
  aa =0 or 1;
  bb =0, 1 or 2;
  cc =0 or 1;
  dd =0 or 1; and
  the sum of aa and cc does not equal 0; and
  D and E each independently denote O, S, NH, N(CH$_3$), N(C$_2$H$_5$) or N[CH(CH3)2];
—C(=O)—R$^8$, or
—S(=O)$_2$—NR$^9$R$^{10}$;
R$^3$ denotes
  —(CHR$^{11}$)—(CH$_2$)$_w$—C(=O)—O—R$^{12}$, wherein
    w=0 or 1;
  —(CHR$^{13}$)—(CH$_2$)$_a$—K$_b$—(CH$_2$)$_c$-L$_d$—R$^{14}$, wherein
    a=0, 1 or 2;
    b=0 or 1;
    c=0, 1 or 2;
    d=0 or 1, and
    K and L each independently denote O, S, NH, N(CH$_3$), N(C$_2$H$_5$) or N[CH(CH$_3$)$_2$];
  a linear or branched, saturated or unsaturated, optionally substituted C$_{1-10}$ aliphatic group;
  an unsaturated or saturated, optionally substituted 3-, 4-, 5-, 6-, 7-, 8- or 9-membered cycloaliphatic group which optionally may be bridged with 1 or 2 linear or branched, optionally substituted C$_{1-5}$ alkylene groups or fused with a saturated, unsaturated or aromatic, optionally substituted mono- or bicyclic ring system, or both;
  an optionally substituted 6- or 10-membered aryl group; or
  an optionally substituted 5- to 14-membered heteroaryl group, wherein the aryl or heteroaryl group optionally may be fused with a saturated or unsaturated, optionally substituted mono- or bicyclic ring system;
R$^4$ denotes
  —(CHR$^{15}$)—(CH$_2$)$_e$-M$_f$-(CH$_2$)$_g$—P$_h$—R$^{16}$, wherein
    e=0, 1 or 2;
    f=0 or 1;
    g=0, 1 or 2;
    h=0 or 1; and
    M and P each independently denote O, S, NH, N(CH$_3$), N(C$_2$H$_5$) or N[CH(CH$_3$)$_2$];
  a linear or branched, saturated or unsaturated, optionally substituted C$_{1-10}$ aliphatic group;
  an unsaturated or saturated, optionally substituted 3-, 4-, 5-, 6-, 7-, 8- or 9-membered cycloaliphatic group which optionally may be bridged with 1 or 2 linear or branched, optionally substituted C$_{1-5}$ alkylene groups or fused with a saturated, unsaturated or aromatic, optionally substituted mono- or bicyclic ring system, or both; or
  an optionally substituted 6- or 10-membered aryl group or optionally substituted 5- to 14-membered heteroaryl group, wherein said aryl or heteroaryl group optionally may be fused with a saturated or unsaturated, optionally substituted mono- or bicyclic ring system;
R$^5$ denotes
  —(CHR$^{17}$)—(CH$_2$)$_k$-Q$_l$-(CH$_2$)$_m$-T$_o$-R$^{18}$, wherein
    k=0, 1 or 2;
    l=0 or 1;
    m=0, 1 or 2;
    o=0 or 1; and
    Q and T each independently denote O, S, NH, N(CH$_3$), N(C$_2$H$_5$) or N[CH(CH$_3$)$_2$];
  a linear or branched, saturated or unsaturated, optionally substituted C$_{1-10}$ aliphatic group;
  an unsaturated or saturated, optionally substituted 3-, 4-, 5-, 6-, 7-, 8- or 9-membered cycloaliphatic group which optionally may be bridged with 1 or 2 linear or branched, optionally substituted C$_{1-5}$ alkylene groups or fused with a saturated, unsaturated or aromatic, optionally substituted mono- or bicyclic ring system, or both; or
  an optionally substituted 6- or 10-membered aryl group or optionally substituted 5- to 14-membered heteroaryl group, wherein the aryl or heteroaryl group optionally may be fused with a saturated or unsaturated, optionally substituted mono- or bicyclic ring system;
R$^6$ denotes
  a linear or branched, saturated or unsaturated, optionally substituted C$_{1-10}$ aliphatic group;
  an unsaturated or saturated, optionally substituted 3-, 4-, 5-, 6-, 7-, 8- or 9-membered cycloaliphatic group which optionally may be bridged with 1 or 2 linear or branched, optionally substituted C$_{1-5}$ alkylene groups or fused with a saturated, unsaturated or aromatic, optionally substituted mono- or bicyclic ring system, or both;
  an optionally substituted 6- or 10-membered aryl group or optionally substituted 5- to 14-membered heteroaryl group, wherein the aryl or heteroaryl group optionally may be fused with a saturated or unsaturated, optionally substituted mono- or bicyclic ring system;
R$^7$ denotes
  a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein said group optionally may be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$; or
  a group selected from the group consisting of phenyl, naphthyl, and [1,2,3,4]-tetrahydronaphthyl, wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, —S(=O)$_2$—NH-phenyl, phenyl and benzyl, wherein the cyclic moiety of the groups —S(=O)$_2$—NH-phenyl, phenyl and benzyl optionally may be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

R$^8$ denotes
—(CHR$^{19}$)—V$_p$—(CH$_2$)$_q$—(CH$_2$)$_r$—W$_s$—R$^{20}$, wherein
p=0 or 1;
q=0, 1 or 2;
r=0, 1 or 2;
s=0 or 1; and
V and W each independently denote O, S, NH, N(CH$_3$), N(C$_2$H$_5$) or N[CH(CH$_3$)$_2$];
—(CH=CH)—R$^{21}$;
—(CR$^{22}$R$^{23}$)—Y$_t$—(CR$^{24}$R$^{25}$)$_u$—(CH$_2$)$_v$—C(=O)—OR$^{26}$, wherein
t=0 or 1,
u=0 or 1;
v=0 or 1, and
Y denotes O, S, NH, N(CH$_3$), N(C$_2$H$_5$) or N[CH(CH$_3$)$_2$];
—(CHR$^{27}$)—O—C(=O)—R$^{28}$;
—CH[(CH$_2$)R$^{29}$][NH—S(=O)$_2$—R$^{30}$];
—CH[(CH$_2$)R$^{31}$][NH—C(=O)—O—R$^{32}$];
a linear or branched, saturated or unsaturated, optionally substituted C$_{1-10}$ aliphatic group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl;
an unsaturated or saturated, optionally substituted 3-, 4-, 5-, 6-, 7-, 8- or 9-membered cycloaliphatic group which optionally may be bridged with 1 or 2 linear or branched, optionally substituted C$_{1-5}$ alkylene groups, or fused with a saturated, unsaturated or aromatic, optionally substituted mono- or bicyclic ring system, or both; or
an optionally substituted 6- or 10-membered aryl group or optionally substituted 5- to 14-membered heteroaryl group, wherein the aryl or heteroaryl group optionally may be fused with a saturated or unsaturated, optionally substituted mono- or bicyclic ring system;

R$^9$ and R$^{10}$ each independently denote a linear or branched, saturated or unsaturated, optionally substituted C$_{1-10}$ aliphatic group;

R$^{11}$, R$^{13}$, R$^{15}$, R$^{17}$, R$^{19}$, R$^{22}$, R$^{23}$, R$^{24}$, R$^{25}$ and R$^{26}$ each independently denote a hydrogen or a linear or branched, saturated or unsaturated, optionally substituted C$_{1-10}$ aliphatic group;

R$^{12}$, R$^{28}$ and R$^{32}$ each independently denote a linear or branched, saturated or unsaturated, optionally substituted C$_{1-10}$ aliphatic group;

R$^{14}$, R$^{16}$, R$^{18}$ and R$^{20}$ each independently denote
a linear or branched, saturated or unsaturated, optionally substituted C$_{1-10}$ aliphatic group;
an unsaturated or saturated, optionally substituted 3-, 4-, 5-, 6-, 7-, 8- or 9-membered cycloaliphatic group which optionally may be bridged with 1 or 2 linear or branched, optionally substituted C$_{1-5}$ alkylene groups, or fused with a saturated, unsaturated or aromatic, optionally substituted mono- or bicyclic ring system, or both; or
an optionally substituted 6- or 10-membered aryl group or optionally substituted 5- to 14-membered heteroaryl group, wherein the aryl or heteroaryl group optionally may be fused with a saturated or unsaturated, optionally substituted mono- or bicyclic ring system; and R$^{21}$, R$^{27}$, R$^{29}$, R$^{30}$ and R$^{31}$ each independently denote
an unsaturated or saturated, optionally substituted 3-, 4-, 5-, 6-, 7-, 8- or 9-membered cycloaliphatic group which optionally may be bridged with 1 or 2 linear or branched, optionally substituted C$_{1-5}$ alkylene groups, or fused with a saturated, unsaturated or aromatic, optionally substituted mono- or bicyclic ring system, or both; or
an optionally substituted 6- or 10-membered aryl group or optionally substituted 5- to 14-membered heteroaryl group, wherein the aryl or heteroaryl group optionally may be fused with a saturated or unsaturated, optionally substituted mono- or bicyclic ring system;

wherein
the above-stated C$_{1-10}$ aliphatic groups each independently may optionally be substituted with 1, 2, 3, 4 or 5 substituents independently selected from the group consisting of F, Cl, Br, I, —CN, —NO$_2$, —OH, —SH and —NH$_2$;
the above-stated cycloaliphatic groups each independently may optionally be substituted with 1, 2, 3, 4 or 5 substituents independently selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —S—CF$_2$H, —S—CFH$_2$, —SH, —S—C$_{1-5}$-alkyl, —C$_{1-5}$-alkyl, —C(=O)—OH, —(CH$_2$)—C(=O)—OH, —C(=O)—O—C$_{1-5}$-alkyl, —(CH$_2$)—C(=O)—O—C$_{1-5}$-alkyl, —O—C(=O)—C$_{1-5}$-alkyl, —NH—C$_{1-5}$-alkyl, —N(—C$_{1-5}$-alkyl)$_2$, —NH-phenyl, —NH-pyridinyl, —N(—C$_{1-5}$-alkyl)-phenyl, —N(—C$_{1-5}$-alkyl)-pyridinyl, —NH—C(=O)—O—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(—C$_{1-5}$-alkyl)$_2$, —S(=O)$_2$—C$_{1-5}$-alkyl, —S(=O)$_2$-phenyl, —NH—S(=O)$_2$—C$_{1-5}$-alkyl, —S(=O)$_2$—NH—C$_{1-5}$-alkyl, —S(=O)$_2$—NH$_2$, —S(=O)$_2$—NH-phenyl, cyclohexyl, cyclopentyl, pyridinyl, [1,2,5]-thiadiazolyl, pyridazinyl, —(CH$_2$)-benzo[b]furanyl, —O-phenyl, —O-benzyl, phenyl and benzyl, wherein the cyclic moiety of the groups —S(=O)$_2$—NH-phenyl, —NH-phenyl, —NH-pyridinyl, —N(—C$_{1-5}$-alkyl)-phenyl, —N(—C$_{1-5}$-alkyl)-pyridinyl, pyridinyl, cyclopentyl, [1,2,5]-thiadiazolyl, cyclohexyl, pyridazinyl, —S(=O)$_2$-phenyl, —O-phenyl, —O-benzyl, phenyl, —(CH$_2$)-benzo[b]furanyl and benzyl optionally may be substituted with 1, 2, 3, 4 or 5 substituents independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and comprise 1, 2, 3, 4 or 5 heteroatom(s) mutually independently selected from the group consisting of oxygen, nitrogen and sulfur;

the above-stated C$_{1-5}$-alkylene groups each independently may optionally be substituted with 1, 2, 3, 4 or 5 substituents independently selected from the group consisting of F, Cl, Br, I, —CN, —NO$_2$, —OH, —SH and —NH$_2$;

the rings of the above-stated mono- or polycyclic ring systems each independently may optionally be substituted with 1, 2, 3, 4 or 5 substituents independently selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —S—CF$_2$H, —S—CFH$_2$, —SH, —S—C$_{1-5}$-alkyl, —C$_{1-5}$-alkyl, —C(=O)—OH, —(CH$_2$)—C(=O)—OH; —C(=O)—O—C$_{1-5}$-alkyl, —(CH$_2$)—C(=O)—O—C$_{1-5}$-alkyl, —O—C(=O)—C$_{1-5}$-alkyl, —NH—C$_{1-5}$-alkyl, —N(—C$_{1-5}$-alkyl)$_2$, —NH-phenyl, —NH-pyridinyl, —N(—C$_{1-5}$-alkyl)-phenyl, —N(—C$_{1-5}$-alkyl)-pyridinyl, —NH—C(=O)—O—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, C(=O)—N—(—C$_{1-5}$-alkyl)$_2$, —S(=O)$_2$—C$_{1-5}$-alkyl, —S(=O)$_2$-phenyl, —NH—S(=O)$_2$—C$_{1-5}$-alkyl, —S(=O)$_2$—NH—C$_{1-5}$-alkyl, —S(=O)$_2$—NH$_2$, —S(=O)$_2$—NH-phenyl, cyclohexyl, cyclopentyl, pyridinyl, [1,2,5]-thiadiazolyl, pyridazinyl, —(CH$_2$)-benzo[b]furanyl, —O-phenyl, —O-benzyl, phenyl and benzyl, wherein the cyclic moiety of the groups —S(=O)$_2$—NH-phenyl, —NH-phenyl, —NH-pyridinyl, —N(—C$_{1-5}$-alkyl)-phenyl, —N(—C$_{1-5}$-alkyl)-pyridinyl, pyridinyl, cyclopentyl, [1,2,5]-thiadiazolyl, cyclohexyl, pyridazinyl, —S(=O)$_2$-phenyl, —O-phenyl, —O-benzyl, phenyl, —(CH$_2$)-benzo[b]furanyl and benzyl optionally may be substituted with 1, 2, 3, 4 or 5 substituents independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl;

the rings of the above-stated mono- or bicyclic ring systems are each independently 5-, 6- or 7-membered and each independently may optionally comprise as ring member(s), 1, 2, 3, 4 or 5 heteroatom(s) independently selected from the group consisting of oxygen, nitrogen and sulfur;

the above-stated aryl or heteroaryl groups each independently may optionally be substituted with 1, 2, 3, 4 or 5 substituents independently selected from the group consisting of F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —S—CF$_2$H, —S—CFH$_2$, SH, —S—C$_{1-5}$-alkyl, —C$_{1-10}$-alkyl, —C(=O)—OH, —(CH$_2$)—C(=O)—OH, —C(=O)—O—C$_{1-5}$-alkyl, —(CH$_2$)—C(=O)—O—C$_{1-5}$-alkyl, —O—C(=O)—C$_{1-5}$-alkyl, —NH—C$_{1-5}$-alkyl, —N(—C$_{1-5}$-alkyl)$_2$, —NH—C(=O)—O—C$_{1-5}$-alkyl, —NH—C(=O)—C$_{1-5}$-alkyl, —C(=O)—H, —C(=O)—C$_{1-5}$-alkyl, —C(=O)—C$_{1-5}$-perfluoroalkyl, —C(=O)—NH$_2$, —C(=O)—NH—C$_{1-5}$-alkyl, —C(=O)—N—(—C$_{1-5}$-alkyl)$_2$, —S(=O)$_2$—C$_{1-5}$-alkyl, —S(=O)$_2$-phenyl, —NH—S(=O)$_2$—C$_{1-5}$-alkyl, —S(=O)$_2$—NH—C$_{1-5}$-alkyl, —S(=O)$_2$—NH$_2$, —S(=O)$_2$—NH-phenyl, cyclohexyl, cyclopentyl, pyridinyl, pyridazinyl, —(CH$_2$)-benzo[b]furanyl, —O-phenyl, —O-benzyl, phenyl and benzyl, wherein the cyclic moiety of the groups pyridinyl, cyclopentyl, cyclohexyl, pyridazinyl, —S(=O)$_2$-phenyl, —S(=O)$_2$—NH-phenyl, —O-phenyl, —O-benzyl, phenyl, —(CH$_2$)-benzo[b]furanyl and benzyl optionally may be substituted with 1, 2, 3, 4 or 5 substituents independently selected from the group consisting of F, Cl, Br, —OH, —CF$_3$, —SF$_5$, —NO$_2$, —C$_{1-5}$-alkyl, —O—C$_{1-5}$-alkyl, —O—CF$_3$, —S—CF$_3$, phenyl and —O-benzyl; and the above-stated heteroaryl groups each independently may optionally comprise as ring member(s), 1, 2, 3, 4 or 5 heteroatom(s) independently selected from the group consisting of oxygen, nitrogen and sulfur;

or a pharmaceutically acceptable salt or solvate thereof.

2. A compound as claimed in claim 1, wherein said compound contains at least one chiral carbon atom and is present in the form of an isolated or purified stereoisomer.

3. A compound as claimed in claim 1, wherein said compound contains at least one chiral carbon atom and is present in the form of a mixture of stereoisomers in any mixing ratio.

4. A compound as claimed in claim 1, wherein said compound is present in the form of a racemic mixture.

5. A compound as claimed in claim 1 wherein $R^1$ denotes a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl, oxazolyl, isoxazolyl, pyridazinyl, pyrazinyl, pyrimidinyl, indazolyl, quinazolinyl, quinolinyl and isoquinolinyl, wherein said group may in optionally be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, n-hexyl, n-heptyl, —NH—C(=O)—O—CH$_3$, —NH—C(=O)—O—C$_2$H$_5$, —NH—C(=O)—O—C(CH$_3$)$_3$, —NH—C(=O)—CH$_3$, —NH—C(=O)—C$_2$H$_5$, —NH—C(=O)—C(CH$_3$)$_3$, —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, phenyl and benzyl, wherein the cyclic moiety of each phenyl or benzyl group independently may optionally be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl.

6. A compound as claimed in claim 1, wherein
R$^2$ denotes —C(=S)—NH—R$^3$; —C(=O)—NH—R$^4$; —S(=O)$_2$—R$^5$; —(CH$_2$)—C(=O)—NH—R$^6$; —(CH$_2$)—O—R$^7$, —(CH$_2$)—S—R$^7$, —(CH$_2$)—NH—R$^7$, —(CH$_2$)—N(CH$_3$)—R$^7$, —(CH$_2$)—(CH$_2$)—O—R$^7$, —(CH$_2$)—(CH$_2$)—S—R$^7$, —(CH$_2$)—NH—R$^7$, —(CH$_2$)—N(CH$_3$)—R$^7$, —(CH$_2$)—(CH$_2$)—(CH$_2$)—O—R$^7$, —(CH$_2$)—(CH$_2$)—(CH$_2$)—S—R$^7$, —(CH$_2$)—(CH$_2$)—(CH$_2$)—NH—R$^7$, —(CH$_2$)—(CH$_2$)—(CH$_2$)—N(CH$_3$)—R$^7$, —(CH$_2$)—O—(CH$_2$)—R$^7$, —(CH$_2$)—S—(CH$_2$)—R$^7$; —(CH$_2$)—NH—(CH$_2$)—R$^7$; —C(=O)—R$^8$ or —S(=O)$_2$—NR$^9$R$^{10}$.

7. A compound as claimed in claim 1, wherein
R$^3$ denotes
—(CHR$^{11}$)—C(=O)—O—R$^{12}$ or —(CHR$^{11}$)—(CH$_2$)—C(=O)—O—R$^{12}$;
—(CHR$^{13}$)—R$^{14}$, —(CHR$^{13}$)—(CH$_2$)—R$^{14}$, —(CHR$^{13}$)—(CH$_2$)—(CH$_2$)—R$^{14}$, —(CHR$^{13}$)—O—R$^{14}$, —(CHR$^{13}$)—S—R$^{14}$, —(CHR$^{13}$)—NH—R$^{14}$, —(CHR$^{13}$)—N(CH$_3$)—R$^{14}$, —(CHR$^{13}$)—(CH$_2$)—O—R$^{14}$, —(CHR$^{13}$)—(CH$_2$)—S—R$^{14}$, —(CHR$^{13}$)—NH—R$^{14}$, —(CHR$^{13}$)—N(CH$_3$)—R$^{14}$, —(CHR$^{13}$)—(CH$_2$)—(CH$_2$)—O—R$^{14}$, —(CHR$^{13}$)—(CH$_2$)—(CH$_2$)—S—R$^{14}$, —(CHR$^{13}$)—(CH$_2$)—(CH$_2$)—NH—R$^{14}$, —(CHR$^{13}$)—(CH$_2$)—(CH$_2$)—N(CH$_3$)—R$^{14}$, —(CHR$^{13}$)—O—(CH$_2$)—R$^{14}$, —(CHR$^{13}$)—S—(CH$_2$)—R$^{14}$ or —(CHR$^{13}$)—NH—(CH$_2$)—R$^{14}$;
a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein said group optionally may be substituted with 1, 2, 3, 4 or 5 substituents independently selected from the group consisting of F, Cl, Br, I, —CN, —NO$_2$, —OH, —SH and —NH$_2$;
a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein said group optionally may be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$; or
a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, phenyl and benzyl, wherein the cyclic moiety of each phenyl or benzyl group independently may optionally be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl.

8. A compound as claimed in claim 1, wherein
R$^4$ denotes
—(CHR$^{15}$)—R$^{16}$, —(CHR$^{15}$)—(CH$_2$)—R$^{16}$, —(CHR$^{15}$)—(CH$_2$)—(CH$_2$)—R$^{16}$, —(CHR$^{15}$)—O—R$^{16}$, —(CHR$^{15}$)—S—R$^{16}$, —(CHR$^{15}$)—NH—R$^{16}$, —(CHR$^{15}$)—N(CH$_3$)—R$^{16}$, —(CHR$^{15}$)—(CH$_2$)—O—R$^{16}$, —(CHR$^{15}$)—(CH$_2$)—S—R$^{16}$, —(CHR$^{15}$)—NH—R$^{16}$, —(CHR$^{15}$)—N(CH$_3$)—R$^{16}$, —(CHR$^{15}$)—(CH$_2$)—(CH$_2$)—O—R$^{16}$, —(CHR$^{15}$)—(CH$_2$)—(CH$_2$)—S—R$^{16}$, —(CHR$^{15}$)—(CH$_2$)—(CH$_2$)—NH—R$^{16}$, —(CHR$^{15}$)—(CH$_2$)—(CH$_2$)—N(CH$_3$)—R$^{16}$, —(CHR$^{15}$)—O—(CH$_2$)—R$^{16}$, —(CHR$^{15}$)—S—(CH$_2$)—R$^{16}$ or —(CHR$^{15}$)—NH—(CH$_2$)—R$^{16}$;
a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein said group optionally may be substituted with 1, 2, 3, 4 or 5 substituents independently selected from the group consisting of F, Cl, Br, I, —CN, —NO$_2$, —OH, —SH and —NH$_2$;

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein said group optionally may be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$; or a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, oxazolyl, isoxazolyl, pyridazinyl, pyrazinyl, pyrimidinyl, indazolyl, quinazolinyl, quinolinyl and isoquinolinyl, wherein the said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, phenyl and benzyl, wherein the cyclic moiety of each phenyl or benzyl group independently may optionally be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl.

9. A compound as claimed in claim 1, wherein R$^5$ denotes

—(CHR$^{17}$)—R$^{18}$, —(CHR$^{17}$)—(CH$_2$)—R$^{18}$, —(CHR$^{17}$)—(CH$_2$)—(CH$_2$)—R$^{18}$, —(CHR$^{17}$)—O—R$^{18}$, —(CHR$^{17}$)—S—R$^{18}$, —(CHR$^{17}$)—NH—R$^{18}$, —(CHR$^{17}$)—N(CH$_3$)—R$^{18}$, —(CHR$^{17}$)—(CH$_2$)—O—R$^{18}$, —(CHR$^{17}$)—(CH$_2$)—S—R$^{18}$, —(CHR$^{17}$)—NH—R$^{18}$, —(CHR$^{17}$)—N(CH$_3$)—R$^{18}$, —(CHR$^{17}$)—(CH$_2$)—(CH$_2$)—O—R$^{18}$, —(CHR$^{17}$)—(CH$_2$)—(CH$_2$)—S—R$^{18}$, —(CHR$^{17}$)—(CH$_2$)—(CH$_2$)—NH—R$^{18}$, —(CHR$^{17}$)—(CH$_2$)—(CH$_2$)—N(CH$_3$)—R$^{18}$, —(CHR$^{17}$)—O—(CH$_2$)—R$^{18}$, —(CHR$^{17}$)—S—(CH$_2$)—R$^{18}$ or —(CHR$^{17}$)—NH—(CH$_2$)—R$^{18}$;

a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein said group optionally may be substituted with 1, 2, 3, 4 or 5 substituents independently selected from the group consisting of F, Cl, Br, I, —CN, —NO$_2$, —OH, —SH and —NH$_2$;

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein said group optionally may be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$; or a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, [1,2,3,4]-tetrahydronaphthyl, [1,2,3,4]-tetrahydroquinolinyl, [1,2,3,4]-tetrahydroisoquinolinyl, [1,2,3,4]- tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, phenyl and benzyl, wherein the cyclic moiety of each phenyl or benzyl group independently may optionally be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl.

10. A compound as claimed in claim 1, wherein R$^6$ denotes a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein said group optionally may be substituted with 1, 2, 3, 4 or 5 substituents independently selected from the group consisting of F, Cl, Br, I, —CN, —NO$_2$, —OH, —SH and —NH$_2$;

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein said group optionally may be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$; or a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, —S(=O)$_2$—NH-phenyl, phenyl and benzyl, wherein in each case the cyclic moiety of the groups —S(=O)$_2$—NH-phenyl, phenyl and benzyl may be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl.

11. A compound as claimed in claim 1 wherein R$^8$ denotes

—(CHR$^{19}$)—R$^{20}$, —(CHR$^{19}$)—(CH$_2$)—R$^{20}$, —(CHR$^{19}$)—(CH$_2$)—(CH$_2$)—R$^{20}$, —(CHR$^{19}$)—O—R$^{20}$, —(CHR$^{19}$)—S—R$^{20}$, —(CHR$^{19}$)—NH—R$^{20}$, —(CHR$^{19}$)—N(CH$_3$)—R$^{20}$, —(CHR$^{19}$)—(CH$_2$)—O—R$^{20}$, —(CHR$^{19}$)—(CH$_2$)—S—R$^{20}$,

—(CHR$^{19}$)—NH—R$^{20}$, —(CHR$^{19}$)—N(CH$_3$)—R$^{20}$, —(CHR$^{19}$)—(CH$_2$)—(CH$_2$)—O—R$^{20}$, —(CHR$^{19}$)—(CH$_2$)—(CH$_2$)—S—R$^{20}$, —(CHR$^{19}$)—(CH$_2$)—(CH$_2$)—NH—R$^{20}$, —(CHR$^{19}$)—(CH$_2$)—(CH$_2$)—N(CH$_3$)—R$^{20}$, —(CHR$^{19}$)—O—(CH$_2$)—R$^{20}$, —(CHR$^{19}$)—S—(CH$_2$)—R$^{20}$, —(CHR$^{19}$)—NH—(CH$_2$)—R$^{20}$, —(CHR$^{19}$)—O—(CH$_2$)—(CH$_2$)—O—R$^{20}$, —(CHR$^{19}$)—O—(CH$_2$)—(CH$_2$)—S—R$^{20}$ or —(CHR$^{19}$)—S—(CH$_2$)—(CH$_2$)—S—R$^{20}$;
—(CH=CH)—R$^{21}$; —(CR$^{22}$R$^{23}$)—C(=O)—O—R$^{26}$, —(CR$^{22}$R$^{23}$)—(CR$^{24}$R$^{25}$)—C(=O)—O—R$^{26}$, —(CR$^{22}$R$^{23}$)—(CR$^{24}$R$^{25}$)—(CH$_2$)—C(=O)—O—R$^{26}$, —(CR$^{22}$R$^{23}$)—O(CR$^{24}$R$^{25}$)—C(=O)—O—R$^{26}$, —(CR$^{22}$R$^{23}$)—S—(CR$^{24}$R$^{25}$)—C(=O)—O—R$^{26}$ or denotes —(CR$^{22}$R$^{23}$)—NH—(CR$^{24}$R$^{25}$)—C(=O)—O—R$^{26}$;
—(CHR$^{27}$)—O—C(=O)—R$^{28}$;
—CH[(CH$_2$)R$^{29}$][NH—S(=O)$_2$—R$^{30}$];
—CH[(CH$_2$)R$^{31}$][NH—C(=O)—O—R$^{32}$];
a group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl, wherein said group optionally may be substituted with 1, 2, 3, 4 or 5 substituents independently selected from the group consisting of F, Cl, Br, I, —CN, —NO$_2$, —OH, —SH and —NH$_2$;
a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, adamantyl and bicyclo[2.2.1]heptyl, wherein said group optionally may be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, —(CH$_2$)—C(=O)—OH, —C(=O)—OH, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, phenyl and —S(=O)$_2$—NH$_2$; wherein the phenyl group optionally may be substituted with 1, 2, 3, 4 or 5 substituents independently selected from the group consisting of F, Cl, Br, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$; or
a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tyl, tert-butyl, n-pentyl, —C(CH$_3$)$_2$—C$_2$H$_5$, n-hexyl, n-heptyl, —NH—C(=O)—O—CH$_3$, —NH—C(=O)—O—C$_2$H$_5$, —NH—C(=O)—O—C(CH$_3$)$_3$, —O—CH$_2$—CH$_2$—CH$_2$—CH$_3$, —NH—C(=O)—CH$_3$, —NH—C(=O)—C$_2$H$_5$, —NH—C(=O)—C(CH$_3$)$_3$, —C(=O)—OH, —(CH$_2$)—C(=O)—OH, —C(=O)—O—CH$_3$, —C(=O)—O—CH$_2$—CH$_3$, —C(=O)—O—CH(CH$_3$)$_2$, —C(=O)—O—C(CH$_3$)$_3$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —C(=O)—H, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$, —S(=O)$_2$—NH$_2$, —S(=O)$_2$—NH-phenyl, phenyl, —O-phenyl, —O-benzyl and benzyl, wherein the cyclic moiety of the groups —S(=O)$_2$—NH-phenyl, phenyl, —O-phenyl, —O-benzyl and benzyl optionally may be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl.

12. A compound as claimed in claim 1 wherein R$^9$ and R$^{10}$ each independently denote a group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl.

13. A compound as claimed in claim 1 wherein R$^{11}$, R$^{13}$, R$^{15}$, R$^{17}$, R$^{19}$, R$^{22}$, R$^{23}$, R$^{24}$, R$^{25}$ and R$^{26}$ each independently denote hydrogen or a group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl.

14. A compound as claimed in claim 1 wherein
$R^{12}$, $R^{28}$ and $R^{32}$ each independently denote a group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl.

15. A compound as claimed in claim 1 wherein
$R^{14}$, $R^{16}$, $R^{18}$ and $R^{20}$ each independently denote
a group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;
a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, adamantyl and bicyclo[2.2.1]heptyl, wherein said group optionally may be substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, —(CH$_2$)—C(=O)—OH, —C(=O)—OH, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$, —C(=O)—C$_2$F$_5$, —C(=O)—NH$_2$, —C(=O)—NH—CH$_3$, —C(=O)—NH—C$_2$H$_5$, —C(=O)—NH—C(CH$_3$)$_3$, —C(=O)—N(CH$_3$)$_2$, —C(=O)—N(C$_2$H$_5$)$_2$, —S(=O)$_2$—CH$_3$, —S(=O)$_2$—C$_2$H$_5$, —NH—S(=O)$_2$—CH$_3$, —S(=O)$_2$—NH—CH$_3$ and —S(=O)$_2$—NH$_2$; or
a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—CH$_3$, —NH—C(=O)—C$_2$H$_5$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$) and S(=O)$_2$—NH$_2$.

16. A compound as claimed in claim 1 wherein
$R^{21}$, $R^{27}$, $R^{29}$, $R^{30}$ and $R^{31}$ each independently denote a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —SH, —S—CH$_3$, —S—C$_2$H$_5$, —S—CH(CH$_3$)$_2$, —S—CH$_2$—CH$_2$—CH$_3$, —S—C(CH$_3$)$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—CH$_3$, —NH—C(=O)—C$_2$H$_5$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$) and S(=O)$_2$—NH$_2$.

17. A compound as claimed in claim 1 wherein n is 1, 2 or 3;
$R^1$ denotes a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —SF$_5$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, methyl, ethyl, n-propyl, isopropyl, n-butyl, sec-butyl, isobutyl, tert-butyl, n-pentyl, n-hexyl, n-heptyl, phenyl and benzyl, wherein the cyclic moiety of the phenyl and benzyl groups optionally may be substituted with 1, 2, 3, 4 or 5 substituents independently selected from the group consisting of F, Cl, Br, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$ and —O—C(CH$_3$)$_3$;
$R^2$ denotes
—C(=S)—NH—R$^3$;
—C(=O)—NH—R$^4$;
—S(=O)$_2$—R$^5$;
—(CH$_2$)—C(=O)—NH—R$^6$;
—(CH$_2$)—O—R$^7$, —(CH$_2$)—S—R$^7$, —(CH$_2$)—NH—R$^7$, —(CH$_2$)—N(CH$_3$)—R$^7$, —(CH$_2$)—(CH$_2$)—O—R$^7$, —(CH$_2$)—(CH$_2$)—S—R$^7$, —(CH$_2$)—NH—R$^7$, —(CH$_2$)—N(CH$_3$)—R$^7$, —(CH$_2$)—(CH$_2$)—(CH$_2$)—O—R$^7$, —(CH$_2$)—(CH$_2$)—(CH$_2$)—S—R$^7$, —(CH$_2$)—(CH$_2$)—(CH$_2$)—NH—R$^7$, —(CH$_2$)—(CH$_2$)—(CH$_2$)—N(CH$_3$)—R$^7$, —(CH$_2$)—O—(CH$_2$)—R$^7$, —(CH$_2$)—S—(CH$_2$)—R$^7$, or —(CH$_2$)—NH—(CH$_2$)—R$^7$;
—C(=O)—R$^8$, or
—S(=O)$_2$—NR$^9$R$^{10}$;

R$^3$ denotes
—(CHR$^{11}$)—C(=O)—O—R$^{12}$ or —(CHR$^{11}$)—(CH$_2$)—C(=O)—O—R$^{12}$;
—(CHR$^{13}$)—R$^{14}$, —(CHR$^{13}$)—(CH$_2$)—R$^{14}$, —(CHR$^{13}$)—(CH$_2$)—(CH$_2$)—R$^{14}$, —(CHR$^{13}$)—O—R$^{14}$, —(CHR$^{13}$)—(CH$_2$)—O—R$^{14}$, —(CHR$^{13}$)—(CH$_2$)—(CH$_2$)—O—R$^{14}$ or —(CHR$^{13}$)—O—(CH$_2$)—R$^{14}$;

a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl and 3-butenyl; or a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$ and —C(=O)—C$_2$F$_5$;

R$^4$ denotes
—(CHR$^{15}$)—R$^{16}$, —(CHR$^{15}$)—(CH$_2$)—R$^{16}$ or —(CHR$^{15}$)—(CH$_2$)—(CH$_2$)—R$^{16}$; or a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —NO$_2$, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, n-hexyl, n-heptyl, —C(=O)—O—CH$_3$, —C(=O)—O—CH$_2$—CH$_3$, —C(=O)—O—CH(CH$_3$)$_2$, —C(=O)—O—C(CH$_3$)$_3$, —C(=O)—CH$_3$, —C(=O)—C$_2$H$_5$, —C(=O)—C(CH$_3$)$_3$, —C(=O)—CF$_3$ and —C(=O)—C$_2$F$_5$;

R$^5$ denotes
—(CHR$^{17}$)—R$^{18}$, —(CHR$^{17}$)—(CH$_2$)—R$^{18}$ or —(CHR$^{17}$)—(CH$_2$)—(CH$_2$)—R$^{18}$;

a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$); or a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —C(=O)—O—CH$_3$, —C(=O)—O—CH$_2$—CH$_3$, —C(=O)—O—CH(CH$_3$)$_2$, —C(=O)—O—C(CH$_3$)$_3$, —C(=O)—CF$_3$, —C(=O)—C$_2$F$_5$, —S(=O)$_2$—CH$_3$ and —S(=O)$_2$—C$_2$H$_5$;

R$^6$ denotes a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, —CF$_3$, —CN, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —S(=O)$_2$—NH-phenyl, phenyl and benzyl, wherein the cyclic moiety of the —S(=O)$_2$—NH-phenyl, phenyl and benzyl groups optionally may be substituted with 1, 2, 3, 4 or 5 substituents independently selected from the group consisting of F, Cl and Br;

R$^7$ denotes a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, imidazolyl, indolyl, isoindolyl, benzo[b]furanyl, benzo[b]thiophenyl, thiazolyl, [1,2,4]-oxadiazolyl, [1,2,3]-thiadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, —CN, —CF$_3$, —SF$_5$, —OH, —O—CH$_3$, —O—C$_2$H$_5$, —NO$_2$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, phenyl and benzyl, wherein the cyclic moiety of the phenyl and benzyl groups optionally may be substituted with 1, 2, 3, 4 or 5 substituents independently selected from the group consisting of F, Cl, Br, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$;

$R^8$ denotes
- —(CHR$^{19}$)—R$^{20}$, —(CHR$^{19}$)—(CH$_2$)—R$^{20}$, —(CHR$^{19}$)—(CH$_2$)—(CH$_2$)—R$^{20}$, —(CHR$^{19}$)—O—R$^{20}$, —(CHR$^{19}$)—(CH$_2$)—O—R$^{20}$, —(CHR$^{19}$)—(CH$_2$)—(CH$_2$)—O—R$^{20}$, —(CHR$^{19}$)—O—(CH$_2$)—R$^{20}$ or —(CHR$^{19}$)—O—(CH$_2$)—(CH$_2$)—O—R$^{20}$;
- —(CH=CH)—R$^{21}$;
- —(CR$^{22}$R$^{23}$)—C(=O)—O—R$^{26}$, —(CR$^{22}$R$^{23}$)—(CR$^{24}$R$^{25}$)—C(=O)—O—R$^{26}$, —(CR$^{22}$R$^{23}$)—(CR$^{24}$R$^{25}$)—(CH$_2$)—C(=O)—O—R$^{26}$ or —(CR$^{22}$R$^{23}$)—O—(CR$^{24}$R$^{25}$)—C(=O)—O—R$^{26}$;
- —(CHR$^{27}$)—O—C(=O)—R$^{28}$;
- —CH[(CH$_2$)R$^{29}$][NH—S(=O)$_2$—R$^{30}$];
- —CH[(CH$_2$)R$^{31}$][NH—C(=O)—O—R$^{32}$];
- a group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;
- a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, adamantyl and bicyclo[2.2.1]heptyl, wherein said group optionally may be substituted with 1, 2, 3, 4 or 5 substituents independently selected from the group consisting of —C(=O)—CH$_3$, —C(=O)—C$_2$H$_5$, —C(=O)—C(CH$_3$)$_3$ and phenyl; or
- a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, oxazolyl, isoxazolyl, pyridazinyl, pyrazinyl, pyrimidinyl, indazolyl, quinazolinyl, quinolinyl and isoquinolinyl, wherein said group optionally may be substituted with 1, 2, 3, 4 or 5 substituents independently selected from the group consisting of F, Cl, Br, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —S—CH$_3$, —S—C$_2$H$_5$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—CH$_3$, —NH—C(=O)—C$_2$H$_5$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —S(=O)$_2$—NH$_2$, phenyl, —O-phenyl, —O-benzyl and benzyl, wherein the cyclic moiety of the phenyl, —O-phenyl, —O-benzyl, and benzyl groups optionally may be substituted with 1, 2, 3, 4 or 5 substituents independently selected from the group consisting of F, Cl, Br, —OH, —CF$_3$, —SF$_5$, —NO$_2$, methyl, ethyl, n-propyl, isopropyl, n-butyl, sec-butyl, isobutyl, tert-butyl, n-pentyl, n-hexyl, n-heptyl, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, phenyl and —O-benzyl;

$R^9$ and $R^{10}$ each independently denote a group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;

$R^{11}$, $R^{13}$, $R^{15}$, $R^{17}$, $R^{19}$, $R^{22}$, $R^{23}$, $R^{24}$, $R^{25}$ and $R^{26}$ each independently denote hydrogen or a group selected from the group consisting of methyl, ethyl, n-propyl, isopropyl, n-butyl, sec-butyl, isobutyl and tert-butyl;

$R^{12}$, $R^{28}$ and $R^{32}$ each independently denote a group selected from the group consisting of methyl, ethyl, n-propyl, isopropyl, n-butyl, sec-butyl, isobutyl and tert-butyl;

$R^{14}$, $R^{16}$, $R^{18}$ and $R^{20}$ each independently denote
- a group selected from the group consisting of methyl, ethyl, n-propyl, isopropyl, n-butyl, sec-butyl, isobutyl and tert-butyl;
- a group selected from the group consisting of cyclopropyl, cyclobutyl, cyclopentyl, cyclohexyl, cycloheptyl, tetrahydrofuranyl, tetrahydrothiophenyl, tetrahydropyranyl and bicyclo[2.2.1]heptyl, wherein said group optionally may be substituted with 1, 2, 3, 4 or 5 substituents independently selected from the group consisting of oxo (=O), thioxo (=S), methyl, ethyl, n-propyl, isopropyl, n-butyl, sec-butyl, isobutyl, tert-butyl, n-pentyl, n-hexyl, n-heptyl, —(CH$_2$)—C(=O)—OH and —C(=O)—OH; or
- a group selected from the group consisting of phenyl, and naphthyl, wherein said phenyl or naphthyl group optionally may be substituted with 1, 2, 3, 4 or 5 substituents independently selected from the group consisting of F, Cl, Br, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl and n-heptyl; and $R^{21}$, $R^{27}$, $R^{29}$, $R^{30}$ and $R^{31}$ each independently denote a group selected from the group consisting of phenyl, naphthyl, indolyl and isoindolyl, wherein said group optionally may be substituted with 1, 2, 3, 4 or 5 substituents independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, —C(CH$_3$)$_2$—C$_2$H$_5$, n-hexyl and n-heptyl.

18. A compound as claimed in claim 1 wherein n is 1 or 2; $R^1$ denotes a group selected from the group consisting of phenyl and naphthyl, wherein said group optionally may be substituted with 1, 2, 3, 4 or 5 substituents independently selected from the group consisting of F, Cl, Br, I, —CN, —CF$_3$, —SF$_5$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, methyl, ethyl, n-propyl, isopropyl, n-butyl, sec-butyl, isobutyl, tert-butyl, n-pentyl, n-hexyl, n-heptyl, phenyl and benzyl;

R$^2$ denotes
- —C(=S)—NH—R$^3$;
- —C(=O)—NH—R$^4$;
- —S(=O)$_2$—R$^5$;
- —(CH$_2$)—C(=O)—NH—R$^6$;
- —(CH$_2$)—O—R$^7$, —(CH$_2$)—(CH$_2$)—O—R$^7$ or —(CH$_2$)—(CH$_2$)—(CH$_2$)—O—R$^7$;
- —C(=O)—R$^8$, or
- —S(=O)$_2$—NR$^9$R$^{10}$;

R$^3$ denotes
- —(CHR$^{11}$)—(CH$_2$)—C(=O)—O—R$^{12}$;
- —(CHR$^{13}$)—R$^{14}$, —(CHR$^{13}$)—(CH$_2$)—R$^{14}$, —(CHR$^{13}$)—(CH$_2$)—(CH$_2$)—R$^{14}$ or denotes —(CHR$^{13}$)—(CH$_2$)—O—R$^{14}$;
- a group selected from the group consisting of vinyl, 1-propenyl, 2-propenyl, 1-butenyl, 2-butenyl and 3-butenyl; or
- a phenyl group, wherein said phenyl group optionally may be substituted with 1, 2, 3, 4 or 5 substituents independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, n-hexyl, n-heptyl, —C(=O)—CH$_3$, —C(=O)—C$_2$H$_5$, —C(=O)—C(CH$_3$)$_3$, —C(=O)—CF$_3$ and —C(=O)—C$_2$F$_5$;

R$^4$ denotes
- —(CHR$^{15}$)—R$^{16}$, —(CHR$^{15}$)—(CH$_2$)—R$^{16}$ or —(CHR$^{15}$)—(CH$_2$)—(CH$_2$)—R$^{16}$; or
- a group selected from the group consisting of phenyl and naphthyl, wherein said phenyl or naphthyl group optionally may be substituted with 1, 2, 3, 4 or 5 substituents independently selected from the group consisting of F, Cl, Br, —NO$_2$, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, methyl, ethyl, n-propyl, isopropyl, n-butyl, sec-butyl, isobutyl, tert-butyl, n-pentyl, n-hexyl, n-heptyl, —C(=O)—O—CH$_3$, —C(=O)—O—CH$_2$—CH$_3$, —C(=O)—O—CH(CH$_3$)$_2$, —C(=O)—O—C(CH$_3$)$_3$, —C(=O)—CH$_3$, —C(=O)—C$_2$H$_5$, —C(=O)—C(CH$_3$)$_3$, —C(=O)—CF$_3$ and —C(=O)—C$_2$F$_5$;

R$^5$ denotes
- —(CHR$^{17}$)—R$^{18}$, —(CHR$^{17}$)—(CH$_2$)—R$^{18}$ or —(CHR$^{17}$)—(CH$_2$)—(CH$_2$)—R$^{18}$;
- a group selected from the group consisting of methyl, ethyl, n-propyl, isopropyl, n-butyl, sec-butyl, isobutyl, tert-butyl, n-pentyl, sec-pentyl, —(CH$_2$)—(CH$_2$)—(C(CH$_3$)$_3$), n-hexyl, n-heptyl, n-octyl and —(CH$_2$)—(CH)(C$_2$H$_5$)—(CH$_2$)—(CH$_2$)—(CH$_2$)—(CH$_3$); or
- a group selected from the group consisting of phenyl, naphthyl, pyrazolyl, thiophenyl, [1,2,3,4]-tetrahydroquinolinyl and [1,2,3,4]-tetrahydroisoquinolinyl, wherein said group optionally may be substituted with 1, 2, 3, 4 or 5 substituents independently selected from the group consisting of F, Cl, Br, I, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —C(=O)—O—CH$_3$, —C(=O)—O—CH$_2$—CH$_3$, —C(=O)—O—CH(CH$_3$)$_2$, —C(=O)—O—C(CH$_3$)$_3$, —C(=O)—CF$_3$, —C(=O)—C$_2$F$_5$, —S(=O)$_2$—CH$_3$ and —S(=O)$_2$—C$_2$H$_5$;

R$^6$ denotes a group selected from the group consisting of phenyl, naphthyl, pyrazolyl, thiophenyl and thiazolyl, wherein said group optionally may be substituted with 1, 2, 3, 4 or 5 substituents independently selected from the group consisting of F, Cl, Br, —CF$_3$, —CN, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —O—CF$_3$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —S(=O)$_2$—NH-phenyl, phenyl and benzyl, wherein the cyclic moiety of the —S(=O)$_2$—NH-phenyl, phenyl and benzyl groups optionally may be substituted with 1, 2, 3, 4 or 5 substituents independently selected from the group consisting of F, Cl and Br;

R$^7$ denotes a group selected from the group consisting of phenyl, naphthyl, benzo[b]furanyl, benzo[b]thiophenyl and [1,2,4]-oxadiazolyl, wherein said group optionally may be substituted with 1, 2, 3, 4 or 5 substituents independently selected from the group consisting of F, Cl, Br, —CN, —CF$_3$, —SF$_5$, —OH, —O—CH$_3$, —O—C$_2$H$_5$, —NO$_2$, —O—CF$_3$, —S—CF$_3$, —S—CF$_2$H, —S—CFH$_2$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, phenyl and benzyl, wherein the cyclic moiety of the phenyl and benzyl groups optionally may be substituted with 1, 2, 3, 4 or 5 substituents independently selected from the group consisting of F, Cl, Br, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$;

R$^8$ denotes
- —(CHR$^{19}$)—R$^{20}$, —(CHR$^{19}$)—(CH$_2$)—R$^{20}$, —(CHR$^{19}$)—(CH$_2$)—(CH$_2$)—R$^{20}$, —(CHR$^{19}$)—O—R$^{20}$, —(CHR$^{19}$)—(CH$_2$)—O—R$^{20}$, —(CHR$^{19}$)—(CH$_2$)—(CH$_2$)—O—R$^{20}$, —(CHR$^{19}$)—O—(CH$_2$)—R$^{20}$ or —(CHR$^{19}$)—O—(CH$_2$)—(CH$_2$)—O—R$^{20}$;
- —(CH=CH)—R$^{21}$;
- —(CR$^{22}$R$^{23}$)—C(=O)—O—R$^{26}$, —(CR$^{22}$R$^{23}$)—(CR$^{24}$R$^{25}$)—C(=O)—O—R$^{26}$, —(CR$^{22}$R$^{23}$)—(CR$^{24}$R$^{25}$)—(CH$_2$)—C(=O)—O—R$^{26}$ or —(CR$^{22}$R$^{23}$)—O—(CR$^{24}$R$^{25}$)—C(=O)—O—R$^{26}$;
- —(CHR$^{27}$)—O—C(=O)—R$^{28}$;
- —CH[(CH$_2$)R$^{29}$][NH—S(=O)$_2$—R$^{30}$];
- —CH[(CH$_2$)R$^{31}$][NH—C(=O)—O—R$^{32}$];
- a group selected from the group consisting of methyl, ethyl, n-propyl, isopropyl, n-butyl, sec-butyl, isobutyl, tert-butyl, n-pentyl, sec-pentyl, 3-pentyl, —(CH$_2$)—(CH$_2$)—(C(CH$_3$)$_3$), n-hexyl, 2-hexyl, 3-hexyl, n-heptyl, 2-heptyl, 3-heptyl, 4-heptyl and n-octyl;
- a group selected from the group consisting of cyclopropyl, cyclobutyl, cyclopentyl, cyclohexyl, cycloheptyl, pyrrolidinyl, piperidinyl and adamantyl, wherein said group optionally may be substituted with 1, 2, 3, 4 or 5 substituents independently selected from the group consisting of —C(=O)—CH$_3$, —C(=O)—C$_2$H$_5$, —C(=O)—C(CH$_3$)$_3$ and phenyl; or a group selected from the group consisting of phenyl, naphthyl, 2H-chromenyl, thiophenyl, furanyl, pyrazolyl, triazolyl, pyridinyl, [1,2,3]-thiadiazolyl, [2,1,3]-benzoxadiazolyl, [1,2,3]-benzoxadiazolyl, oxazolyl and isoxazolyl, wherein said group optionally may be substituted with 1, 2, 3, 4 or 5 substituents independently selected from the group consisting of F, Cl, Br, —CN, —CF$_3$, —O—CH$_3$, —O—C$_2$H$_5$, —O—CH(CH$_3$)$_2$, —O—CH$_2$—CH$_2$—CH$_3$, —O—C(CH$_3$)$_3$, —O—CH$_2$—CH$_2$—CH$_2$—CH$_3$, —NO$_2$, —O—CF$_3$, —S—CF$_3$, —S—CF$_2$H, —S—CFH$_2$, —S—CH$_3$, —S—C$_2$H$_5$, methyl, ethyl, n-propyl, isopropyl, n-butyl, sec-butyl, isobutyl, tert-butyl, n-pentyl, —C(CH$_3$)$_2$—C$_2$H$_5$, n-hexyl, n-heptyl, —NH—C(=O)—CH$_3$, —NH—C(=O)—C$_2$H$_5$, —NH—CH$_3$, —NH—C$_2$H$_5$, —NH—CH(CH$_3$)$_2$, —NH—C(CH$_3$)$_3$, —N(CH$_3$)$_2$, —N(C$_2$H$_5$)$_2$, —N(CH$_3$)(C$_2$H$_5$), —S(=O)$_2$—NH$_2$, phenyl, —O-phenyl, —O-benzyl and benzyl; wherein the cyclic moiety of the phenyl, —O-phenyl, —O-benzyl and benzyl groups optionally may be substituted with 1, 2, 3, 4 or 5 substituents independently selected from the group consisting of F, Cl and Br;

R$^9$ and R$^{10}$ each independently denote a group selected from the group consisting of methyl, ethyl, n-propyl, isopropyl, n-butyl, sec-butyl, isobutyl and tert-butyl;

R$^{11}$, R$^{13}$, R$^{15}$, R$^{17}$, R$^{19}$, R$^{22}$, R$^{23}$, R$^{24}$, R$^{25}$ and R$^{26}$ each independently denote hydrogen or a group selected from the group consisting of methyl, ethyl and n-propyl;

R$^{12}$, R$^{28}$ and R$^{32}$, mutually independently, in each case denote a group selected from the group consisting of methyl, ethyl, n-propyl, isopropyl, n-butyl, sec-butyl, isobutyl and tert-butyl;

R$^{14}$ denotes a group selected from the group consisting of methyl, ethyl, n-propyl, isopropyl, n-butyl, sec-butyl, isobutyl and tert-butyl;

a group selected from the group consisting of cyclopropyl, cyclobutyl, cyclopentyl, cyclohexyl, cycloheptyl, tetrahydrofuranyl, tetrahydrothiophenyl and tetrahydropyranyl; or a phenyl group which may be substituted with 1, 2, 3, 4 or 5 substituents selected from the group consisting of F, Cl and Br;

R$^{16}$ denotes a group selected from the group consisting of phenyl and naphthyl, wherein the group may in each case be substituted with 1, 2, 3, 4 or 5 substituents mutually independently selected from the group consisting of F, Cl and Br;

R$^{18}$ denotes a 7,7-dimethyl-2-oxobicyclo[2.2.1]hept-1-yl group;

R$^{20}$ denotes a group selected from the group consisting of methyl, ethyl, n-propyl, isopropyl, n-butyl, sec-butyl, isobutyl and tert-butyl;

a group selected from the group consisting of cyclopropyl, cyclobutyl, cyclopentyl, cyclohexyl and cycloheptyl; wherein the group may in each case be substituted with a substituent selected from the group consisting of —(CH$_2$)—C(=O)—OH and —C(=O)—OH; or a phenyl group which optionally may be substituted with 1, 2, 3, 4 or 5 substituents independently selected from the group consisting of F, Cl, Br, —O—CH$_3$, —O—C$_2$H$_5$, —O—CH(CH$_3$)$_2$, —O—CH$_2$—CH$_2$—CH$_3$, —O—C(CH$_3$)$_3$ and —O—CH$_2$—CH$_2$—CH$_2$—CH$_3$;

R$^{21}$ denotes a phenyl group which may be substituted with 1, 2, 3, 4 or 5 substituents selected from the group consisting of F, Cl, and Br;

R$^{27}$ denotes a phenyl group;

R$^{29}$ denotes a phenyl group;

R$^{30}$ denotes a phenyl group which optionally may be substituted with 1, 2, 3, 4 or 5 substituents selected from the group consisting of methyl, ethyl, n-propyl, isopropyl, n-butyl, sec-butyl, and tert-butyl; and R$^{31}$ denotes an indolyl group.

19. A compound as claimed in claim 1 selected from the group consisting of

[1] 3-(4-methylbenzyl)-2-oxo-1-oxa-3,8-diazaspiro[4.5]decane-8-carbothioic acid pentafluorophenylamide

[2] 3-(3-bromobenzyl)-2-oxo-1-oxa-3,8-diazaspiro[4.5]decane-8-carbothioic acid (2,5-dichlorophenyl)amide

[3] 2-oxo-3-(4-trifluoromethylbenzyl)-1-oxa-3,8-diazaspiro[4.5]decane-8-carbothioic acid benzylamide

[4] 3-(3,5-dimethylbenzyl)-2-oxo-1-oxa-3,8-diazaspiro[4.5]decane-8-carbothioic acid (tetrahydrofuran-2-ylmethyl)amide

[5] 3-(3-bromobenzyl)-2-oxo-1-oxa-3,8-diazaspiro[4.5]decane-8-carbothioic acid (2-methoxyethyl)amide

[6] 3-(3-bromobenzyl)-2-oxo-1-oxa-3,8-diazaspiro[4.5]decane-8-carbothioic acid (2-methoxyphenyl)amide

[7] 3-(3,5-dimethylbenzyl)-2-oxo-1-oxa-3,8-diazaspiro[4.5]decane-8-carbothioic acid (3-acetylphenyl)amide

[8] 3-benzyl-2-oxo-1-oxa-3,8-diazaspiro[4.5]decane-8-carbothioic acid o-tolylamide

[9] 3-{[3-(3-bromobenzyl)-2-oxo-1-oxa-3,8-diazaspiro[4.5]decane-8-carbothioyl]amino}butanoic acid ethyl ester

[10] 3-naphthalen-2-ylmethyl-2-oxo-1-oxa-3,8-diazaspiro[4.5]decane-8-carbothioic acid allylamide

[11] 3-(3,4-difluorobenzyl)-2-oxo-1-oxa-3,8-diazaspiro[4.5]decane-8-carbothioic acid benzylamide

[12] 3-biphenyl-2-ylmethyl-2-oxo-1-oxa-3,8-diazaspiro[4.5]decane-8-carbothioic acid (1-phenylethyl)amide

[13] 3-(3,4-difluorobenzyl)-2-oxo-1-oxa-3,8-diazaspiro[4.5]decane-8-carbothioic acid (4-ethoxyphenyl)amide

[14] 3-(3-cyanobenzyl)-2-oxo-1-oxa-3,8-diazaspiro[4.5]decane-8-carbothioic acid (3,5-dichlorophenyl)amide

[15] 3-(3-cyanobenzyl)-2-oxo-1-oxa-3,8-diazaspiro[4.5]decane-8-carbothioic acid (3-trifluoromethylphenyl)amide

[16] 3-(3-bromobenzyl)-2-oxo-1-oxa-3,8-diazaspiro[4.5]decane-8-carbothioic acid benzylamide

[17] 3-(2-methoxy-5-nitrobenzyl)-2-oxo-1-oxa-3,8-diazaspiro[4.5]decane-8-carbothioic acid (tetrahydrofuran-2-ylmethyl)amide

[18] 3-biphenyl-2-ylmethyl-2-oxo-1-oxa-3,8-diazaspiro[4.5]decan-8-carbothioic acid phenylamide

[19] 3-(3-cyanobenzyl)-2-oxo-1-oxa-3,8-diazaspiro[4.5]decane-8-carbothioic acid cyclohexylmethylamide

[20] 3-(2-fluorobenzyl)-2-oxo-1-oxa-3,8-diazaspiro[4.5]decane-8-carbothioic acid (3-acetylphenyl)amide

[21] 3-(2-methoxy-5-nitrobenzyl)-2-oxo-1-oxa-3,8-diazaspiro[4.5]decane-8-carbothioic acid cyclohexylmethylamide

[22] 3-(3-cyanobenzyl)-2-oxo-1-oxa-3,8-diazaspiro[4.5]decane-8-carbothioic acid 4-chlorobenzylamide

[23] 3-(2-methoxy-5-nitrobenzyl)-2-oxo-1-oxa-3,8-diazaspiro[4.5]decane-8-carbothioic acid benzylamide

[24] 3-(2-fluorobenzyl)-2-oxo-1-oxa-3,8-diazaspiro[4.5]decane-8-carboxylic acid (4-ethoxyphenyl)amide
[25] 3-biphenyl-2-ylmethyl-2-oxo-1-oxa-3,8-diazaspiro[4.5]decane-8-carboxylic acid (2,5-dichlorophenyl)amide
[26] 3-(2-methoxy-5-nitrobenzyl)-2-oxo-1-oxa-3,8-diazaspiro[4.5]decane-8-carboxylic acid (2,5-difluorophenyl)amide
[27] 3-(4-methylbenzyl)-2-oxo-1-oxa-3,8-diazaspiro[4.5]decane-8-carboxylic acid (4-methyl-3-nitrophenyl)amide
[28] 3-(3,4-difluorobenzyl)-2-oxo-1-oxa-3,8-diazaspiro[4.5]decane-8-carboxylic acid 4-fluorobenzylamide
[29] 3-(3-bromobenzyl)-2-oxo-1-oxa-3,8-diazaspiro[4.5]decane-8-carboxylic acid (2,5-difluorophenyl)amide
[30] 4-[(3-naphthalen-2-ylmethyl-2-oxo-1-oxa-3,8-diazaspiro[4.5]decane-8-carbonyl)amino]benzoic acid ethyl ester
[31] 2-oxo-3-(4-trifluoromethylbenzyl)-1-oxa-3,8-diazaspiro[4.5]decane-8-carboxylic acid (4-chloro-3-trifluoromethylphenyl)amide
[32] 3-(2-cyanobenzyl)-2-oxo-1-oxa-3,8-diazaspiro[4.5]decane-8-carboxylic acid (2,5-difluorophenyl)amide
[33] 3-benzyl-2-oxo-1-oxa-3,8-diazaspiro[4.5]decane-8-carboxylic acid (3-cyanophenyl)amide
[34] 3-(3,4-difluorobenzyl)-2-oxo-1-oxa-3,8-diazaspiro[4.5]decane-8-carboxylic acid (4-methyl-3-nitrophenyl)amide
[35] 3-(3,4-difluorobenzyl)-2-oxo-1-oxa-3,8-diazaspiro[4.5]decane-8-carboxylic acid (3-methoxyphenyl)amide
[36] 3-(4-methylbenzyl)-2-oxo-1-oxa-3,8-diazaspiro[4.5]decane-8-carboxylic acid 3,4-dichlorobenzylamide
[37] 3-benzyl-2-oxo-1-oxa-3,8-diazaspiro[4.5]decane-8-carboxylic acid (4-chloro-3-trifluoromethylphenyl)amide
[38] 2-oxo-3-(4-trifluoromethylsulfanylbenzyl)-1-oxa-3,8-diazaspiro[4.5]decane-8-carboxylic acid (3-cyanophenyl)amide
[39] 3-benzyl-2-oxo-1-oxa-3,8-diazaspiro[4.5]decane-8-carboxylic acid (4-methoxyphenyl)amide
[40] 2-oxo-3-(4-trifluoromethylsulfanylbenzyl)-1-oxa-3,8-diazaspiro[4.5]decane-8-carboxylic acid (4-methyl-3-nitrophenyl)amide
[41] 3-(4-iodobenzyl)-2-oxo-1-oxa-3,8-diazaspiro[4.5]decane-8-carboxylic acid (4-butoxyphenyl)amide
[42] 3-(3-bromobenzyl)-2-oxo-1-oxa-3,8-diazaspiro[4.5]decane-8-carboxylic acid 3,4-dichlorobenzylamide
[43] 3-benzyl-2-oxo-1-oxa-3,8-diazaspiro[4.5]decane-8-carboxylic acid (1-phenylethyl)amide
[44] 3-naphthalen-2-ylmethyl-2-oxo-1-oxa-3,8-diazaspiro[4.5]decane-8-carboxylic acid 3,4-dichlorobenzylamide
[45] 3-(4-methylbenzyl)-2-oxo-1-oxa-3,8-diazaspiro[4.5]decane-8-carboxylic acid phenethylamide
[46] 2-oxo-3-(2-trifluoromethylbenzyl)-1-oxa-3,8-diazaspiro[4.5]decane-8-carboxylic acid (3-methoxyphenyl)amide
[47] 3-(4-cyanobenzyl)-2-oxo-1-oxa-3,8-diazaspiro[4.5]decane-8-carboxylic acid (4-methoxyphenyl)amide
[48] 2-oxo-3-(4-trifluoromethylbenzyl)-1-oxa-3,8-diazaspiro[4.5]decane-8-carboxylic acid (1-naphthalen-1-ylethyl)amide
[49] 2-oxo-3-(2-trifluoromethylbenzyl)-1-oxa-3,8-diazaspiro[4.5]decane-8-carboxylic acid phenethylamide
[50] 3-(4-iodobenzyl)-2-oxo-1-oxa-3,8-diazaspiro[4.5]decane-8-carboxylic acid (4-methyl-3-nitrophenyl)amide
[51] 3-(2-methoxy-5-nitrobenzyl)-2-oxo-1-oxa-3,8-diazaspiro[4.5]decane-8-carboxylic acid (3-cyanophenyl)amide
[52] 3-naphthalen-2-ylmethyl-2-oxo-1-oxa-3,8-diazaspiro[4.5]decane-8-carboxylic acid (4-methoxyphenyl)amide
[53] 3-{[3-(4-methylbenzyl)-2-oxo-1-oxa-3,8-diazaspiro[4.5]decane-8-carbonyl]amino}benzoic acid ethyl ester
[54] 2-oxo-3-(2-trifluoromethylbenzyl)-1-oxa-3,8-diazaspiro[4.5]decane-8-carboxylic acid (1-naphthalen-1-ylethyl)amide
[55] 3-naphthalen-2-ylmethyl-2-oxo-1-oxa-3,8-diazaspiro[4.5]decane-8-carboxylic acid (2,5-dimethoxyphenyl)amide
[56] 3-(4-cyanobenzyl)-2-oxo-1-oxa-3,8-diazaspiro[4.5]decane-8-carboxylic acid (3-acetylphenyl)amide
[57] 3-biphenyl-2-ylmethyl-2-oxo-1-oxa-3,8-diazaspiro[4.5]decane-8-carboxylic acid phenethylamide
[58] 3-(4-cyanobenzyl)-2-oxo-1-oxa-3,8-diazaspiro[4.5]decane-8-carboxylic acid (5-chloro-2-methoxyphenyl)amide
[59] 3-{[2-oxo-3-(2-trifluoromethylbenzyl)-1-oxa-3,8-diazaspiro[4.5]decane-8-carbonyl]amino}benzoic acid ethyl ester
[60] 3-benzyl-2-oxo-1-oxa-3,8-diazaspiro[4.5]decane-8-carboxylic acid (3-fluorophenyl)amide
[61] 3-{[3-(3-cyanobenzyl)-2-oxo-1-oxa-3,8-diazaspiro[4.5]decane-8-carbonyl]amino}benzoic acid ethyl ester
[62] 3-biphenyl-2-ylmethyl-2-oxo-1-oxa-3,8-diazaspiro[4.5]decane-8-carboxylic acid (3-methoxyphenyl)amide
[63] 3-(2-methoxy-5-nitrobenzyl)-2-oxo-1-oxa-3,8-diazaspiro[4.5]decane-8-carboxylic acid (1-naphthalen-1-ylethyl)amide
[64] {2-[3-(3,4-difluorobenzyl)-2-oxo-1-oxa-3,8-diazaspiro[4.5]dec-8-yl]-2-oxoethoxy}acetic acid
[65] 4-[3-(3,4-difluorobenzyl)-2-oxo-1-oxa-3,8-diazaspiro[4.5]dec-8-yl]-3,3-dimethyl-4-oxobutanoic acid
[66] [2-[3-(3-bromobenzyl)-2-oxo-1-oxa-3,8-diazaspiro[4.5]dec-8-yl]-1-(1H-indol-3-ylmethyl)-2-oxoethyl]carbamic acid tert-butyl ester
[67] 5-[3-(2-fluorobenzyl)-2-oxo-1-oxa-3,8-diazaspiro[4.5]dec-8-yl]-3-methyl-5-oxopentanoic acid
[68] 3,3-dimethyl-5-[3-(4-methylbenzyl)-2-oxo-1-oxa-3,8-diazaspiro[4.5]dec-8-yl]-5-oxopentanoic acid
[69] 5-[3-(3,4-difluorobenzyl)-2-oxo-1-oxa-3,8-diazaspiro[4.5]dec-8-yl]-3-methyl-5-oxopentanoic acid
[70] {2-oxo-2-[2-oxo-3-(4-trifluoromethylbenzyl)-1-oxa-3,8-diazaspiro[4.5]dec-8-yl]ethoxy}acetic acid
[71] (1-{2-[3-(2-cyanobenzyl)-2-oxo-1-oxa-3,8-diazaspiro[4.5]dec-8-yl]-2-oxoethyl}cyclopentyl)acetic acid
[72] (1-{2-[3-(3,4-difluorobenzyl)-2-oxo-1-oxa-3,8-diazaspiro[4.5]dec-8-yl]-2-oxoethyl}cyclopentyl)acetic acid
[73] 5-(3-biphenyl-2-ylmethyl-2-oxo-1-oxa-3,8-diazaspiro[4.5]dec-8-yl)-3-methyl-5-oxopentanoic acid
[75] N-[4-(3,5-dichlorophenylsulfamoyl)phenyl]-2-[3-(4-methylbenzyl)-2-oxo-1-oxa-3,8-diazaspiro[4.5]dec-8-yl]acetamide
[76] N-(2,5-dimethyl-2H-pyrazol-3-yl)-2-[3-(2-methoxy-5-nitrobenzyl)-2-oxo-1-oxa-3,8-diazaspiro[4.5]dec-8-yl]acetamide

[80] N-(3-cyano-4-methylthiophen-2-yl)-2-[3-(3,4-difluorobenzyl)-2-oxo-1-oxa-3,8-diazaspiro[4.5]dec-8-yl]acetamide
[85] 2-[2-oxo-3-(4-trifluoromethylsulfanylbenzyl)-1-oxa-3,8-diazaspiro[4.5]dec-8-yl]-N-(4-phenyl-5-trifluoromethylthiophen-3-yl)acetamide
[86] 2-[3-(2-fluorobenzyl)-2-oxo-1-oxa-3,8-diazaspiro[4.5]dec-8-yl]-N-(4-phenyl-thiazolyl-2-yl)acetamide
[87] 2-[2-oxo-3-(2-trifluoromethylbenzyl)-1-oxa-3,8-diazaspiro[4.5]dec-8-yl]-N-(4-trifluoromethoxyphenyl)acetamide
[91] N-{4-[3-(3-cyanobenzyl)-2-oxo-1-oxa-3,8-diazaspiro[4.5]decane-8-carbonyl]phenyl}acetamide
[92] 8-(4-ethoxybenzoyl)-3-(4-methylbenzyl)-1-oxa-3,8-diazaspiro[4.5]decan-2-one
[93] 3-[3-(4-cyanobenzyl)-2-oxo-1-oxa-3,8-diazaspiro[4.5]dec-8-yl]-3-oxopropionic acid methyl ester
[94] 2-[8-(2,4-difluorobenzoyl)-2-oxo-1-oxa-3,8-diazaspiro[4.5]dec-3-ylmethyl]benzonitrile
[95] 8-(3-dimethylaminobenzoyl)-3-(3,5-dimethylbenzyl)-1-oxa-3,8-diazaspiro[4.5]decan-2-one
[96] N-{4-[3-(3,4-difluorobenzyl)-2-oxo-1-oxa-3,8-diazaspiro[4.5]decane-8-carbonyl]phenyl}acetamide
[97] 8-(4-bromobenzoyl)-3-(4-fluorobenzyl)-1-oxa-3,8-diazaspiro[4.5]decan-2-one
[98] 4-[8-(adamantane-1-carbonyl)-2-oxo-1-oxa-3,8-diazaspiro[4.5]dec-3-ylmethyl]benzonitrile
[99] 3-(3,5-dimethylbenzyl)-8-(2-ethylsulfanylpyridine-3-carbonyl)-1-oxa-3,8-diazaspiro[4.5]decan-2-one
[100] 3-(3-bromobenzyl)-8-(4-chlorobenzoyl)-1-oxa-3,8-diazaspiro[4.5]decan-2-one
[101] 8-[3-(2-chlorophenyl)-5-methylisoxazole-4-carbonyl]-3-(3,5-dimethylbenzyl)-1-oxa-3,8-diazaspiro[4.5]decan-2-one
[102] 3-(3-bromobenzyl)-8-(4-ethylbenzylsulfonyl)-1-oxa-3,8-diazaspiro[4.5]decan-2-one
[103] 8-(4-butoxybenzylsulfonyl)-3-(3,5-dimethylbenzyl)-1-oxa-3,8-diazaspiro[4.5]decan-2-one
[104] 8-(biphenyl-4-carbonyl)-3-(3-bromobenzyl)-1-oxa-3,8-diazaspiro[4.5]decan-2-one
[105] acetic acid 2-[3-(3,5-dimethylbenzyl)-2-oxo-1-oxa-3,8-diazaspiro[4.5]dec-8-yl]-2-oxo-1-phenylethyl ester
[106] 4-[2-oxo-8-(2-phenylcyclopropanecarbonyl)-1-oxa-3,8-diazaspiro[4.5]dec-3-ylmethyl]benzonitrile
[107] 8-(2,5-dimethoxybenzylsulfonyl)-3-(3,5-dimethylbenzyl)-1-oxa-3,8-diazaspiro[4.5]decan-2-one
[108] 8-(2-chlorobenzoyl)-3-(3,5-dimethylbenzyl)-1-oxa-3,8-diazaspiro[4.5]decan-2-one
[109] 3-(3-bromobenzyl)-8-(4-nitrobenzoyl)-1-oxa-3,8-diazaspiro[4.5]decan-2-one
[110] N-{1-benzyl-2-[3-(3-cyanobenzyl)-2-oxo-1-oxa-3,8-diazaspiro[4.5]dec-8-yl]-2-oxoethyl}-4-methylbenzylsulfonamide
[111] 8-(2-ethylsulfanylpyridine-3-carbonyl)-3-(3-methoxybenzyl)-1-oxa-3,8-diazaspiro[4.5]decan-2-one
[112] 8-(2,4-dimethoxybenzoyl)-3-(3-methoxybenzyl)-1-oxa-3,8-diazaspiro[4.5]decan-2-one
[113] 3-(3,5-dimethylbenzyl)-8-[2-(3-methoxyphenyl)acetyl]-1-oxa-3,8-diazaspiro[4.5]decan-2-one
[114] 3-(3,5-dimethylbenzyl)-8-(4-methoxy-2,3,6-trimethylbenzylsulfonyl)-1-oxa-3,8-diazaspiro[4.5]decan-2-one
[115] 4-[8-(biphenyl-4-carbonyl)-2-oxo-1-oxa-3,8-diazaspiro[4.5]dec-3-ylmethyl]benzonitrile
[116] 8-(2-chlorobenzylsulfonyl)-3-(3,5-dimethylbenzyl)-1-oxa-3,8-diazaspiro[4.5]decan-2-one
[117] 8-(benzo[1,2,5]oxadiazole-5-carbonyl)-3-(3,5-dimethylbenzyl)-1-oxa-3,8-diazaspiro[4.5]decan-2-one
[118] 8-(biphenyl-4-carbonyl)-3-(4-iodobenzyl)-1-oxa-3,8-diazaspiro[4.5]decan-2-one
[119] 3-(3,5-dimethylbenzyl)-8-(pyridine-2-carbonyl)-1-oxa-3,8-diazaspiro[4.5]decan-2-one
[120] 8-(6-chloropyridine-3-carbonyl)-3-naphthalen-2-ylmethyl-1-oxa-3,8-diazaspiro[4.5]decan-2-one
[121] 3-(3-bromobenzyl)-8-(2-ethylsulfanylpyridine-3-carbonyl)-1-oxa-3,8-diazaspiro[4.5]decan-2-one
[122] 3-(3,5-dimethylbenzyl)-8-(5-methylisoxazole-3-carbonyl)-1-oxa-3,8-diazaspiro[4.5]decan-2-one
[123] 3-(2-methoxy-5-nitrobenzyl)-8-pentanoyl-1-oxa-3,8-diazaspiro[4.5]decan-2-one
[124] 8-(4-bromobenzoyl)-3-(3,5-dimethylbenzyl)-1-oxa-3,8-diazaspiro[4.5]decan-2-one
[125] 8-(5-tert-butyl-2-methylfuran-3-carbonyl)-3-(2-methoxy-5-nitrobenzyl)-1-oxa-3,8-diazaspiro[4.5]decan-2-one
[126] 8-(3-chlorobenzoyl)-3-(3,5-dimethylbenzyl)-1-oxa-3,8-diazaspiro[4.5]decan-2-one
[127] 8-(2-ethylsulfanylpyridine-3-carbonyl)-3-(2-trifluoromethylbenzyl)-1-oxa-3,8-diazaspiro[4.5]decan-2-one
[128] 3-(3,5-dimethylbenzyl)-8-(isoxazole-5-carbonyl)-1-oxa-3,8-diazaspiro[4.5]decan-2-one
[129] 3-(3-bromobenzyl)-8-(pyridine-2-carbonyl)-1-oxa-3,8-diazaspiro[4.5]decan-2-one
[130] 3-(3,5-dimethylbenzyl)-8-(thiophene-2-carbonyl)-1-oxa-3,8-diazaspiro[4.5]decan-2-one
[131] 8-(3-chloro-4-fluorobenzoyl)-3-(3,5-dimethylbenzyl)-1-oxa-3,8-diazaspiro[4.5]decan-2-one
[132] 8-(2,6-difluoro-3-methylbenzoyl)-3-(3,5-dimethylbenzyl)-1-oxa-3,8-diazaspiro[4.5]decan-2-one
[133] 4-[3-(3-bromobenzyl)-2-oxo-1-oxa-3,8-diazaspiro[4.5]dec-8-yl]-4-oxobutanoic acid methyl ester
[134] 3-[8-(2-ethylbutyryl)-2-oxo-1-oxa-3,8-diazaspiro[4.5]dec-3-ylmethyl]benzonitrile
[135] 3-[8-(3-bromobenzylsulfonyl)-2-oxo-1-oxa-3,8-diazaspiro[4.5]dec-3-ylmethyl]benzonitrile
[136] 3-(3,4-difluorobenzyl)-8-(4-methylbenzoyl)-1-oxa-3,8-diazaspiro[4.5]decan-2-one
[137] 3-(3-bromobenzyl)-8-(3,5-dimethoxybenzoyl)-1-oxa-3,8-diazaspiro[4.5]decan-2-one
[138] 8-(3-dimethylaminobenzoyl)-3-(2-methoxy-5-nitrobenzyl)-1-oxa-3,8-diazaspiro[4.5]decan-2-one
[139] 8-(2,6-dichlorobenzoyl)-3-(2-fluorobenzyl)-1-oxa-3,8-diazaspiro[4.5]decan-2-one
[140] 3-(2-methoxy-5-nitrobenzyl)-8-(2-phenoxypyridine-3-carbonyl)-1-oxa-3,8-diazaspiro[4.5]decan-2-one
[141] 8-[2-(3-methoxyphenyl)acetyl]-3-naphthalen-2-ylmethyl-1-oxa-3,8-diazaspiro[4.5]decan-2-one
[142] 4-{2-oxo-8-[2-(2,2,2-trifluoroacetyl)-1,2,3,4-tetrahydroisoquinoline-7-sulfonyl]-1-oxa-3,8-diazaspiro[4.5]dec-3-ylmethyl}benzonitrile
[143] 8-(3,5-bis-trifluoromethylbenzoyl)-3-(4-trifluoromethylbenzyl)-1-oxa-3,8-diazaspiro[4.5]decan-2-one
[144] 3-(3-bromobenzyl)-8-(2-phenoxypyridine-3-carbonyl)-1-oxa-3,8-diazaspiro[4.5]decan-2-one
[145] 3-(2-methoxy-5-nitrobenzyl)-8-[2-(3-methoxyphenyl)acetyl]-1-oxa-3,8-diazaspiro[4.5]decan-2-one
[146] 3-(3,4-difluorobenzyl)-8-(2-phenoxypyridine-3-carbonyl)-1-oxa-3,8-diazaspiro[4.5]decan-2-one
[147] 3-[8-(4-bromo-3-methylbenzoyl)-2-oxo-1-oxa-3,8-diazaspiro[4.5]dec-3-ylmethyl]benzonitrile

[148] 3-(3-bromobenzyl)-8-(4-propylbenzoyl)-1-oxa-3,8-diazaspiro[4.5]decan-2-one
[149] 3-biphenyl-2-ylmethyl-8-(3-chlorobenzylsulfonyl)-1-oxa-3,8-diazaspiro[4.5]decan-2-one
[150] 8-[2-(3,4-dimethoxyphenyl)acetyl]-3-(2-methoxy-5-nitrobenzyl)-1-oxa-3,8-diazaspiro[4.5]decan-2-one
[151] 2-[8-(2-chloro-4-nitrobenzoyl)-2-oxo-1-oxa-3,8-diazaspiro[4.5]dec-3-ylmethyl]benzonitrile
[152] 3-[2-oxo-8-(2,4,6-trimethylbenzylsulfonyl)-1-oxa-3,8-diazaspiro[4.5]dec-3-ylmethyl]benzonitrile
[153] 3-benzyl-8-(4-fluorobenzylsulfonyl)-1-oxa-3,8-diazaspiro[4.5]decan-2-one
[154] 3-(4-fluorobenzyl)-8-(toluene-4-sulfonyl)-1-oxa-3,8-diazaspiro[4.5]decan-2-one
[155] 4-[2-oxo-8-(toluene-4-sulfonyl)-1-oxa-3,8-diazaspiro[4.5]dec-3-ylmethyl]benzonitrile
[156] 3-(2-fluorobenzyl)-8-(toluene-4-sulfonyl)-1-oxa-3,8-diazaspiro[4.5]decan-2-one
[157] 3-(3,4-difluorobenzyl)-8-(toluene-4-sulfonyl)-1-oxa-3,8-diazaspiro[4.5]decan-2-one
[158] 3-(4-tert-butylbenzyl)-8-(toluene-4-sulfonyl)-1-oxa-3,8-diazaspiro[4.5]decan-2-one
[159] 8-(toluene-4-sulfonyl)-3-(4-trifluoromethylsulfanylbenzyl)-1-oxa-3,8-diazaspiro[4.5]decan-2-one
[160] 2-[3-(4-fluorobenzyl)-2-oxo-1-oxa-3,8-diazaspiro[4.5]decan-8-sulfonyl]benzoic acid methyl ester
[161] 2-[3-(3-methoxybenzyl)-2-oxo-1-oxa-3,8-diazaspiro[4.5]decan-8-sulfonyl]benzoic acid methyl ester
[162] 2-[3-(3-bromobenzyl)-2-oxo-1-oxa-3,8-diazaspiro[4.5]decan-8-sulfonyl]benzoic acid methyl ester
[163] 3-benzyl-8-(2-methanesulfonylbenzylsulfonyl)-1-oxa-3,8-diazaspiro[4.5]decan-2-one
[164] 8-(2-methanesulfonylbenzylsulfonyl)-3-(2-methoxy-5-nitrobenzyl)-1-oxa-3,8-diazaspiro[4.5]decan-2-one
[165] 3-(4-methylbenzyl)-2-oxo-1-oxa-3,8-diazaspiro[4.5]decane-8-sulfonic acid dimethylamide
[166] 4-[8-(7,7-dimethyl-2-oxobicyclo[2.2.1]hept-1-ylmethanesulfonyl)-2-oxo-1-oxa-3,8-diazaspiro[4.5]dec-3-ylmethyl]benzonitrile
[167] 3-(4-fluorobenzyl)-8-(4-methoxybenzylsulfonyl)-1-oxa-3,8-diazaspiro[4.5]decan-2-one
[168] 3-(4-methylbenzyl)-8-(4-trifluoromethoxybenzylsulfonyl)-1-oxa-3,8-diazaspiro[4.5]decan-2-one
[169] 8-(4-trifluoromethoxybenzylsulfonyl)-3-(4-trifluoromethylsulfanylbenzyl)-1-oxa-3,8-diazaspiro[4.5]decan-2-one
[170] 8-(propane-1-sulfonyl)-3-(4-trifluoromethylsulfanylbenzyl)-1-oxa-3,8-diazaspiro[4.5]decan-2-one
[171] 3-(2-methoxy-5-nitrobenzyl)-8-(4-propylbenzylsulfonyl)-1-oxa-3,8-diazaspiro[4.5]decan-2-one
[172] 3-biphenyl-2-ylmethyl-8-(4-propylbenzylsulfonyl)-1-oxa-3,8-diazaspiro[4.5]decan-2-one
[173] 8-(3-bromobenzylsulfonyl)-3-(2-fluorobenzyl)-1-oxa-3,8-diazaspiro[4.5]decan-2-one
[174] 8-(3-bromobenzylsulfonyl)-3-(3-bromobenzyl)-1-oxa-3,8-diazaspiro[4.5]decan-2-one
[175] 2-{8-[4-(1,1-dimethylpropyl)benzylsulfonyl]-2-oxo-1-oxa-3,8-diazaspiro[4.5]dec-3-ylmethyl}benzonitrile
[176] 3-benzyl-8-[4-(1,1-dimethylpropyl)benzylsulfonyl]-1-oxa-3,8-diazaspiro[4.5]decan-2-one
[177] 8-[4-(1,1-dimethylpropyl)benzylsulfonyl]-3-(4-iodobenzyl)-1-oxa-3,8-diazaspiro[4.5]decan-2-one
[178] 8-[4-(1,1-dimethylpropyl)benzylsulfonyl]-3-(2-methoxy-5-nitrobenzyl)-1-oxa-3,8-diazaspiro[4.5]decan-2-one
[179] 8-[4-(1,1-dimethylpropyl)benzylsulfonyl]-3-(4-trifluoromethylbenzyl)-1-oxa-3,8-diazaspiro[4.5]decan-2-one
[180] 3-biphenyl-2-ylmethyl-8-[4-(1,1-dimethylpropyl)benzylsulfonyl]-1-oxa-3,8-diazaspiro[4.5]decan-2-one
[181] 8-(4,5-dichlorothiophene-2-sulfonyl)-3-(3-methoxybenzyl)-1-oxa-3,8-diazaspiro[4.5]decan-2-one
[182] 8-(4,5-dichlorothiophene-2-sulfonyl)-3-(4-trifluoromethylbenzyl)-1-oxa-3,8-diazaspiro[4.5]decan-2-one
[183] 3-(3-bromobenzyl)-8-(4,5-dichlorothiophene-2-sulfonyl)-1-oxa-3,8-diazaspiro[4.5]decan-2-one
[184] 2-[8-(4-methoxy-2,3,6-trimethylbenzylsulfonyl)-2-oxo-1-oxa-3,8-diazaspiro[4.5]dec-3-ylmethyl]benzonitrile
[185] 3-(2-fluorobenzyl)-8-(4-methoxy-2,3,6-trimethylbenzylsulfonyl)-1-oxa-3,8-diazaspiro[4.5]decan-2-one
[186] 3-(4-tert-butylbenzyl)-8-[2-(2,2,2-trifluoroacetyl)-1,2,3,4-tetrahydroisoquinoline-7-sulfonyl]-1-oxa-3,8-diazaspiro[4.5]decan-2-one
[187] 8-(butane-1-sulfonyl)-3-(3-methoxybenzyl)-1-oxa-3,8-diazaspiro[4.5]decan-2-one
[188] 3-(4-methylbenzyl)-8-(thiophene-2-sulfonyl)-1-oxa-3,8-diazaspiro[4.5]decan-2-one
[189] 8-(4-chloro-2,5-dimethylbenzylsulfonyl)-3-(4-methylbenzyl)-1-oxa-3,8-diazaspiro[4.5]decan-2-one
[190] 3-benzyl-8-(4-chloro-2,5-dimethylbenzylsulfonyl)-1-oxa-3,8-diazaspiro[4.5]decan-2-one
[191] 8-(4-chloro-2,5-dimethylbenzylsulfonyl)-3-(4-trifluoromethylbenzyl)-1-oxa-3,8-diazaspiro[4.5]decan-2-one
[192] 3-biphenyl-2-ylmethyl-8-(4-chloro-2,5-dimethylbenzylsulfonyl)-1-oxa-3,8-diazaspiro[4.5]decan-2-one
[193] 8-(4-chloro-2,5-dimethylbenzylsulfonyl)-3-(4-trifluoromethylsulfanylbenzyl)-1-oxa-3,8-diazaspiro[4.5]decan-2-one
[194] 3-(4-fluorobenzyl)-8-(2-trifluoromethylbenzylsulfonyl)-1-oxa-3,8-diazaspiro[4.5]decan-2-one
[195] 3-(3-methoxybenzyl)-8-(2-trifluoromethylbenzylsulfonyl)-1-oxa-3,8-diazaspiro[4.5]decan-2-one
[196] 3-benzyl-8-(2-methyl-5-nitrobenzylsulfonyl)-1-oxa-3,8-diazaspiro[4.5]decan-2-one
[197] 3-(4-tert-butylbenzyl)-8-(2-methyl-5-nitrobenzylsulfonyl)-1-oxa-3,8-diazaspiro[4.5]decan-2-one
[198] 3-(4-tert-butylbenzyl)-8-(toluene-3-sulfonyl)-1-oxa-3,8-diazaspiro[4.5]decan-2-one
[199] 8-(furan-2-carbonyl)-3-(4-trifluoromethylbenzyl)-1-oxa-3,8-diazaspiro[4.5]decan-2-one
[200] 3-(3-bromobenzyl)-8-(furan-2-carbonyl)-1-oxa-3,8-diazaspiro[4.5]decan-2-one
[201] 4-[8-(naphthalene-1-carbonyl)-2-oxo-1-oxa-3,8-diazaspiro[4.5]dec-3-ylmethyl]benzonitrile
[202] 3-(3,4-difluorobenzyl)-8-(naphthalene-1-carbonyl)-1-oxa-3,8-diazaspiro[4.5]decan-2-one
[203] 3-(3-bromobenzyl)-8-(naphthalene-1-carbonyl)-1-oxa-3,8-diazaspiro[4.5]decan-2-one
[204] 2-[8-(3-nitrobenzoyl)-2-oxo-1-oxa-3,8-diazaspiro[4.5]dec-3-ylmethyl]benzonitrile
[205] 4-[8-(3-nitrobenzoyl)-2-oxo-1-oxa-3,8-diazaspiro[4.5]dec-3-ylmethyl]benzonitrile
[206] 3-(3-bromobenzyl)-8-(3,5-difluorobenzoyl)-1-oxa-3,8-diazaspiro[4.5]decan-2-one
[207] 8-(2-benzyloxy-acetyl)-3-(2-fluorobenzyl)-1-oxa-3,8-diazaspiro[4.5]decan-2-one
[208] 8-(2-chlorobenzoyl)-3-(2-trifluoromethylbenzyl)-1-oxa-3,8-diazaspiro[4.5]decan-2-one

[209] 8-(2-chlorobenzoyl)-3-(4-iodobenzyl)-1-oxa-3,8-diazaspiro[4.5]decan-2-one
[210] 8-(2-chlorobenzoyl)-3-(2-methoxy-5-nitrobenzyl)-1-oxa-3,8-diazaspiro[4.5]decan-2-one
[211] 3-biphenyl-2-ylmethyl-8-(2-chlorobenzoyl)-1-oxa-3,8-diazaspiro[4.5]decan-2-one
[212] 8-(2,6-dichlorobenzoyl)-3-naphthalen-2-ylmethyl-1-oxa-3,8-diazaspiro[4.5]decan-2-one
[213] 3-(4-tert-butylbenzyl)-8-(2,6-dichlorobenzoyl)-1-oxa-3,8-diazaspiro[4.5]decan-2-one
[214] 3-(3-bromobenzyl)-8-(2,6-dichlorobenzoyl)-1-oxa-3,8-diazaspiro[4.5]decan-2-one
[215] 8-(2,6-dichlorobenzoyl)-3-(4-trifluoromethylsulfanylbenzyl)-1-oxa-3,8-diazaspiro[4.5]decan-2-one
[216] 2-[8-(2-methylbenzoyl)-2-oxo-1-oxa-3,8-diazaspiro[4.5]dec-3-ylmethyl]benzonitrile
[217] 8-(2-methylbenzoyl)-3-(4-methylbenzyl)-1-oxa-3,8-diazaspiro[4.5]decan-2-one
[218] 8-(2-methylbenzoyl)-3-(2-trifluoromethylbenzyl)-1-oxa-3,8-diazaspiro[4.5]decan-2-one
[219] 3-(2-methoxy-5-nitrobenzyl)-8-(2-methylbenzoyl)-1-oxa-3,8-diazaspiro[4.5]decan-2-one
[220] 3-(3,4-difluorobenzyl)-8-(2-methylbenzoyl)-1-oxa-3,8-diazaspiro[4.5]decan-2-one
[221] 8-(2-methylbenzoyl)-3-(4-trifluoromethylbenzyl)-1-oxa-3,8-diazaspiro[4.5]decan-2-one
[222] 8-(2-methylbenzoyl)-3-(4-trifluoromethylsulfanylbenzyl)-1-oxa-3,8-diazaspiro[4.5]decan-2-one
[223] 8-(3-bromobenzoyl)-3-(4-fluorobenzyl)-1-oxa-3,8-diazaspiro[4.5]decan-2-one
[224] 8-(3-bromobenzoyl)-3-(2-trifluoromethylbenzyl)-1-oxa-3,8-diazaspiro[4.5]decan-2-one
[225] 8-(3-bromobenzoyl)-3-(2-fluorobenzyl)-1-oxa-3,8-diazaspiro[4.5]decan-2-one
[226] 8-(3-bromobenzoyl)-3-(3,4-difluorobenzyl)-1-oxa-3,8-diazaspiro[4.5]decan-2-one
[227] 8-(3-bromobenzoyl)-3-naphthalen-2-ylmethyl-1-oxa-3,8-diazaspiro[4.5]decan-2-one
[228] 8-(3-bromobenzoyl)-3-(4-tert-butylbenzyl)-1-oxa-3,8-diazaspiro[4.5]decan-2-one
[229] 3-benzyl-8-(3-fluorobenzoyl)-1-oxa-3,8-diazaspiro[4.5]decan-2-one
[230] 8-(3-fluorobenzoyl)-3-(2-fluorobenzyl)-1-oxa-3,8-diazaspiro[4.5]decan-2-one
[231] 3-(3,4-difluorobenzyl)-8-(3-fluorobenzoyl)-1-oxa-3,8-diazaspiro[4.5]decan-2-one
[232] 8-(3-fluorobenzoyl)-3-(4-trifluoromethylbenzyl)-1-oxa-3,8-diazaspiro[4.5]decan-2-one
[233] 3-(3-bromobenzyl)-8-(3-fluorobenzoyl)-1-oxa-3,8-diazaspiro[4.5]decan-2-one
[234] 8-(3-chlorobenzoyl)-3-(3,5-dimethylbenzyl)-1-oxa-3,8-diazaspiro[4.5]decan-2-one
[235] 3-benzyl-8-(3-chlorobenzoyl)-1-oxa-3,8-diazaspiro[4.5]decan-2-one
[236] 4-[8-(3,4-dichlorobenzoyl)-2-oxo-1-oxa-3,8-diazaspiro[4.5]dec-3-ylmethyl]benzonitrile
[237] 3-(4-iodobenzyl)-8-(3-methoxybenzoyl)-1-oxa-3,8-diazaspiro[4.5]decan-2-one
[238] 3-(2-fluorobenzyl)-8-(3-methoxybenzoyl)-1-oxa-3,8-diazaspiro[4.5]decan-2-one
[239] 3-(4-tert-butylbenzyl)-8-(3-methoxybenzoyl)-1-oxa-3,8-diazaspiro[4.5]decan-2-one
[240] 3-benzyl-8-(3-methylbenzoyl)-1-oxa-3,8-diazaspiro[4.5]decan-2-one
[241] 3-(2-methoxy-5-nitrobenzyl)-8-(3-methylbenzoyl)-1-oxa-3,8-diazaspiro[4.5]decan-2-one
[242] 3-(4-tert-butylbenzyl)-8-(3-methylbenzoyl)-1-oxa-3,8-diazaspiro[4.5]decan-2-one
[243] 8-(3-methylbenzoyl)-3-(4-trifluoromethylbenzyl)-1-oxa-3,8-diazaspiro[4.5]decan-2-one
[244] 3-(3,4-difluorobenzyl)-8-(2-phenyl-butyryl)-1-oxa-3,8-diazaspiro[4.5]decan-2-one
[245] 3-benzyl-8-[3-(2-chlorophenyl)-5-methylisoxazole-4-carbonyl]-1-oxa-3,8-diazaspiro[4.5]decan-2-one
[246] 4-[8-(2,3-dichlorobenzoyl)-2-oxo-1-oxa-3,8-diazaspiro[4.5]dec-3-ylmethyl]benzonitrile
[247] 8-[2-(4-chlorophenyl)acetyl]-3-(3,4-difluorobenzyl)-1-oxa-3,8-diazaspiro[4.5]decan-2-one
[248] 3-biphenyl-2-ylmethyl-8-[2-(4-chlorophenyl)acetyl]-1-oxa-3,8-diazaspiro[4.5]decan-2-one
[249] 8-[2-(4-chlorophenyl)acetyl]-3-(4-trifluoromethylsulfanylbenzyl)-1-oxa-3,8-diazaspiro[4.5]decan-2-one
[250] 3-(4-tert-butylbenzyl)-8-[3-(2-chlorophenyl)acryloyl]-1-oxa-3,8-diazaspiro[4.5]decan-2-one
[251] 3-biphenyl-2-ylmethyl-8-[3-(2-chlorophenyl)acryloyl]-1-oxa-3,8-diazaspiro[4.5]decan-2-one
[252] 3-(3-bromobenzyl)-8-[3-(2-chlorophenyl)acryloyl]-1-oxa-3,8-diazaspiro[4.5]decan-2-one
[253] 4-[8-(2,3-difluorobenzoyl)-2-oxo-1-oxa-3,8-diazaspiro[4.5]dec-3-ylmethyl]benzonitrile
[254] 8-(2,3-difluorobenzoyl)-3-(2-trifluoromethylbenzyl)-1-oxa-3,8-diazaspiro[4.5]decan-2-one
[255] 8-(2,3-difluorobenzoyl)-3-(4-iodobenzyl)-1-oxa-3,8-diazaspiro[4.5]decan-2-one
[256] 2-[2-oxo-8-(2-propylpentanoyl)-1-oxa-3,8-diazaspiro[4.5]dec-3-ylmethyl]benzonitrile
[257] 3-(3,4-difluorobenzyl)-8-(2-propylpentanoyl)-1-oxa-3,8-diazaspiro[4.5]decan-2-one
[258] 8-(2-chloro-4-nitrobenzoyl)-3I-(4-methylbenzyl)-1-oxa-3,8-diazaspiro[4.5]decan-2-one
[259] 8-(2-chloro-4-nitrobenzoyl)-3I-(2-trifluoromethylbenzyl)-1-oxa-3,8-diazaspiro[4.5]decan-2-one
[260] 3-(4-tert-butylbenzyl)-8-(2-chloro-4-nitrobenzoyl)-1-oxa-3,8-diazaspiro[4.5]decan-2-one
[261] 8-(2-chloro-4-nitrobenzoyl)-3I-(4-trifluoromethylbenzyl)-1-oxa-3,8-diazaspiro[4.5]decan-2-one
[262] 3-biphenyl-2-ylmethyl-8-(2-chloro-4-nitrobenzoyl)-1-oxa-3,8-diazaspiro[4.5]decan-2-one
[263] 3-(3-bromobenzyl)-8-(2-chloro-4-nitrobenzoyl)-1-oxa-3,8-diazaspiro[4.5]decan-2-one
[264] 8-(2-chloro-4-nitrobenzoyl)-3I-(4-trifluoromethylsulfanylbenzyl)-1-oxa-3,8-diazaspiro[4.5]decan-2-one
[265] 8-(2-chloropyridine-3-carbonyl)-3-(4-fluorobenzyl)-1-oxa-3,8-diazaspiro[4.5]decan-2-one
[266] 2-[8-(2-chloropyridine-3-carbonyl)-2-oxo-1-oxa-3,8-diazaspiro[4.5]dec-3-ylmethyl]benzonitrile
[267] 8-(2-chloropyridine-3-carbonyl)-3-(4-methylbenzyl)-1-oxa-3,8-diazaspiro[4.5]decan-2-one
[268] 8-(2-chloropyridine-3-carbonyl)-3-(4-trifluoromethylbenzyl)-1-oxa-3,8-diazaspiro[4.5]decan-2-one
[269] 3-(3-methoxybenzyl)-8-(2-methylsulfanylpyridine-3-carbonyl)-1-oxa-3,8-diazaspiro[4.5]decan-2-one
[270] 3-(4-methylbenzyl)-8-(2-methylsulfanylpyridine-3-carbonyl)-1-oxa-3,8-diazaspiro[4.5]decan-2-one
[271] 3-(4-iodobenzyl)-8-(2-methylsulfanylpyridine-3-carbonyl)-1-oxa-3,8-diazaspiro[4.5]decan-2-one
[272] 3-(3,4-difluorobenzyl)-8-(2-methylsulfanylpyridine-3-carbonyl)-1-oxa-3,8-diazaspiro[4.5]decan-2-one
[273] 3-(4-tert-butylbenzyl)-8-(2-methylsulfanylpyridine-3-carbonyl)-1-oxa-3,8-diazaspiro[4.5]decan-2-one

[274] 8-(2-methylsulfanylpyridine-3-carbonyl)-3-(4-trifluoromethylbenzyl)-1-oxa-3,8-diazaspiro[4.5]decan-2-one
[275] 8-(2-ethylsulfanylpyridine-3-carbonyl)-3-(4-fluorobenzyl)-1-oxa-3,8-diazaspiro[4.5]decan-2-one
[276] 3-[8-(2-ethylsulfanylpyridine-3-carbonyl)-2-oxo-1-oxa-3,8-diazaspiro[4.5]dec-3-ylmethyl]benzonitrile
[277] 2-[8-(2-ethylsulfanylpyridine-3-carbonyl)-2-oxo-1-oxa-3,8-diazaspiro[4.5]dec-3-ylmethyl]benzonitrile
[278] 8-(2-ethylsulfanylpyridine-3-carbonyl)-3-(4-methylbenzyl)-1-oxa-3,8-diazaspiro[4.5]decan-2-one
[279] 3-benzyl-8-(2-ethylsulfanylpyridine-3-carbonyl)-1-oxa-3,8-diazaspiro[4.5]decan-2-one
[280] 8-(2-ethylsulfanylpyridine-3-carbonyl)-3-(2-fluorobenzyl)-1-oxa-3,8-diazaspiro[4.5]decan-2-one
[281] 4-[8-(6-chloropyridine-3-carbonyl)-2-oxo-1-oxa-3,8-diazaspiro[4.5]dec-3-ylmethyl]benzonitrile
[282] 8-(6-chloropyridine-3-carbonyl)-3-(2-trifluoromethylbenzyl)-1-oxa-3,8-diazaspiro[4.5]decan-2-one
[283] 8-(6-chloropyridine-3-carbonyl)-3-(4-iodobenzyl)-1-oxa-3,8-diazaspiro[4.5]decan-2-one
[284] 3-(4-tert-butylbenzyl)-8-(6-chloropyridine-3-carbonyl)-1-oxa-3,8-diazaspiro[4.5]decan-2-one
[285] 3-biphenyl-2-ylmethyl-8-(6-chloropyridine-3-carbonyl)-1-oxa-3,8-diazaspiro[4.5]decan-2-one
[286] 3-(3-methoxybenzyl)-8-(4-trifluoromethoxybenzoyl)-1-oxa-3,8-diazaspiro[4.5]decan-2-one
[287] 3-(3,4-difluorobenzyl)-8-(4-trifluoromethoxybenzoyl)-1-oxa-3,8-diazaspiro[4.5]decan-2-one
[288] 8-[3-(2-chloro-6-fluorophenyl)-5-methylisoxazole-4-carbonyl]-3-(4-fluorobenzyl)-1-oxa-3,8-diazaspiro[4.5]decan-2-one
[289] 8-[3-(2-chloro-6-fluorophenyl)-5-methylisoxazole-4-carbonyl]-3-(3-methoxybenzyl)-1-oxa-3,8-diazaspiro[4.5]decan-2-one
[290] 8-[3-(2-chloro-6-fluorophenyl)-5-methylisoxazole-4-carbonyl]-3-(4-trifluoromethylbenzyl)-1-oxa-3,8-diazaspiro[4.5]decan-2-one
[291] 8-[3-(2-chloro-6-fluorophenyl)-5-methylisoxazole-4-carbonyl]-3-(4-trifluoromethylsulfanylbenzyl)-1-oxa-3,8-diazaspiro[4.5]decan-2-one
[292] 3-(4-methylbenzyl)-8-(3-trifluoromethoxybenzoyl)-1-oxa-3,8-diazaspiro[4.5]decan-2-one
[293] 3-(4-iodobenzyl)-8-(3-trifluoromethoxybenzoyl)-1-oxa-3,8-diazaspiro[4.5]decan-2-one
[294] 3-(3,4-difluorobenzyl)-8-(3-trifluoromethoxybenzoyl)-1-oxa-3,8-diazaspiro[4.5]decan-2-one
[295] 3-naphthalen-2-ylmethyl-8-(3-trifluoromethoxybenzoyl)-1-oxa-3,8-diazaspiro[4.5]decan-2-one
[296] 4-[8-(isoxazole-5-carbonyl)-2-oxo-1-oxa-3,8-diazaspiro[4.5]dec-3-ylmethyl]benzonitrile
[297] 8-(isoxazole-5-carbonyl)-3-(2-trifluoromethylbenzyl)-1-oxa-3,8-diazaspiro[4.5]decan-2-one
[298] 8-(isoxazole-5-carbonyl)-3-(2-methoxy-5-nitrobenzyl)-1-oxa-3,8-diazaspiro[4.5]decan-2-one
[299] 3-(3-bromobenzyl)-8-(isoxazole-5-carbonyl)-1-oxa-3,8-diazaspiro[4.5]decan-2-one
[300] 2-[8-(2-chloro-6-fluorobenzoyl)-2-oxo-1-oxa-3,8-diazaspiro[4.5]dec-3-ylmethyl]benzonitrile
[301] 4-[8-(2-chloro-6-fluorobenzoyl)-2-oxo-1-oxa-3,8-diazaspiro[4.5]dec-3-ylmethyl]benzonitrile
[302] 8-(2-chloro-6-fluorobenzoyl)-3-(4-methylbenzyl)-1-oxa-3,8-diazaspiro[4.5]decan-2-one
[303] 3-biphenyl-2-ylmethyl-8-(2-chloro-6-fluorobenzoyl)-1-oxa-3,8-diazaspiro[4.5]decan-2-one
[304] 8-(2,5-dimethylfuran-3-carbonyl)-3-(3-methoxybenzyl)-1-oxa-3,8-diazaspiro[4.5]decan-2-one
[305] 4-[8-(2,5-dimethylfuran-3-carbonyl)-2-oxo-1-oxa-3,8-diazaspiro[4.5]dec-3-ylmethyl]benzonitrile
[306] 4-[8-(4-bromo-3-methylbenzoyl)-2-oxo-1-oxa-3,8-diazaspiro[4.5]dec-3-ylmethyl]benzonitrile
[307] 8-(4-bromo-3-methylbenzoyl)-3-(4-methylbenzyl)-1-oxa-3,8-diazaspiro[4.5]decan-2-one
[308] 3-benzyl-8-(4-bromo-3-methylbenzoyl)-1-oxa-3,8-diazaspiro[4.5]decan-2-one
[309] 8-(4-bromo-3-methylbenzoyl)-3-(2-trifluoromethylbenzyl)-1-oxa-3,8-diazaspiro[4.5]decan-2-one
[310] 8-(4-bromo-3-methylbenzoyl)-3-(3,4-difluorobenzyl)-1-oxa-3,8-diazaspiro[4.5]decan-2-one
[311] 8-(4-bromo-3-methylbenzoyl)-3-(4-tert-butylbenzyl)-1-oxa-3,8-diazaspiro[4.5]decan-2-one
[312] 3-biphenyl-2-ylmethyl-8-(4-bromo-3-methylbenzoyl)-1-oxa-3,8-diazaspiro[4.5]decan-2-one
[313] 8-(4-bromo-3-methylbenzoyl)-3-(4-trifluoromethylsulfanylbenzyl)-1-oxa-3,8-diazaspiro[4.5]decan-2-one
[314] 8-(2,6-difluoro-3-methylbenzoyl)-3-(3-methoxybenzyl)-1-oxa-3,8-diazaspiro[4.5]decan-2-one
[315] 2-[8-(2,6-difluoro-3-methylbenzoyl)-2-oxo-1-oxa-3,8-diazaspiro[4.5]dec-3-ylmethyl]benzonitrile
[316] 4-[8-(2,6-difluoro-3-methylbenzoyl)-2-oxo-1-oxa-3,8-diazaspiro[4.5]dec-3-ylmethyl]benzonitrile
[317] 8-(2,6-difluoro-3-methylbenzoyl)-3-(2-trifluoromethylbenzyl)-1-oxa-3,8-diazaspiro[4.5]decan-2-one
[318] 8-(2,6-difluoro-3-methylbenzoyl)-3-(2-fluorobenzyl)-1-oxa-3,8-diazaspiro[4.5]decan-2-one
[319] 8-(2-chloro-6-fluoro-3-methylbenzoyl)-3-(4-fluorobenzyl)-1-oxa-3,8-diazaspiro[4.5]decan-2-one
[320] 8-(2-chloro-6-fluoro-3-methylbenzoyl)-3-(3-methoxybenzyl)-1-oxa-3,8-diazaspiro[4.5]decan-2-one
[321] 8-(2-chloro-6-fluoro-3-methylbenzoyl)-3-(4-trifluoromethylsulfanylbenzyl)-1-oxa-3,8-diazaspiro[4.5]decan-2-one
[322] 3-biphenyl-2-ylmethyl-8-(6-chloro-2-fluoro-3-methylbenzoyl)-1-oxa-3,8-diazaspiro[4.5]decan-2-one
[323] 3-benzyl-8-(3-difluoromethylsulfanylbenzoyl)-1-oxa-3,8-diazaspiro[4.5]decan-2-one
[324] 8-(3-difluoromethylsulfanylbenzoyl)-3-naphthalen-2-ylmethyl-1-oxa-3,8-diazaspiro[4.5]decan-2-one
[325] 8-(3-difluoromethylsulfanylbenzoyl)-3-(4-trifluoromethylbenzyl)-1-oxa-3,8-diazaspiro[4.5]decan-2-one
[326] 3-(3-bromobenzyl)-8-(3-difluoromethylsulfanylbenzoyl)-1-oxa-3,8-diazaspiro[4.5]decan-2-one
[327] 3-[8-(3-chloro-2-fluorobenzoyl)-2-oxo-1-oxa-3,8-diazaspiro[4.5]dec-3-ylmethyl]benzonitrile
[328] 8-(3-chloro-2-fluorobenzoyl)-3-(4-iodobenzyl)-1-oxa-3,8-diazaspiro[4.5]decan-2-one
[329] 8-(3-chloro-2-fluorobenzoyl)-3-naphthalen-2-ylmethyl-1-oxa-3,8-diazaspiro[4.5]decan-2-one
[330] 3-(3-methoxybenzyl)-8-(4-trifluoromethylsulfanylbenzoyl)-1-oxa-3,8-diazaspiro[4.5]decan-2-one
[331] 2-[2-oxo-8-(4-trifluoromethylsulfanylbenzoyl)-1-oxa-3,8-diazaspiro[4.5]dec-3-ylmethyl]benzonitrile
[332] 4-[2-oxo-8-(4-trifluoromethylsulfanylbenzoyl)-1-oxa-3,8-diazaspiro[4.5]dec-3-ylmethyl]benzonitrile
[333] 3-(4-iodobenzyl)-8-(4-trifluoromethylsulfanylbenzoyl)-1-oxa-3,8-diazaspiro[4.5]decan-2-one
[334] 3-naphthalen-2-ylmethyl-8-(4-trifluoromethylsulfanylbenzoyl)-1-oxa-3,8-diazaspiro[4.5]decan-2-one
[335] 3-(4-trifluoromethylbenzyl)-8-(4-trifluoromethylsulfanylbenzoyl)-1-oxa-3,8-diazaspiro[4.5]decan-2-one

[336] 8-(2-chloro-5-trifluoromethylbenzoyl)-3-(2-trifluoromethylbenzyl)-1-oxa-3,8-diazaspiro[4.5]decan-2-one
[337] 8-(2-chloro-5-trifluoromethylbenzoyl)-3-(2-fluorobenzyl)-1-oxa-3,8-diazaspiro[4.5]decan-2-one
[338] 8-(2-chloro-5-trifluoromethylbenzoyl)-3-(3,4-difluorobenzyl)-1-oxa-3,8-diazaspiro[4.5]decan-2-one
[339] 8-(2,3-difluoro-4-methylbenzoyl)-3-(3-methoxybenzyl)-1-oxa-3,8-diazaspiro[4.5]decan-2-one
[340] 4-[8-(2,3-difluoro-4-methylbenzoyl)-2-oxo-1-oxa-3,8-diazaspiro[4.5]dec-3-ylmethyl]benzonitrile
[341] 3-benzyl-8-(2,3-difluoro-4-methylbenzoyl)-1-oxa-3,8-diazaspiro[4.5]decan-2-one
[342] 8-(2,3-difluoro-4-methylbenzoyl)-3-(4-iodobenzyl)-1-oxa-3,8-diazaspiro[4.5]decan-2-one
[343] 3-(3,4-difluorobenzyl)-8-(2,3-difluoro-4-methylbenzoyl)-1-oxa-3,8-diazaspiro[4.5]decan-2-one
[344] 8-(2,3-difluoro-4-methylbenzoyl)-3-naphthalen-2-ylmethyl-1-oxa-3,8-diazaspiro[4.5]decan-2-one
[345] 3-biphenyl-2-ylmethyl-8-(2,3-difluoro-4-methylbenzoyl)-1-oxa-3,8-diazaspiro[4.5]decan-2-one
[346] 3-(3-bromobenzyl)-8-(2,3-difluoro-4-methylbenzoyl)-1-oxa-3,8-diazaspiro[4.5]decan-2-one
[347] 3-benzyl-8-[2-(2-methoxyethoxy)acetyl]-1-oxa-3,8-diazaspiro[4.5]decan-2-one
[348] 3-(2-fluorobenzyl)-8-[2-(2-methoxyethoxy)acetyl]-1-oxa-3,8-diazaspiro[4.5]decan-2-one
[349] 3-(3,4-difluorobenzyl)-8-[2-(2-methoxyethoxy)acetyl]-1-oxa-3,8-diazaspiro[4.5]decan-2-one
[350] 3-(4-tert-butylbenzyl)-8-[2-(2-methoxyethoxy)acetyl]-1-oxa-3,8-diazaspiro[4.5]decan-2-one
[351] 8-[2-(2-methoxyethoxy)acetyl]-3-(4-trifluoromethylsulfanylbenzyl)-1-oxa-3,8-diazaspiro[4.5]decan-2-one
[352] 8-(1-acetylpiperidine-4-carbonyl)-3-(3,4-difluorobenzyl)-1-oxa-3,8-diazaspiro[4.5]decan-2-one
[353] 4-{8-[2-(3-chlorophenoxy)acetyl]-2-oxo-1-oxa-3,8-diazaspiro[4.5]dec-3-ylmethyl}benzonitrile
[354] 8-[2-(3-chlorophenoxy)acetyl]-3-(3,4-difluorobenzyl)-1-oxa-3,8-diazaspiro[4.5]decan-2-one
[355] 3-(3-bromobenzyl)-8-[2-(3-chlorophenoxy)acetyl]-1-oxa-3,8-diazaspiro[4.5]decan-2-one
[356] 8-[2-(3-chlorophenoxy)acetyl]-3-(4-trifluoromethylsulfanylbenzyl)-1-oxa-3,8-diazaspiro[4.5]decan-2-one
[357] 4-[3-(3-methoxybenzyl)-2-oxo-1-oxa-3,8-diazaspiro[4.5]decane-8-carbonyl]benzylsulfonamide
[358] N-{4-[3-(3,4-difluorobenzyl)-2-oxo-1-oxa-3,8-diazaspiro[4.5]decane-8-carbonyl]phenyl}acetamide
[359] 8-(3-dimethylaminobenzoyl)-3-(3,5-dimethylbenzyl)-1-oxa-3,8-diazaspiro[4.5]decan-2-one
[360] 3-(4-tert-butylbenzyl)-8-(3-dimethylaminobenzoyl)-1-oxa-3,8-diazaspiro[4.5]decan-2-one
[361] 3-(3-bromobenzyl)-8-(3-dimethylaminobenzoyl)-1-oxa-3,8-diazaspiro[4.5]decan-2-one
[362] 3-(4-methylbenzyl)-8-(4-phenoxybutyryl)-1-oxa-3,8-diazaspiro[4.5]decan-2-one
[363] 8-(4-phenoxybutyryl)-3-(2-trifluoromethylbenzyl)-1-oxa-3,8-diazaspiro[4.5]decan-2-one
[364] 3-(2-fluorobenzyl)-8-(4-phenoxybutyryl)-1-oxa-3,8-diazaspiro[4.5]decan-2-one
[365] 8-(2,3-dimethylbenzoyl)-3-(4-fluorobenzyl)-1-oxa-3,8-diazaspiro[4.5]decan-2-one
[366] 3-[8-(2,3-dimethylbenzoyl)-2-oxo-1-oxa-3,8-diazaspiro[4.5]dec-3-ylmethyl]benzonitrile
[367] 8-(2,3-dimethylbenzoyl)-3-(3,5-dimethylbenzyl)-1-oxa-3,8-diazaspiro[4.5]decan-2-one
[368] 8-(2,3-dimethylbenzoyl)-3-(4-methylbenzyl)-1-oxa-3,8-diazaspiro[4.5]decan-2-one
[369] 8-(2,3-dimethylbenzoyl)-3-(2-trifluoromethylbenzyl)-1-oxa-3,8-diazaspiro[4.5]decan-2-one
[370] 8-(2,3-dimethylbenzoyl)-3-(2-methoxy-5-nitrobenzyl)-1-oxa-3,8-diazaspiro[4.5]decan-2-one
[371] 8-(2,3-dimethylbenzoyl)-3-(4-trifluoromethylbenzyl)-1-oxa-3,8-diazaspiro[4.5]decan-2-one
[372] 3-biphenyl-2-ylmethyl-8-(2,3-dimethylbenzoyl)-1-oxa-3,8-diazaspiro[4.5]decan-2-one
[373] 4-[8-(5-methyl-2-phenyl-2H-[1,2,3]triazole-4-carbonyl)-2-oxo-1-oxa-3,8-diazaspiro[4.5]dec-3-ylmethyl]benzonitrile
[374] 3-benzyl-8-(5-methyl-2-phenyl-2H-[1,2,3]triazole-4-carbonyl)-1-oxa-3,8-diazaspiro[4.5]decan-2-one
[375] 3-(3,4-difluorobenzyl)-8-(5-methyl-2-phenyl-2H-[1,2,3]triazole-4-carbonyl)-1-oxa-3,8-diazaspiro[4.5]decan-2-one
[376] 8-(5-methyl-2-phenyl-2H-[1,2,3]triazole-4-carbonyl)-3-naphthalen-2-ylmethyl-1-oxa-3,8-diazaspiro[4.5]decan-2-one
[377] 3-biphenyl-2-ylmethyl-8-(5-methyl-2-phenyl-2H-[1,2,3]triazole-4-carbonyl)-1-oxa-3,8-diazaspiro[4.5]decan-2-one
[378] 3-(4-tert-butylbenzyl)-8-[3-(2,6-dichlorophenyl)-5-methylisoxazole-4-carbonyl]-1-oxa-3,8-diazaspiro[4.5]decan-2-one
[379] 3-[2-oxo-8-(2-phenoxypyridine-3-carbonyl)-1-oxa-3,8-diazaspiro[4.5]dec-3-ylmethyl]benzonitrile
[380] 2-[2-oxo-8-(2-phenoxypyridine-3-carbonyl)-1-oxa-3,8-diazaspiro[4.5]dec-3-ylmethyl]benzonitrile
[381] 3-(4-fluorobenzyl)-8-(pyridine-2-carbonyl)-1-oxa-3,8-diazaspiro[4.5]decan-2-one
[382] 3-(3-methoxybenzyl)-8-(pyridine-2-carbonyl)-1-oxa-3,8-diazaspiro[4.5]decan-2-one
[383] 3-(3,5-dimethylbenzyl)-8-(pyridine-2-carbonyl)-1-oxa-3,8-diazaspiro[4.5]decan-2-one
[384] 2-[2-oxo-8-(pyridine-2-carbonyl)-1-oxa-3,8-diazaspiro[4.5]dec-3-ylmethyl]benzonitrile
[385] 3-(2-fluorobenzyl)-8-(pyridine-2-carbonyl)-1-oxa-3,8-diazaspiro[4.5]decan-2-one
[386] 3-(3,4-difluorobenzyl)-8-(pyridine-2-carbonyl)-1-oxa-3,8-diazaspiro[4.5]decan-2-one
[387] 3-biphenyl-2-ylmethyl-8-(pyridine-2-carbonyl)-1-oxa-3,8-diazaspiro[4.5]decan-2-one
[388] 4-[8-(3-chlorothiophene-2-carbonyl)-2-oxo-1-oxa-3,8-diazaspiro[4.5]dec-3-ylmethyl]benzonitrile
[389] 8-(3-chlorothiophene-2-carbonyl)-3-(3,4-difluorobenzyl)-1-oxa-3,8-diazaspiro[4.5]decan-2-one
[390] 3-biphenyl-2-ylmethyl-8-(3-chlorothiophene-2-carbonyl)-1-oxa-3,8-diazaspiro[4.5]decan-2-one
[391] 8-[1-(4-chlorophenyl)-5-trifluoromethyl-1H-pyrazole-4-carbonyl]-3-(2-fluorobenzyl)-1-oxa-3,8-diazaspiro[4.5]decan-2-one
[392] 8-[1-(4-chlorophenyl)-5-trifluoromethyl-1H-pyrazole-4-carbonyl]-3-(3,4-difluorobenzyl)-1-oxa-3,8-diazaspiro[4.5]decan-2-one
[393] 8-[1-(4-chlorophenyl)-5-trifluoromethyl-1H-pyrazole-4-carbonyl]-3-(4-trifluoromethylsulfanylbenzyl)-1-oxa-3,8-diazaspiro[4.5]decan-2-one
[394] 3-(4-tert-butylbenzyl)-8-(5-tert-butyl-2-methyl-2H-pyrazole-3-carbonyl)-1-oxa-3,8-diazaspiro[4.5]decan-2-one
[395] 3-[8-(5-methylisoxazole-3-carbonyl)-2-oxo-1-oxa-3,8-diazaspiro[4.5]dec-3-ylmethyl]benzonitrile
[396] 3-(3,5-dimethylbenzyl)-8-(5-methylisoxazole-3-carbonyl)-1-oxa-3,8-diazaspiro[4.5]decan-2-one

[397] 2-[8-(5-methylisoxazole-3-carbonyl)-2-oxo-1-oxa-3,8-diazaspiro[4.5]dec-3-ylmethyl]benzonitrile
[398] 4-[8-(5-methylisoxazole-3-carbonyl)-2-oxo-1-oxa-3,8-diazaspiro[4.5]dec-3-ylmethyl]benzonitrile
[399] 3-benzyl-8-(5-methylisoxazole-3-carbonyl)-1-oxa-3,8-diazaspiro[4.5]decan-2-one
[400] 3-(3,4-difluorobenzyl)-8-(5-methylisoxazole-3-carbonyl)-1-oxa-3,8-diazaspiro[4.5]decan-2-one
[401] 3-biphenyl-2-ylmethyl-8-(5-methylisoxazole-3-carbonyl)-1-oxa-3,8-diazaspiro[4.5]decan-2-one
[402] 8-(4-methyl[1,2,3]thiadiazole-5-carbonyl)-3-(2-trifluoromethylbenzyl)-1-oxa-3,8-diazaspiro[4.5]decan-2-one
[403] 3-(4-tert-butylbenzyl)-8-(4-methyl[1,2,3]thiadiazole-5-carbonyl)-1-oxa-3,8-diazaspiro[4.5]decan-2-one
[404] 8-(4-methyl[1,2,3]thiadiazole-5-carbonyl)-3-(4-trifluoromethylsulfanylbenzyl)-1-oxa-3,8-diazaspiro[4.5]decan-2-one
[405] 4-[2-oxo-8-(1-phenyl-5-propyl-1H-pyrazole-4-carbonyl)-1-oxa-3,8-diazaspiro[4.5]dec-3-ylmethyl]benzonitrile
[406] 3-(3,4-difluorobenzyl)-8-(1-phenyl-5-propyl-1H-pyrazole-4-carbonyl)-1-oxa-3,8-diazaspiro[4.5]decan-2-one
[407] 3-naphthalen-2-ylmethyl-8-(1-phenyl-5-propyl-1H-pyrazole-4-carbonyl)-1-oxa-3,8-diazaspiro[4.5]decan-2-one
[408] 8-(1-phenyl-5-propyl-1H-pyrazole-4-carbonyl)-3-(4-trifluoromethylsulfanylbenzyl)-1-oxa-3,8-diazaspiro[4.5]decan-2-one
[409] 3-[8-(2-chloropyridine-4-carbonyl)-2-oxo-1-oxa-3,8-diazaspiro[4.5]dec-3-ylmethyl]benzonitrile
[410] 8-(2-chloropyridine-4-carbonyl)-3-(3-methoxybenzyl)-1-oxa-3,8-diazaspiro[4.5]decan-2-one
[411] 8-(5-tert-butyl-2-methylfuran-3-carbonyl)-3-(4-fluorobenzyl)-1-oxa-3,8-diazaspiro[4.5]decan-2-one
[412] 3-[8-(5-tert-butyl-2-methylfuran-3-carbonyl)-2-oxo-1-oxa-3,8-diazaspiro[4.5]dec-3-ylmethyl]benzonitrile
[413] 2-[8-(5-tert-butyl-2-methylfuran-3-carbonyl)-2-oxo-1-oxa-3,8-diazaspiro[4.5]dec-3-ylmethyl]benzonitrile
[414] 4-[8-(5-tert-butyl-2-methylfuran-3-carbonyl)-2-oxo-1-oxa-3,8-diazaspiro[4.5]dec-3-ylmethyl]benzonitrile
[415] 8-(5-tert-butyl-2-methylfuran-3-carbonyl)-3-(2-trifluoromethylbenzyl)-1-oxa-3,8-diazaspiro[4.5]decan-2-one
[416] 8-(5-tert-butyl-2-methylfuran-3-carbonyl)-3-naphthalen-2-ylmethyl-1-oxa-3,8-diazaspiro[4.5]decan-2-one
[417] 3-biphenyl-2-ylmethyl-8-(5-tert-butyl-2-methylfuran-3-carbonyl)-1-oxa-3,8-diazaspiro[4.5]decan-2-one
[418] 3-(3-bromobenzyl)-8-(5-tert-butyl-2-methylfuran-3-carbonyl)-1-oxa-3,8-diazaspiro[4.5]decan-2-one
[419] 8-(benzo[1,2,5]oxadiazole-5-carbonyl)-3-(3,4-difluorobenzyl)-1-oxa-3,8-diazaspiro[4.5]decan-2-one
[420] 8-(benzo[1,2,5]oxadiazole-5-carbonyl)-3-(4-trifluoromethylbenzyl)-1-oxa-3,8-diazaspiro[4.5]decan-2-one
[421] 3-[8-(2-methyl-6-trifluoromethylpyridine-3-carbonyl)-2-oxo-1-oxa-3,8-diazaspiro[4.5]dec-3-ylmethyl]benzonitrile
[422] 2-[8-(2-methyl-6-trifluoromethylpyridine-3-carbonyl)-2-oxo-1-oxa-3,8-diazaspiro[4.5]dec-3-ylmethyl]benzonitrile
[423] 4-[8-(2-methyl-6-trifluoromethylpyridine-3-carbonyl)-2-oxo-1-oxa-3,8-diazaspiro[4.5]dec-3-ylmethyl]benzonitrile
[424] 8-(2-methyl-6-trifluoromethylpyridine-3-carbonyl)-3-(2-trifluoromethylbenzyl)-1-oxa-3,8-diazaspiro[4.5]decan-2-one
[425] 3-(3,4-difluorobenzyl)-8-(2-methyl-6-trifluoromethylpyridine-3-carbonyl)-1-oxa-3,8-diazaspiro[4.5]decan-2-one
[426] 3-(3-bromobenzyl)-8-(2-methyl-6-trifluoromethylpyridine-3-carbonyl)-1-oxa-3,8-diazaspiro[4.5]decan-2-one
[427] 8-(6-chloro-2H-chromene-3-carbonyl)-3-(3,4-difluorobenzyl)-1-oxa-3,8-diazaspiro[4.5]decan-2-one
[428] 8-(2-chloropyridine-4-carbonyl)-3-(2-fluorobenzyl)-1-oxa-3,8-diazaspiro[4.5]decan-2-one
[429] 8-(2-chloropyridine-4-carbonyl)-3-naphthalen-2-ylmethyl-1-oxa-3,8-diazaspiro[4.5]decan-2-one
[430] 8-acetyl-3-(2-fluorobenzyl)-1-oxa-3,8-diazaspiro[4.5]decan-2-one
[431] 8-acetyl-3-(3-bromobenzyl)-1-oxa-3,8-diazaspiro[4.5]decan-2-one and
[432] 3-(2-methoxy-5-nitrobenzyl)-8-(3-phenoxypropyl)-1-oxa-3,8-diazaspiro[4.5]decan-2-one;
and pharmaceutically acceptable salts thereof.

20. A pharmaceutical composition comprising a compound as claimed in claim 1 and at least one physiologically acceptable auxiliary substance.

\* \* \* \* \*